United States Patent
Jolly et al.

(10) Patent No.: US 9,011,842 B2
(45) Date of Patent: *Apr. 21, 2015

(54) USE OF PROTEASES FOR GLUTEN INTOLERANCE

(75) Inventors: James F. Jolly, Elgin, IL (US); Horoki Ido, Nagoya (JP); Hirotaka Matsubara, Nagoya (JP); Tetsuya Takahashi, Nagoya (JP); Kyoichi Nishio, Nagoya (JP)

(73) Assignees: Amano Enzyme Inc., Nagoya (JP); Amano Enzyme USA Co., Ltd., Elgin, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/520,277

(22) PCT Filed: Feb. 2, 2011

(86) PCT No.: PCT/US2011/023424
§ 371 (c)(1),
(2), (4) Date: Oct. 19, 2012

(87) PCT Pub. No.: WO2011/097266
PCT Pub. Date: Aug. 11, 2011

(65) Prior Publication Data
US 2013/0034531 A1    Feb. 7, 2013

Related U.S. Application Data

(60) Provisional application No. 61/300,726, filed on Feb. 2, 2010.

(51) Int. Cl.
| | |
|---|---|
| A61K 38/48 | (2006.01) |
| A61K 38/17 | (2006.01) |
| A61K 38/22 | (2006.01) |
| A61K 38/24 | (2006.01) |

(52) U.S. Cl.
CPC ........... *A61K 38/4873* (2013.01); *A61K 38/482* (2013.01); *A61K 38/1703* (2013.01); *A61K 38/2242* (2013.01); *A61K 38/24* (2013.01); *A61K 38/4886* (2013.01); *C12Y 304/21063* (2013.01); *C12Y 304/24039* (2013.01)

(58) Field of Classification Search
None
See application file for complete search history.

(56) References Cited

U.S. PATENT DOCUMENTS

| | | | |
|---|---|---|---|
| 5,268,360 A | 12/1993 | Yoshikawa et al. | |
| 5,387,422 A * | 2/1995 | Handel et al. | 426/2 |
| 7,138,252 B2 | 11/2006 | Bachmann et al. | |
| 7,202,216 B2 | 4/2007 | Sollid et al. | |
| 7,252,957 B2 | 8/2007 | Vojdani | |
| 7,303,871 B2 | 12/2007 | Hausch et al. | |
| 7,320,788 B2 | 1/2008 | Shan et al. | |
| 7,354,734 B2 | 4/2008 | Monod et al. | |
| 7,462,688 B2 | 12/2008 | Khosla et al. | |
| 7,468,267 B2 | 12/2008 | Monod et al. | |
| 7,494,656 B2 | 2/2009 | Bachmann et al. | |
| 7,534,426 B2 | 5/2009 | Piper et al. | |
| 7,563,864 B2 | 7/2009 | Marti et al. | |
| 7,910,541 B2 | 3/2011 | Hausch et al. | |
| 7,923,532 B2 | 4/2011 | Hausch et al. | |
| 7,928,056 B2 | 4/2011 | Hausch et al. | |
| 7,943,312 B2 | 5/2011 | Hausch et al. | |
| 2001/0049118 A1 | 12/2001 | Umitsuki et al. | |
| 2002/0082197 A1 | 6/2002 | Aoki et al. | |
| 2002/0091232 A1 * | 7/2002 | Ichikawa et al. | 528/931 |
| 2003/0215438 A1 | 11/2003 | Hausch et al. | |
| 2005/0158298 A1 | 7/2005 | Monod et al. | |
| 2005/0249719 A1 | 11/2005 | Shan et al. | |
| 2005/0256054 A1 | 11/2005 | Sollid et al. | |
| 2006/0002917 A1 | 1/2006 | Piper et al. | |
| 2006/0035838 A1 | 2/2006 | Khosla et al. | |
| 2006/0189540 A1 | 8/2006 | Khosla et al. | |
| 2006/0240475 A1 | 10/2006 | Khosla et al. | |
| 2006/0286601 A1 | 12/2006 | Marti et al. | |
| 2007/0009988 A1 | 1/2007 | Monod et al. | |
| 2007/0031399 A1 | 2/2007 | Edens et al. | |
| 2007/0184049 A1 | 8/2007 | Fox | |
| 2008/0020036 A1 | 1/2008 | Jolly | |
| 2008/0095710 A1 | 4/2008 | Shan et al. | |
| 2008/0145356 A1 | 6/2008 | Hausch et al. | |
| 2008/0193436 A1 | 8/2008 | Shan et al. | |
| 2008/0213245 A1 | 9/2008 | Hausch et al. | |

(Continued)

FOREIGN PATENT DOCUMENTS

| | | |
|---|---|---|
| AU | 2008/100719 | 9/2008 |
| EP | 0 384 303 | 2/1990 |

(Continued)

OTHER PUBLICATIONS

Lee B.R. et al., Aorsin, a novel serine proteinase with trypsin-like specificity at acidic pH, Biochem. J., 2003, vol. 371, pp. 541-548.*
International Search Report and Written Opinion for International Patent Application Serial No. PCT/US2011123424, mailed Jun. 28, 2011.
Messer et al., Oral Papain in Gluten Intolerance. The Lancet. Nov. 1976, vol. 2 (7993), p. 1022, col. 1, para 3-4.
Wehrle et al., Eur Food Res Technol, 1999, vol. 209, pp. 428-433; p. 429, col. 1, para 5, p. 430, col. 2, para 2-3.
Davy et al., Substrate Specificity of Barley Cysteine Endoproteases EP-A and EP-B. Plant Physiol. 1998, vol. 117, pp. 255-261: p. 257, col. 1, para 1.

(Continued)

*Primary Examiner* — Satyendra Singh
(74) *Attorney, Agent, or Firm* — McAndrews, Held & Malloy, Ltd.

(57) ABSTRACT

The present technology relates to an enzyme composition. The enzyme composition may be used to treat gluten intolerant subjects, including suffering from non-Celiac gluten intolerance and/or non-Celiac gluten sensitivity. The enzyme composition may also be used to reduce gluten exposure in certain individuals. For example, the enzyme composition may also be used as a prophylactic to reduce exposure to gluten oligopeptides.

13 Claims, 134 Drawing Sheets

(56) References Cited

U.S. PATENT DOCUMENTS

| | | |
|---|---|---|
| 2008/0213320 A1 | 9/2008 | Eisenstein et al. |
| 2008/0213427 A1 | 9/2008 | Hausch et al. |
| 2008/0213822 A1 | 9/2008 | Hausch et al. |
| 2008/0299108 A1 | 12/2008 | Khosla et al. |
| 2008/0311161 A1 | 12/2008 | Gass |
| 2009/0117255 A1 | 5/2009 | Hays |
| 2009/0130737 A1 | 5/2009 | Monod et al. |
| 2009/0156490 A1 | 6/2009 | Khosla et al. |
| 2009/0304670 A1 | 12/2009 | Edens et al. |

FOREIGN PATENT DOCUMENTS

| | | |
|---|---|---|
| JP | 4401555 | 5/2002 |
| JP | 2009/232835 | 10/2009 |
| WO | WO 2003/068170 | 8/2003 |
| WO | WO 2003/096984 | 11/2003 |
| WO | WO 2004/045392 | 6/2004 |
| WO | WO 2005/019251 | 3/2005 |
| WO | WO 2005/027953 | 3/2005 |
| WO | WO 2005/107786 | 11/2005 |
| WO | WO 2007/019411 | 2/2007 |
| WO | WO 20071056301 | 5/2007 |
| WO | WO 20081090223 | 7/2008 |
| WO | WO 20091035651 | 3/2009 |
| WO | WO 2009/075816 | 6/2009 |

OTHER PUBLICATIONS

A New Diet Villain, Newsweek.com, Dec. 4, 2008.

Agnes Doumas, et al., Characterization of the Prolyl Dipeptidyl Peptidase Gene (dpplV) from the Koji Mold Aspergillus oryzae, Applied and Environmental Microbiology, Dec. 1998, pp. 4809-4815.

Big News: Generation Rescue Funds Study Comparing Vaccinated with non-Vaccinated, Med nauseum blog, Aug. 27, 2009.

Biological Information, Enzyme Stuff, Aug. 27, 2009.

Byung Rho Lee, et al., Aorsin, a novel serine proteinase with trypsin-like specificity at acidic pH, Biochemical Society, (2003) 371, pp. 541-548.

Carlo G. Rizzello, et al., Highly Efficient Gluten Degradation by Lactobacilli and Fungal Proteases during Food Processing: New Perspectives for Celiac Disease, Applied and Environmental Microbiology, Jul. 2007, pp. 4499-4507.

Felix Hausch, et al., Intestinal Digestive Resistance of Immunodominant Gliadin Peptides, AJP-Gastrointest Liver Physiol, vol. 283, Oct. 2002, pp. G996-G1003.

Georg Hartmann, et al., Rapid Degradation of Gliadin Peptides Toxic for Coeliac Disease Patients by Proteases from Germinating Cereals, Journal of Cereal Science 44, 2006. pp. 368-371.

Gluten Intolerance and Celiac Disease, Foodintol.com, Sep. 17, 2008.

H. J. Cornell, et al., Papaya Latex Enzymes Capable of Detoxification of Gliadin, Springer, Jan. 21, 2009.

Jennifer Ehren, et al., a Food-Grade Enzyme Preparation with Modest Gluten Detoxification Properties, PLoS One, vol. 4, Issue 7, Jul. 2009.

Jonathan Gass, et al., Combination Enzyme Therapy for Gastric Digestion of Dietary Gluten in Patients with Celiac Sprue, Gastroenterology, vol. 133, No. 2, Aug. 2007.

Lu Shan, et al., Comparative biochemical analysis of three bacterial prolyl endopeptidases: implications for coeliac sprue, Biochem Society, 2004, pp. 311-318.

Lu Shan, et al., Identification and Analysis of Multivalent Proteolytically Resistant Peptides from Gluten: Implications for Celiac Sprue, Nih PUblic Access, Jan. 20, 2006.

Lu Shan, et al., Structural Basis for Gluten Intolerance in Celiac Sprue, Science Magazine, Sep. 27, 2002, pp. 2275-2279.

Lu Shan, et al., Structural Basis for Gluten Intolerance in Celiac Sprue, www.sciencemag.org, vol. 297, Sep. 27 2002.

Ludvig M. Sollid, et al., Future Therapeutic Options for Celiac Disease, Nature Clinical Practice Gastroentrology & Hepathology, vol. 2, No. 3, Mar. 2005.

Michael T. Bethune, et al., Parallels between Pathogens and Gluten Peptides in Celiac Sprue, PLoS Pathogens, vol. 4, Issue 2, Feb. 2008.

Oral Papain in Gluten Intolerance, the Lancet, Nov. 6, 1976, p. 1022.

Peptizyde, http://livaherb.com/peptizyde, Aug. 27, 2009.

Prolyl Endoprotease Enzyme May Allow Pateints with Celiac Disease to Safely Eat Gluten on Occasion, Celiac.com, Aug. 27, 2009.

Thomas Marti, et al., Prolyl Endopeptidase-Mediated Destruction of T Cell Epitopes in Whole Gluten: Chemcial and Immunological Characterization, JPET, vol. 312, No. 1, 2005.

Working Group on Consumer Allergy Risk from Enzyme Residue in Food, Copenhagen, Aug. 1998.

Sendrejova, E., et al., "Proteolysis as a way of food processing," FEBS Journal, vol. 276, No. Suppl 1, Jul. 1, 2009, p. 294.

Messer, M., et al., "Studies on the mechanism of destruction of the toxic action of wheat gluten in coeliac disease by crude papain," Gut, British Medical Association, vol. 5, 1 Aug. 1964, pp. 295-303.

\* cited by examiner

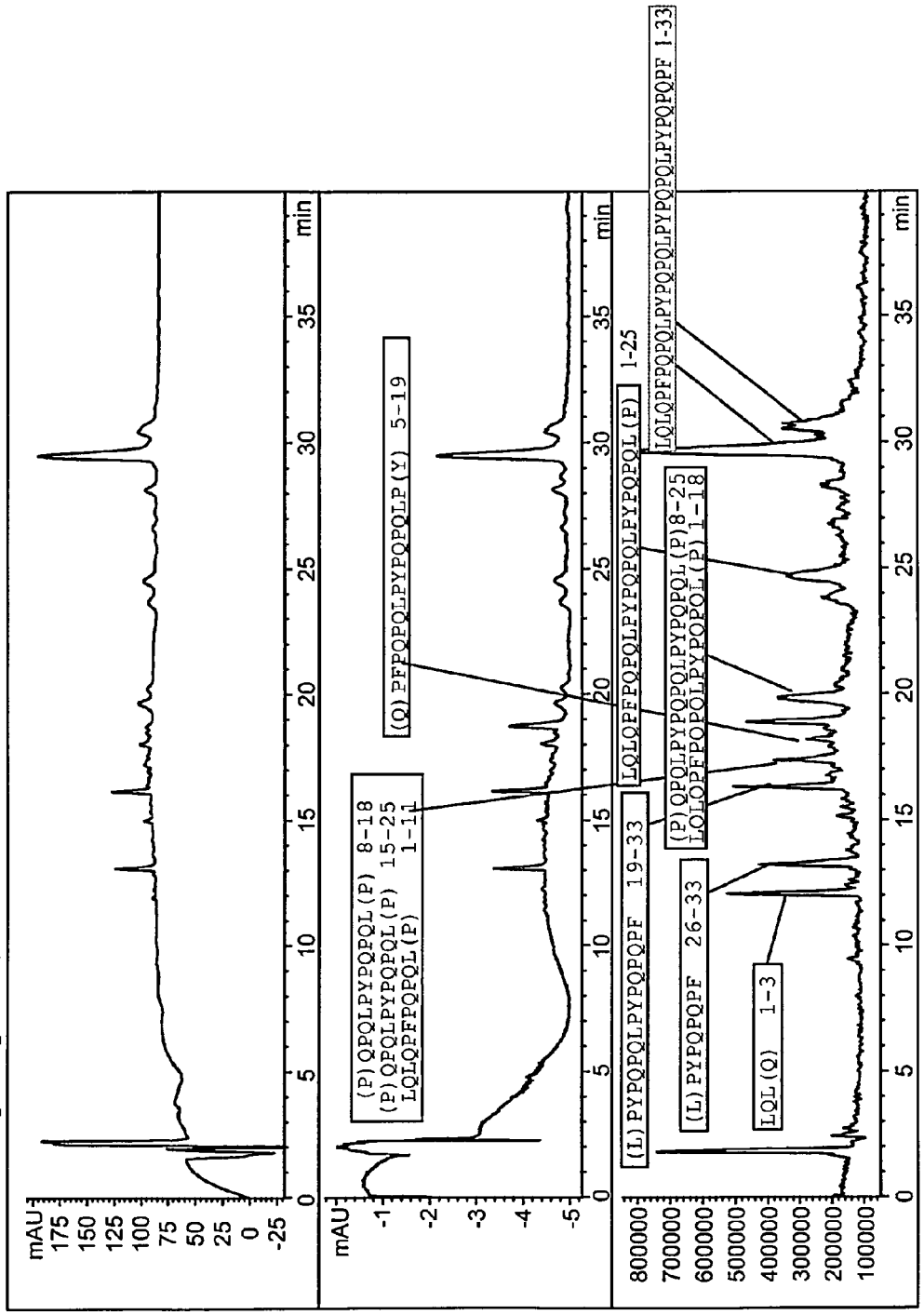

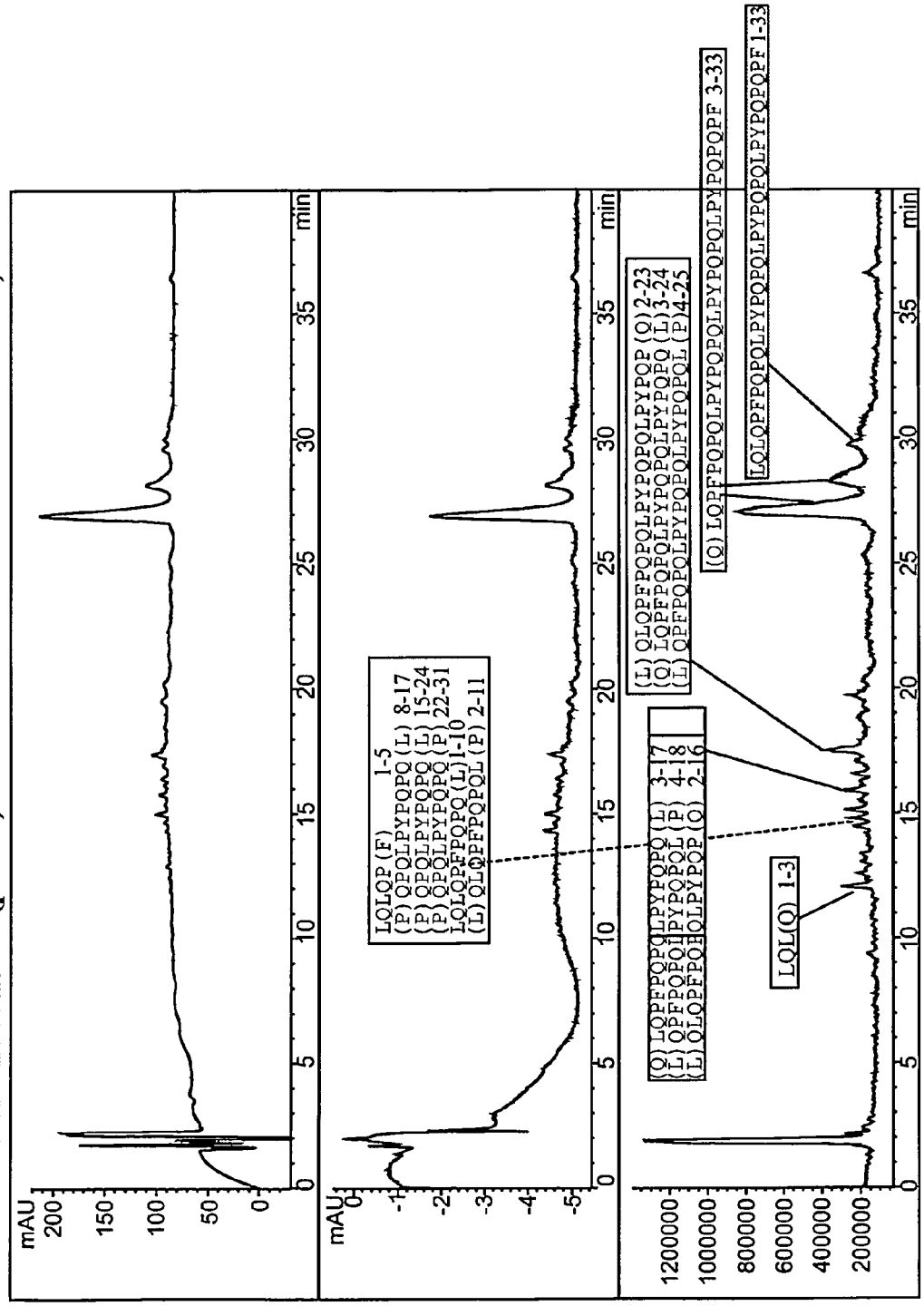
FIG. 4, cont.

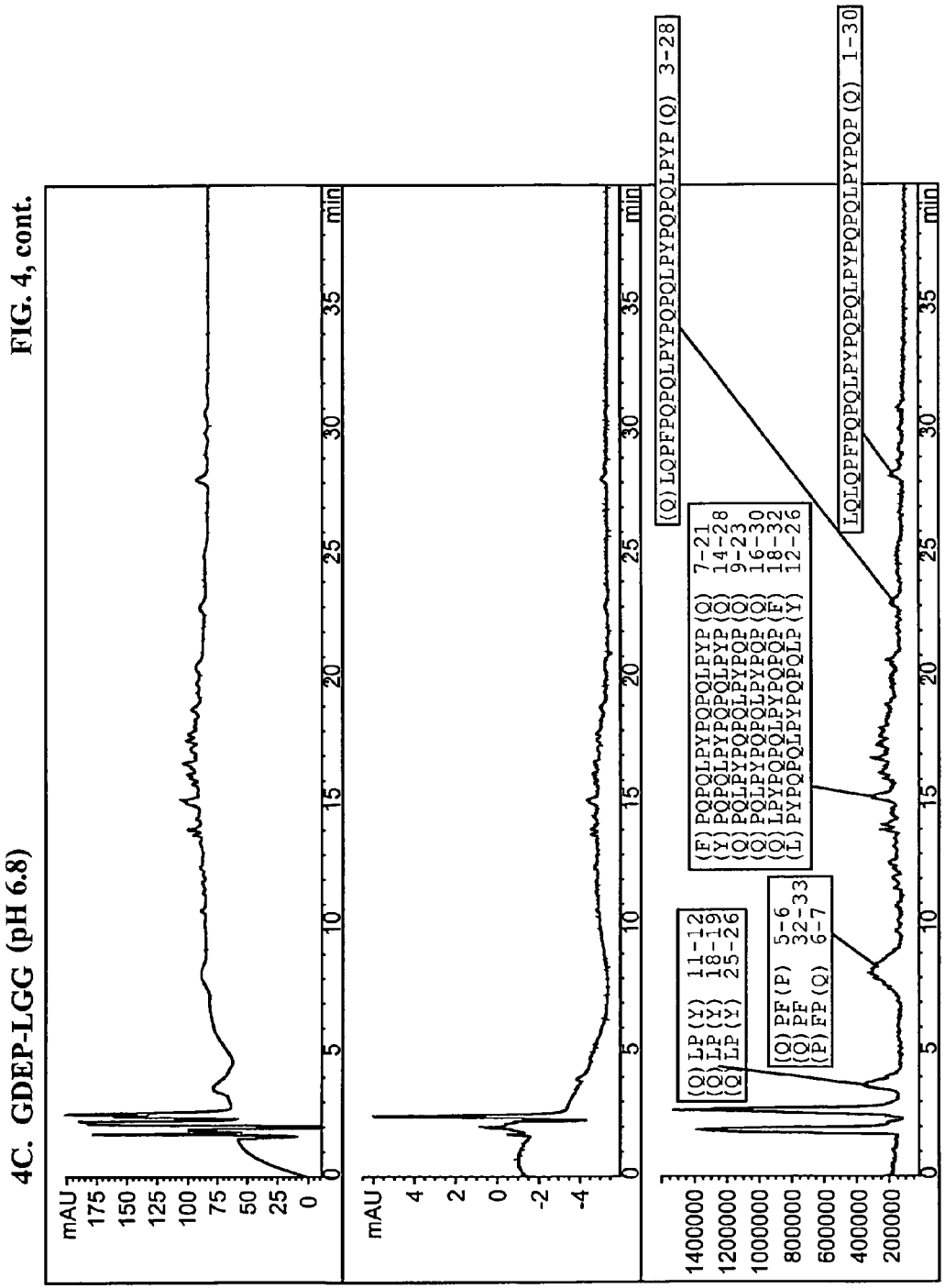
FIG. 4, cont.

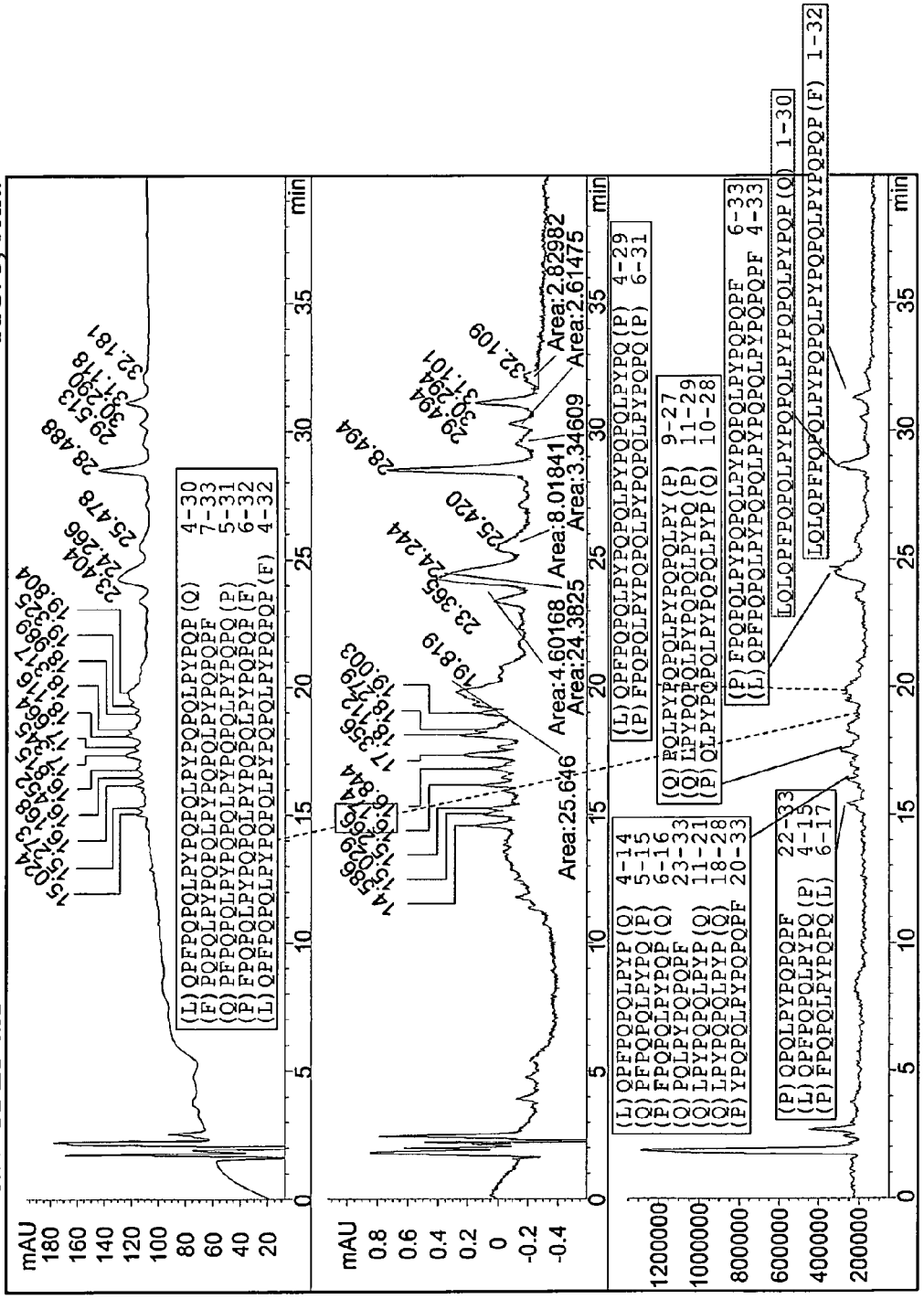
FIG. 5, cont.

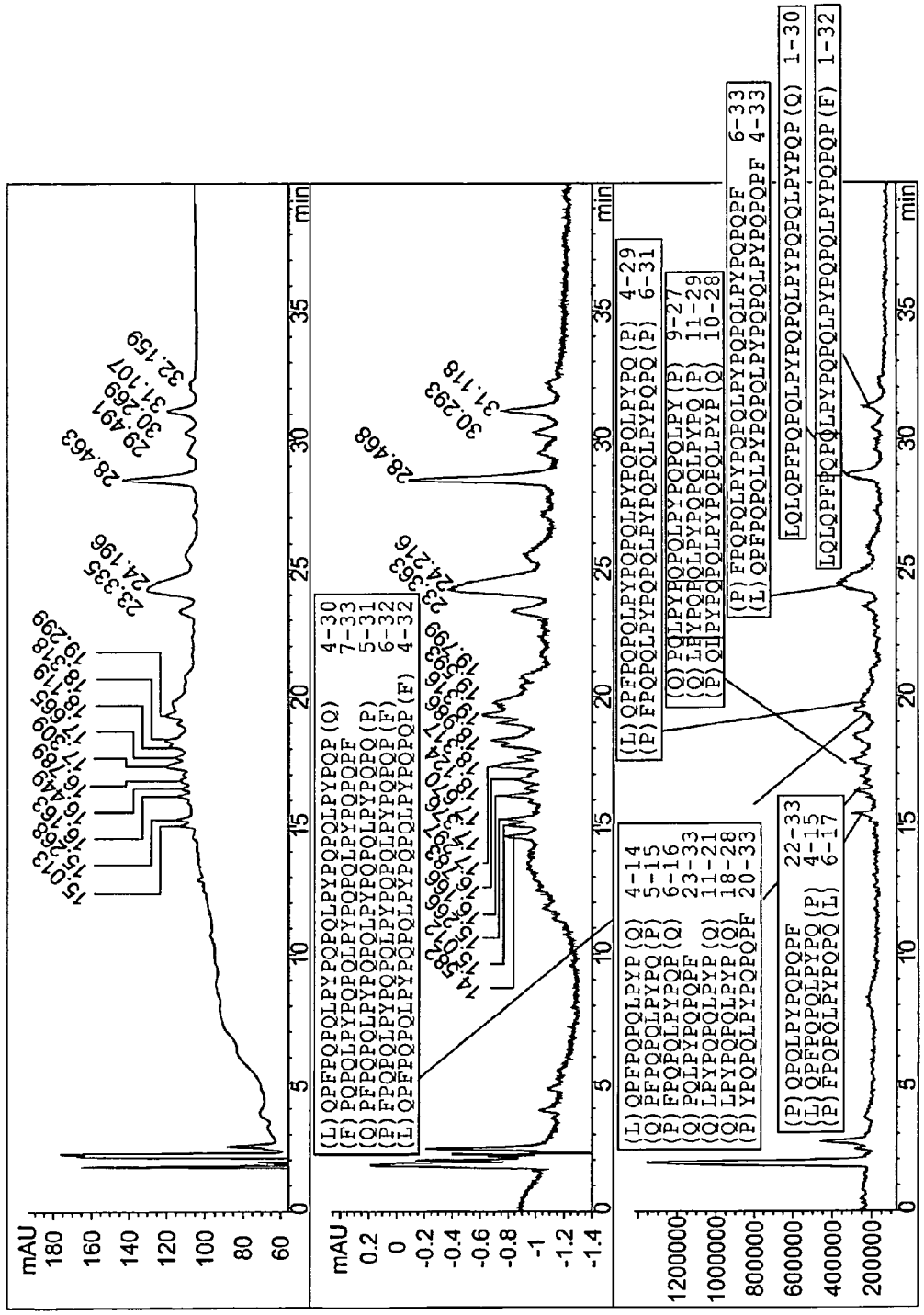
FIG. 5, cont.

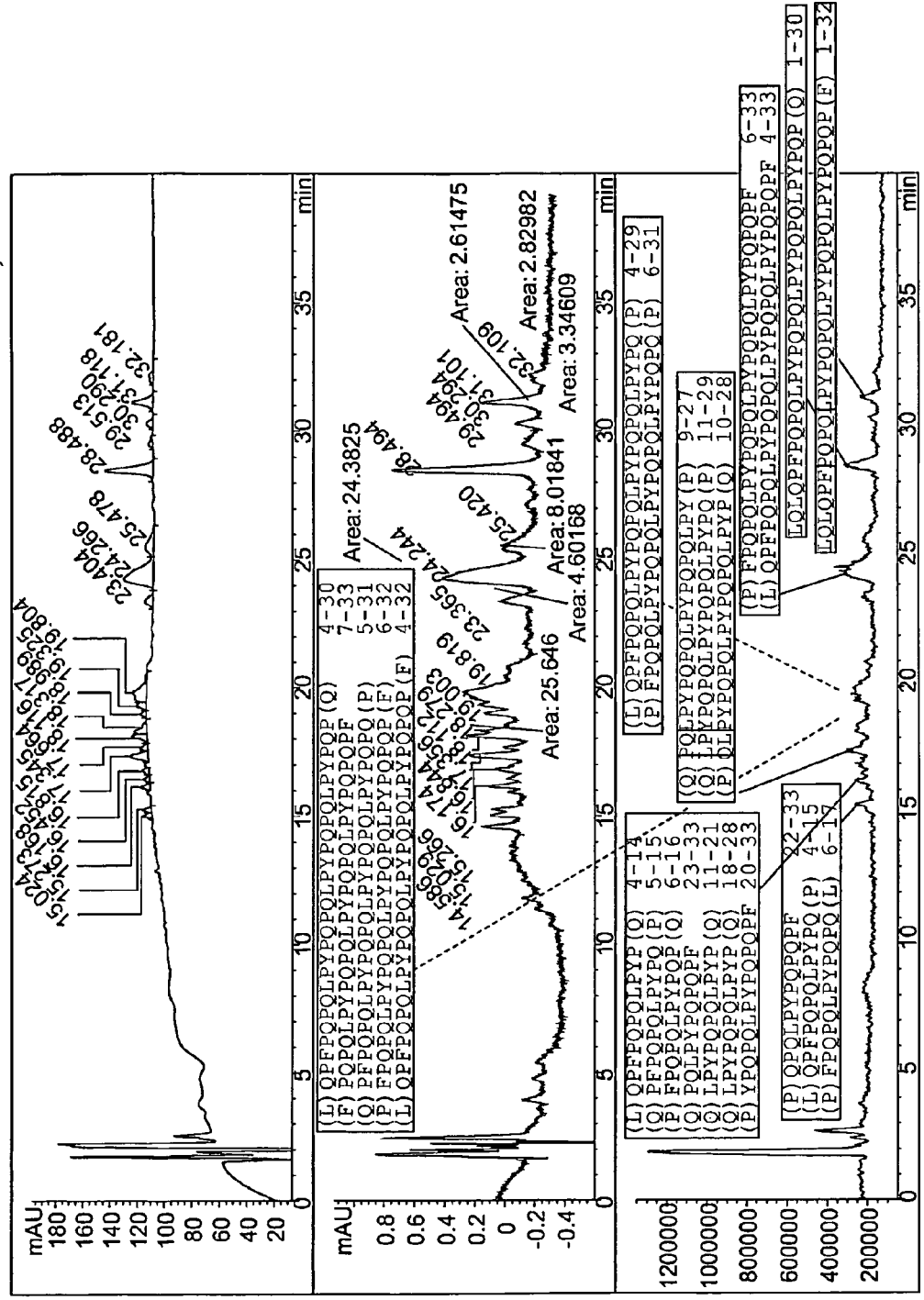
FIG. 5, cont.

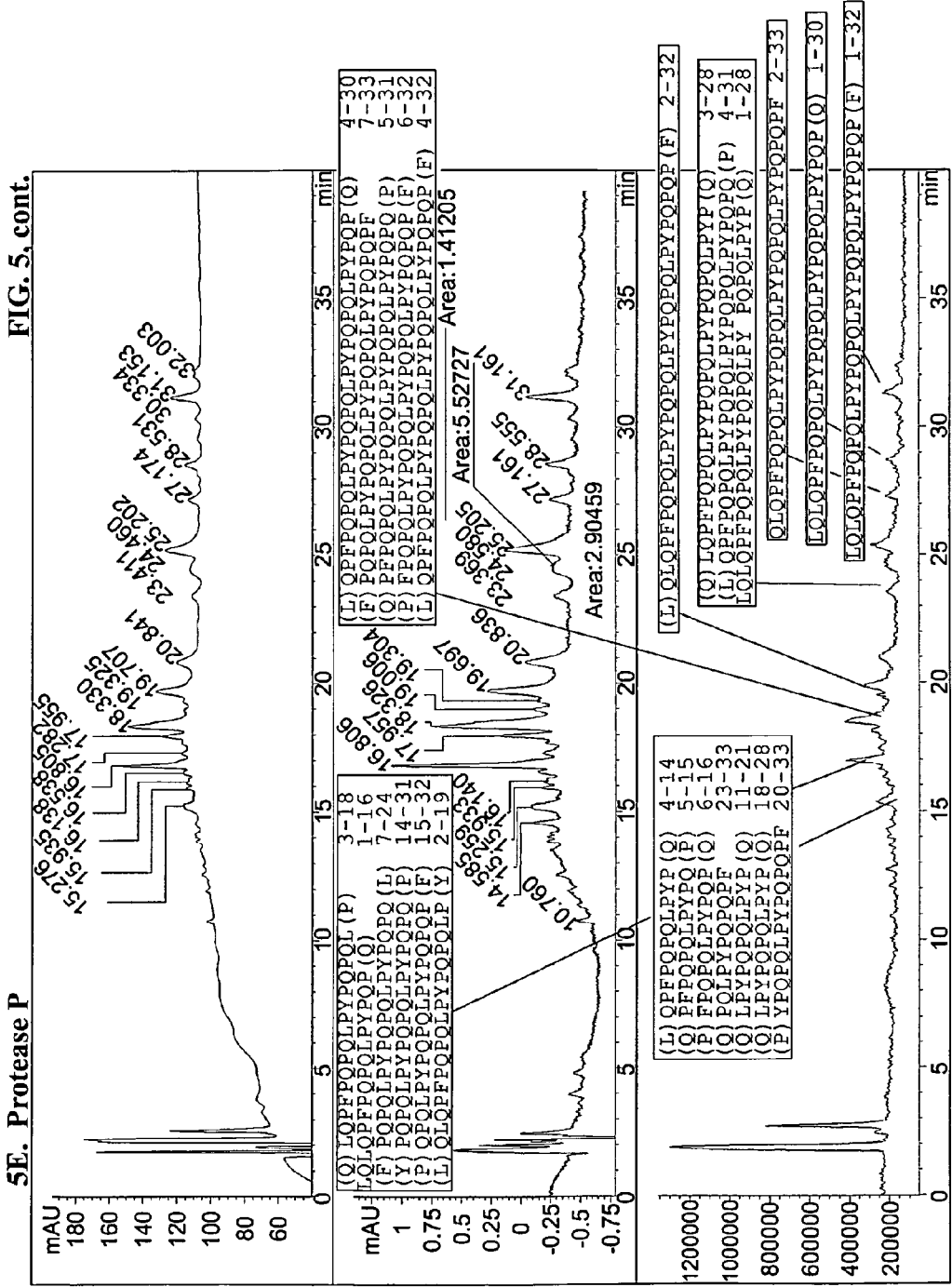

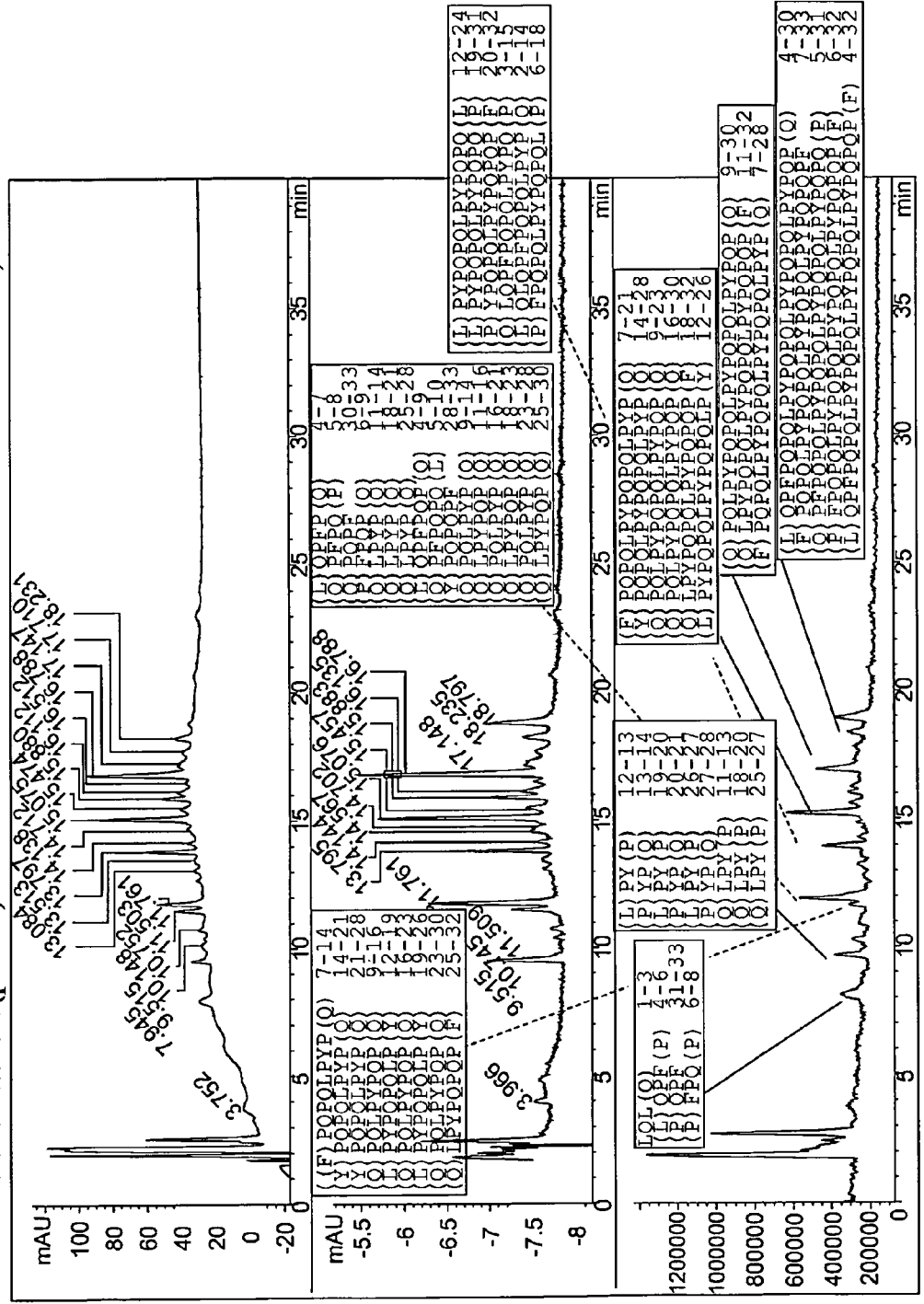
FIG. 6, cont.

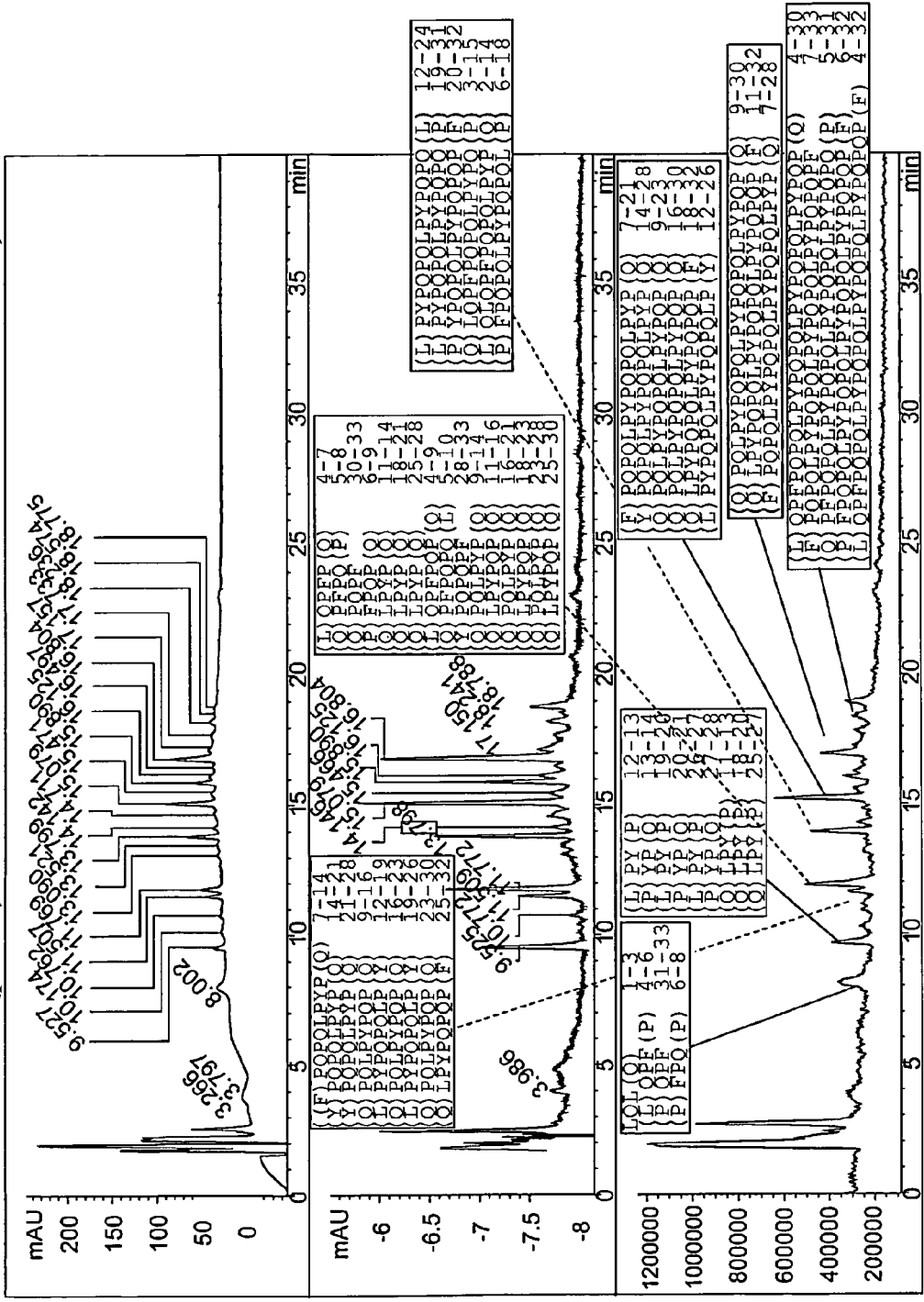

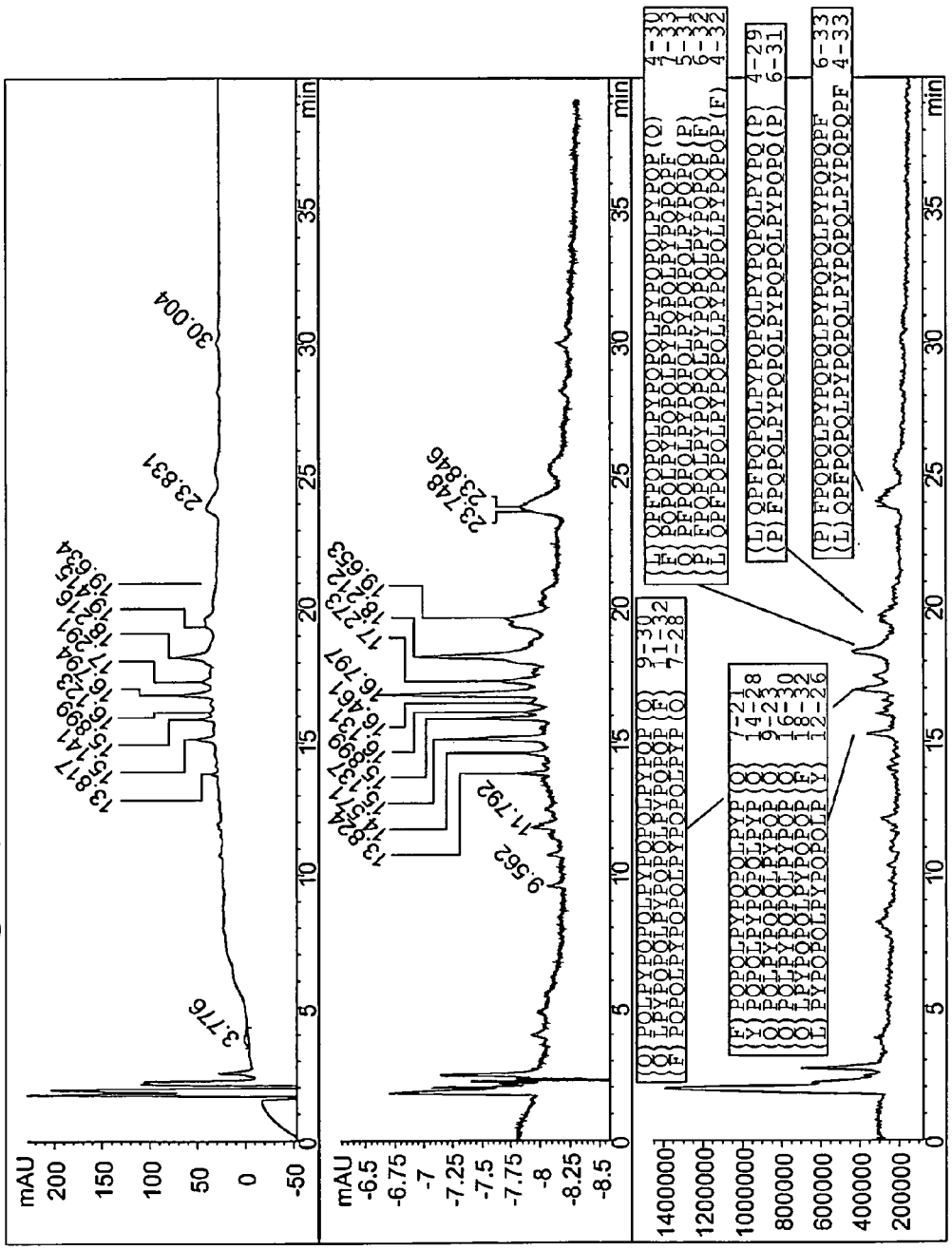

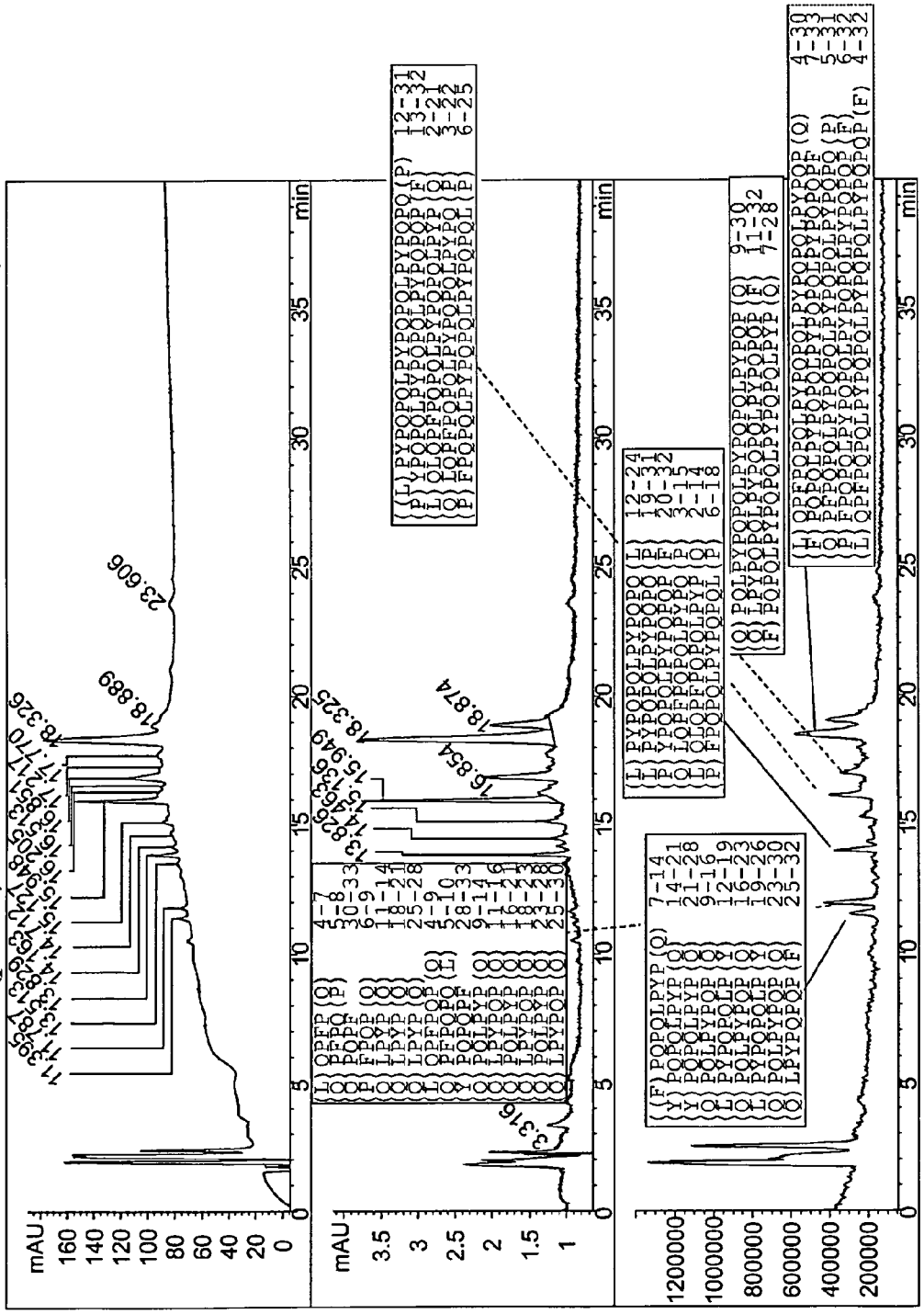
FIG. 6, cont.

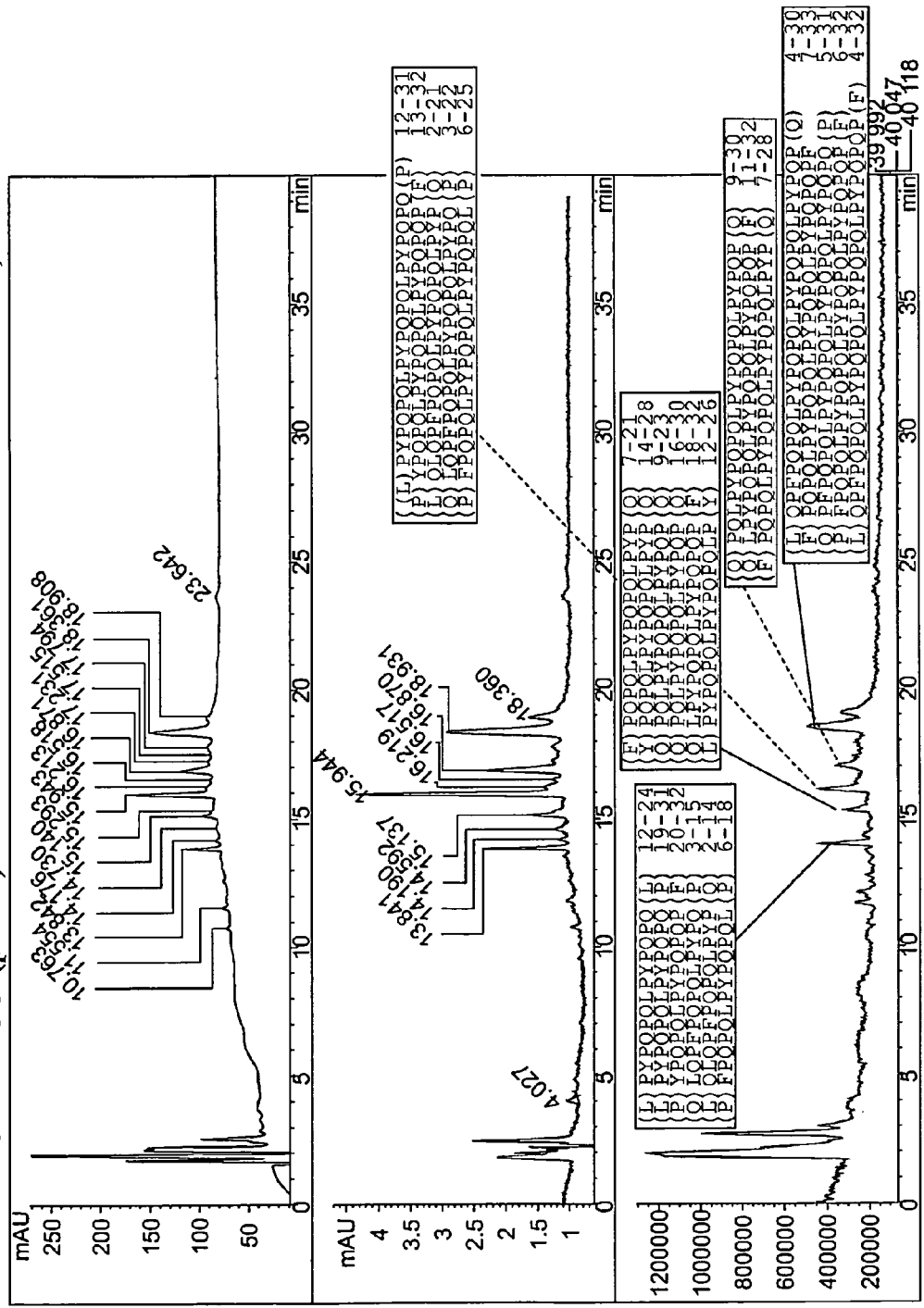
FIG. 6, cont.

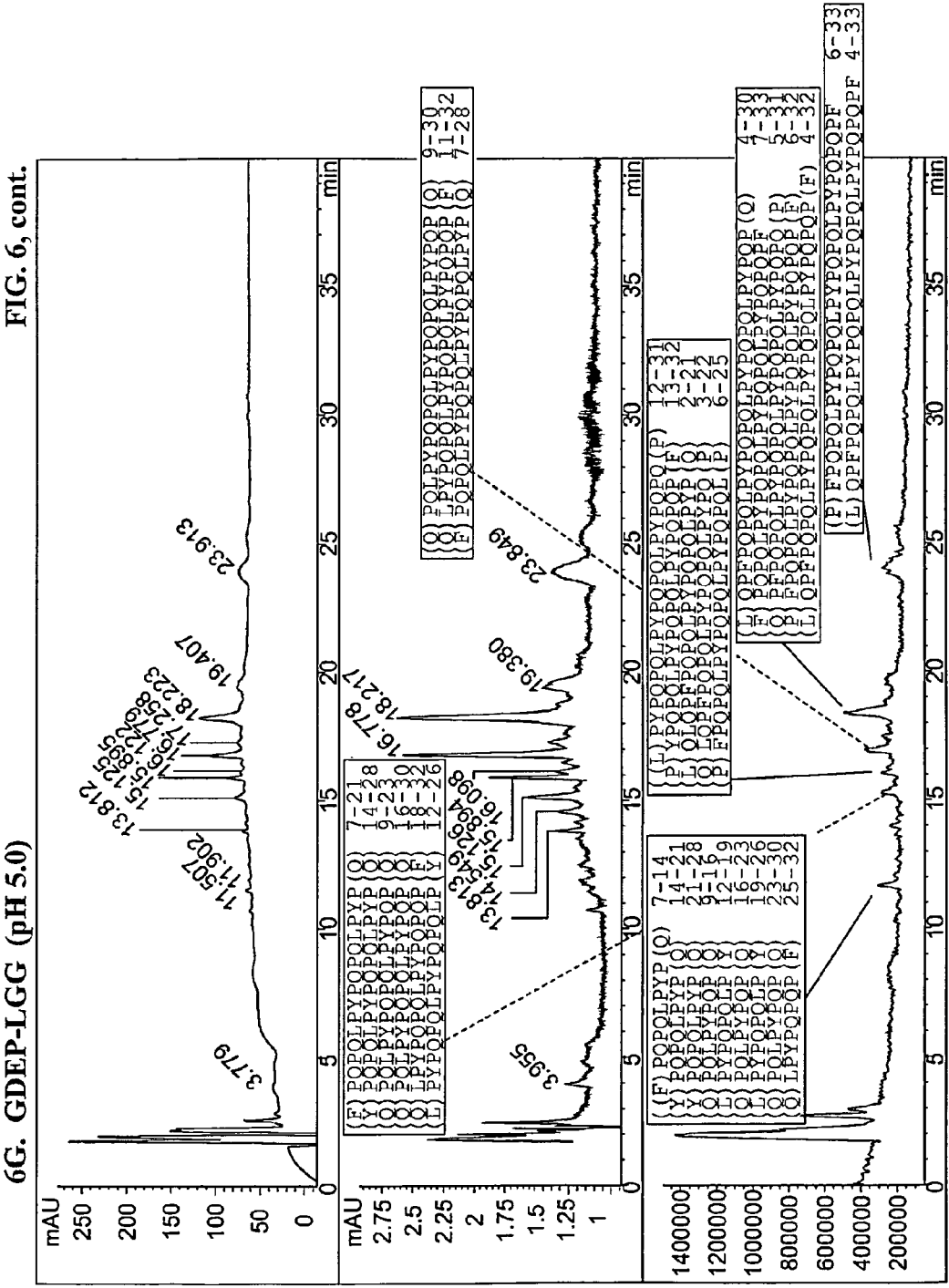
FIG. 6, cont.

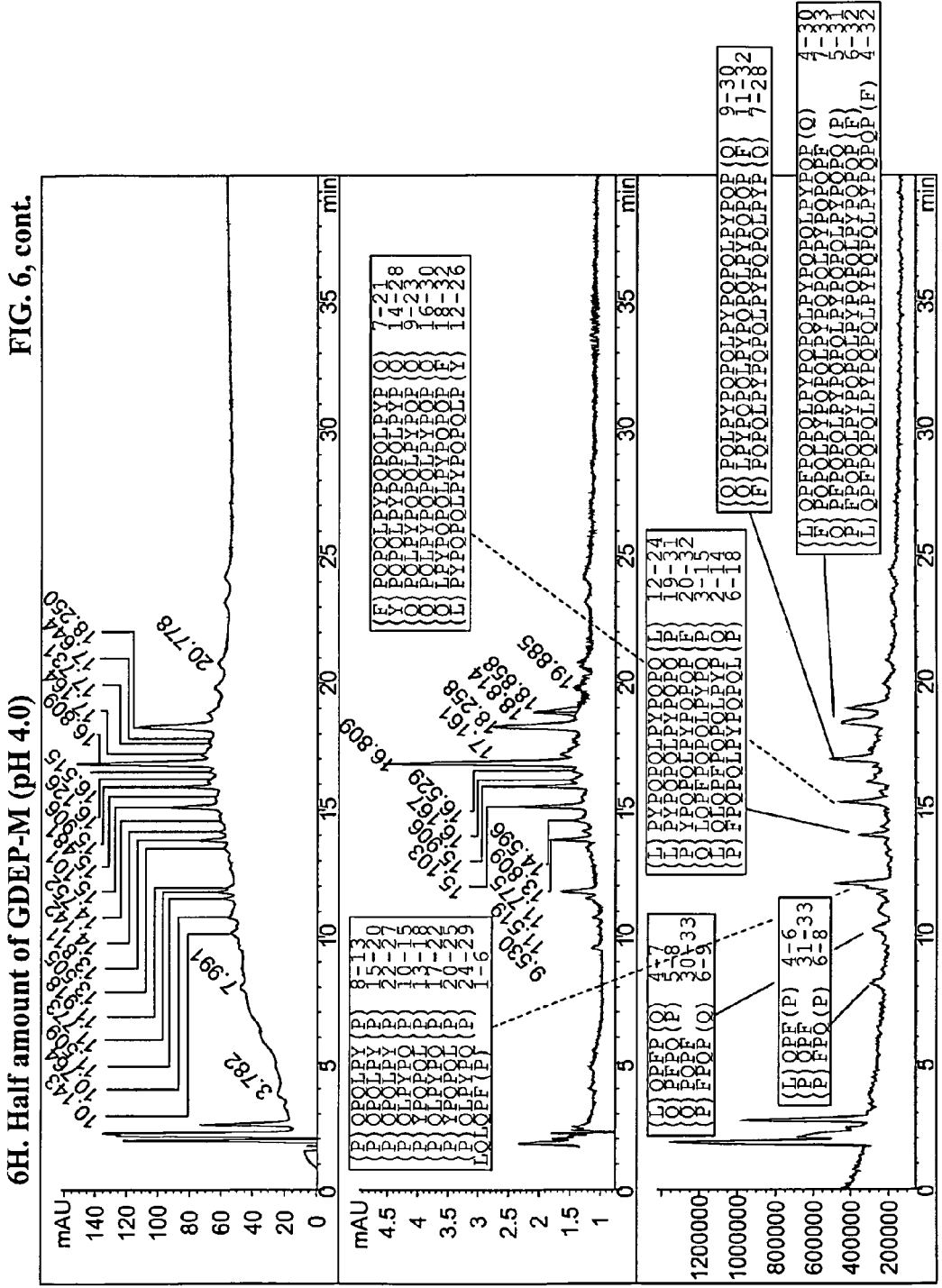
FIG. 6, cont.

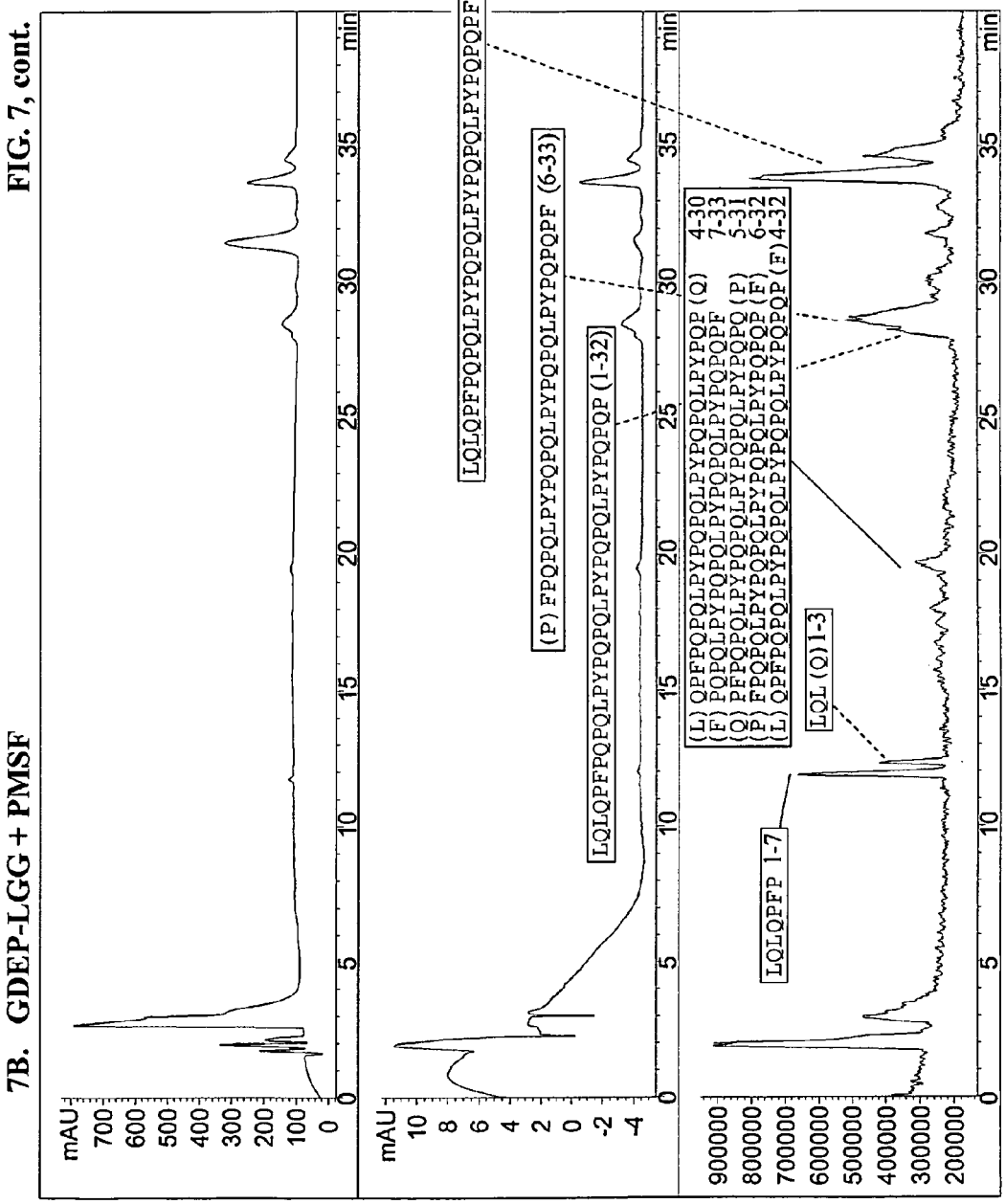

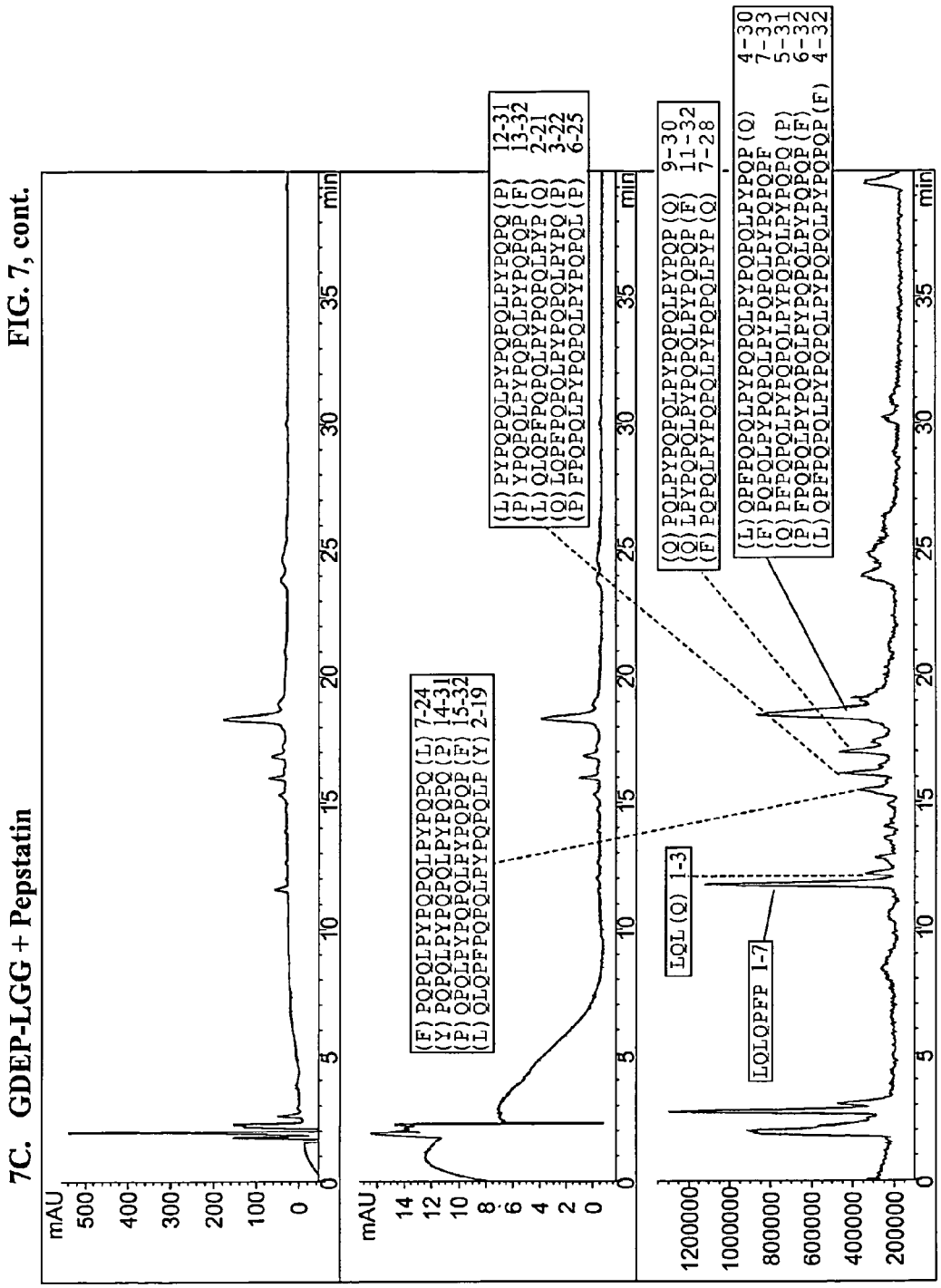

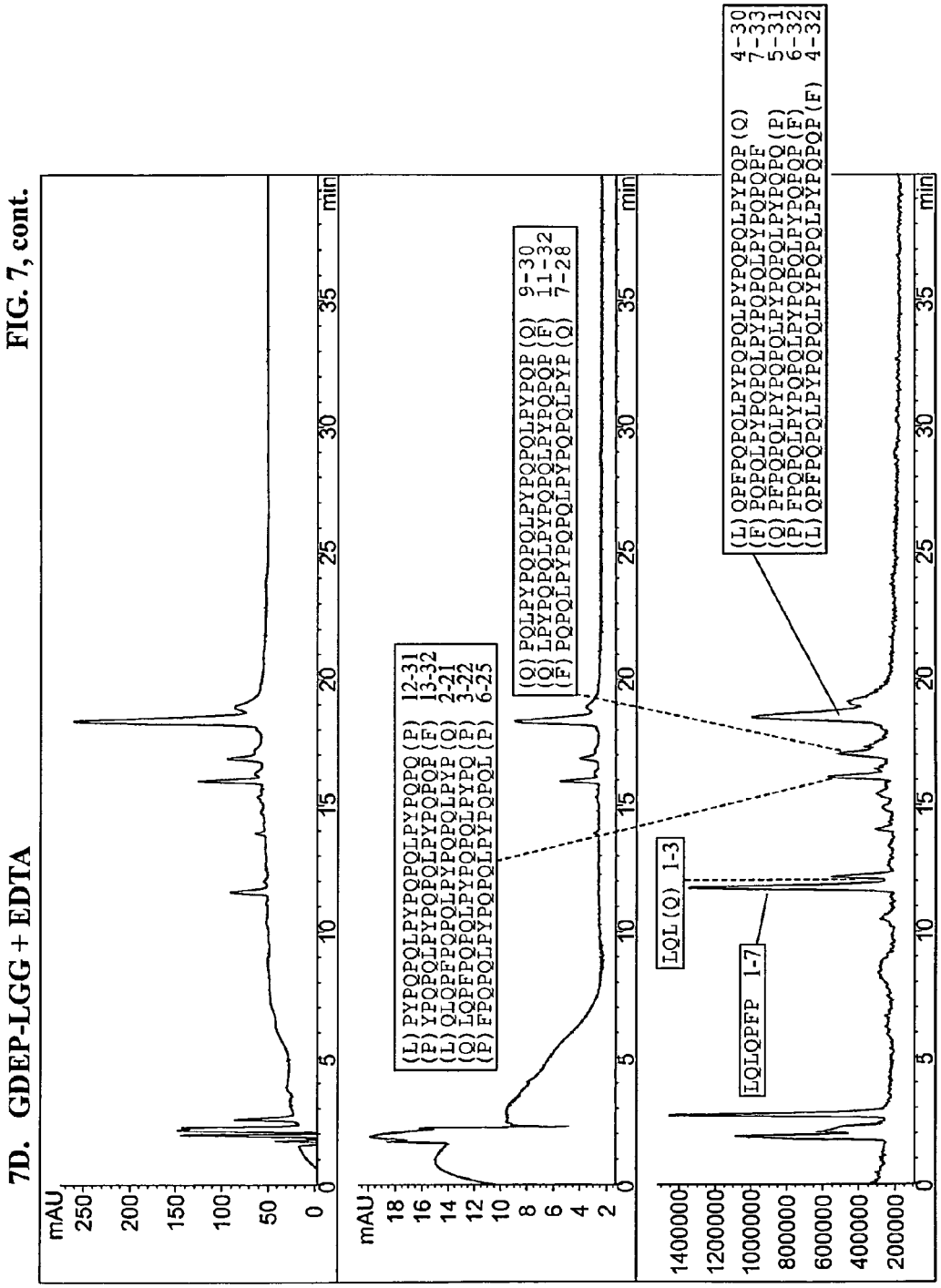

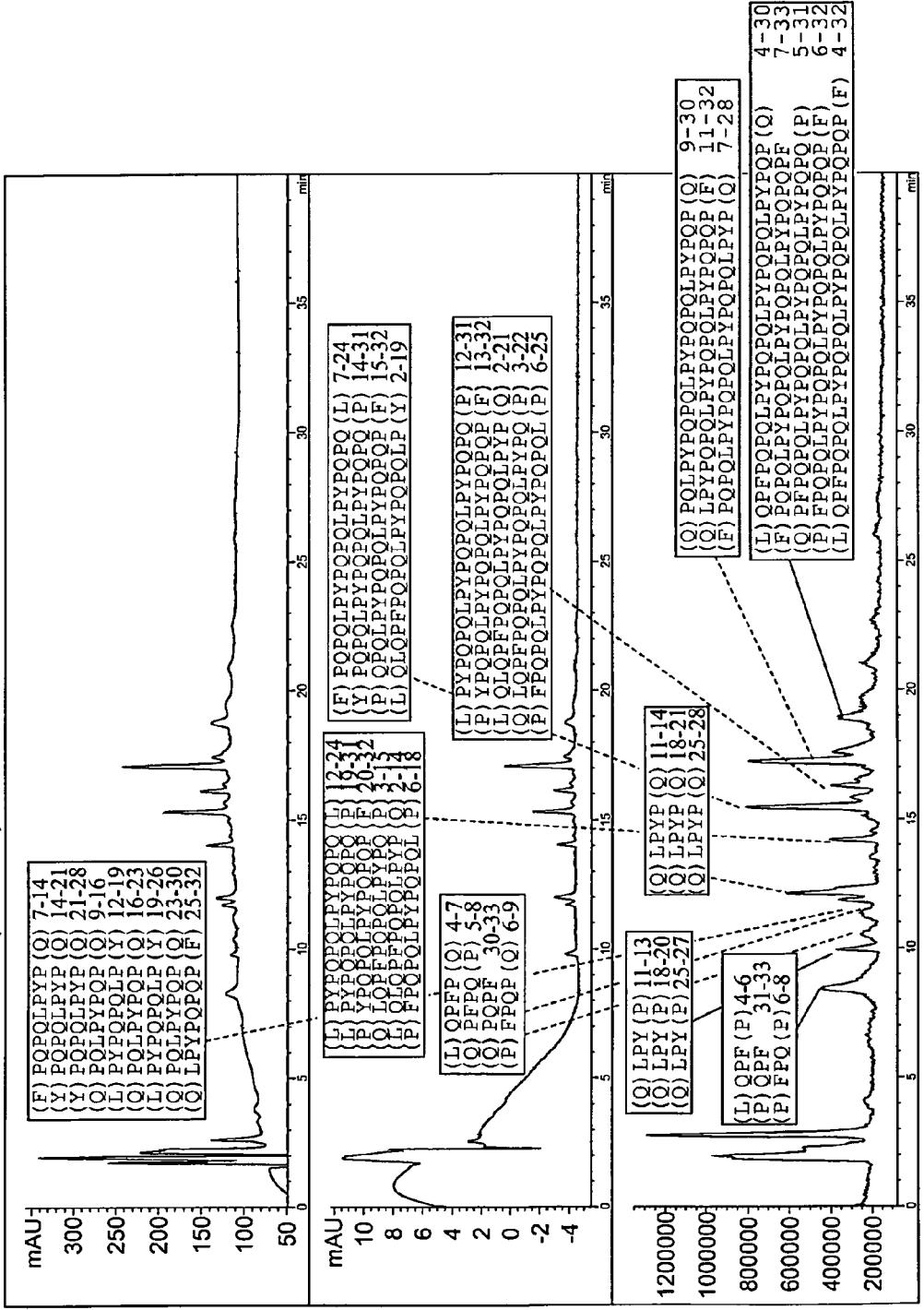
FIG. 7, cont.

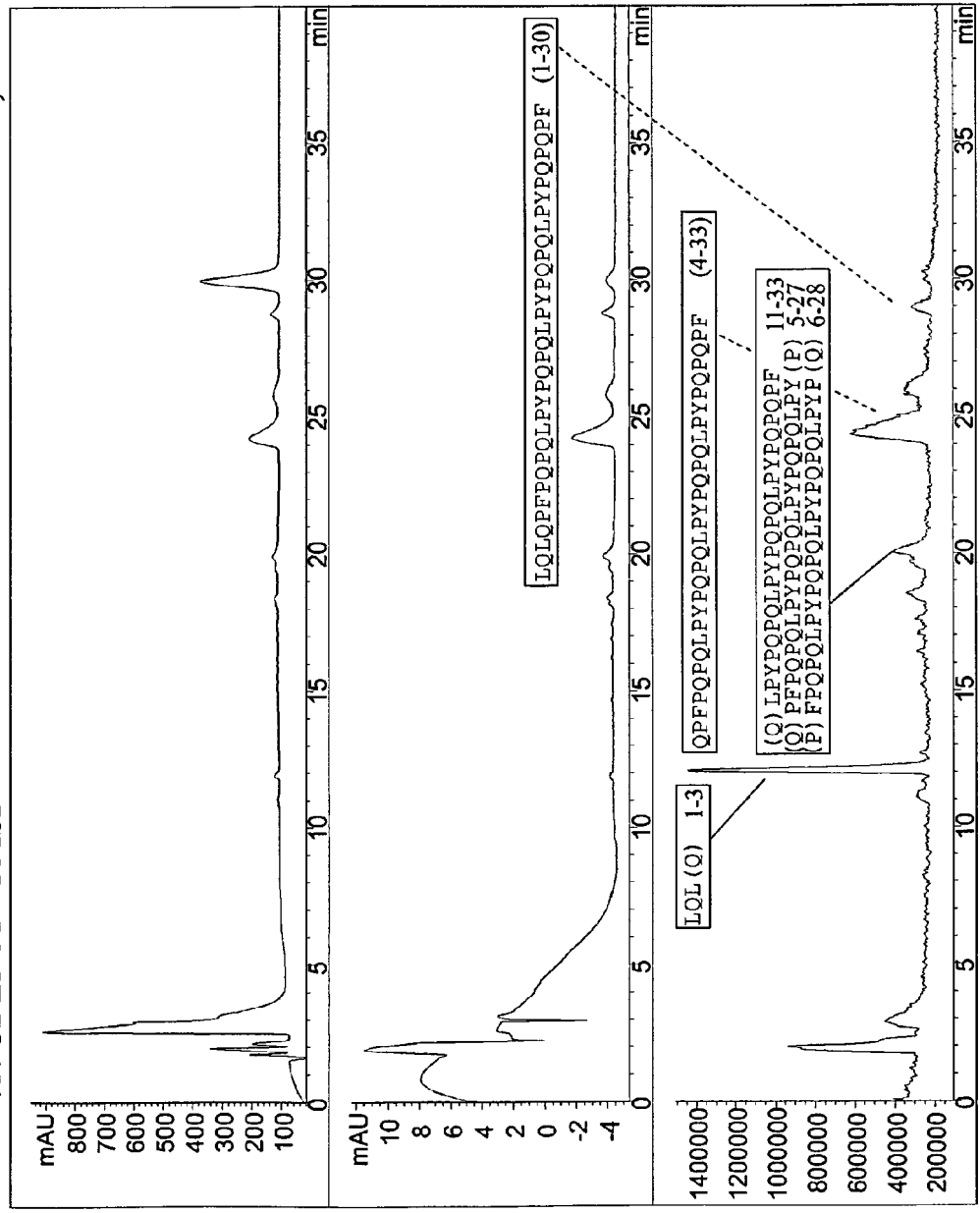
FIG. 7, cont.

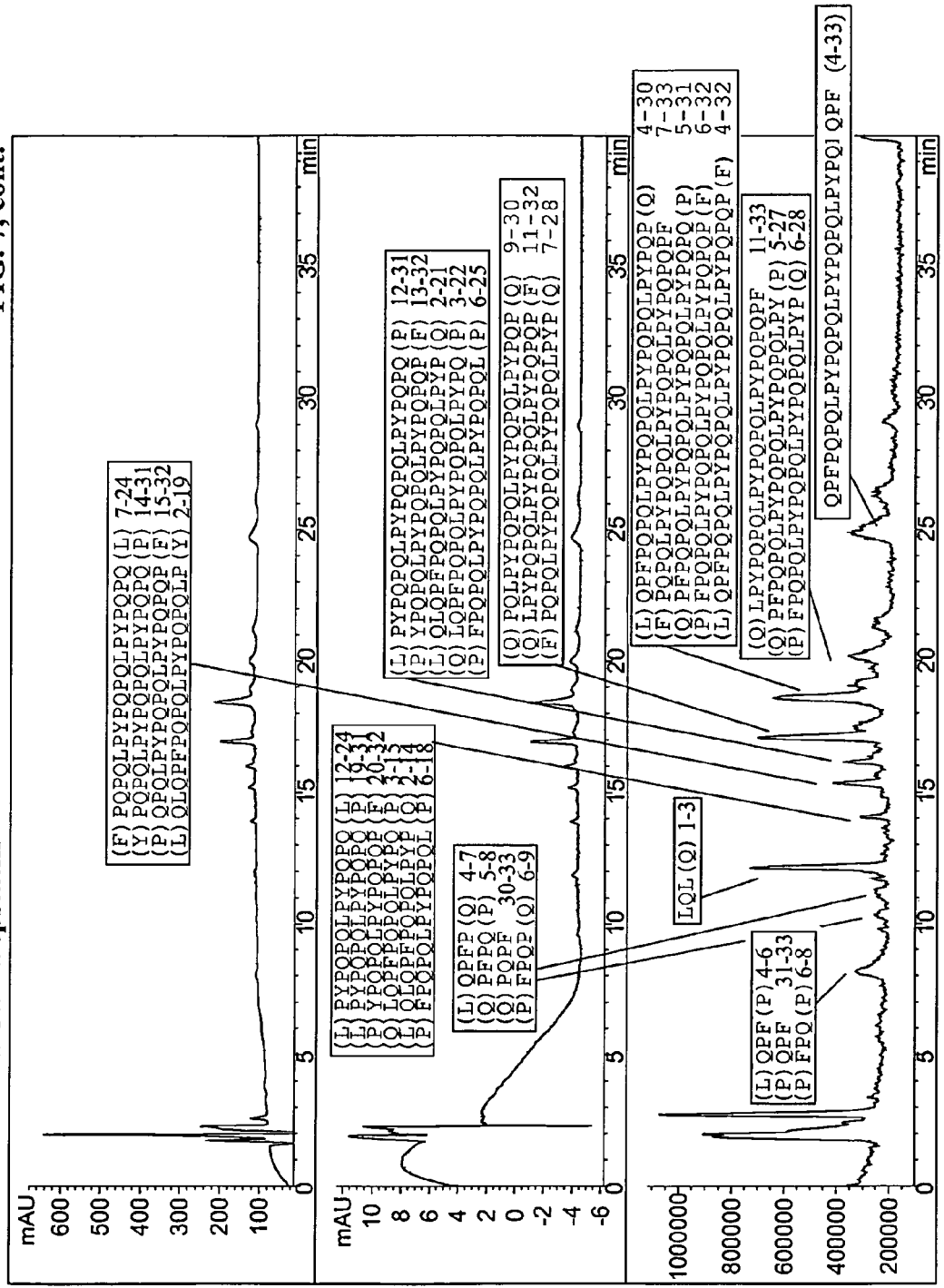
FIG. 7, cont.

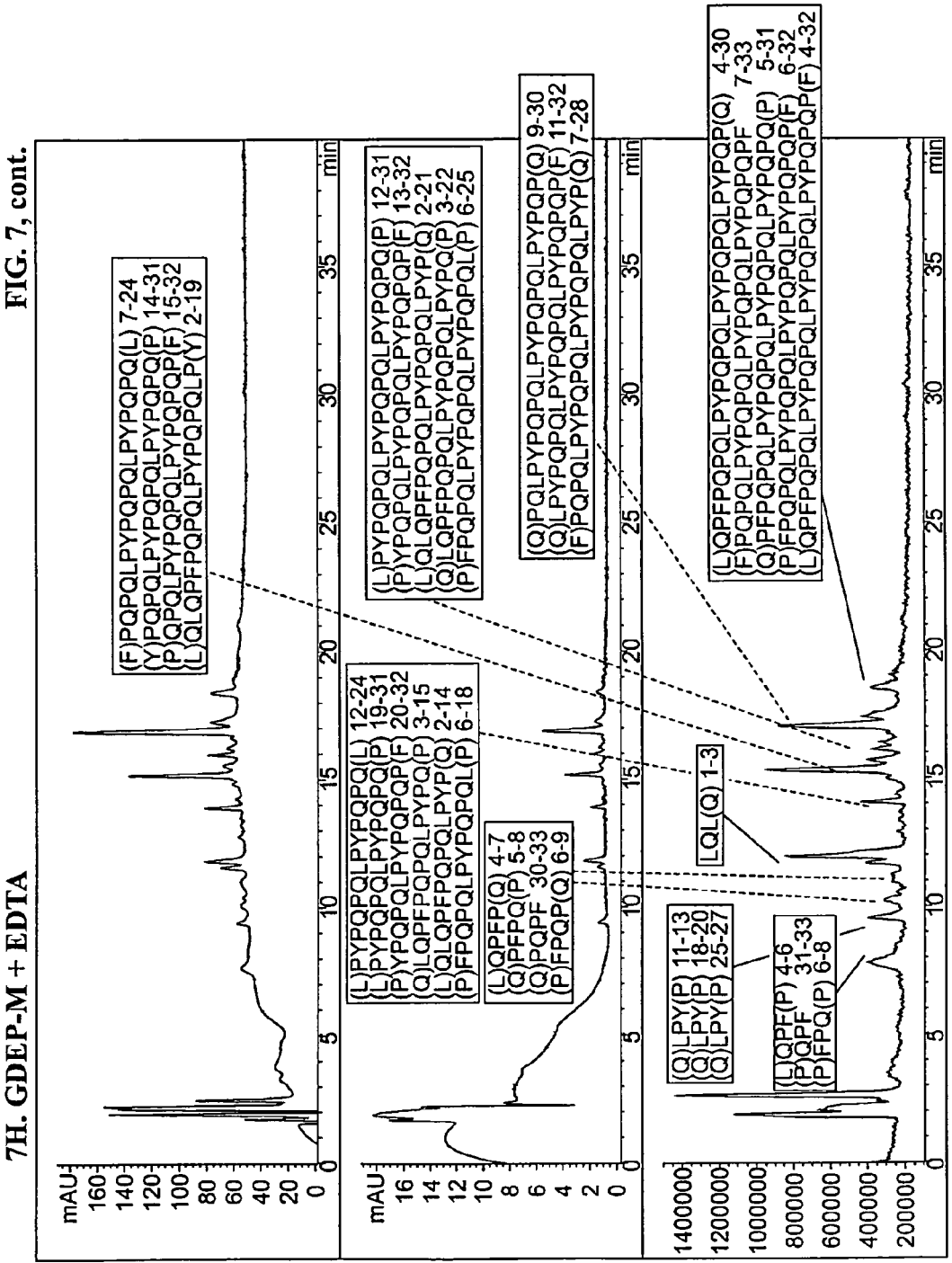

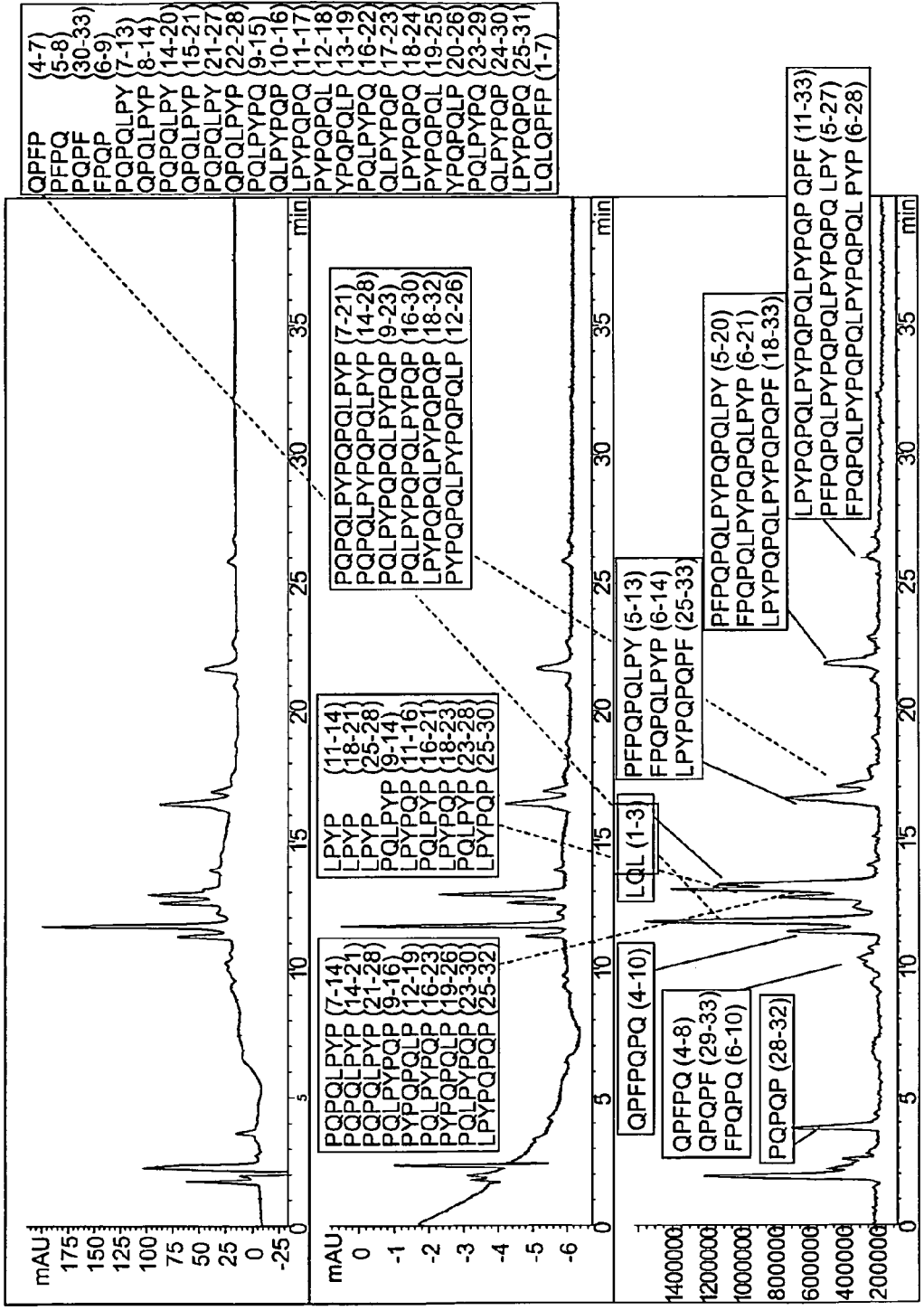
FIG. 8, cont.

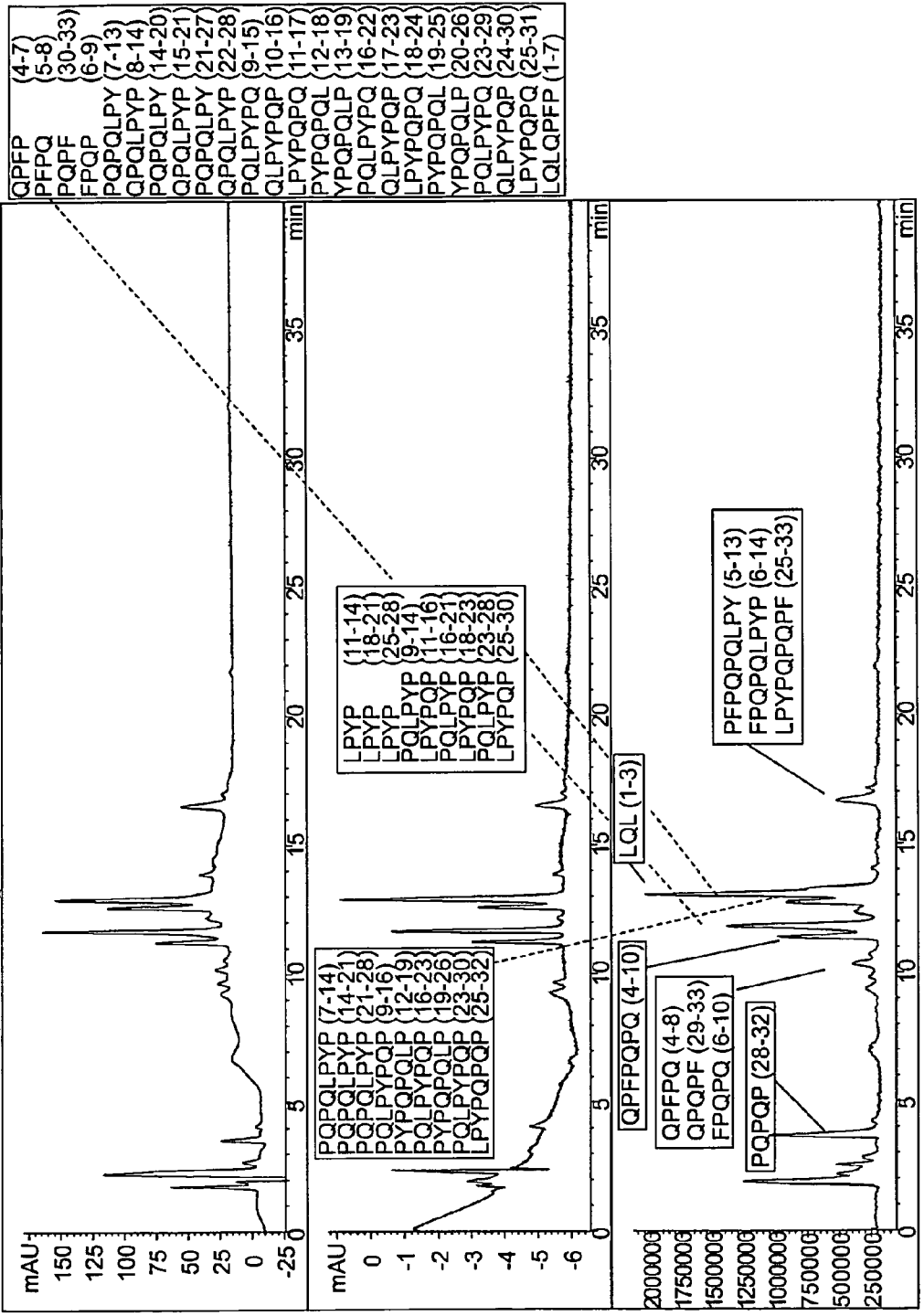
FIG. 8, cont.

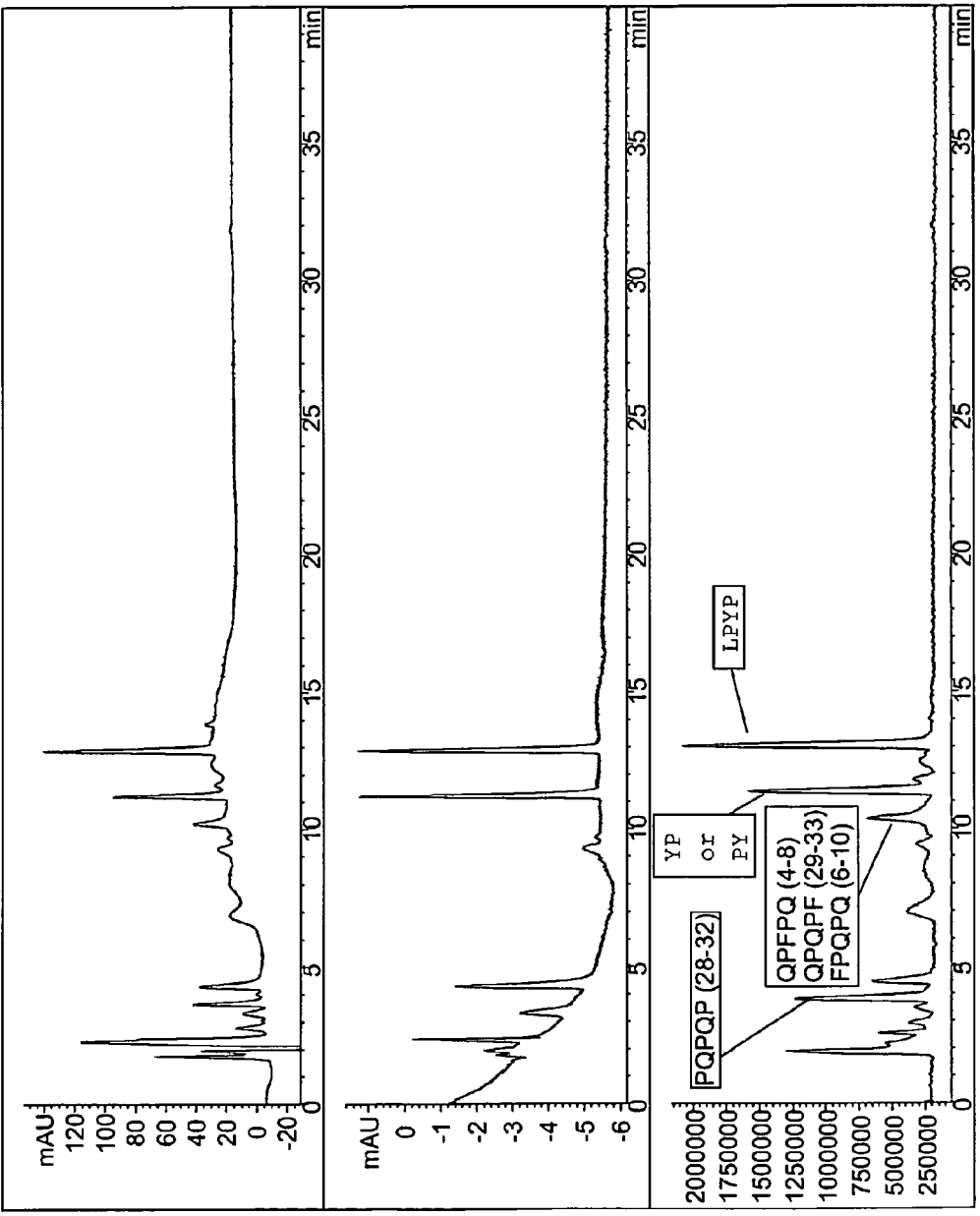
FIG. 8, cont.

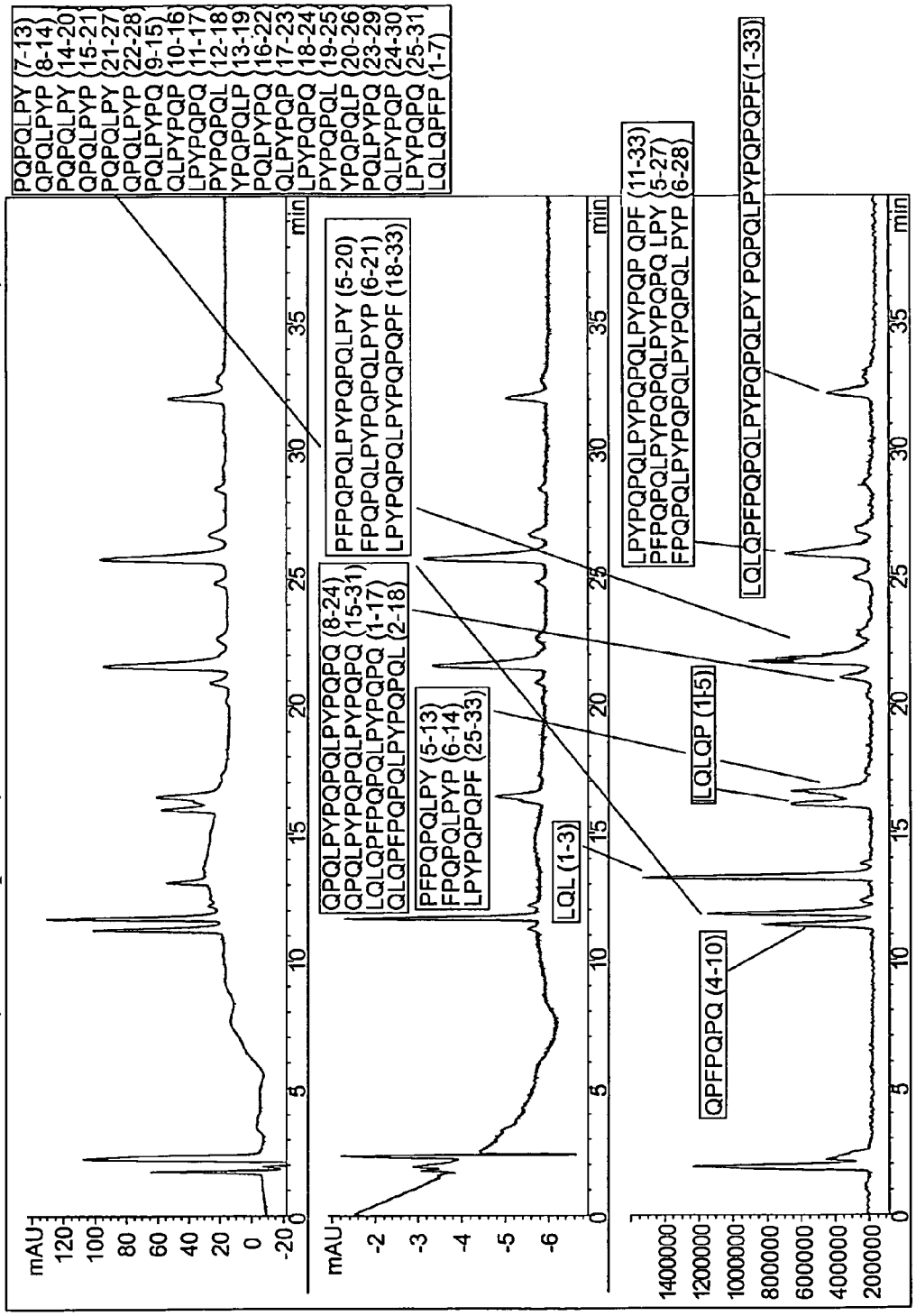

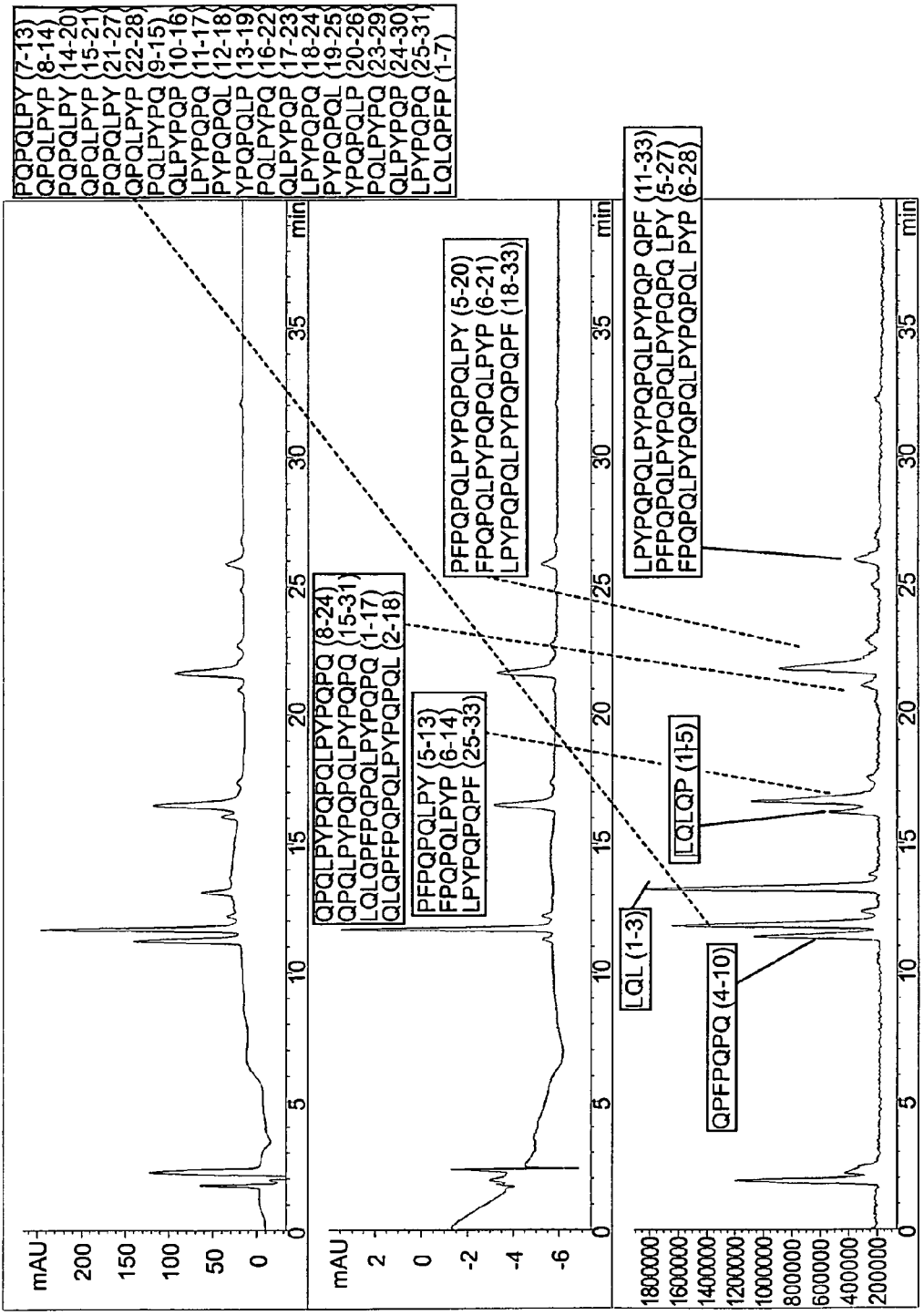
FIG. 8, cont.

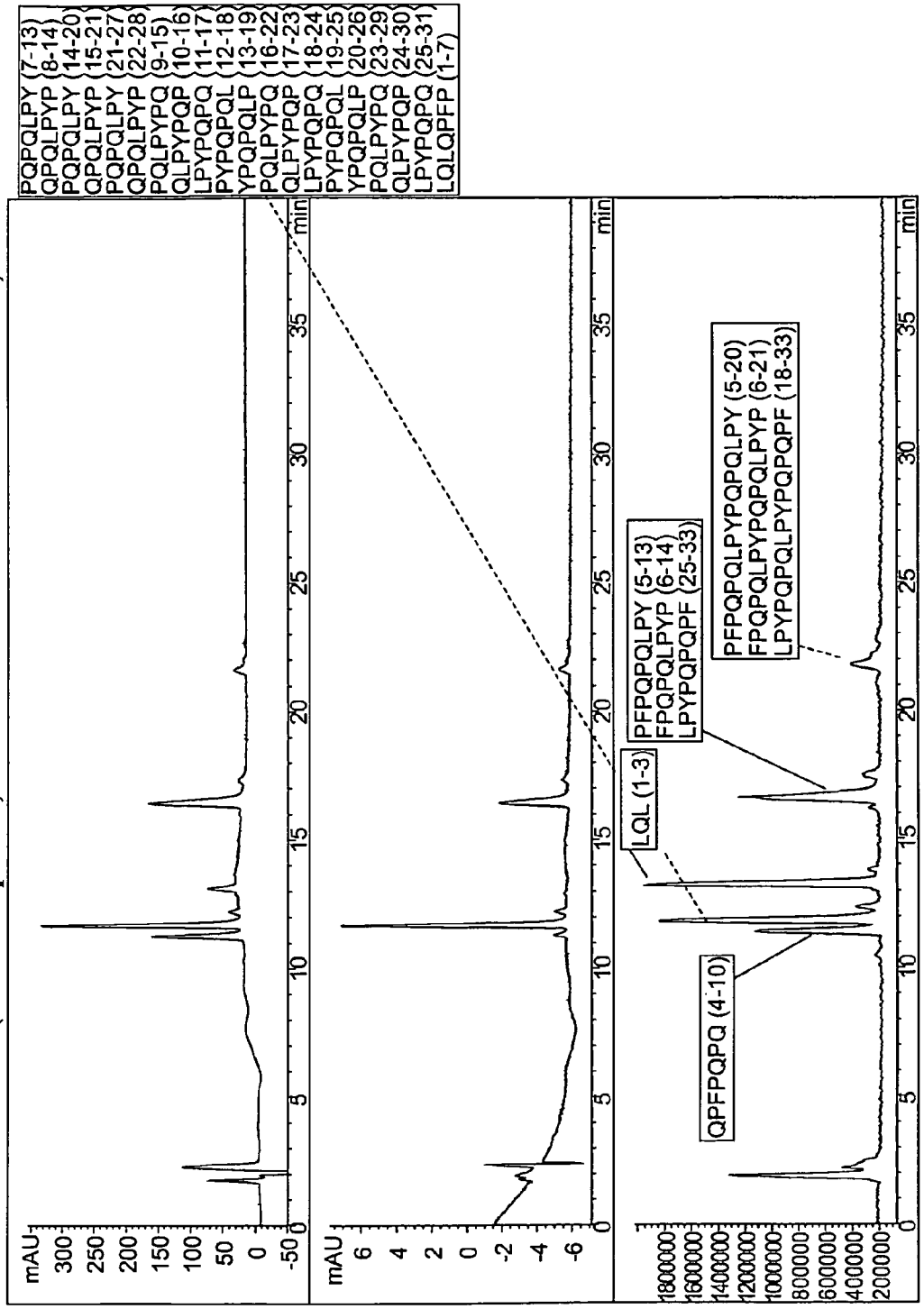
FIG. 8, cont.

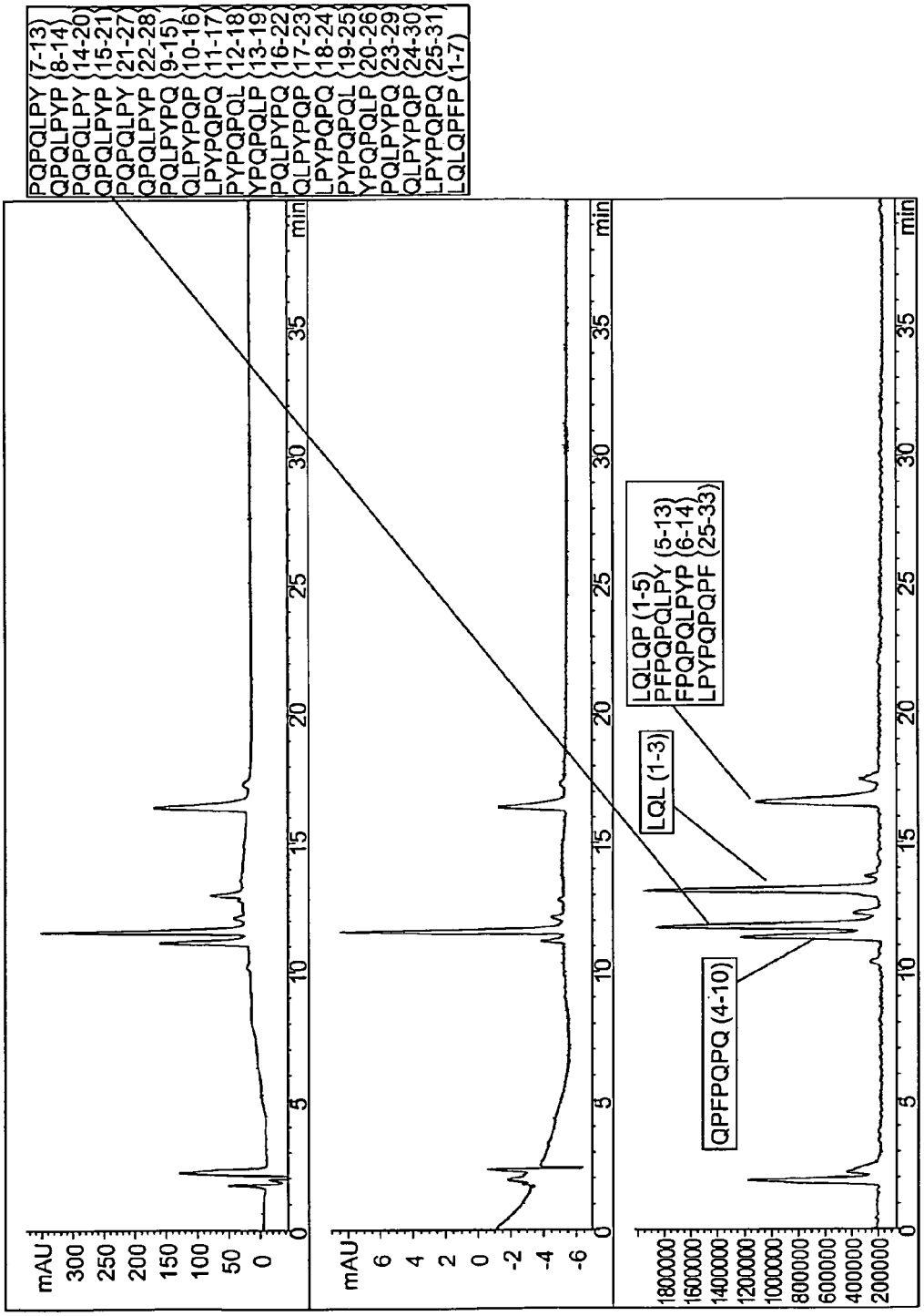

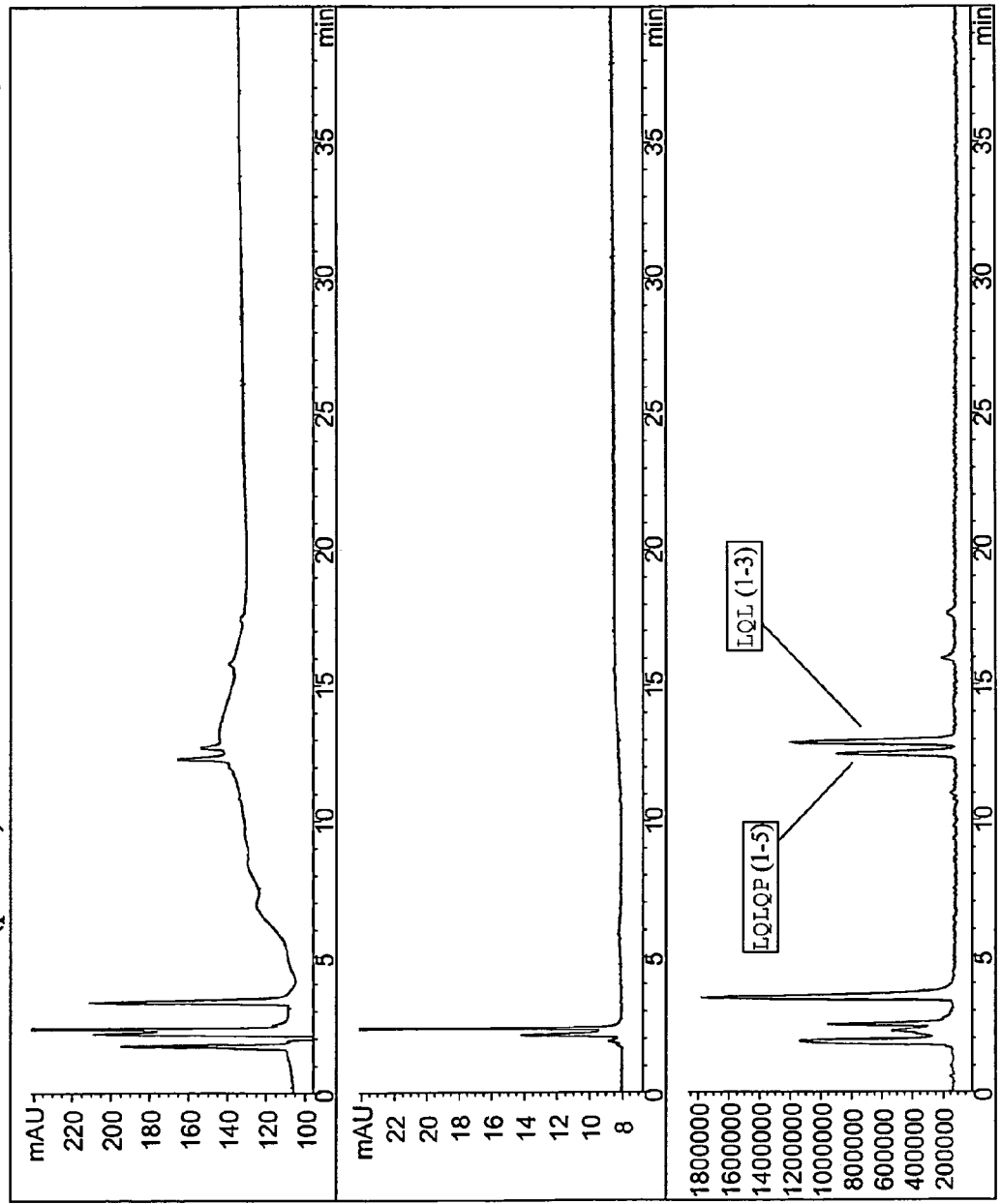

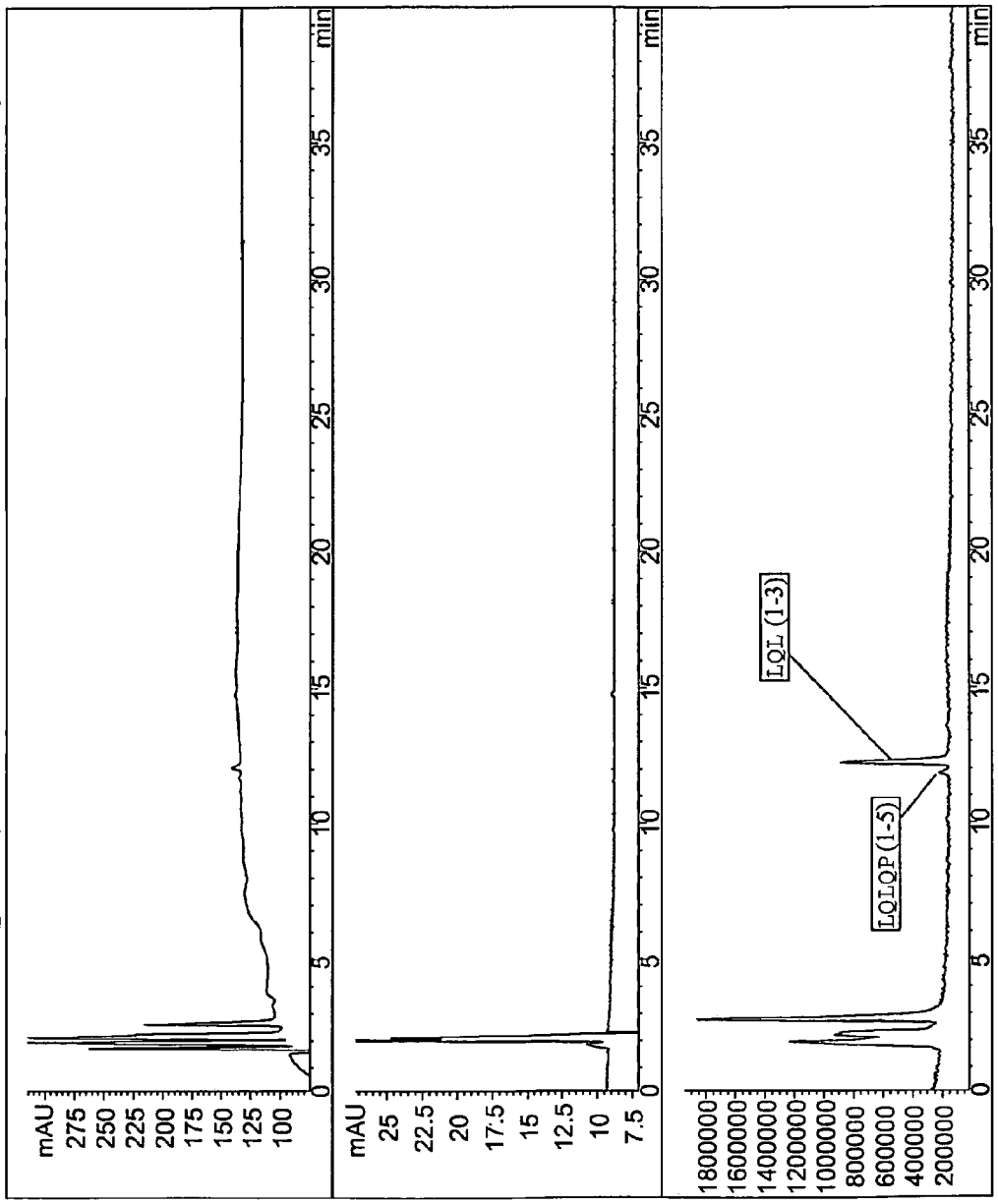
FIG. 10, cont.

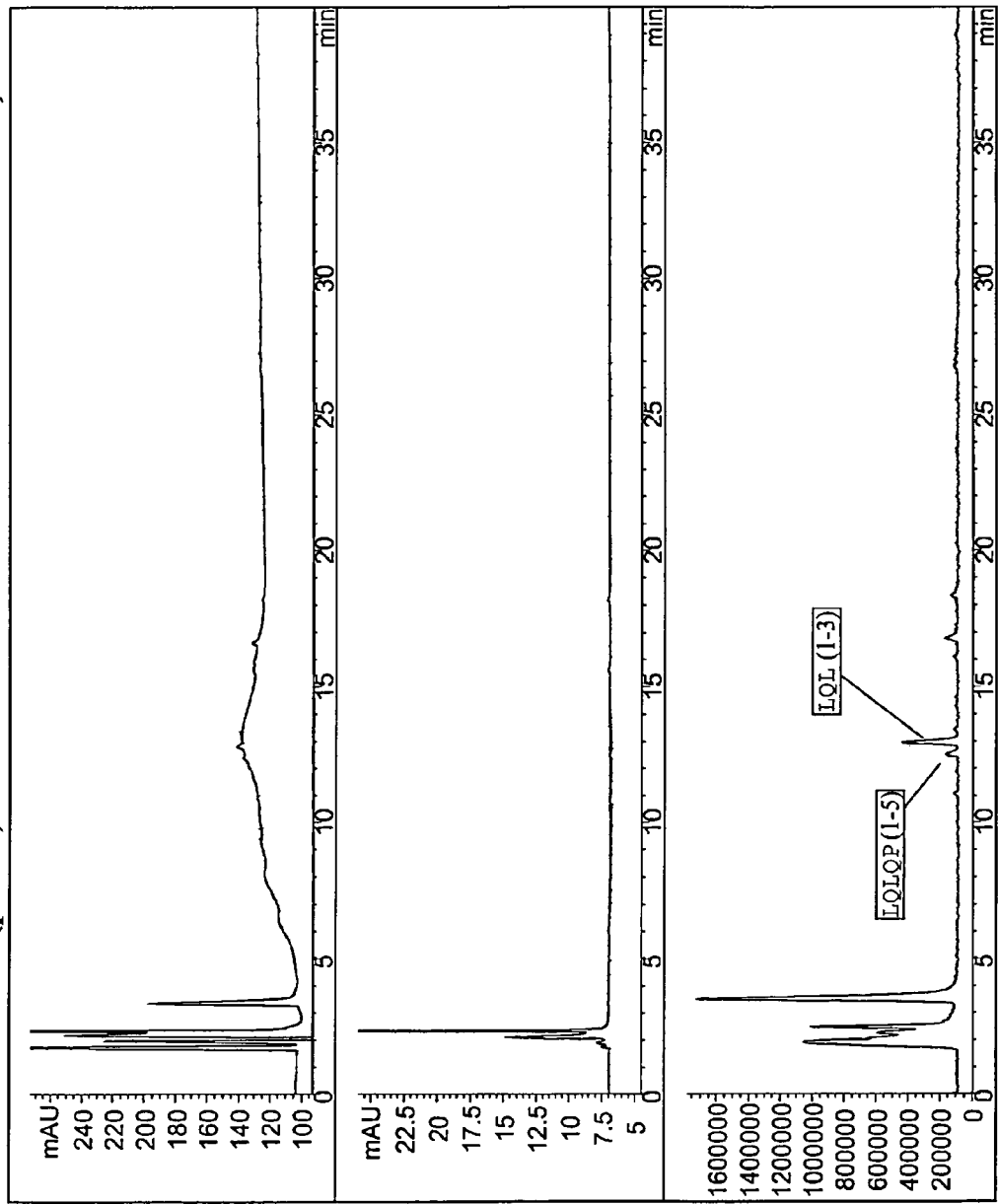
FIG. 10, cont.

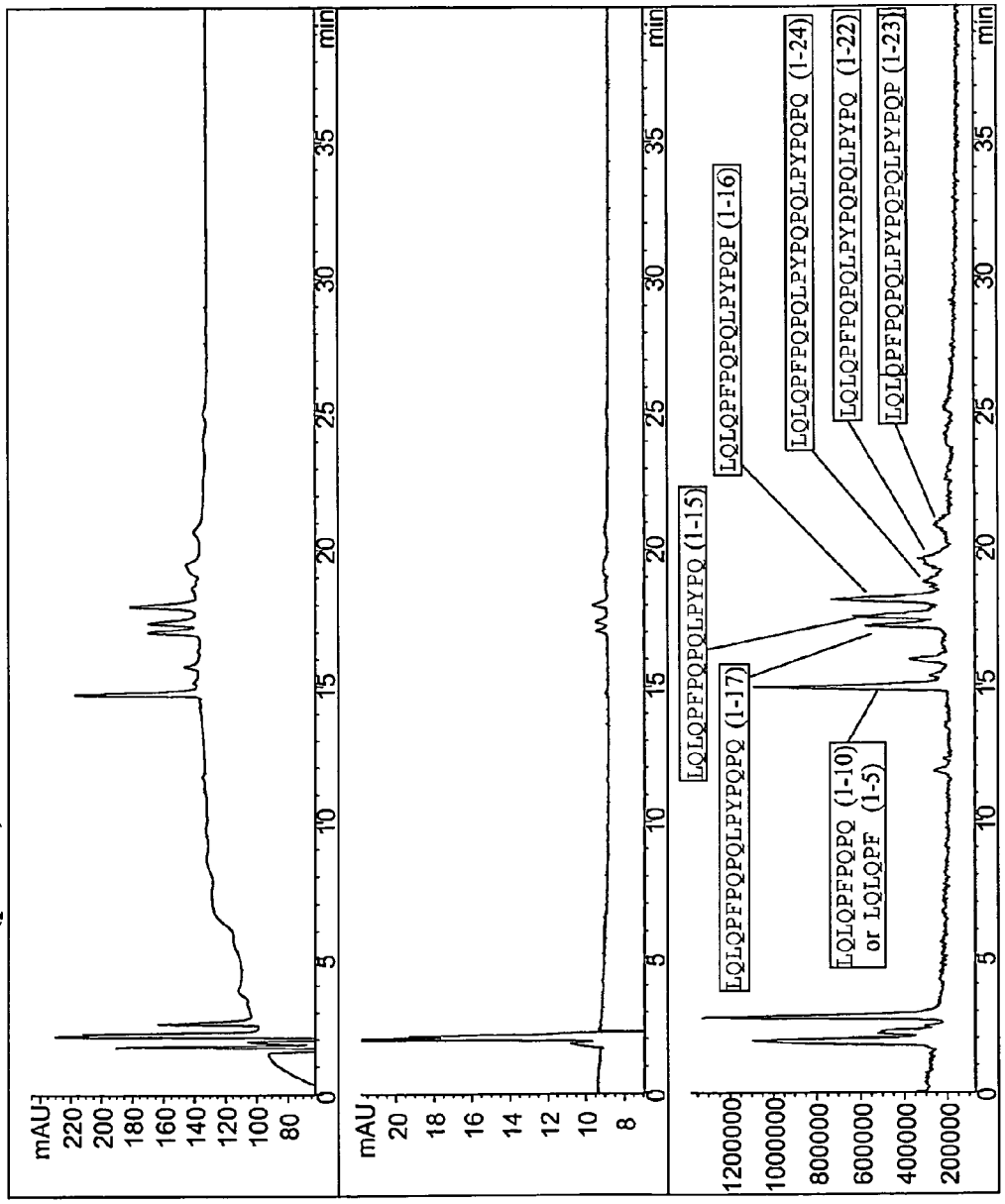

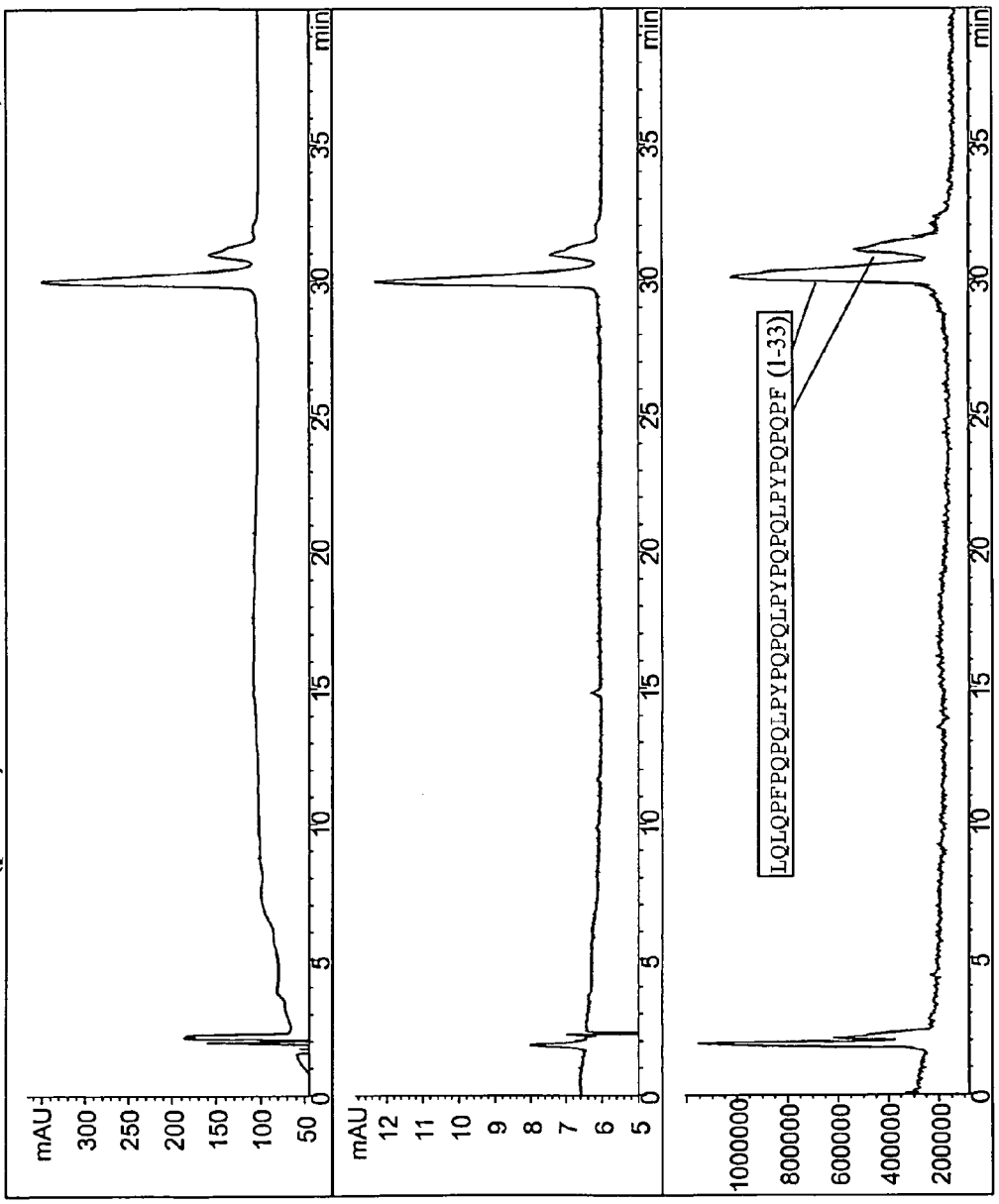

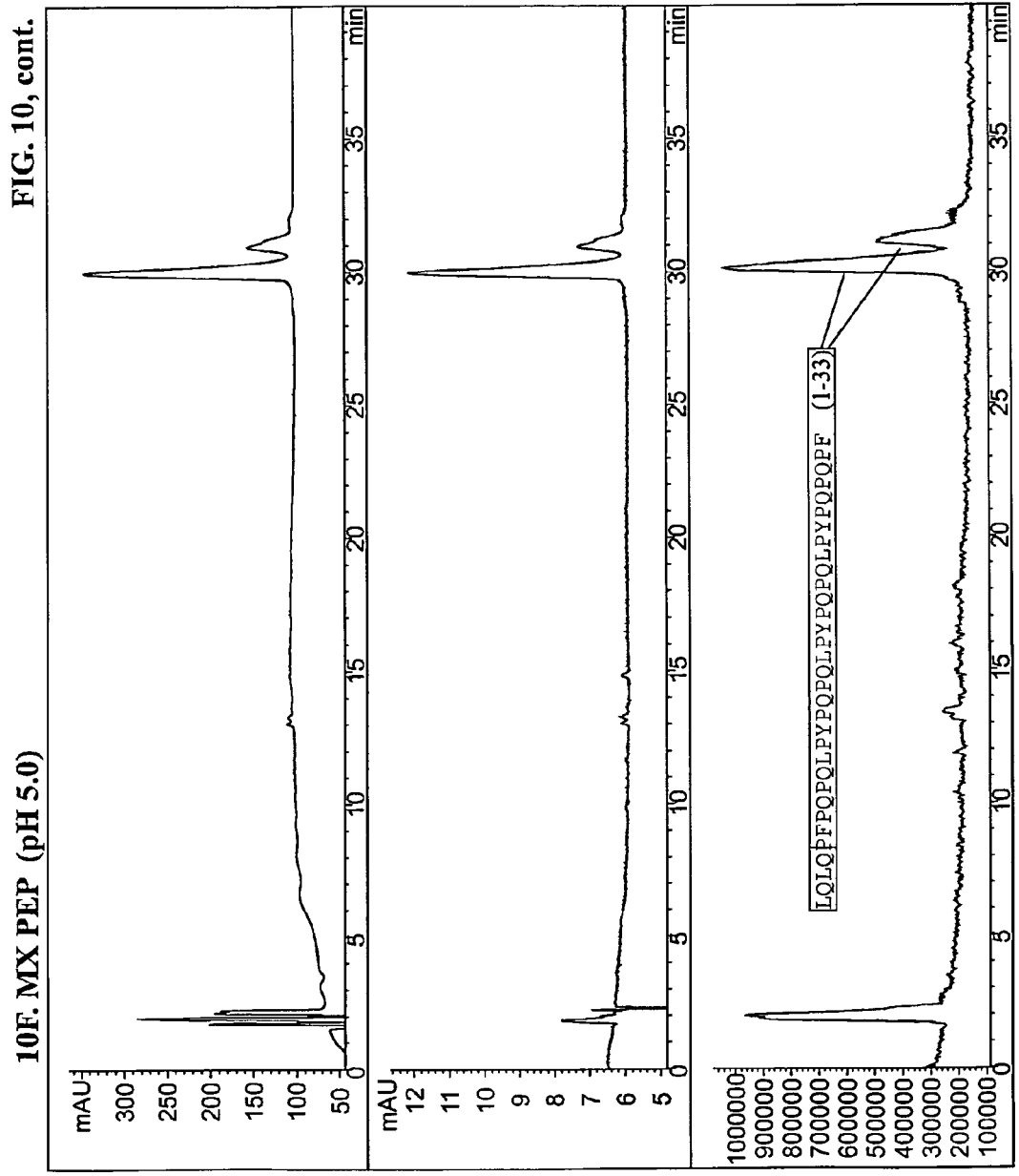
FIG. 10, cont.

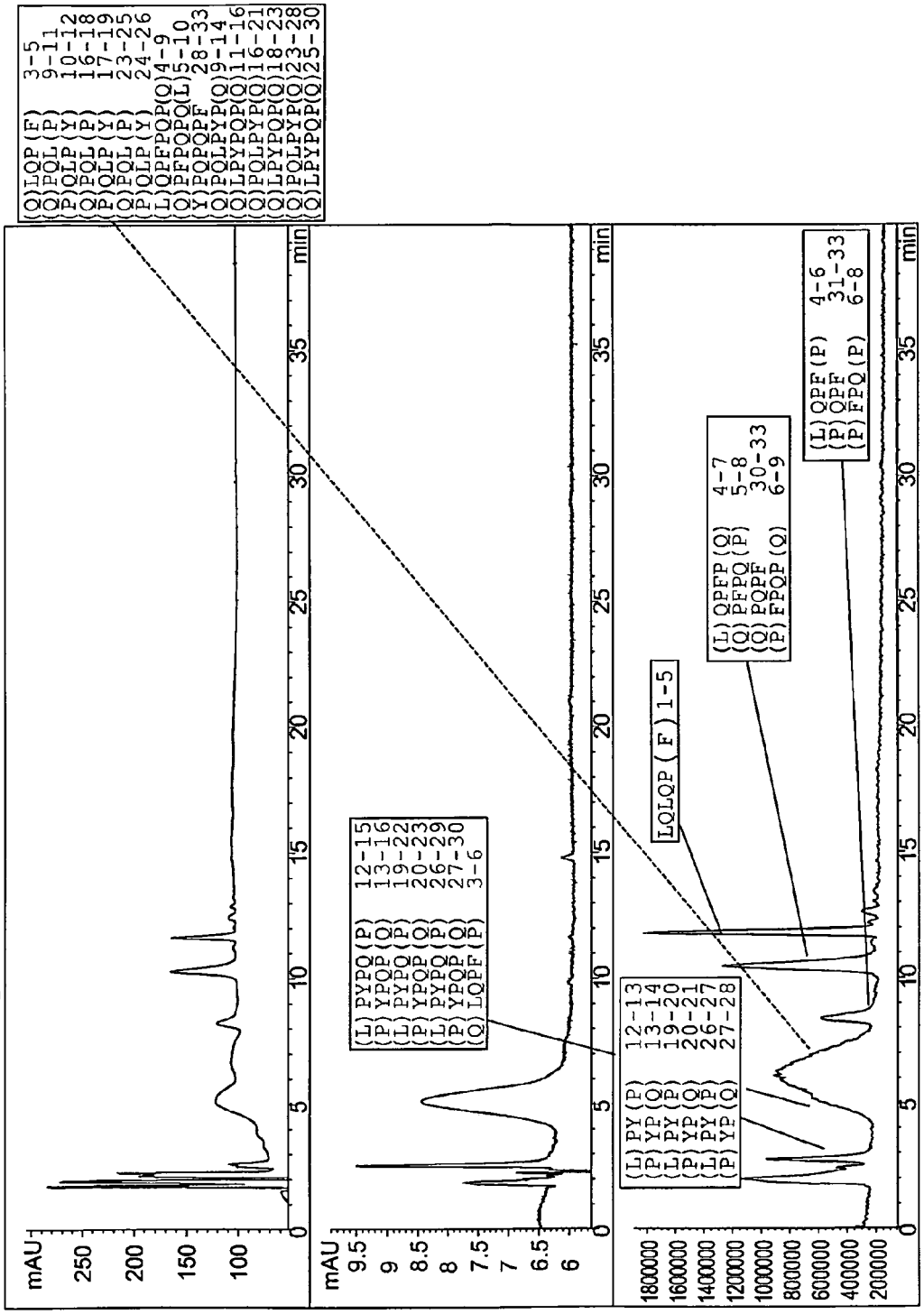
FIG. 10, cont.

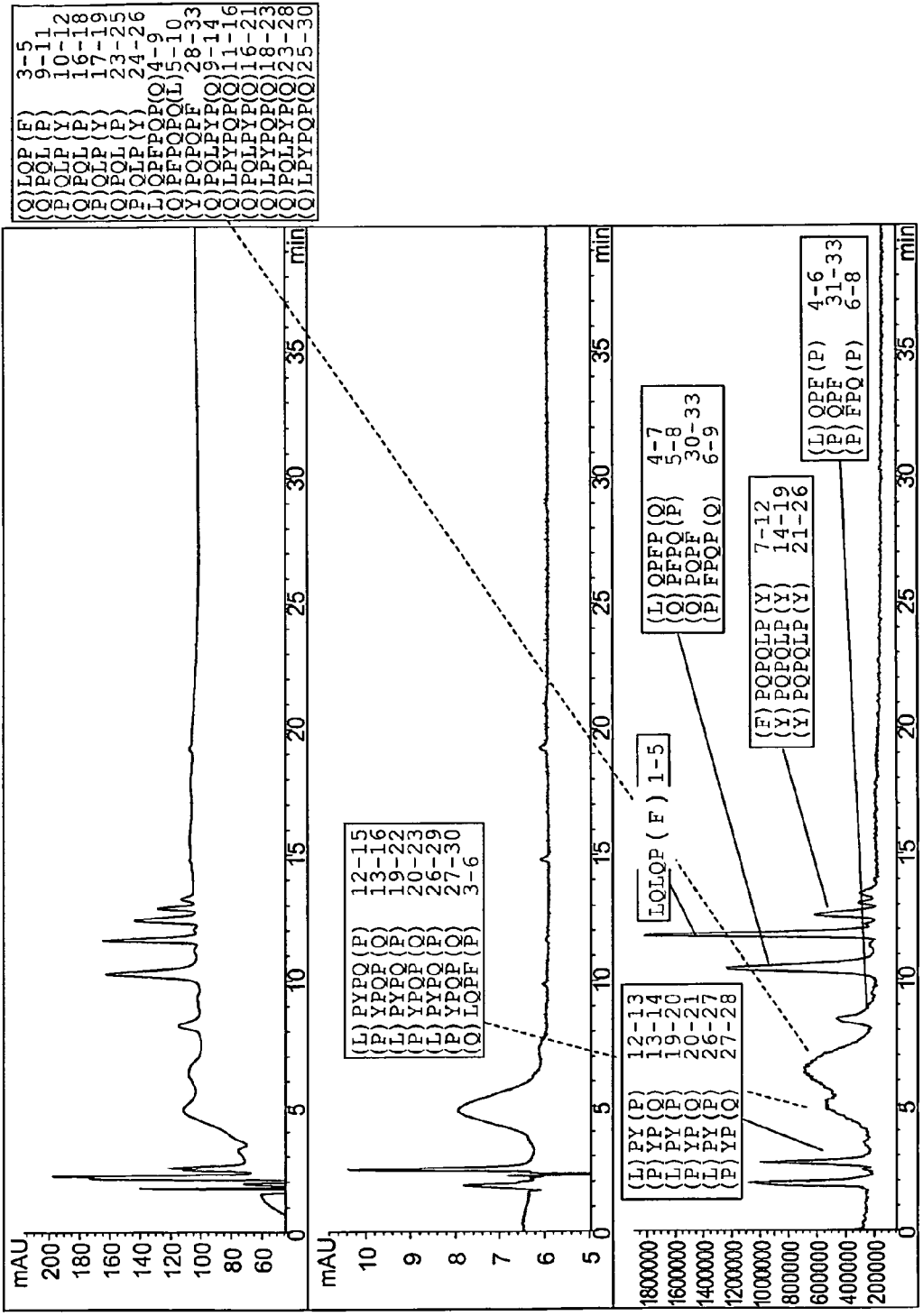

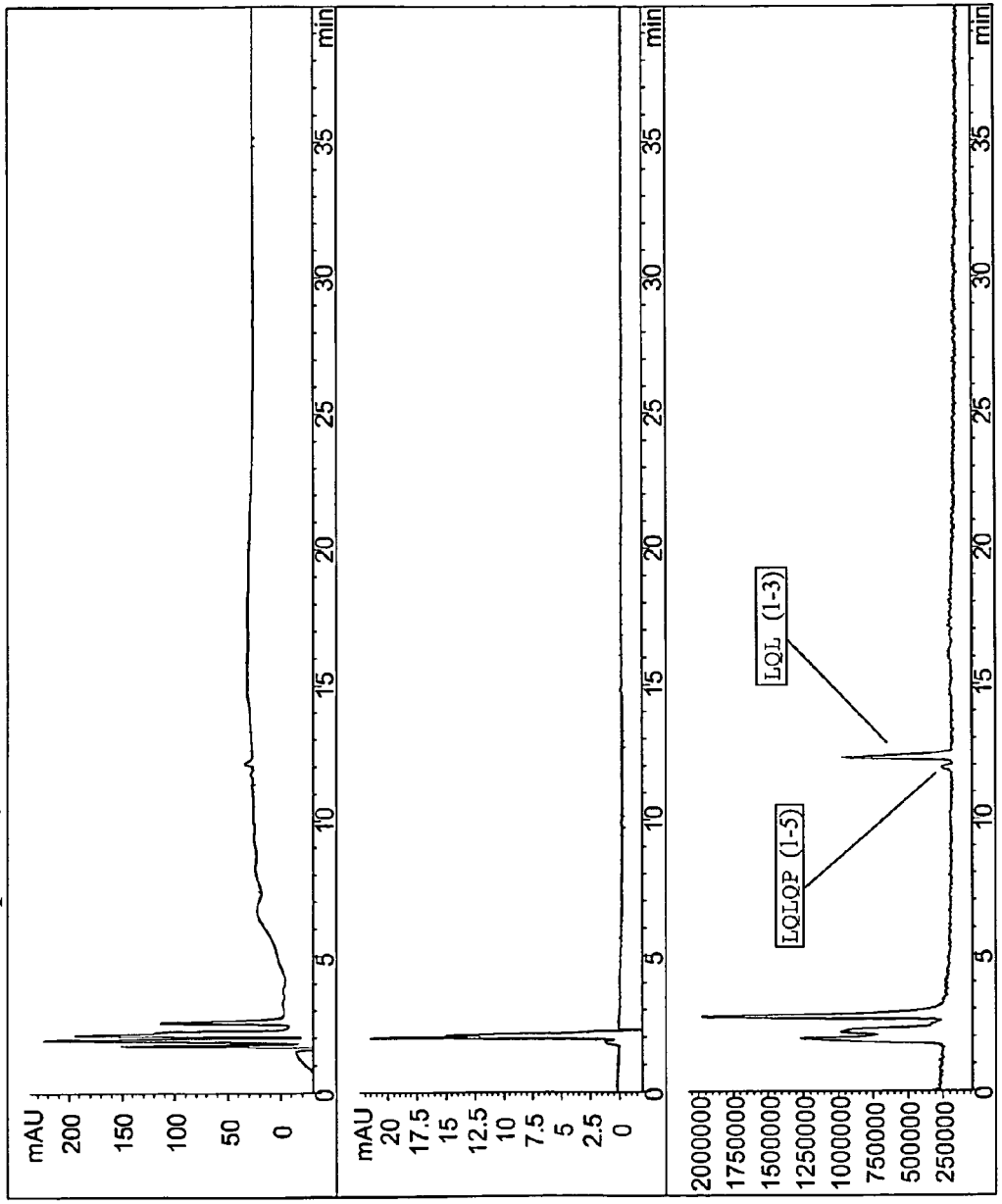

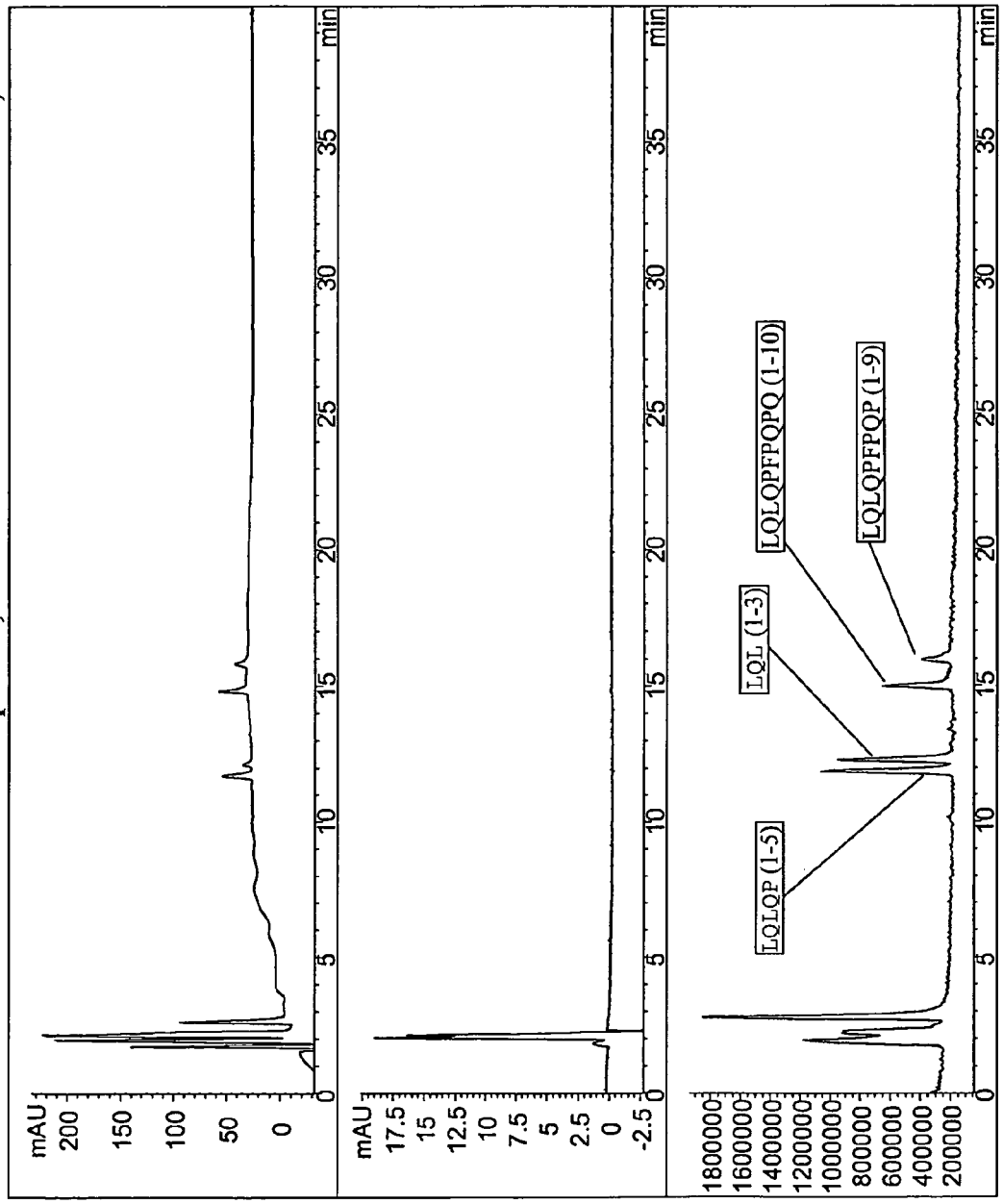
FIG. 11, cont.

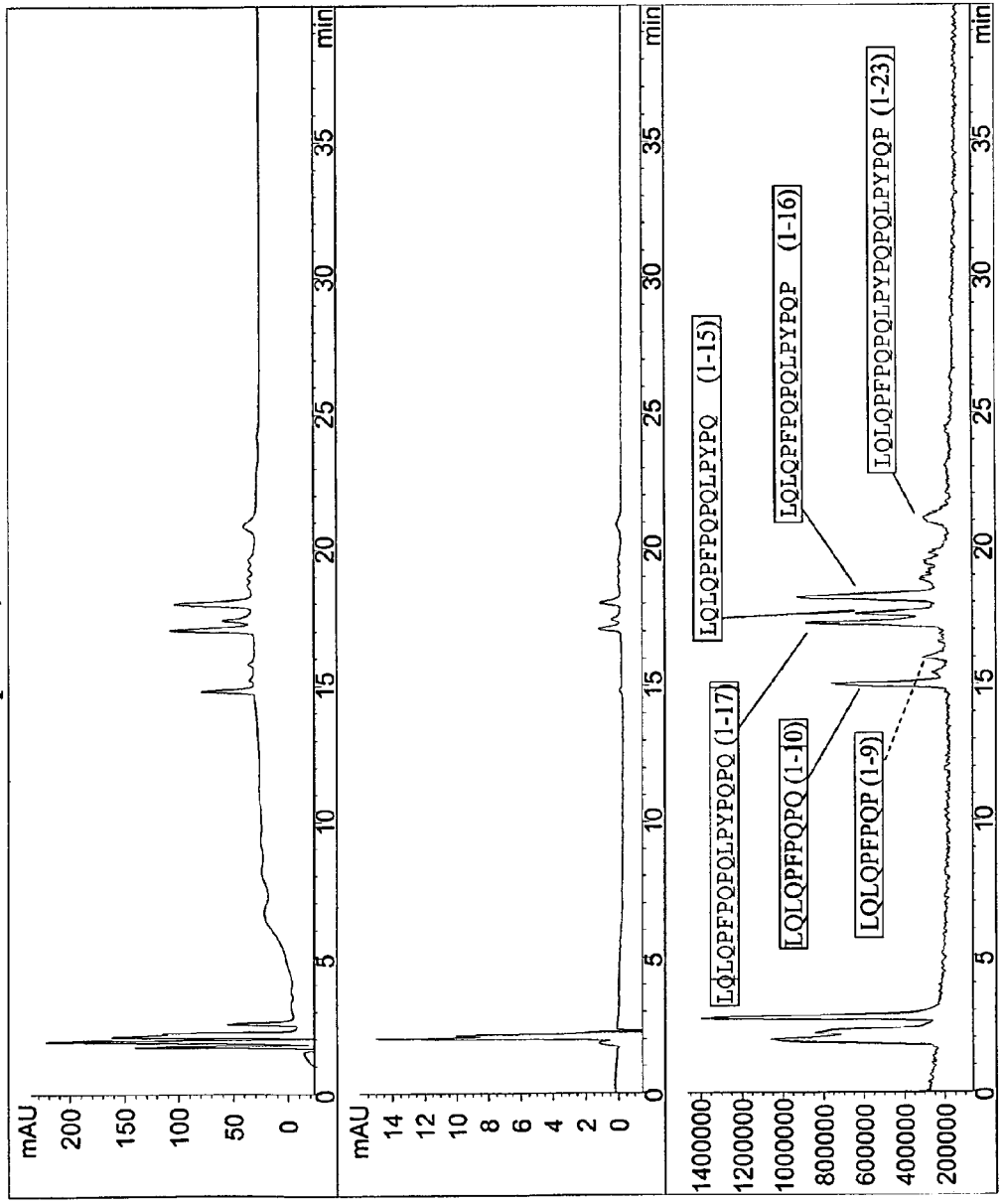

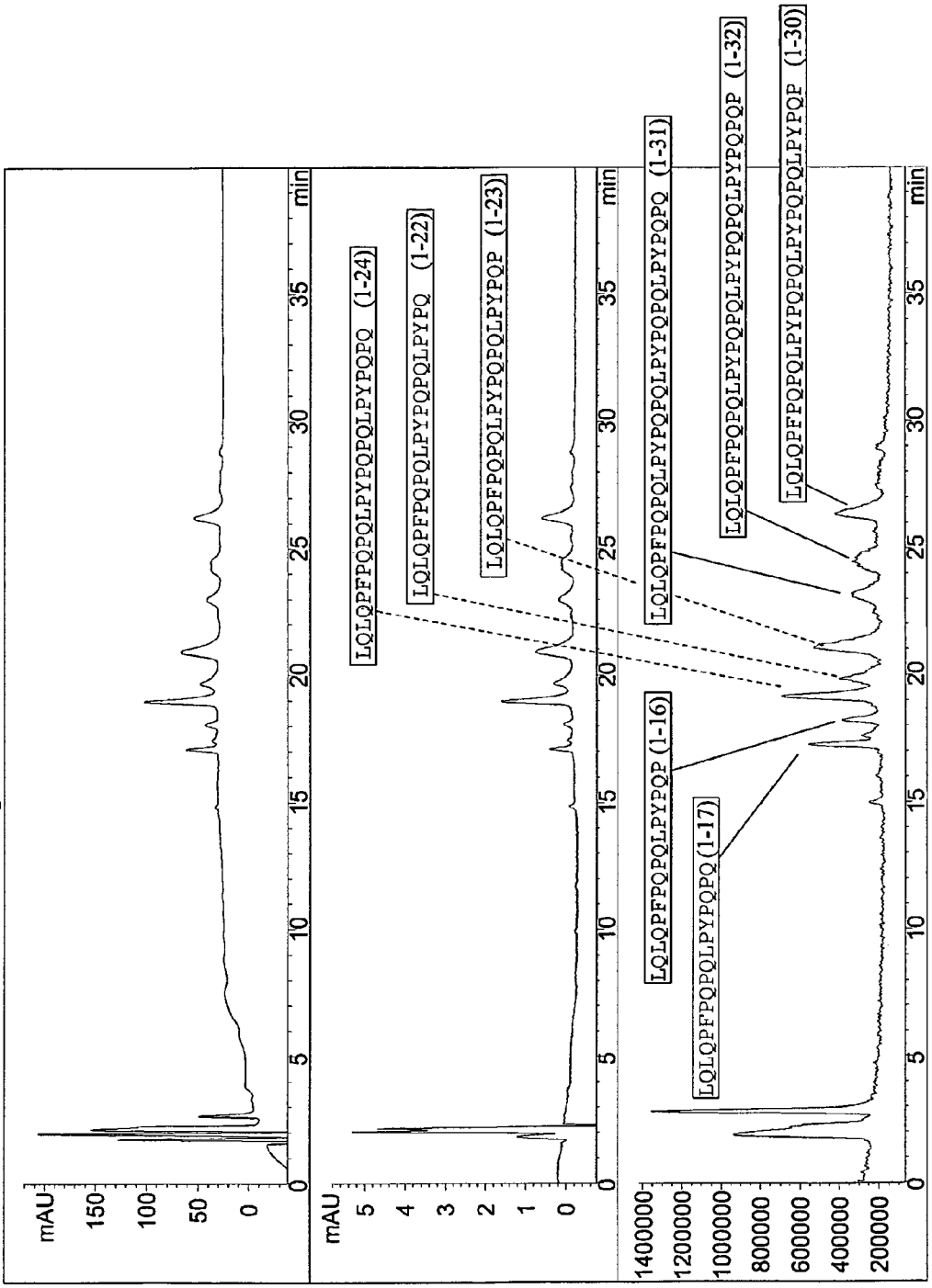

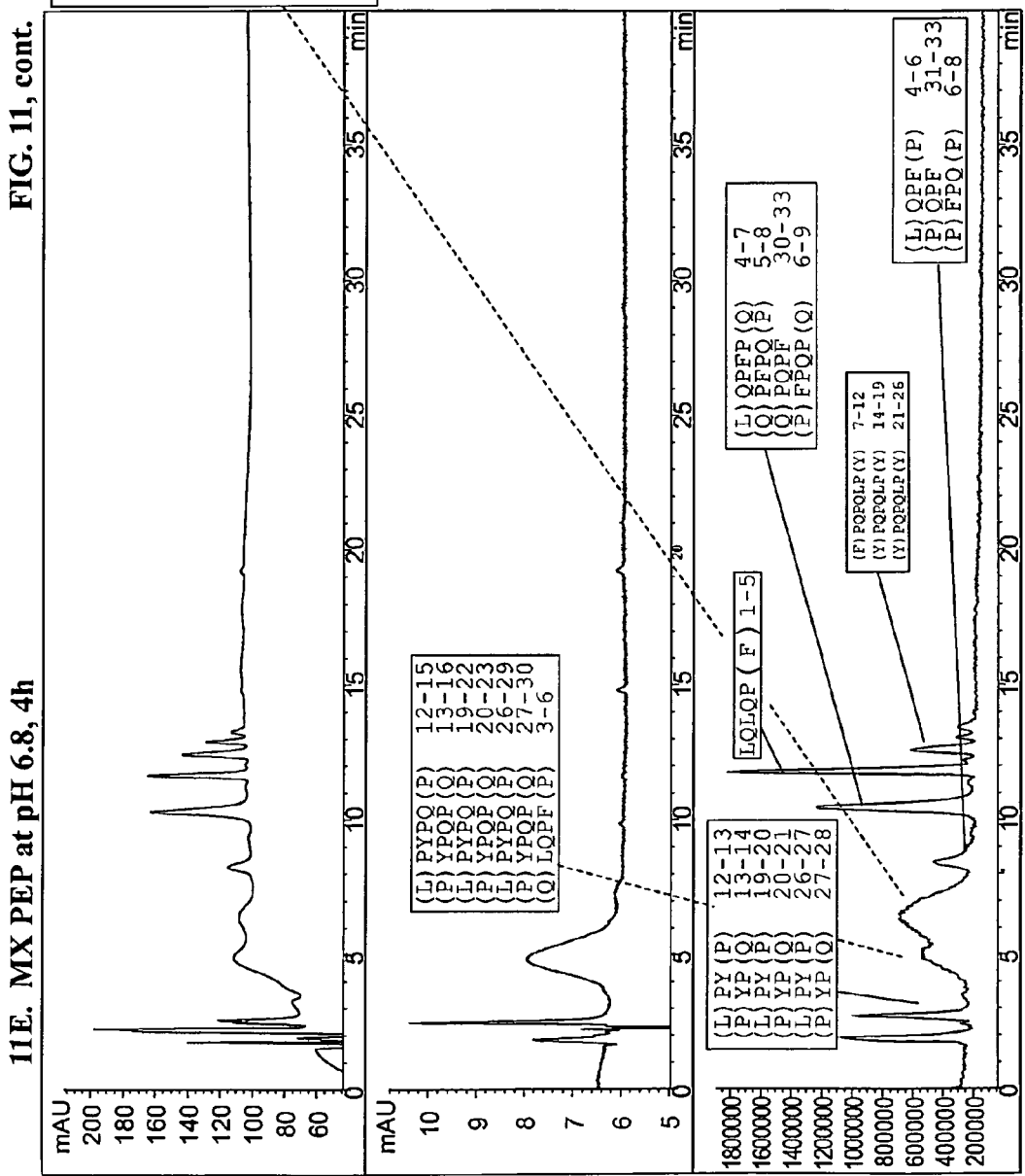
FIG. 11, cont.

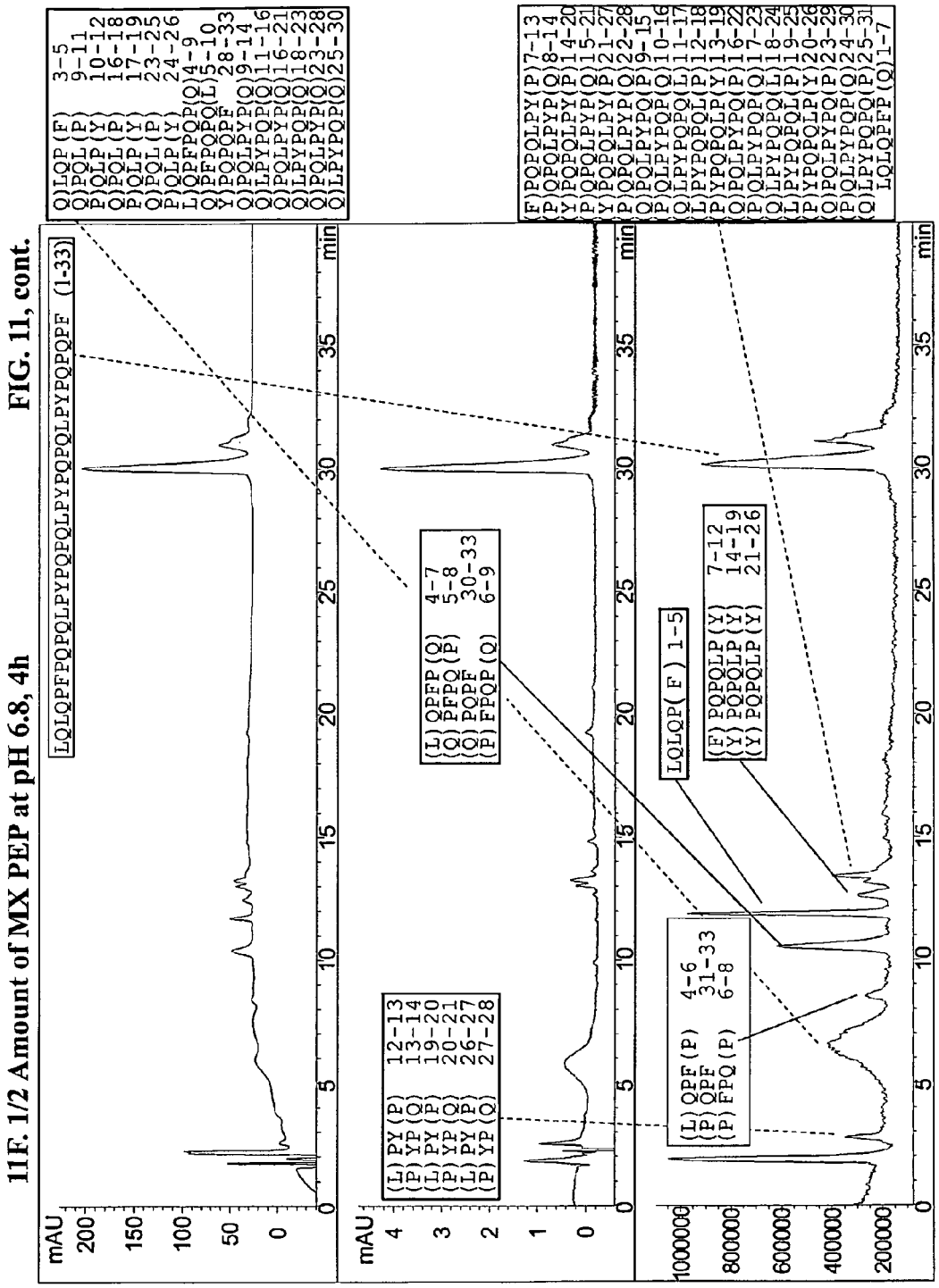

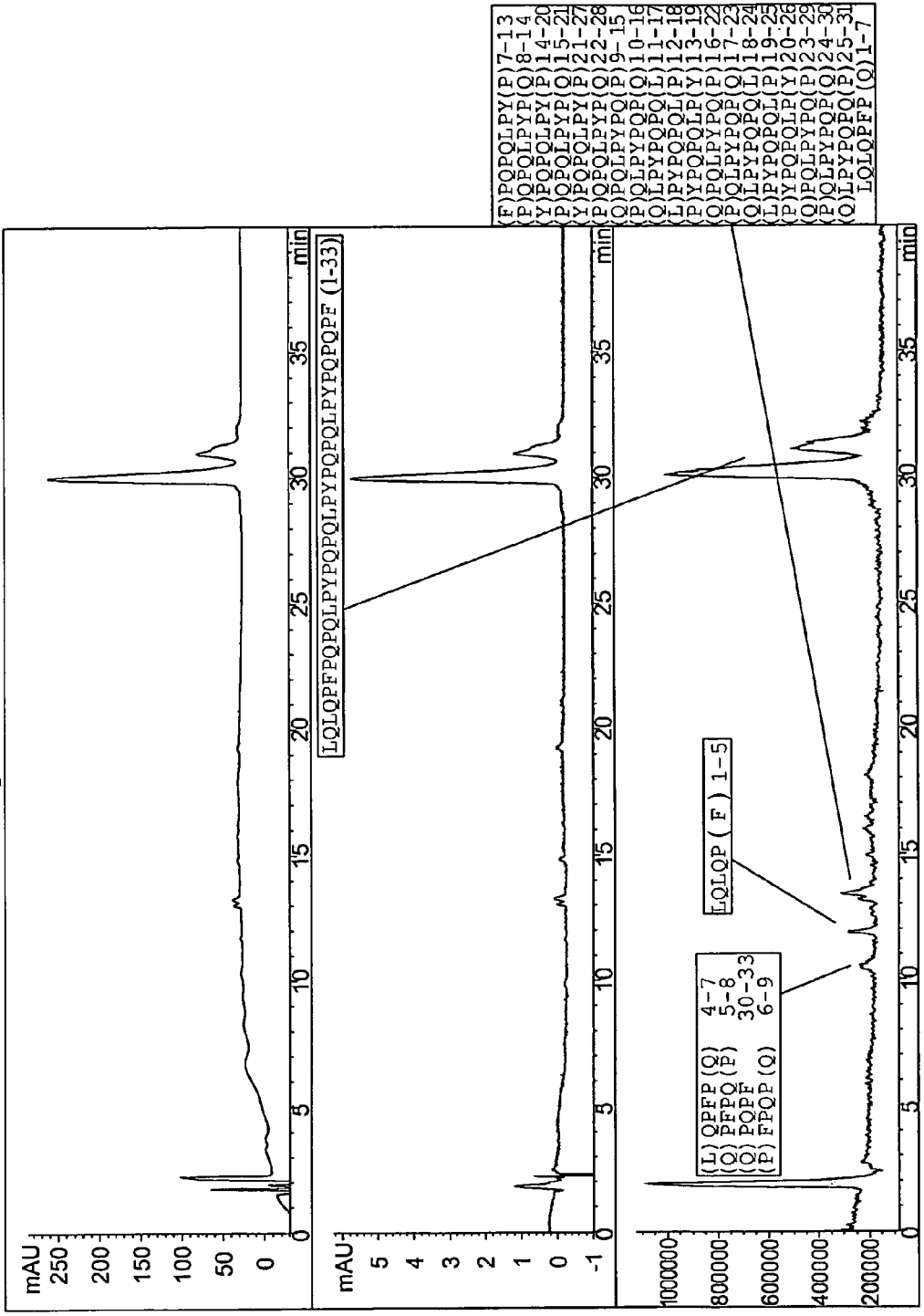
FIG. 11, cont.

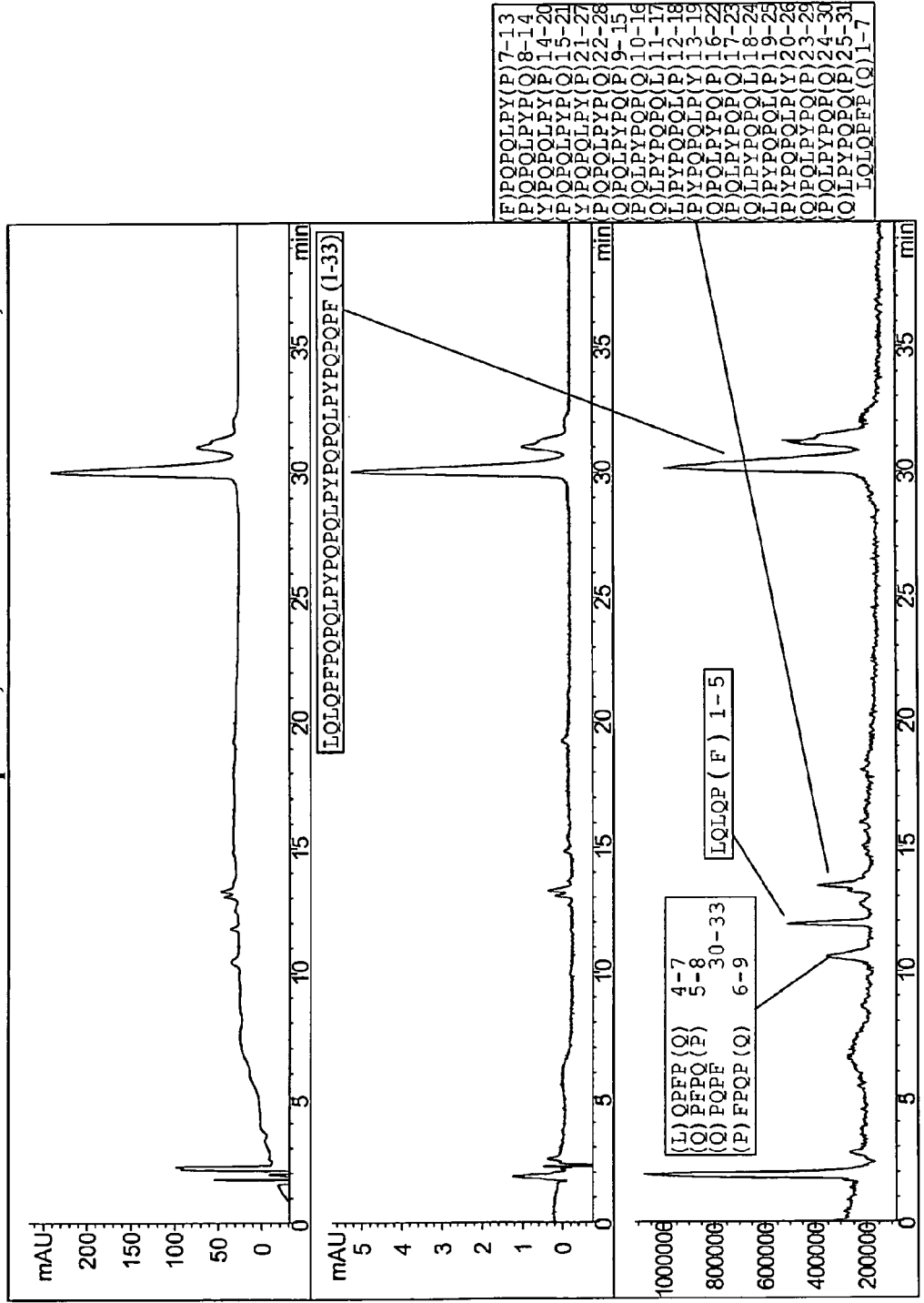
FIG. 11, cont.

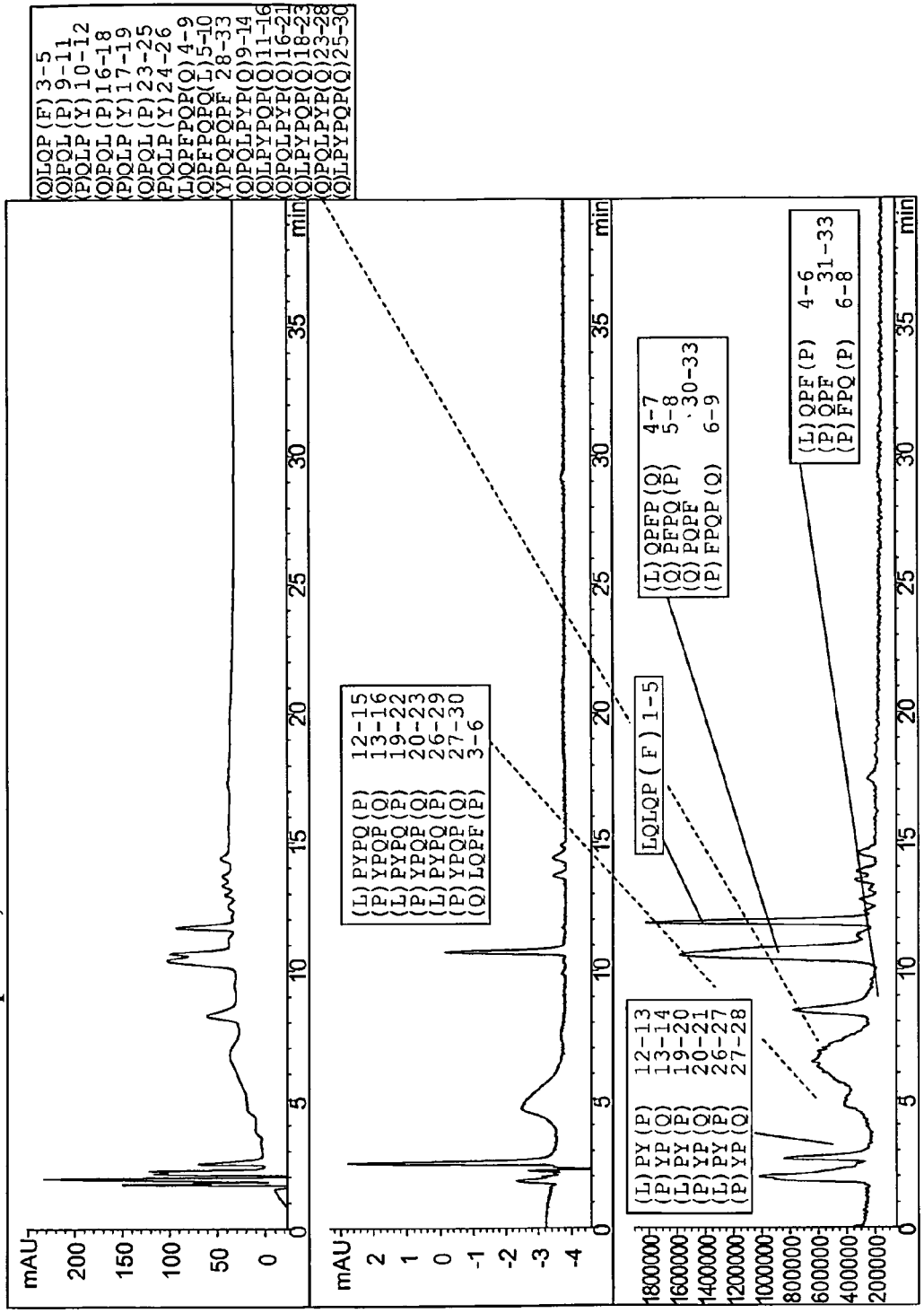
FIG. 11, cont.

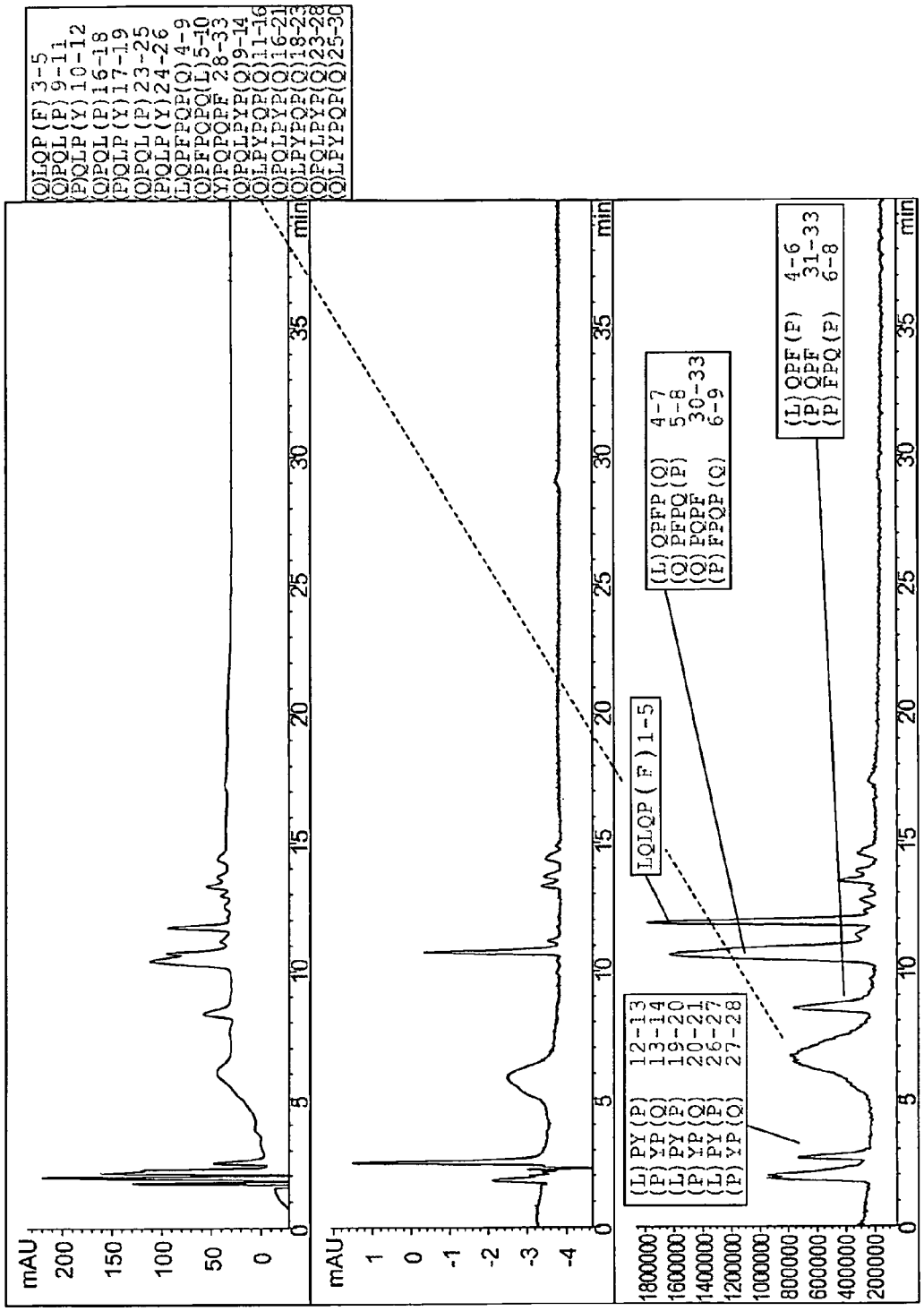
FIG. 11, cont.

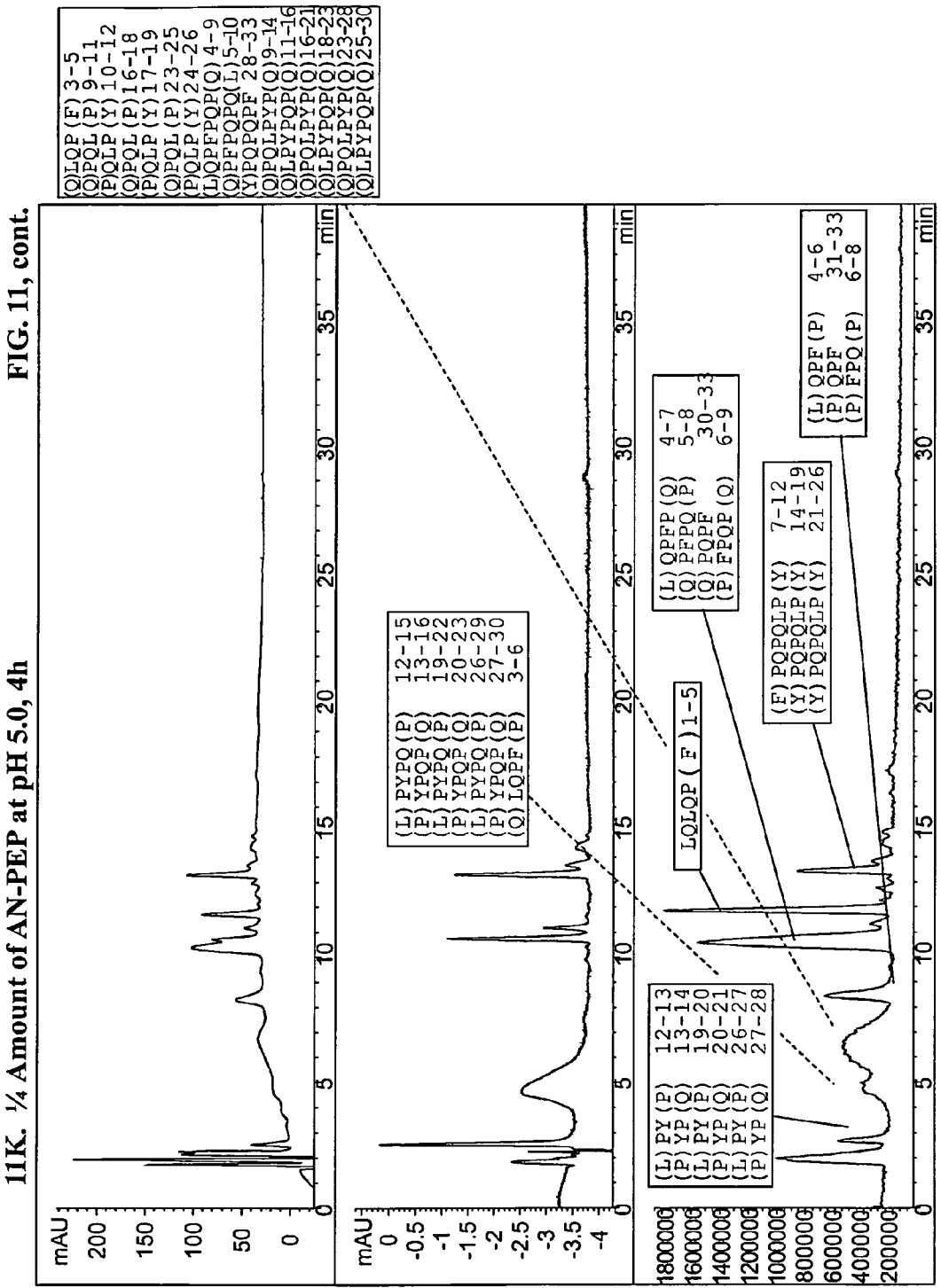

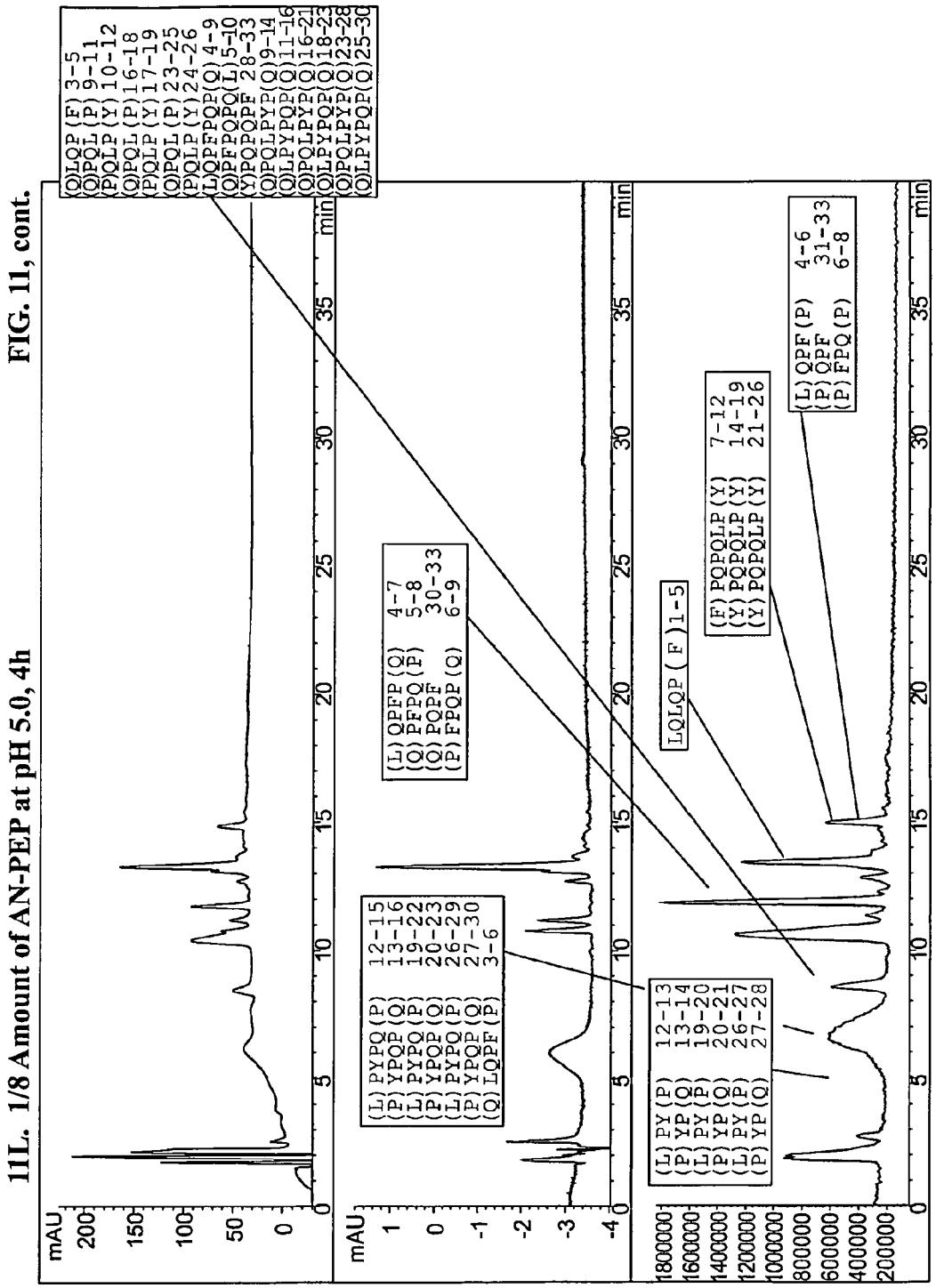
FIG. 11, cont.

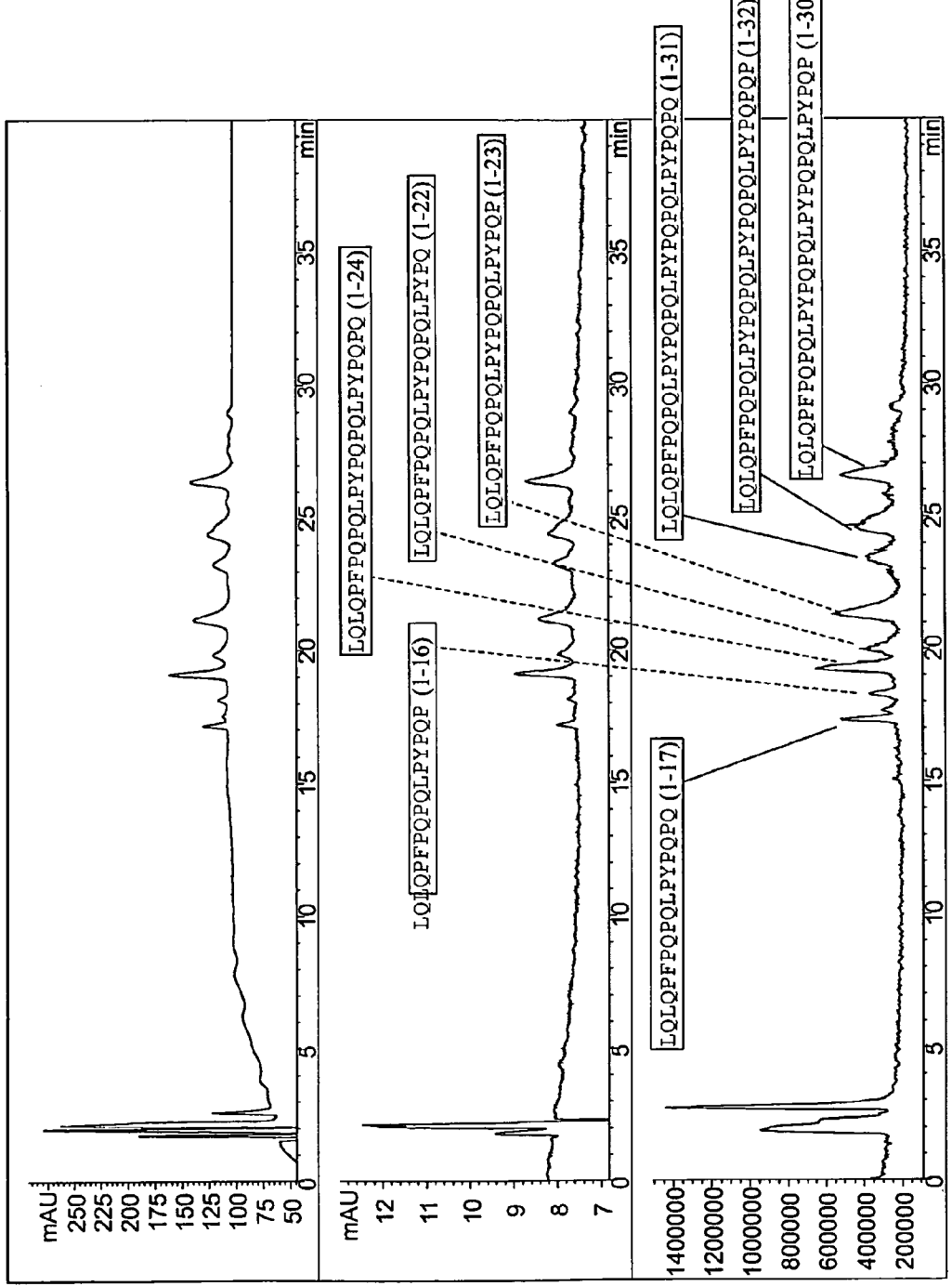
FIG. 11, cont.

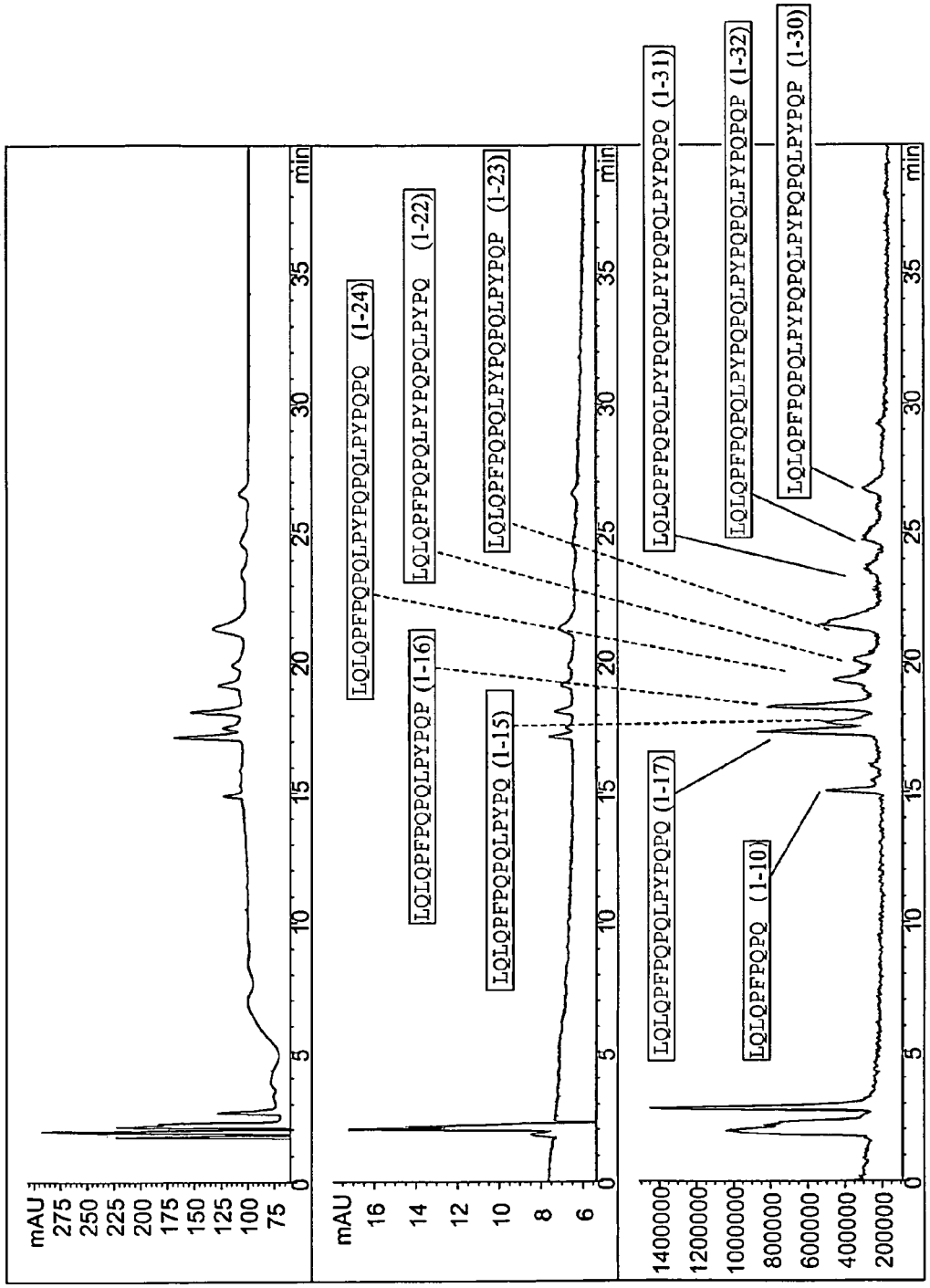
FIG. 11, cont.

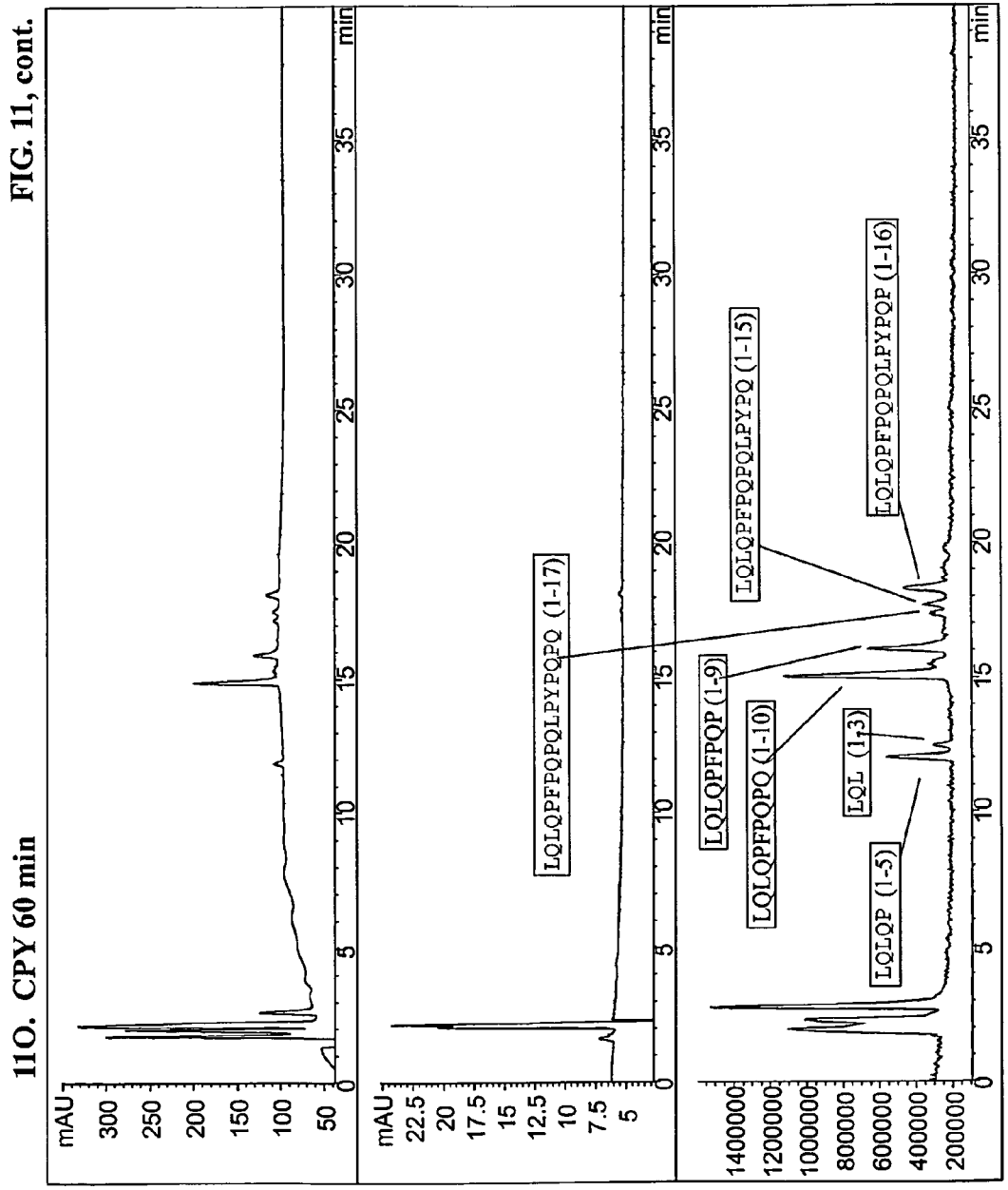
FIG. 11, cont.

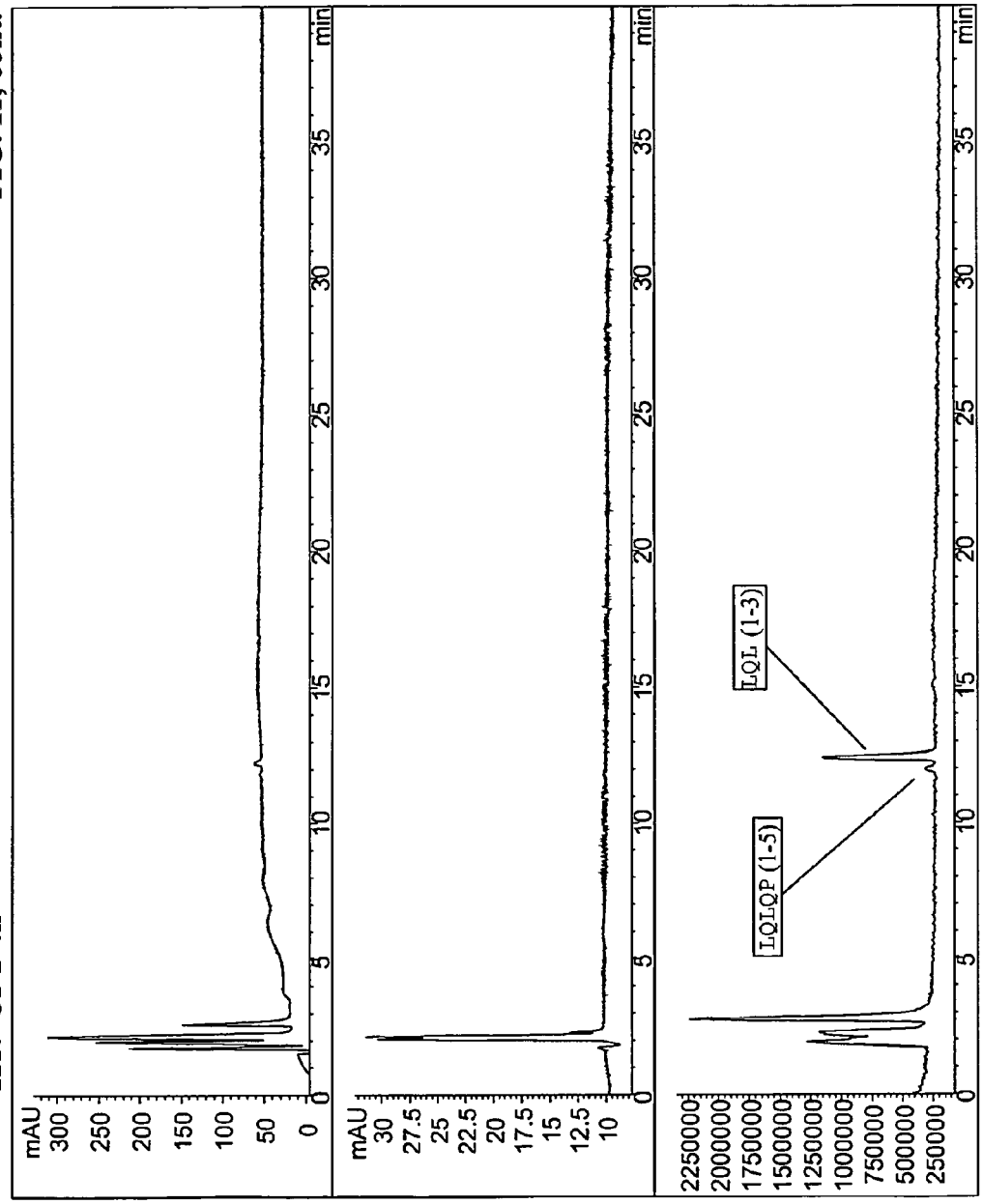
FIG. 11, cont.

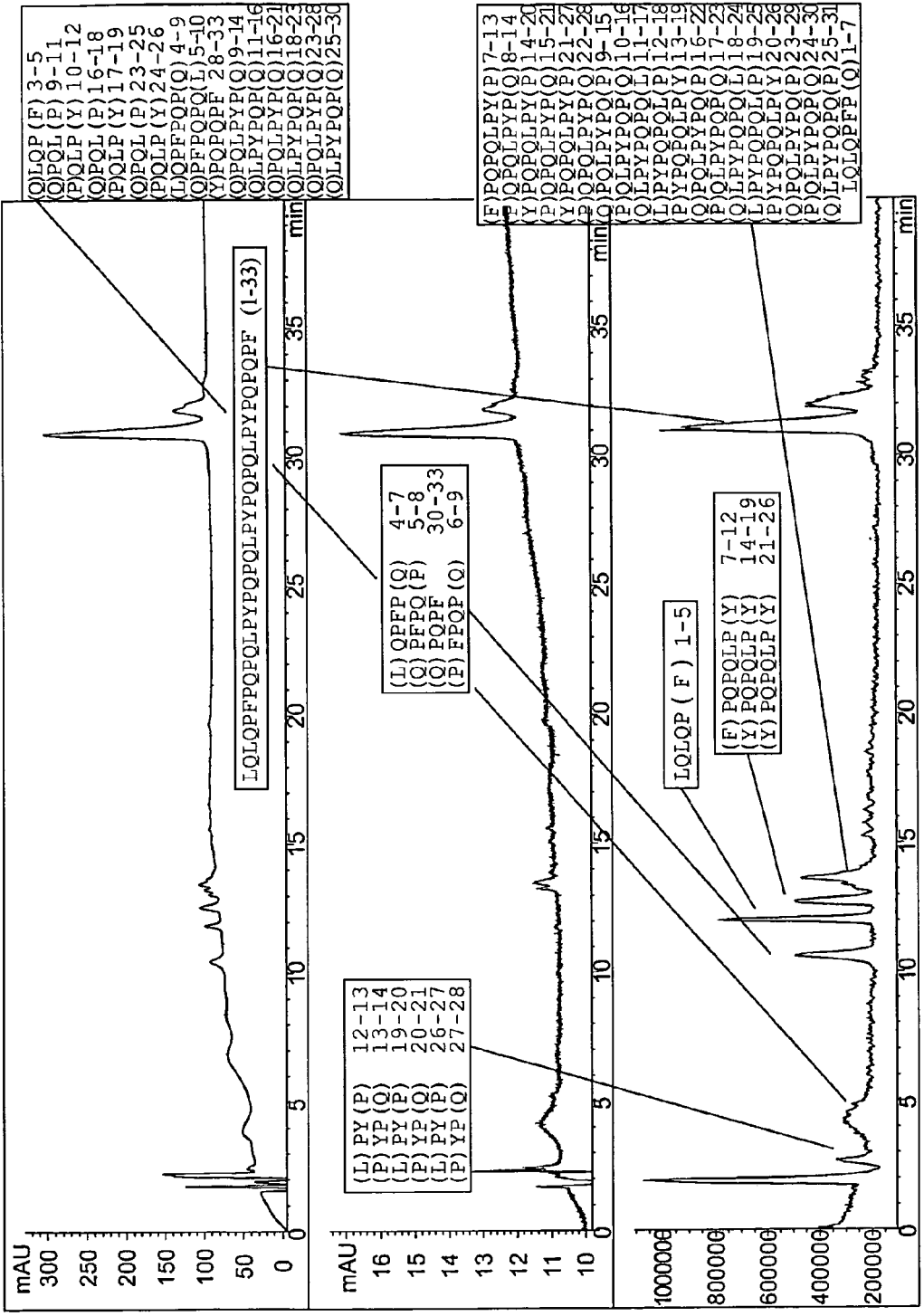
FIG. 11, cont.

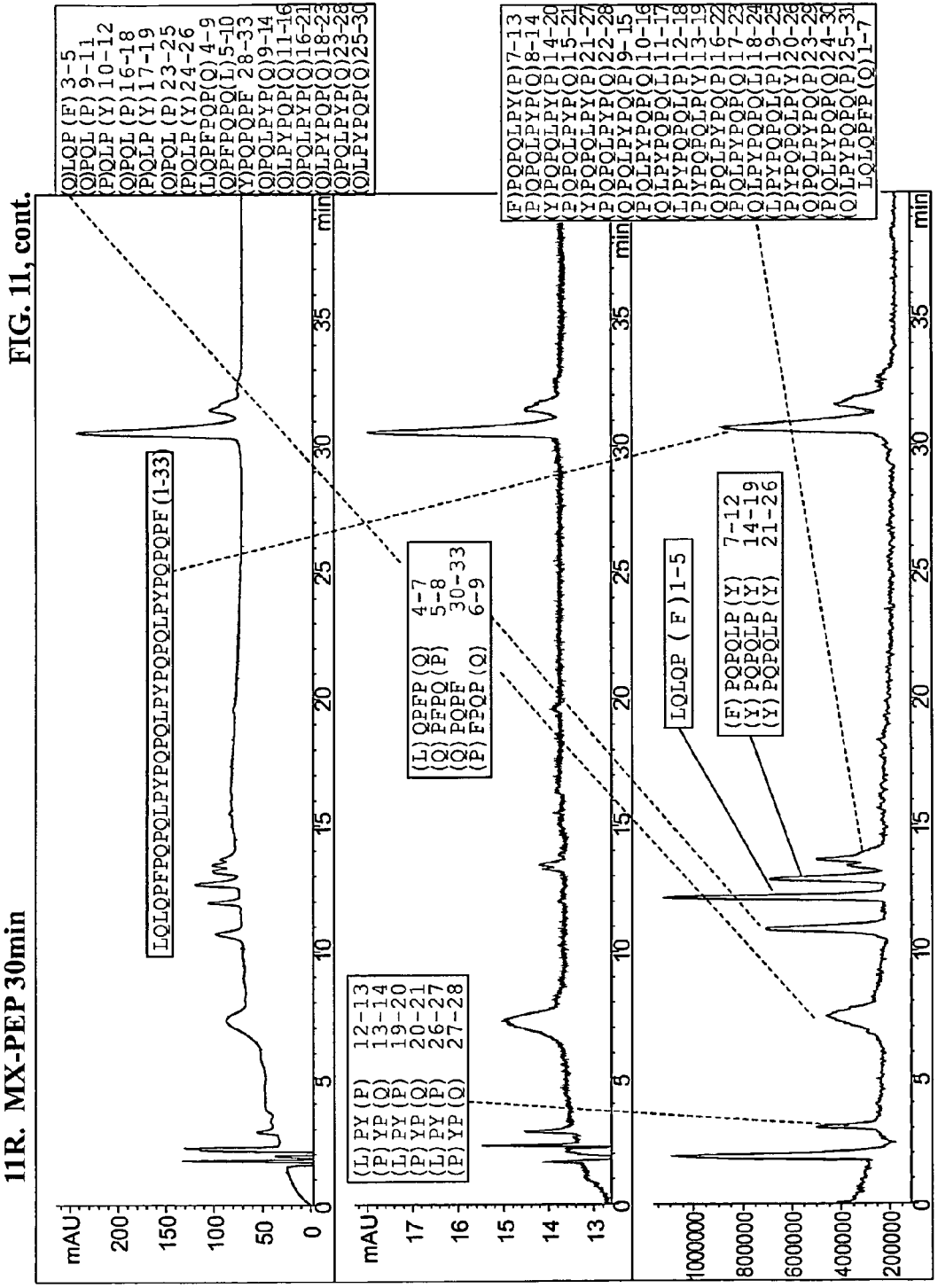
FIG. 11, cont.

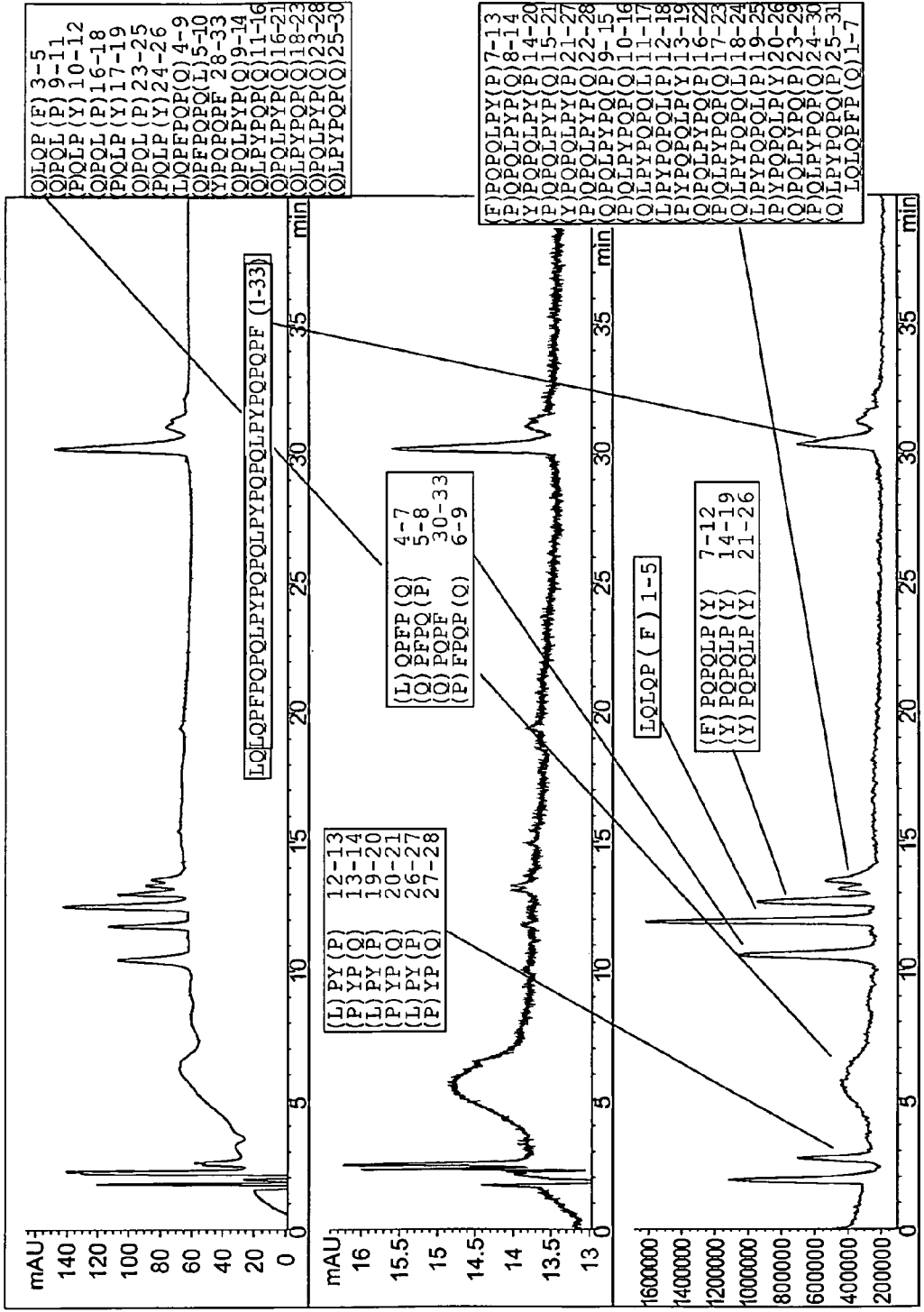
FIG. 11, cont.

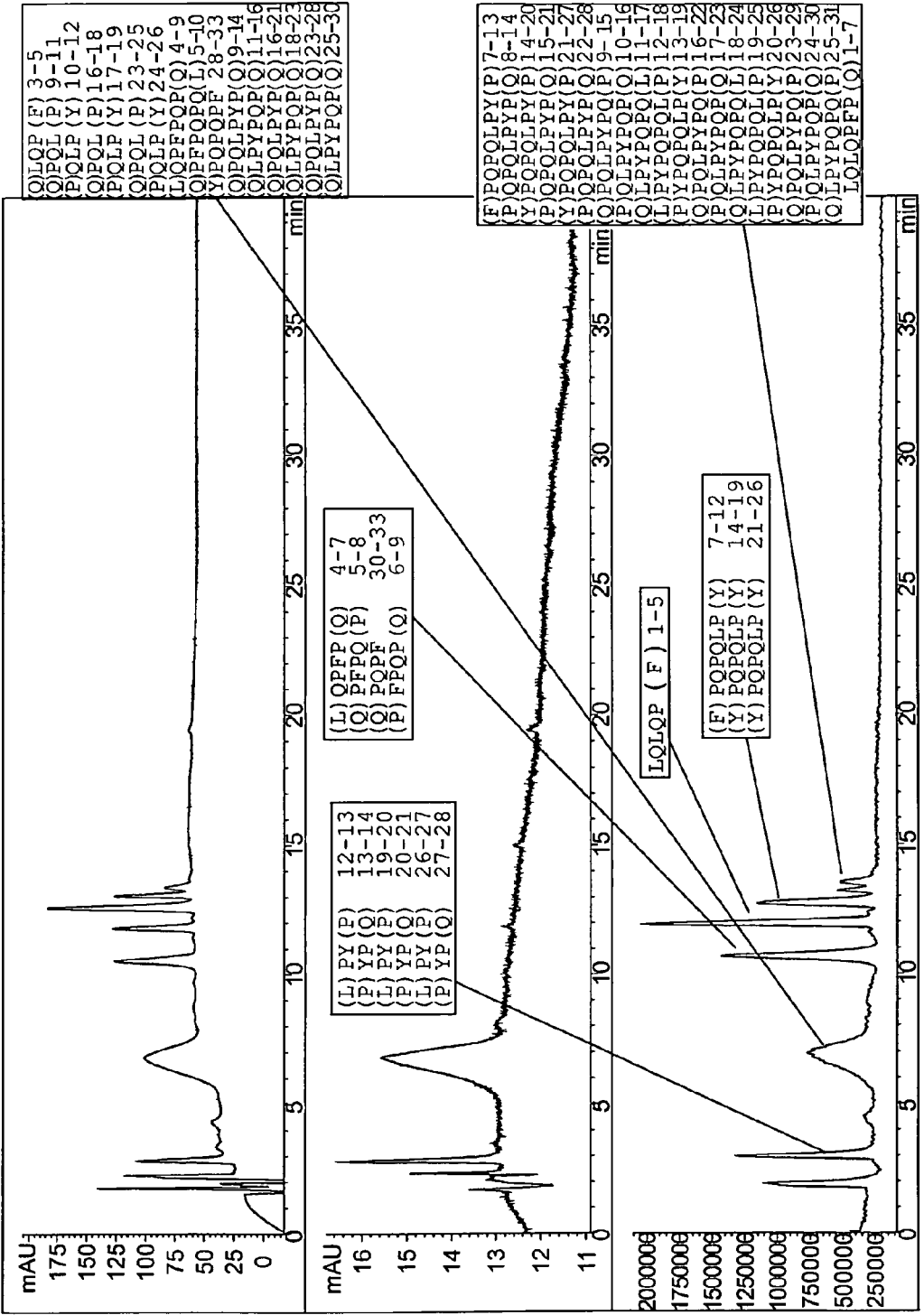
FIG. 11, cont.

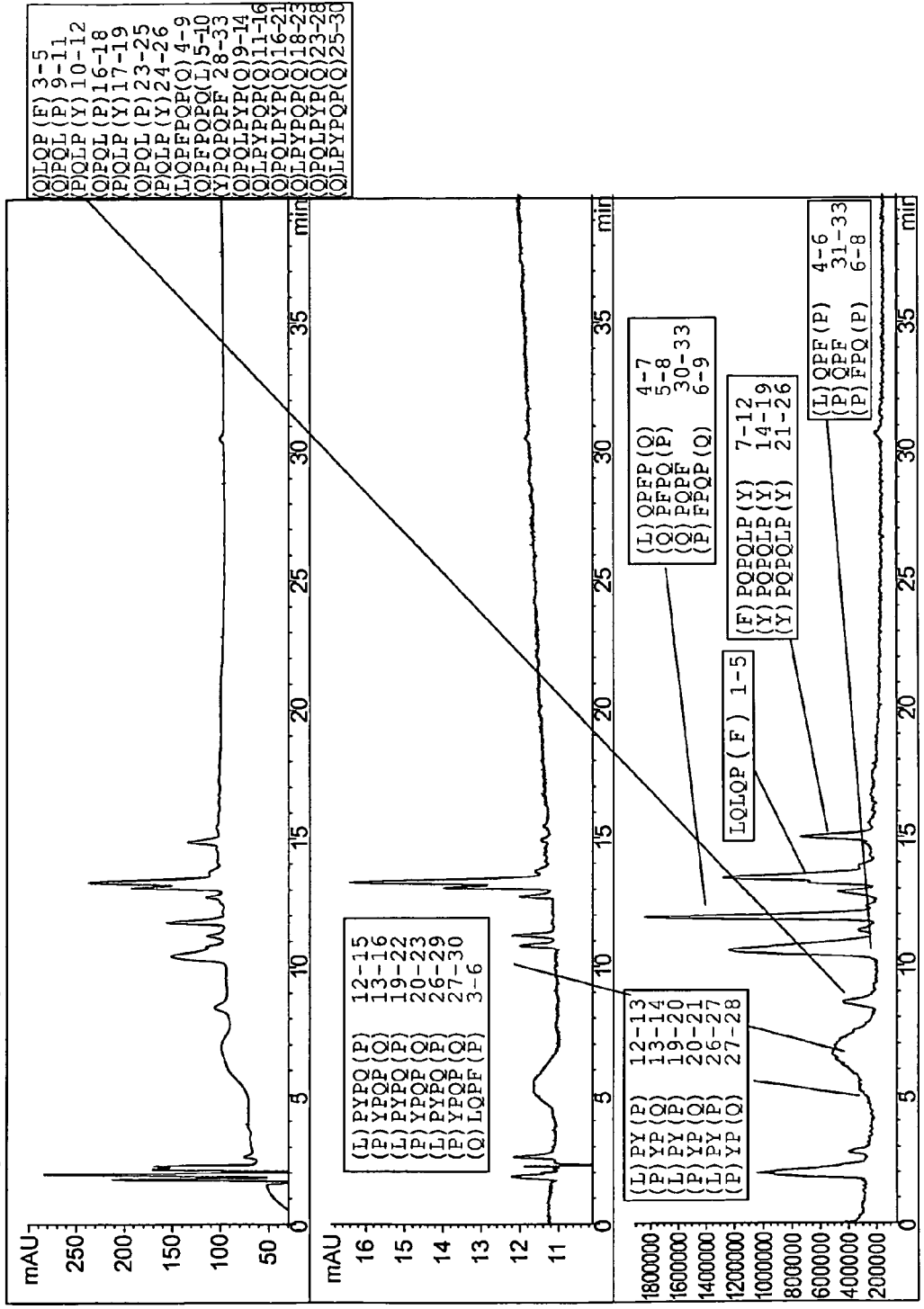
FIG. 11, cont.

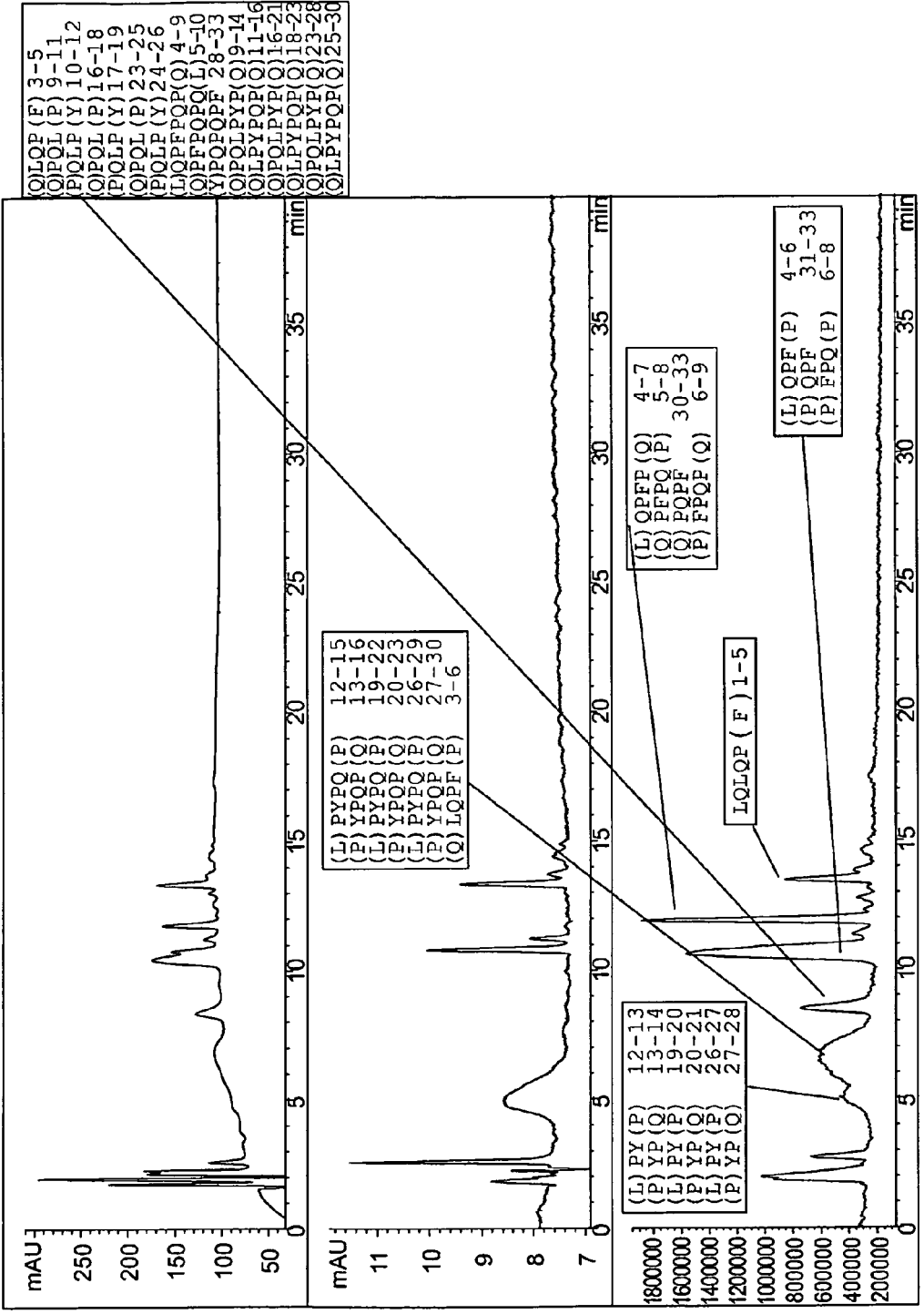

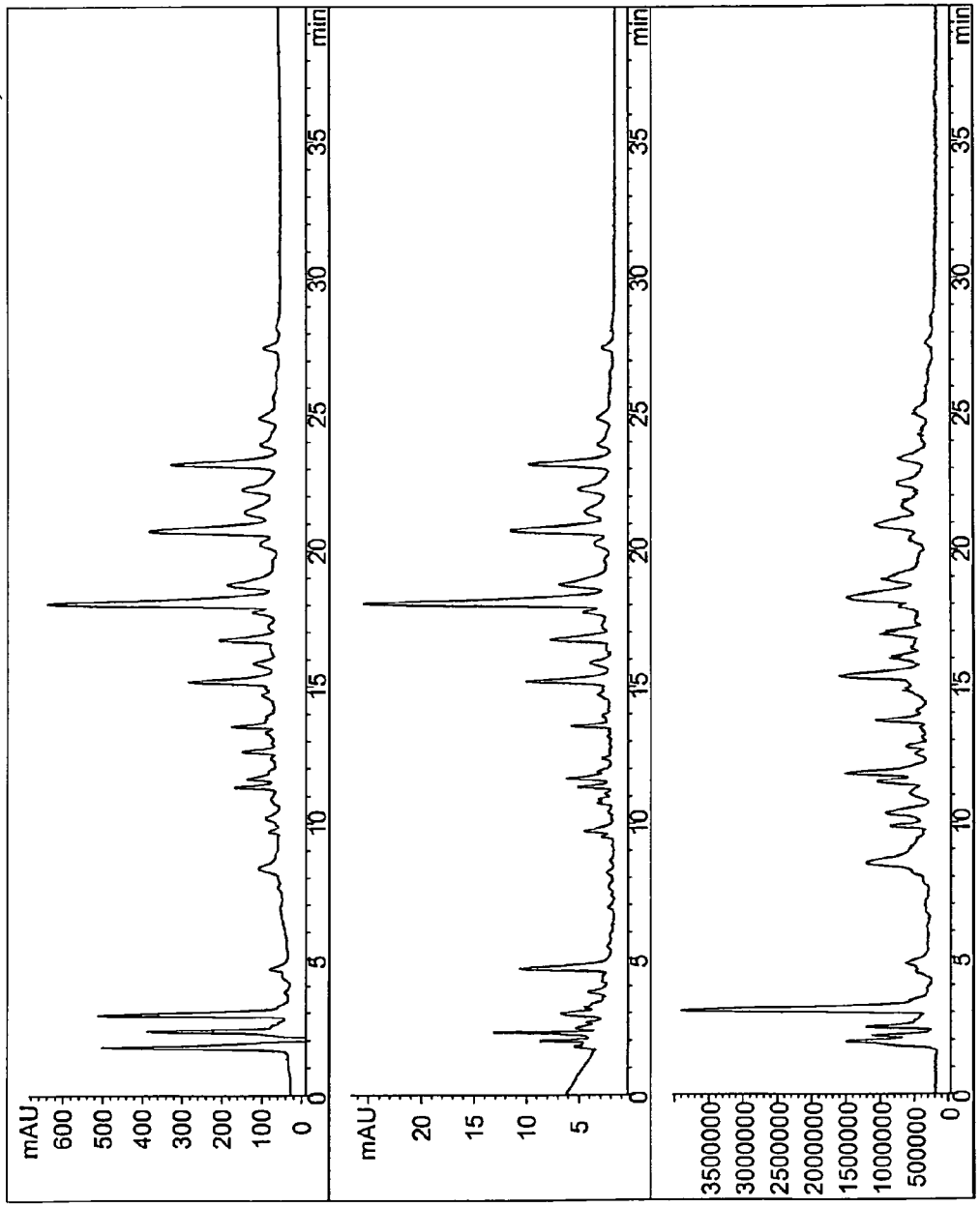
FIG. 14, cont.

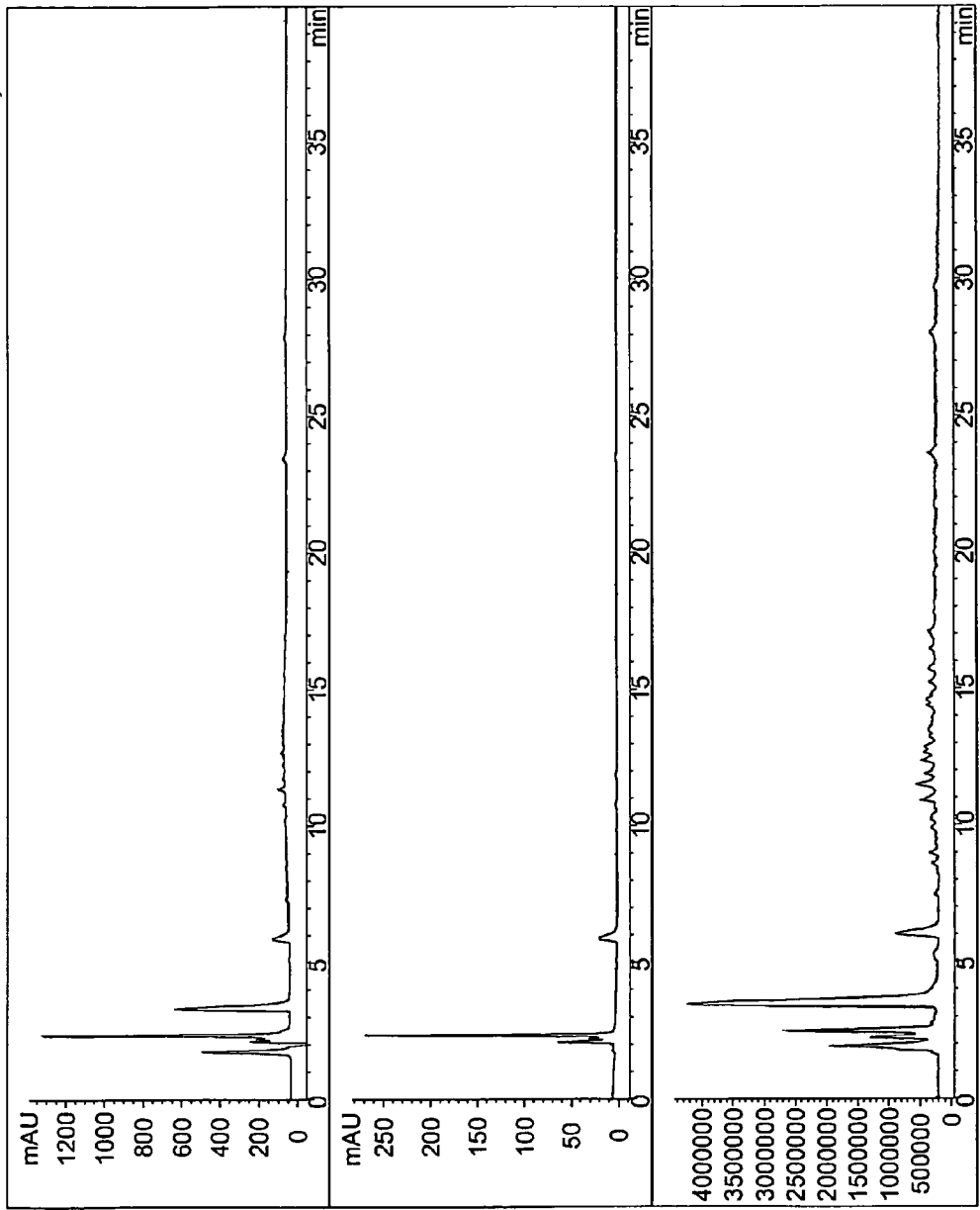
FIG. 14, cont.

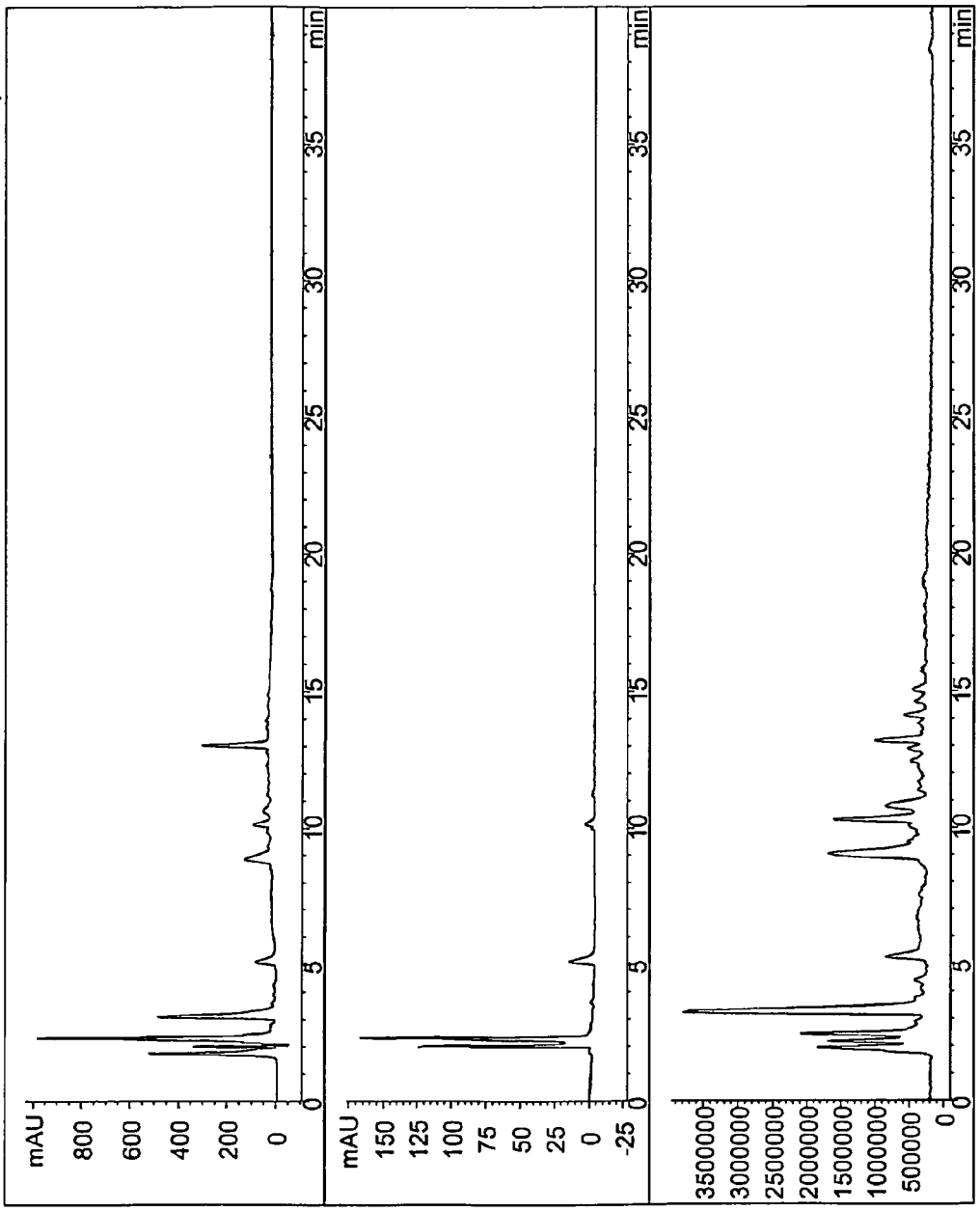

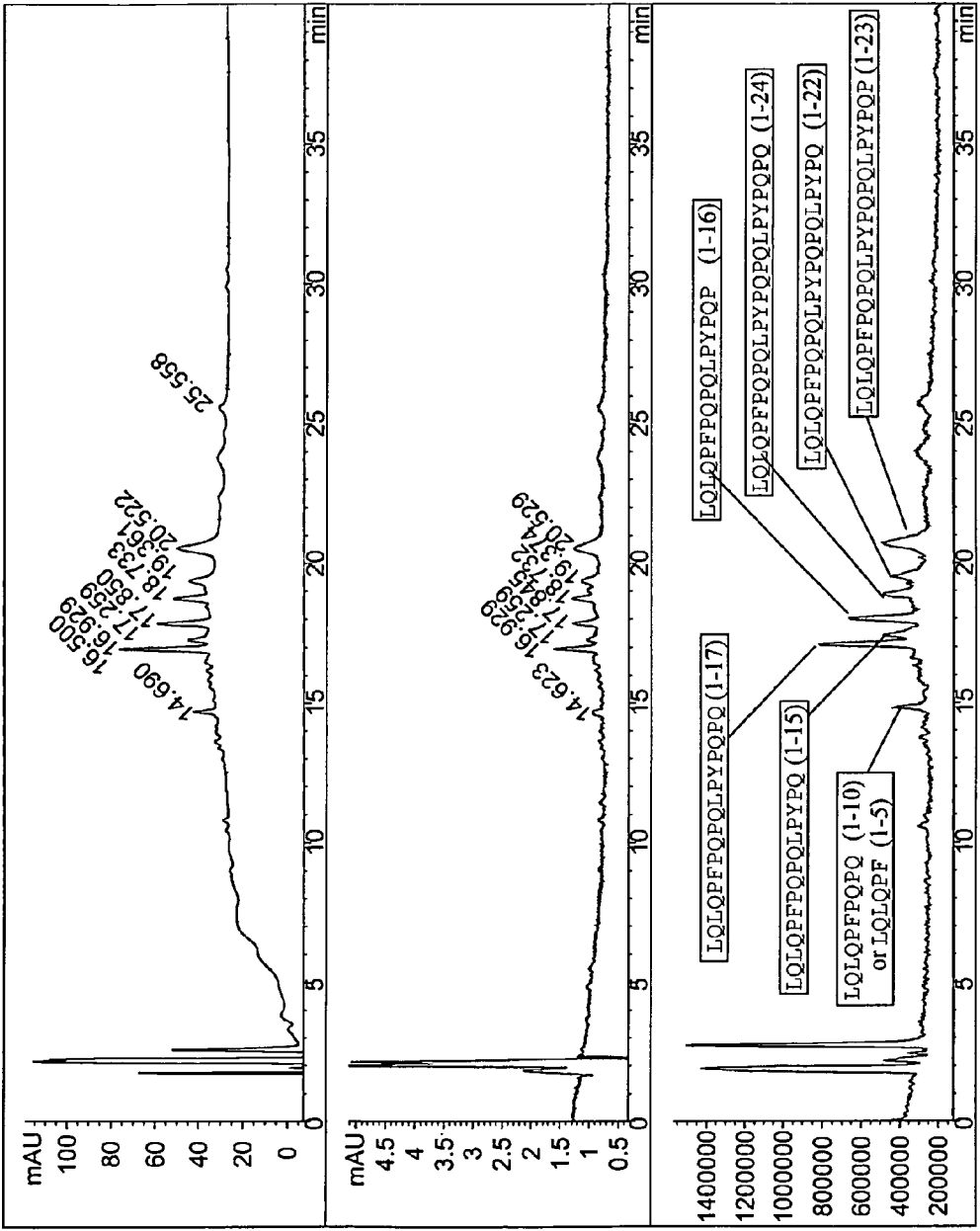
FIG. 16, cont.

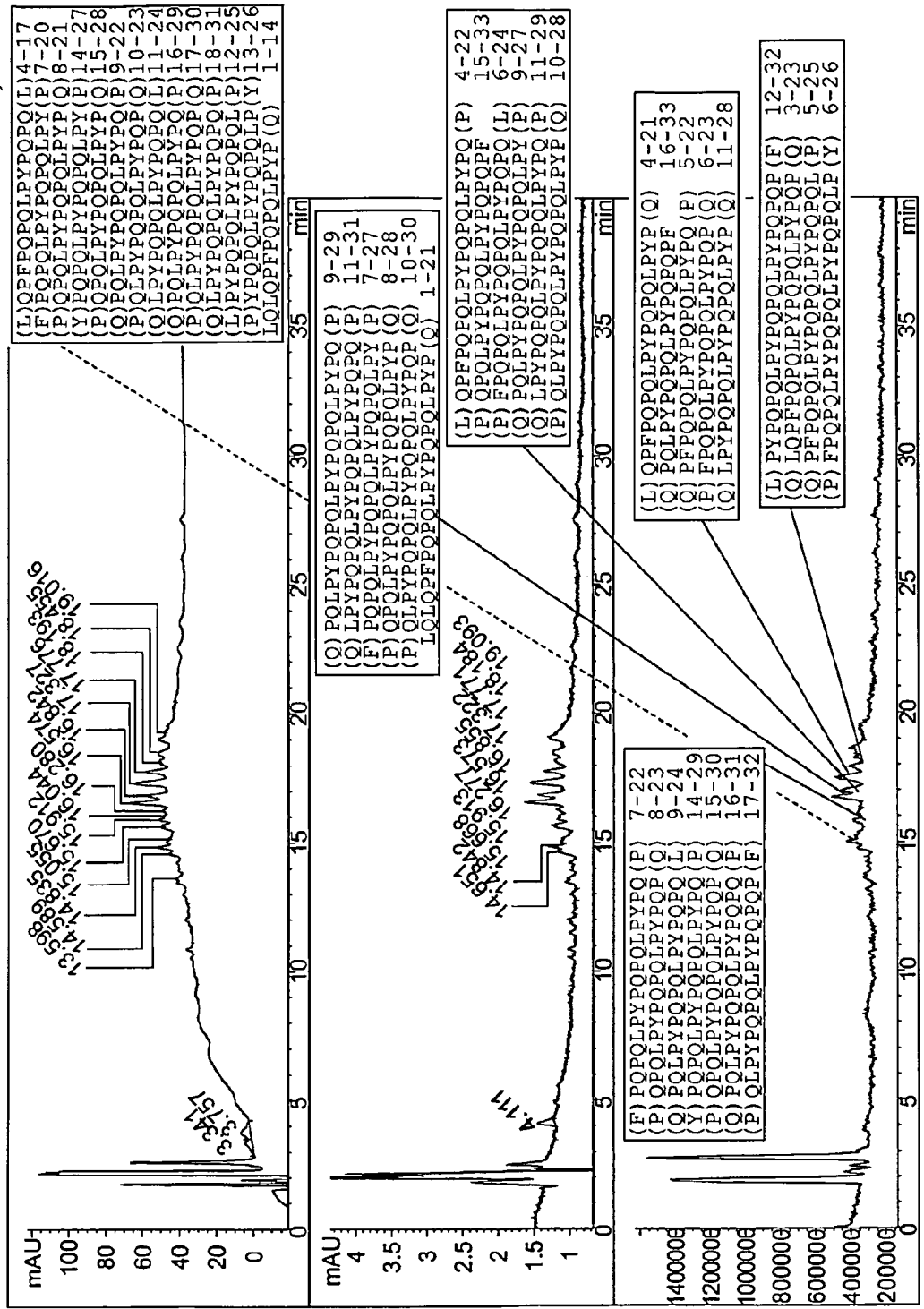

FIG. 18
18A. CPY and AN-pep
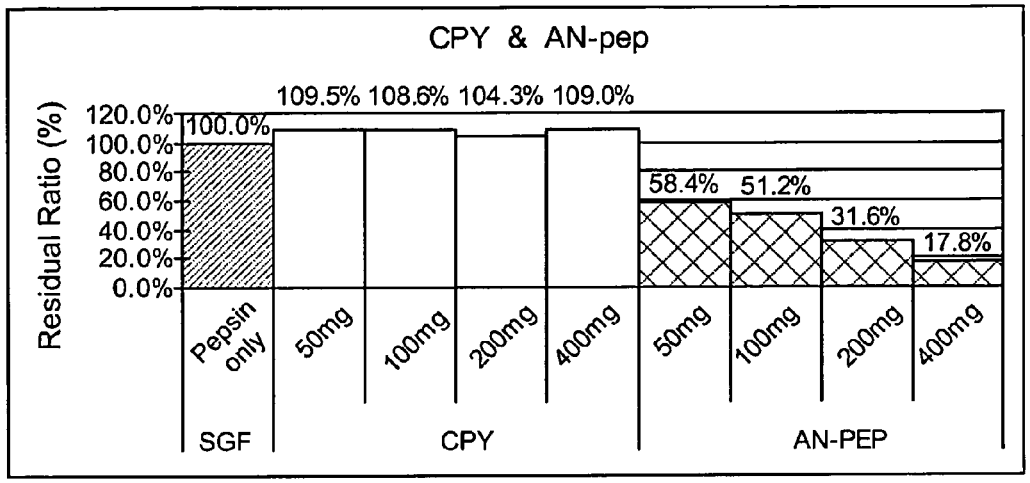
18B. GDEP-M and GDEP-LGG
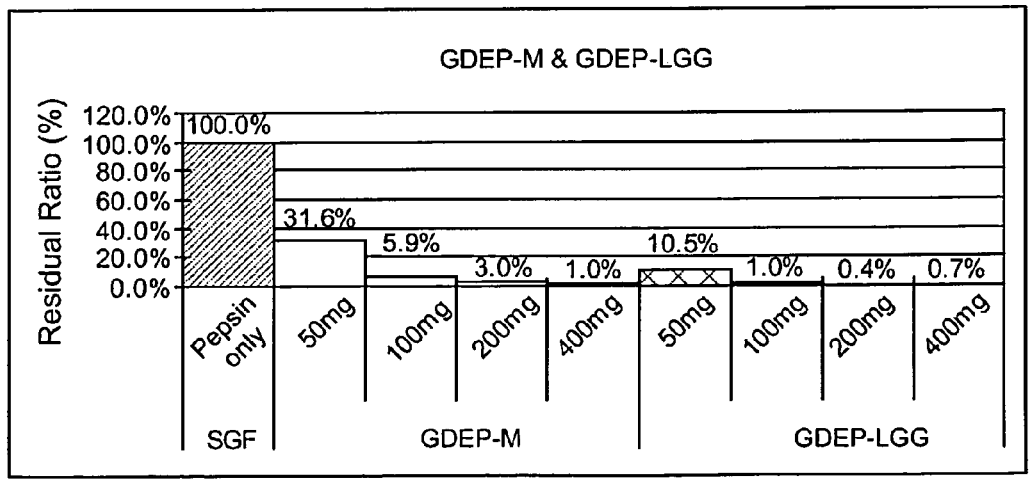

FIG. 18, cont.
18C. Aorsin A and Aorsin B
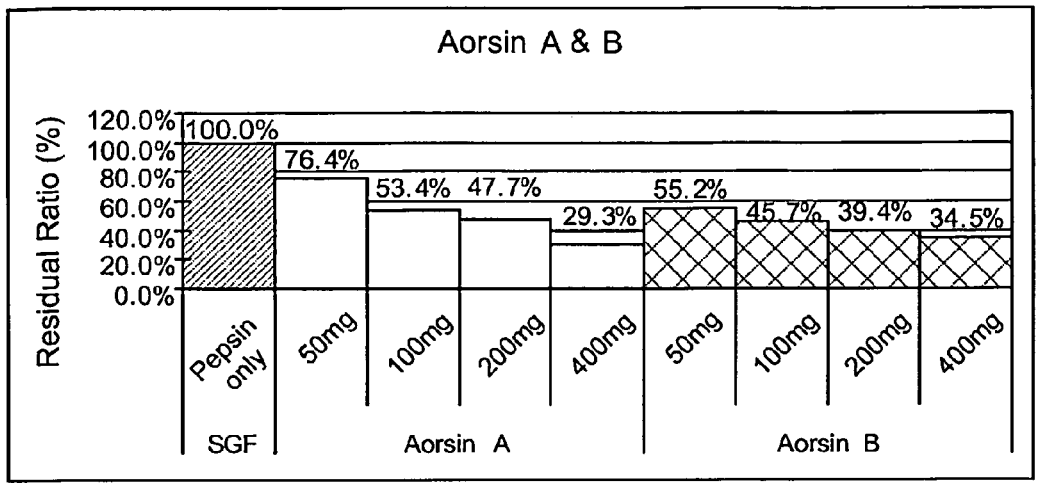
18D. Combination of GDEP-M and Some Peptidases
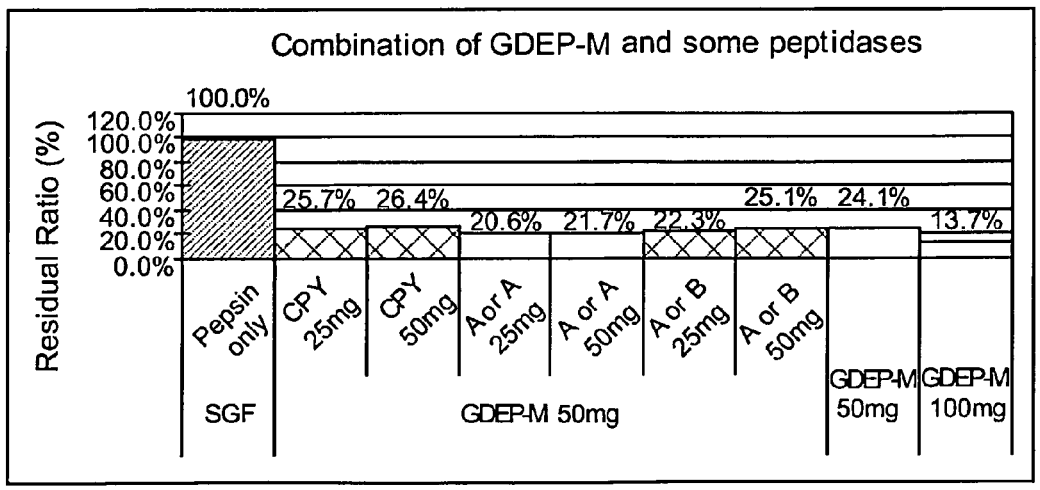

FIG. 18, cont.
18E. Combination of GDEP-LGG and GDEP-M
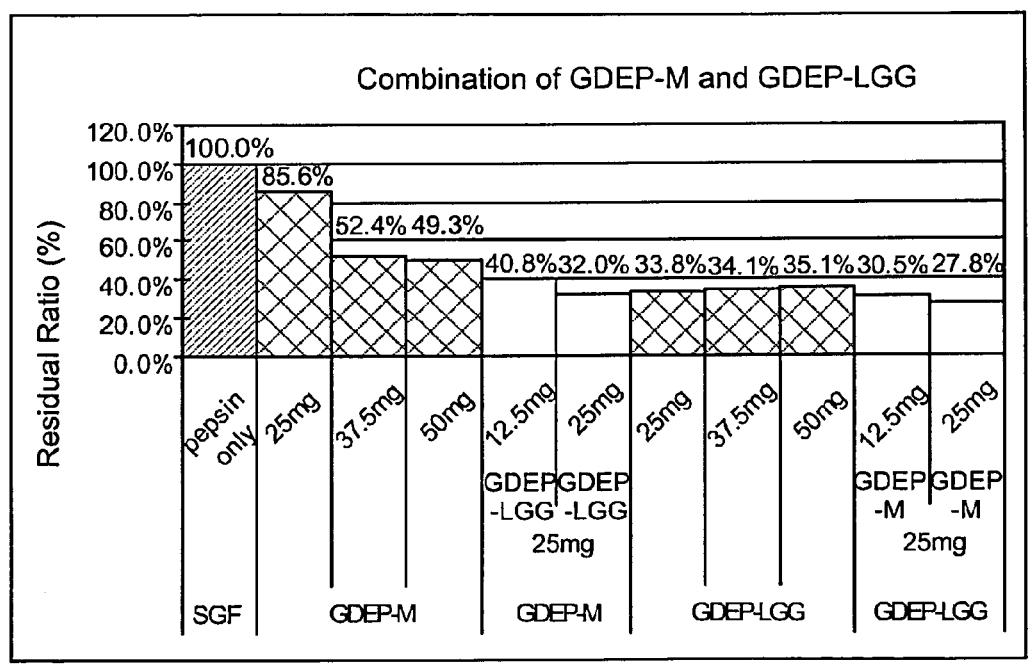

FIG. 19
19A. Commercial 33-mer Peptide
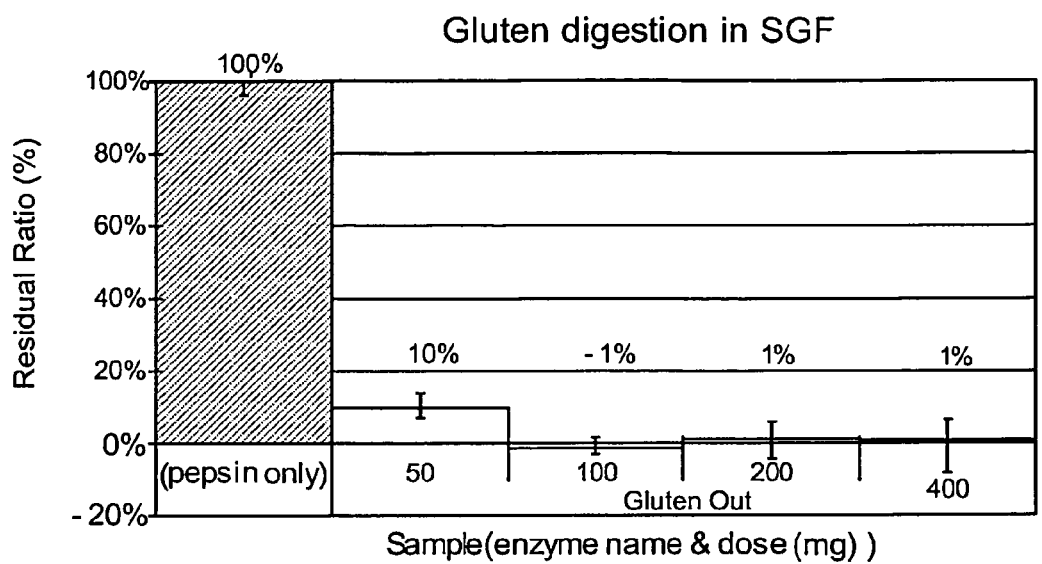
19B. Ravioli
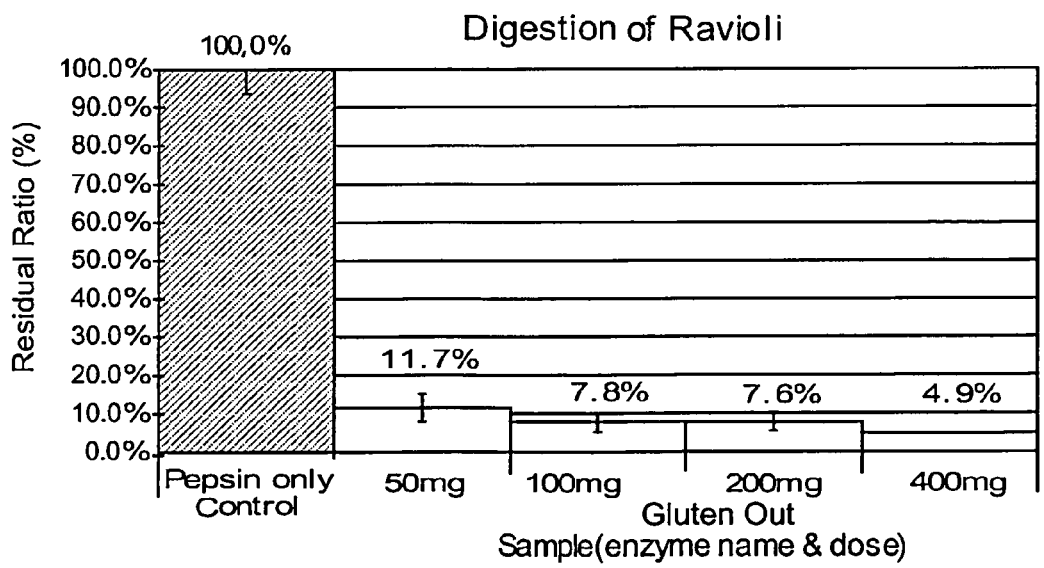

FIG. 19, cont.
19C. Cheese Macaroni
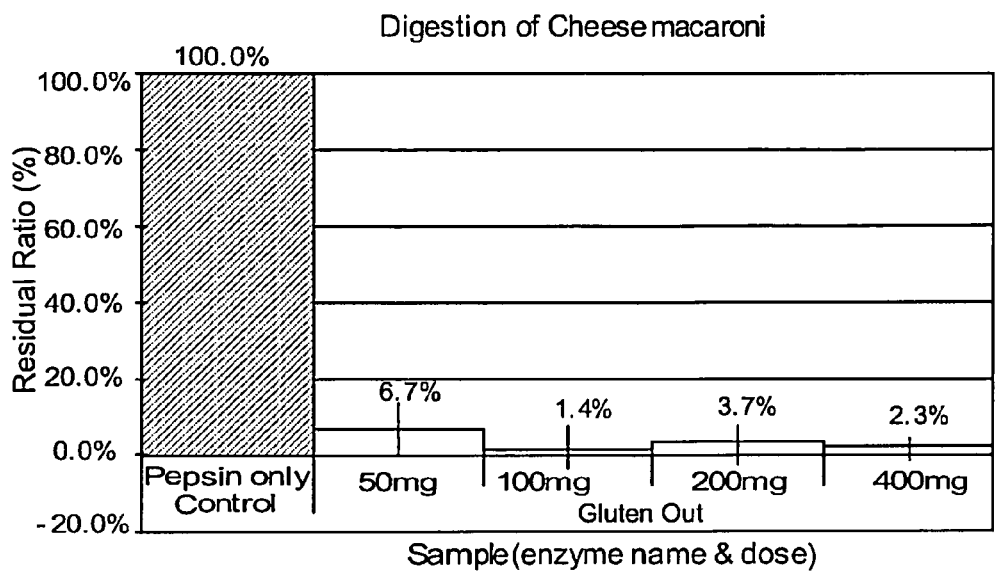
19D. White Bread
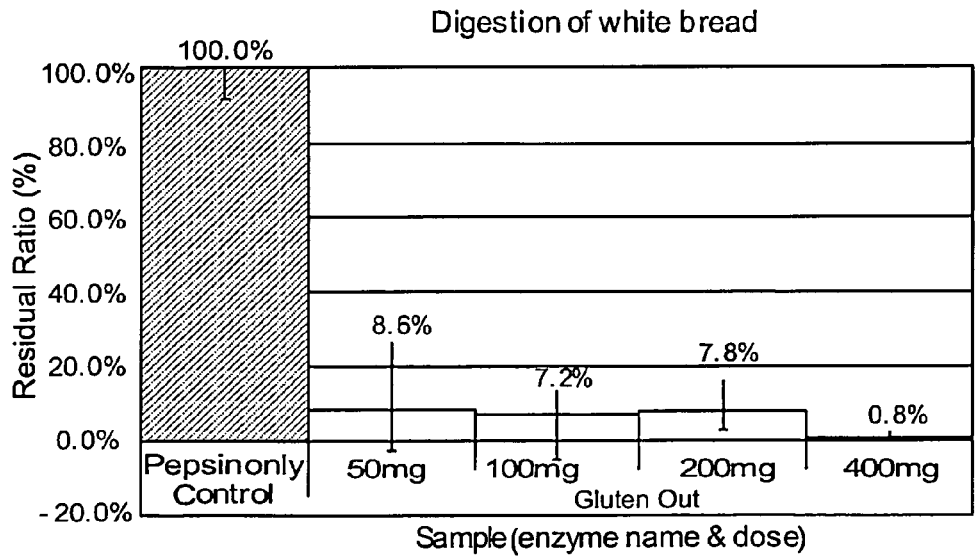

FIG. 19, cont.
19E. Roll of Bread
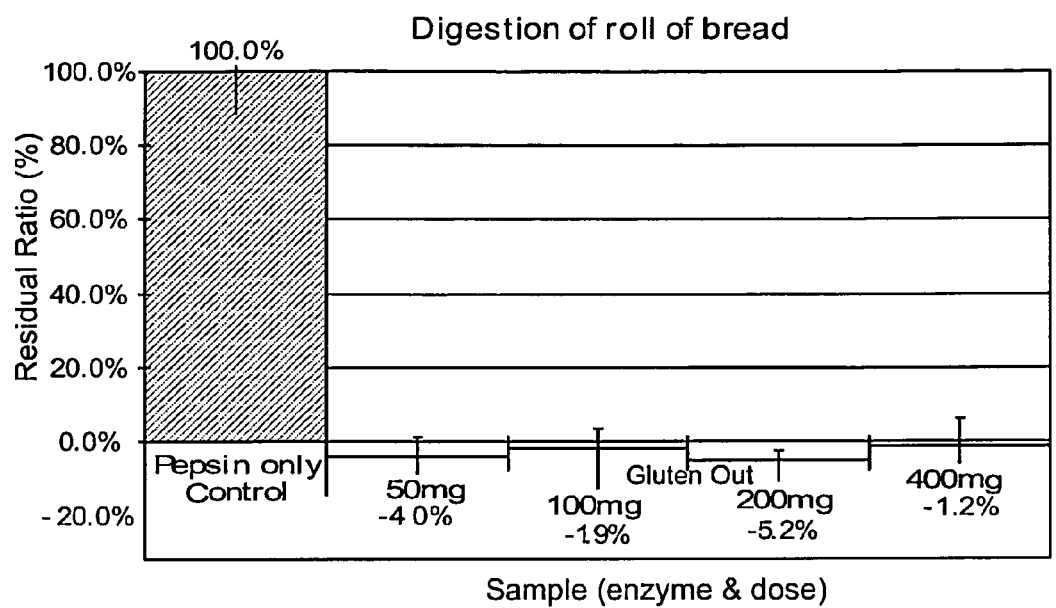

FIG. 20
20A. Ravioli
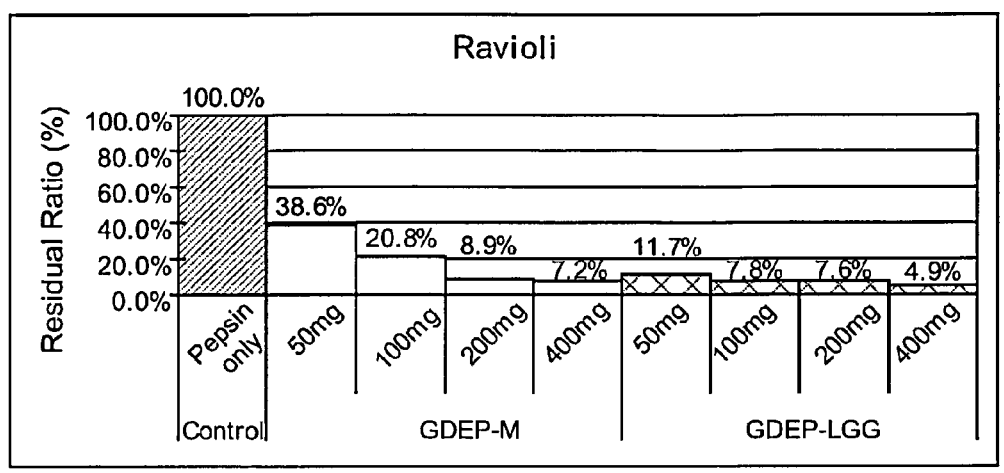
20B. Macaroni
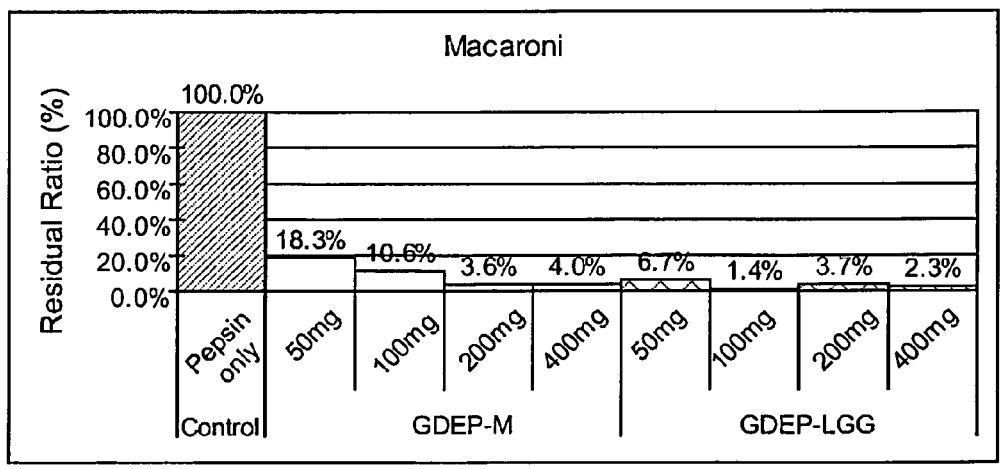

FIG. 20, cont.
20C. White Bread
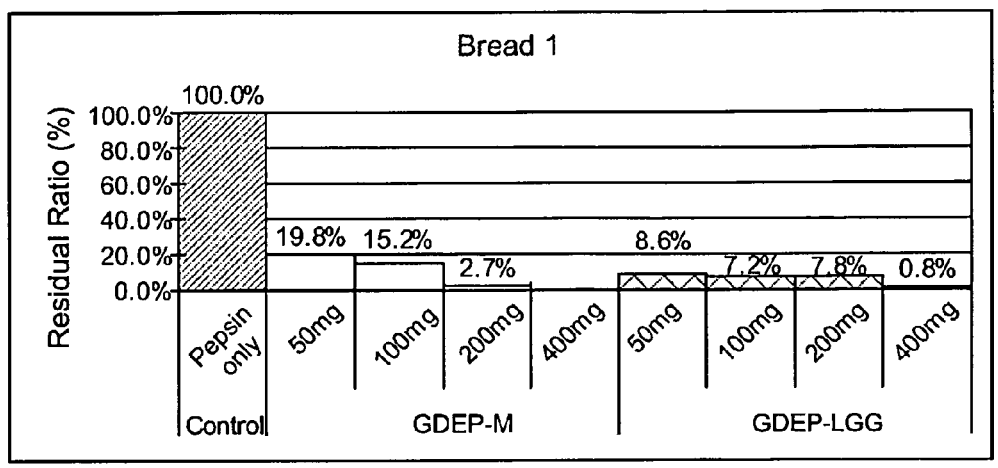
20D. Roll of Bread
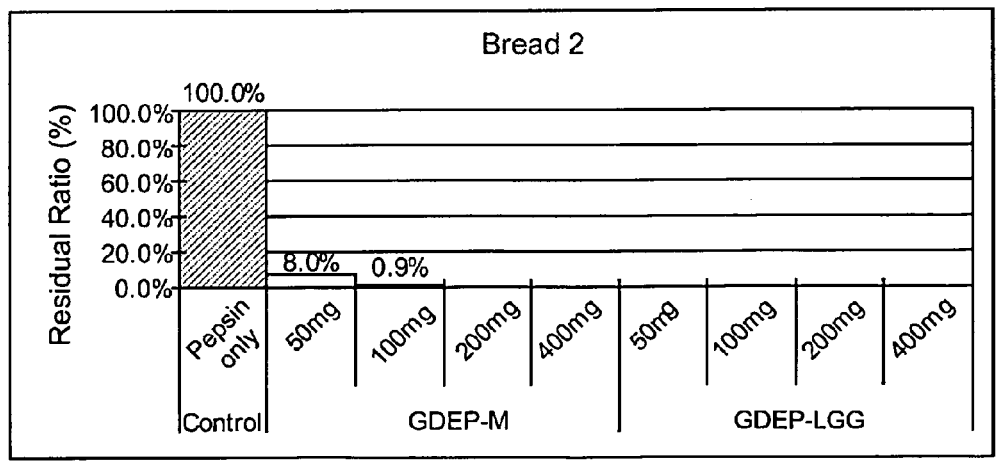

FIG. 20, cont.
20E. Lasagna
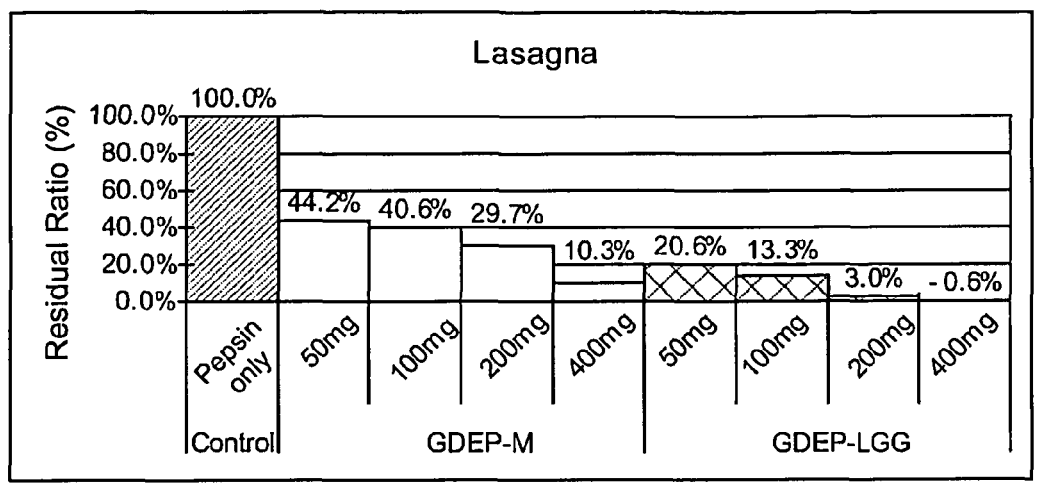
20F. Pasta
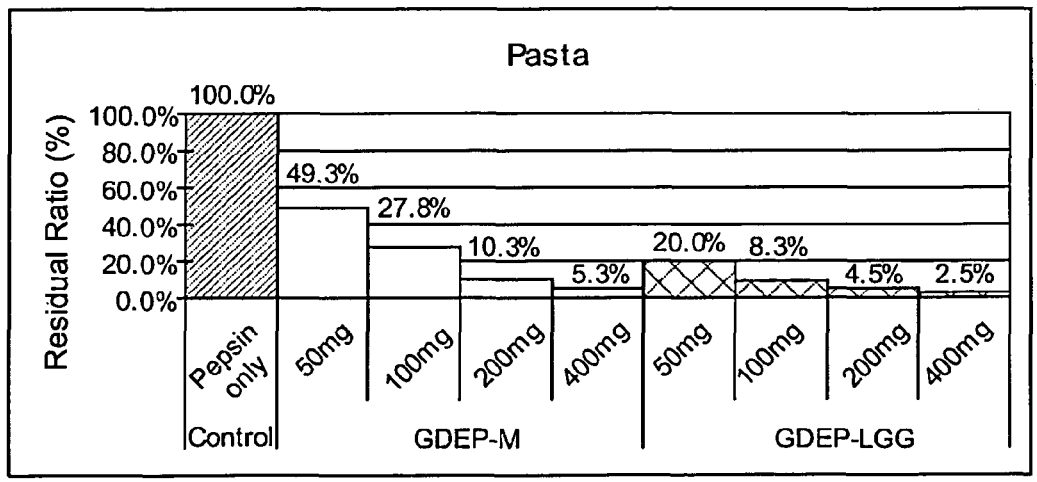

FIG. 20, cont.
20G. Summary
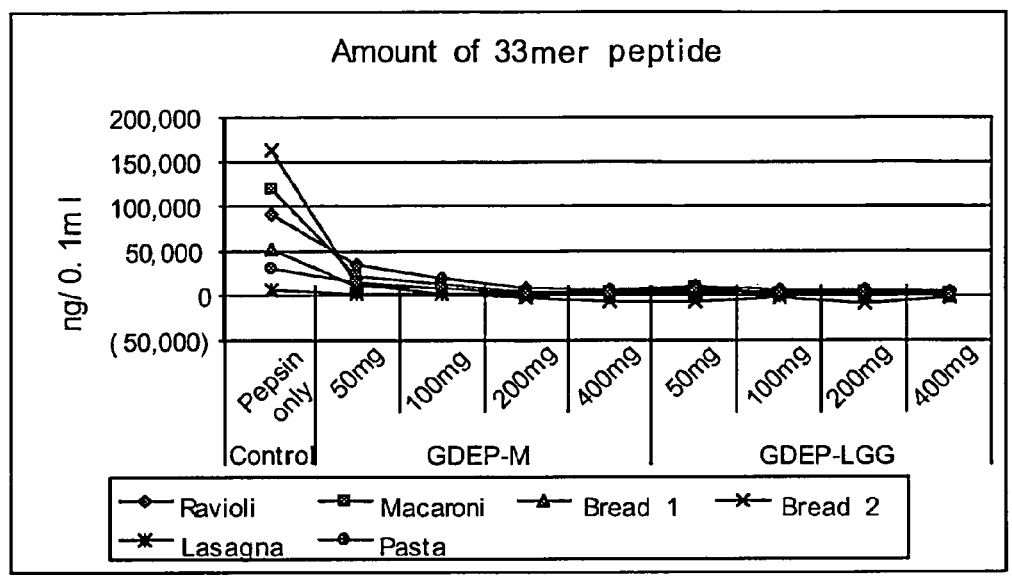
20H. Summary
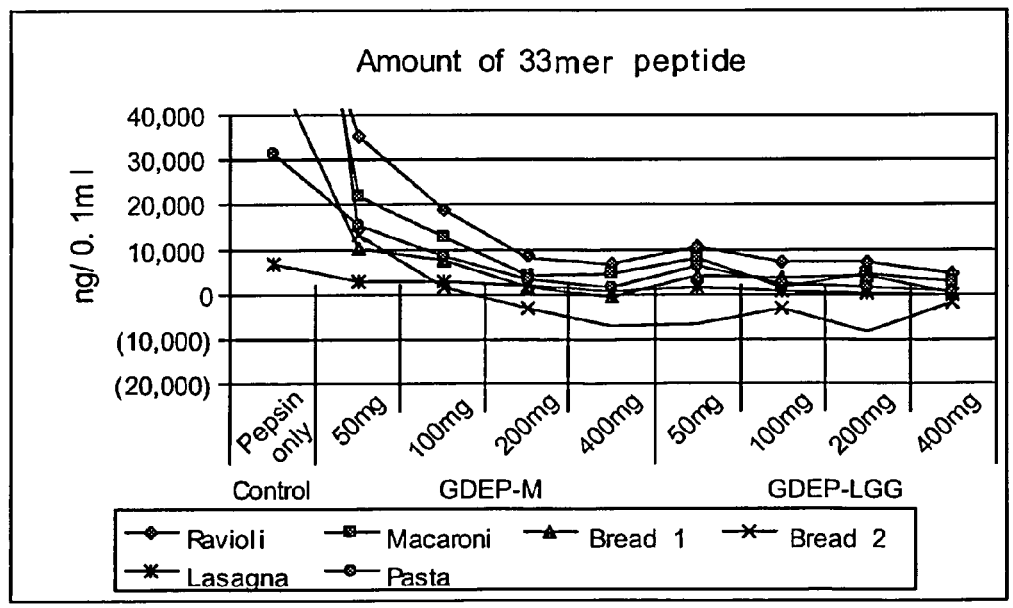

21A.

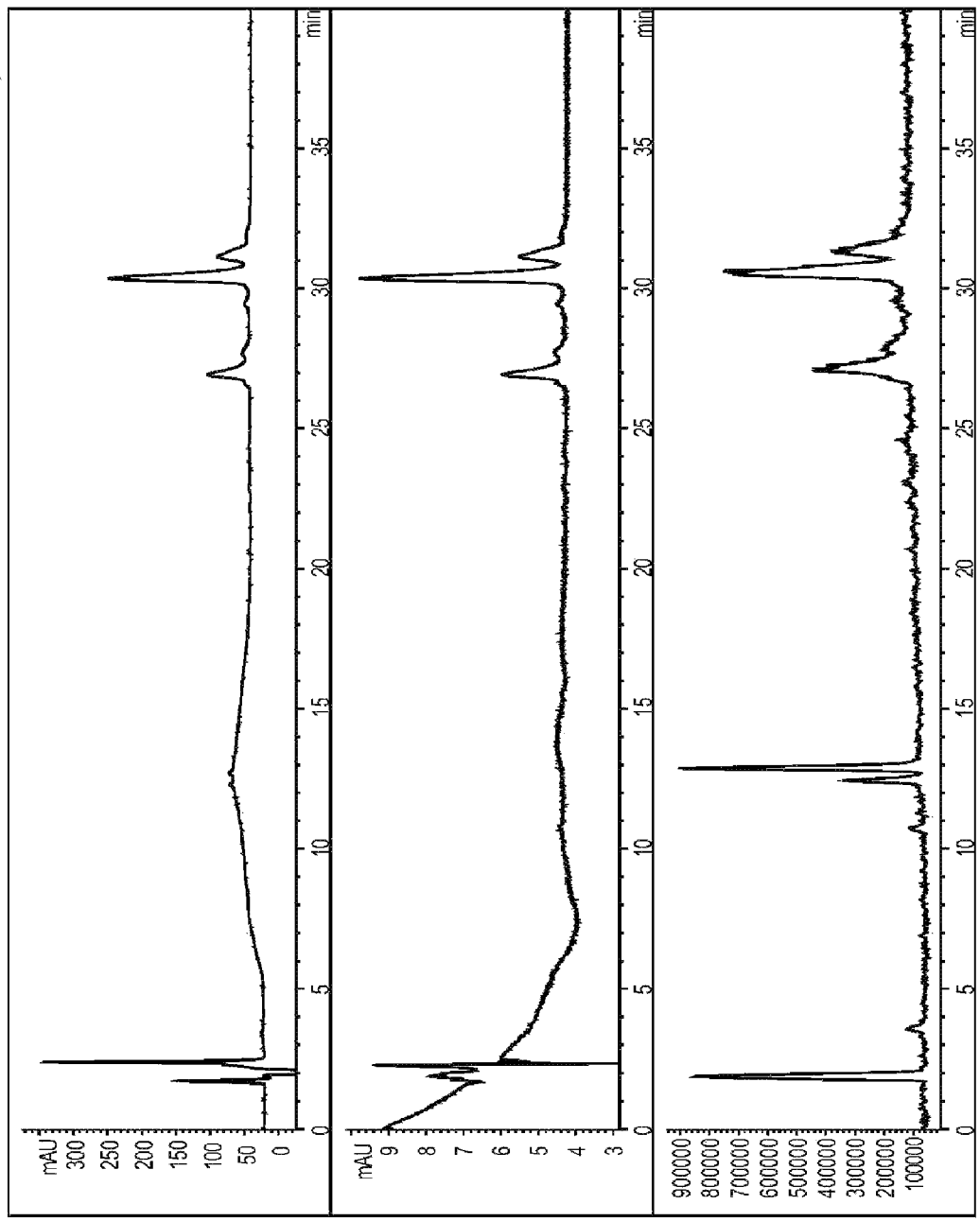
FIG. 21, cont.

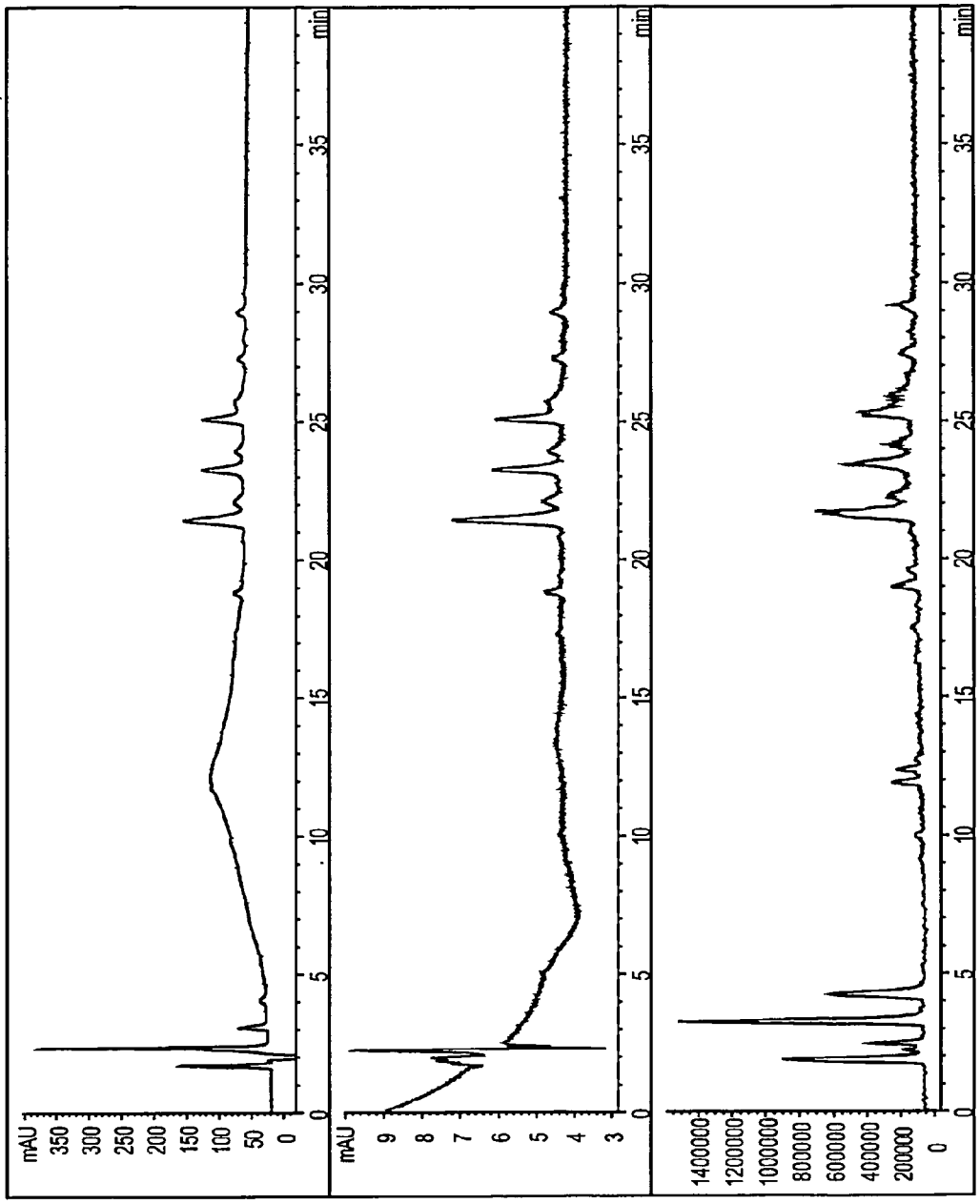

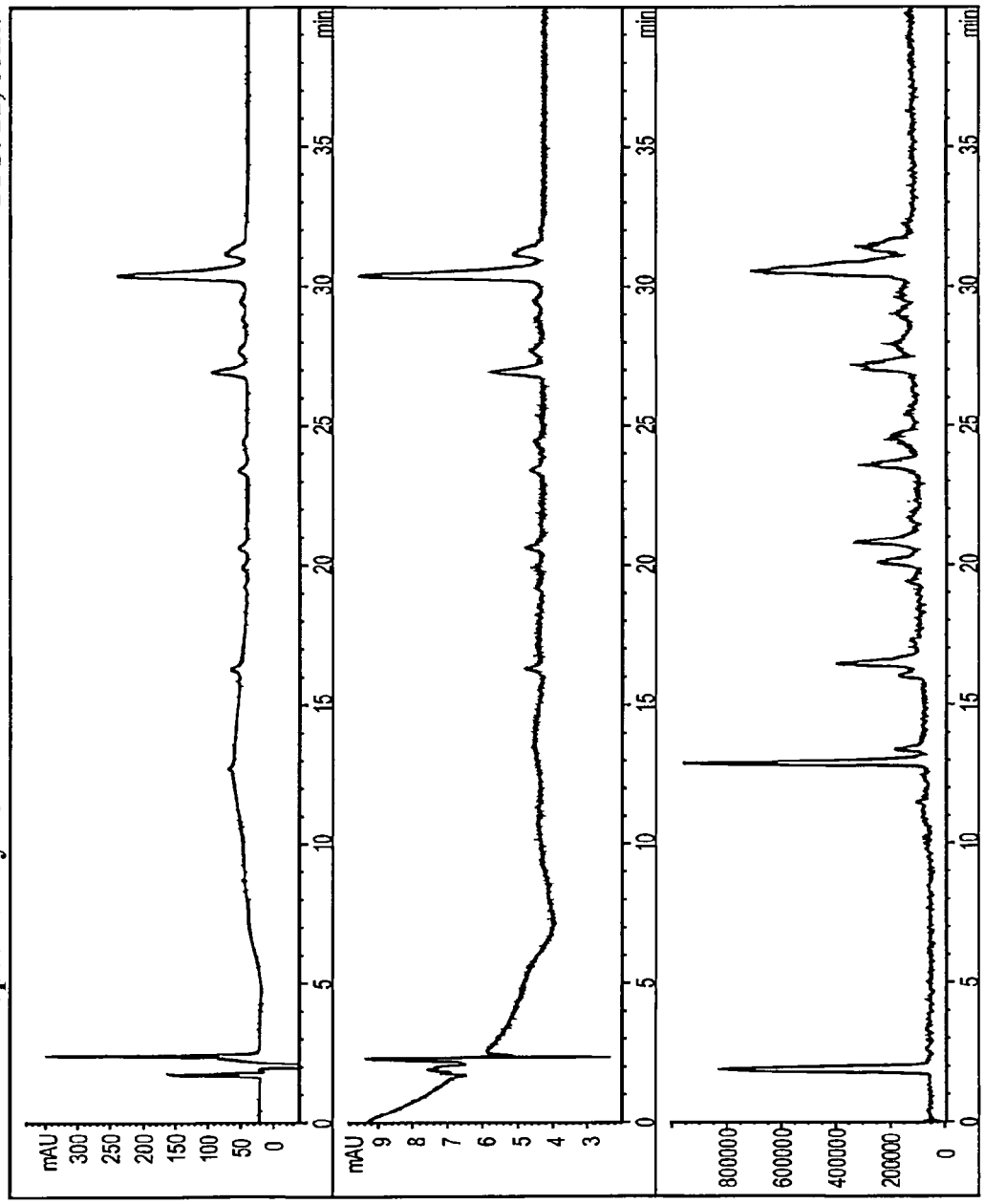
FIG. 21, cont.

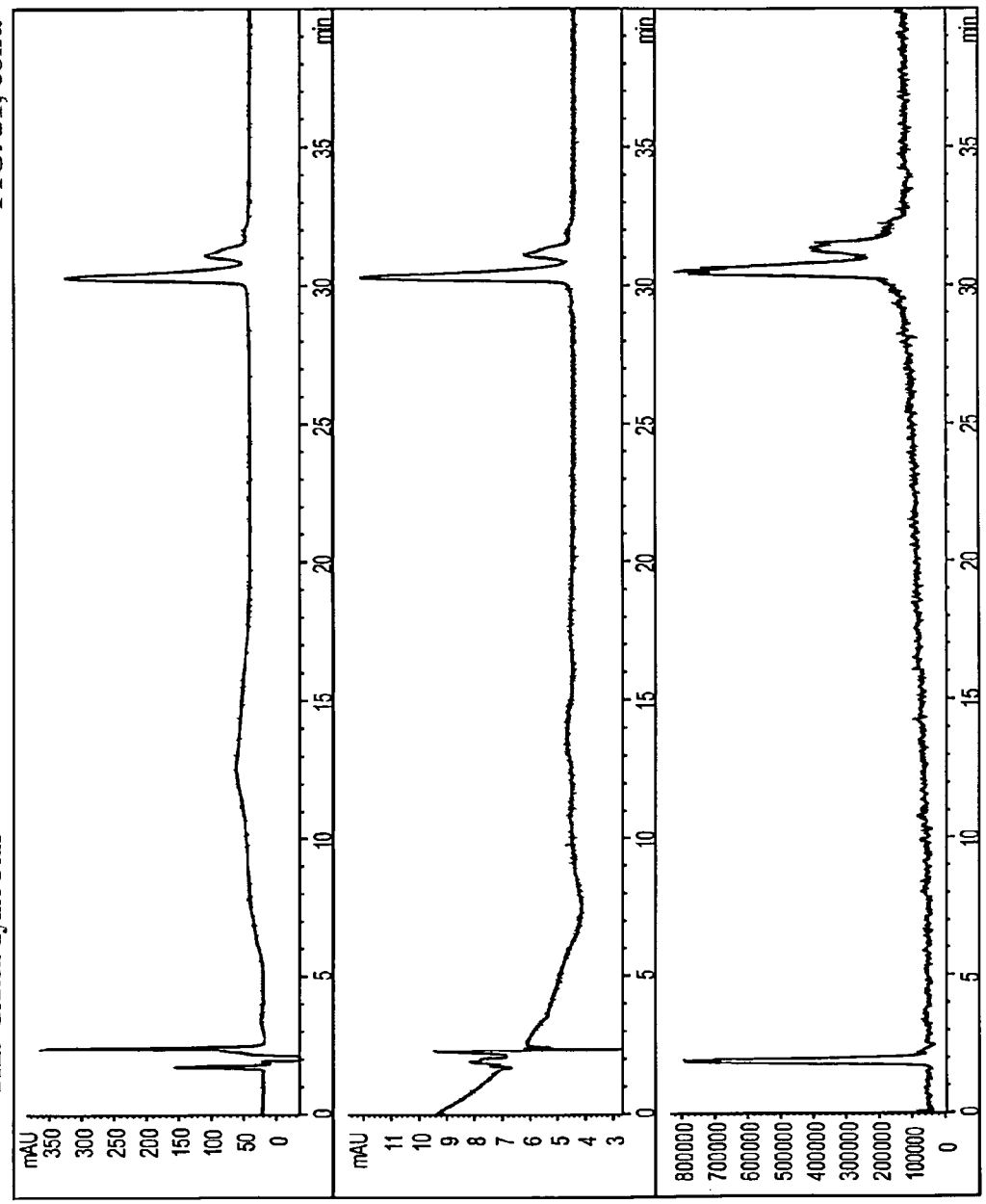
FIG. 21, cont.

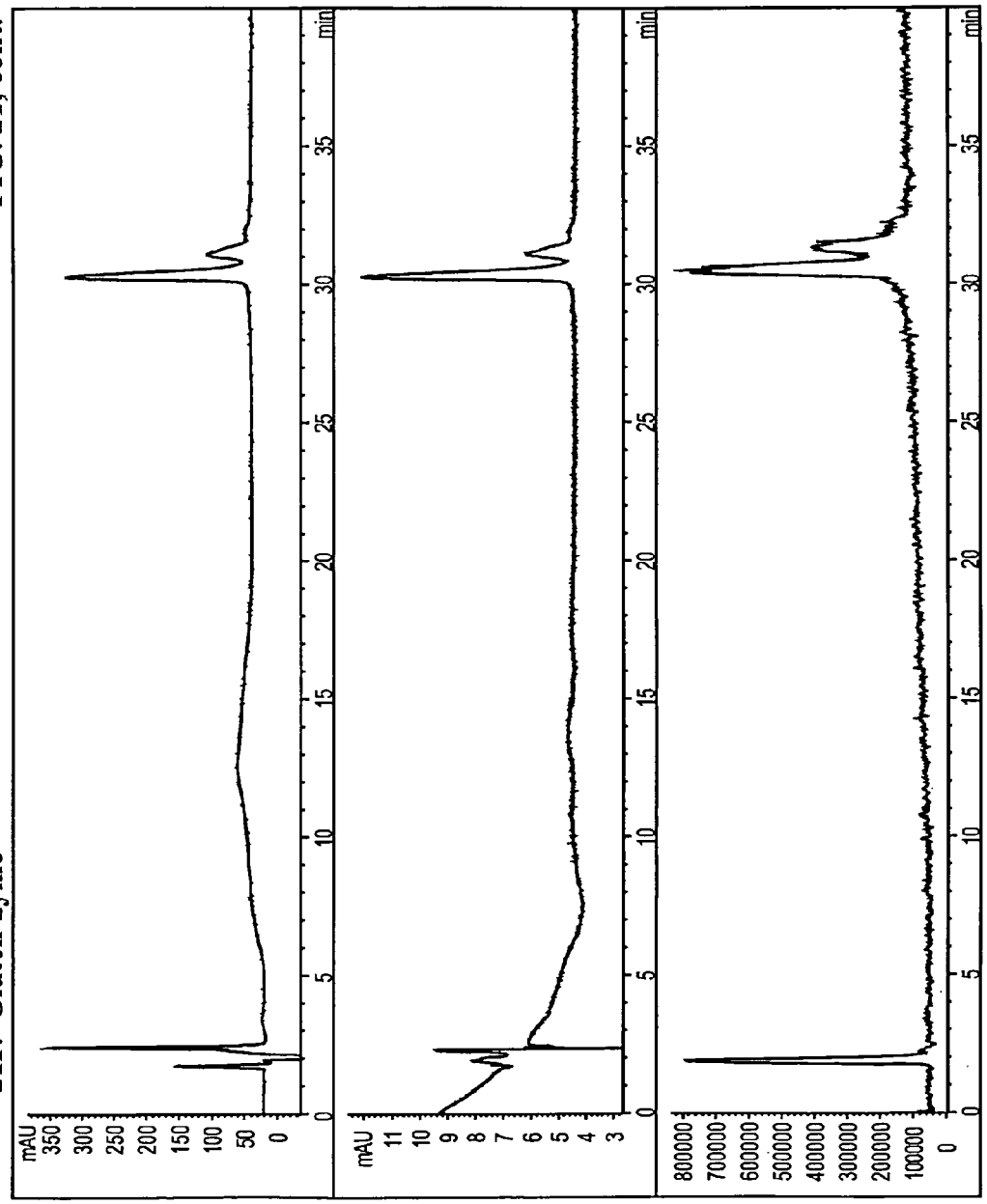

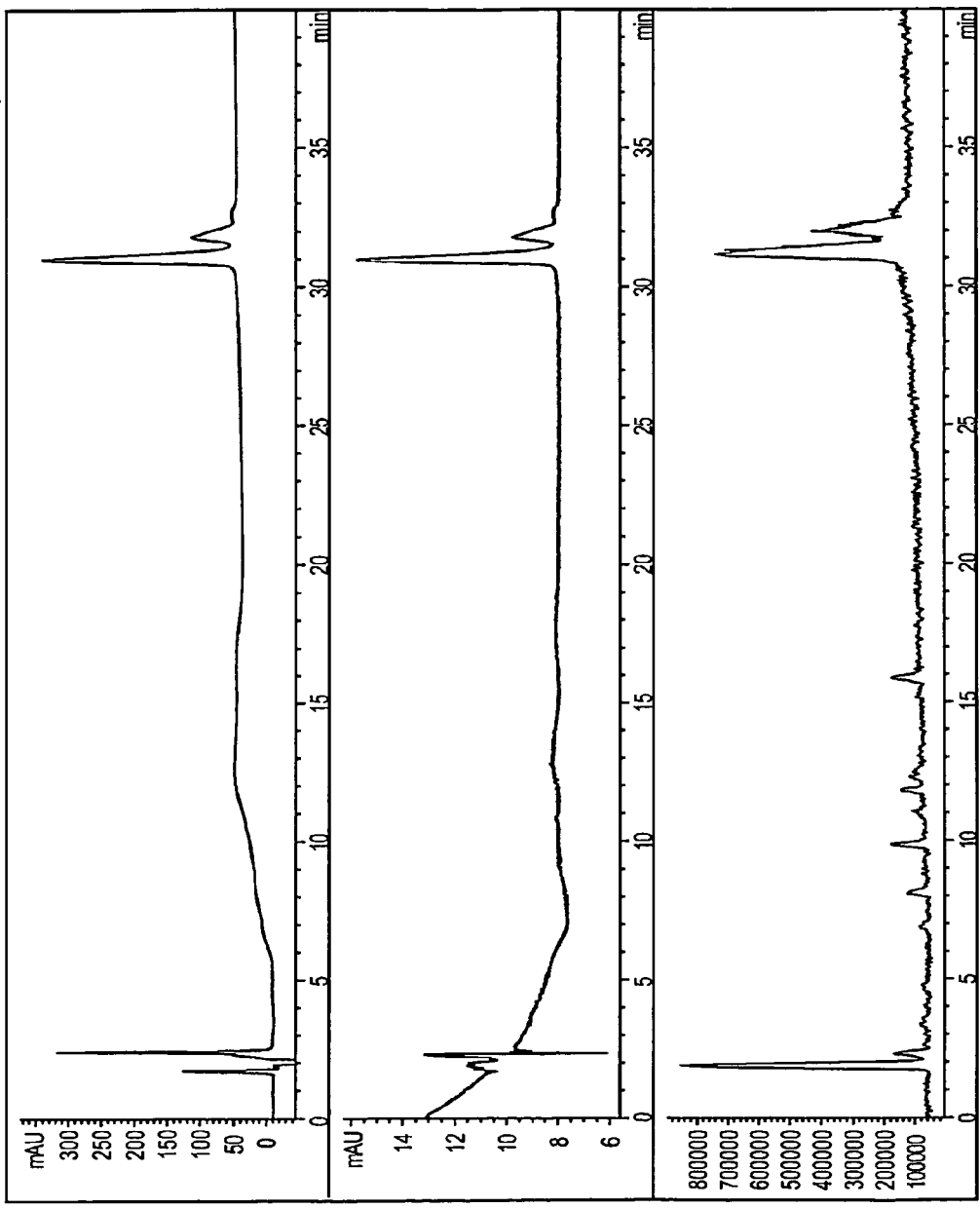
FIG. 21, cont.

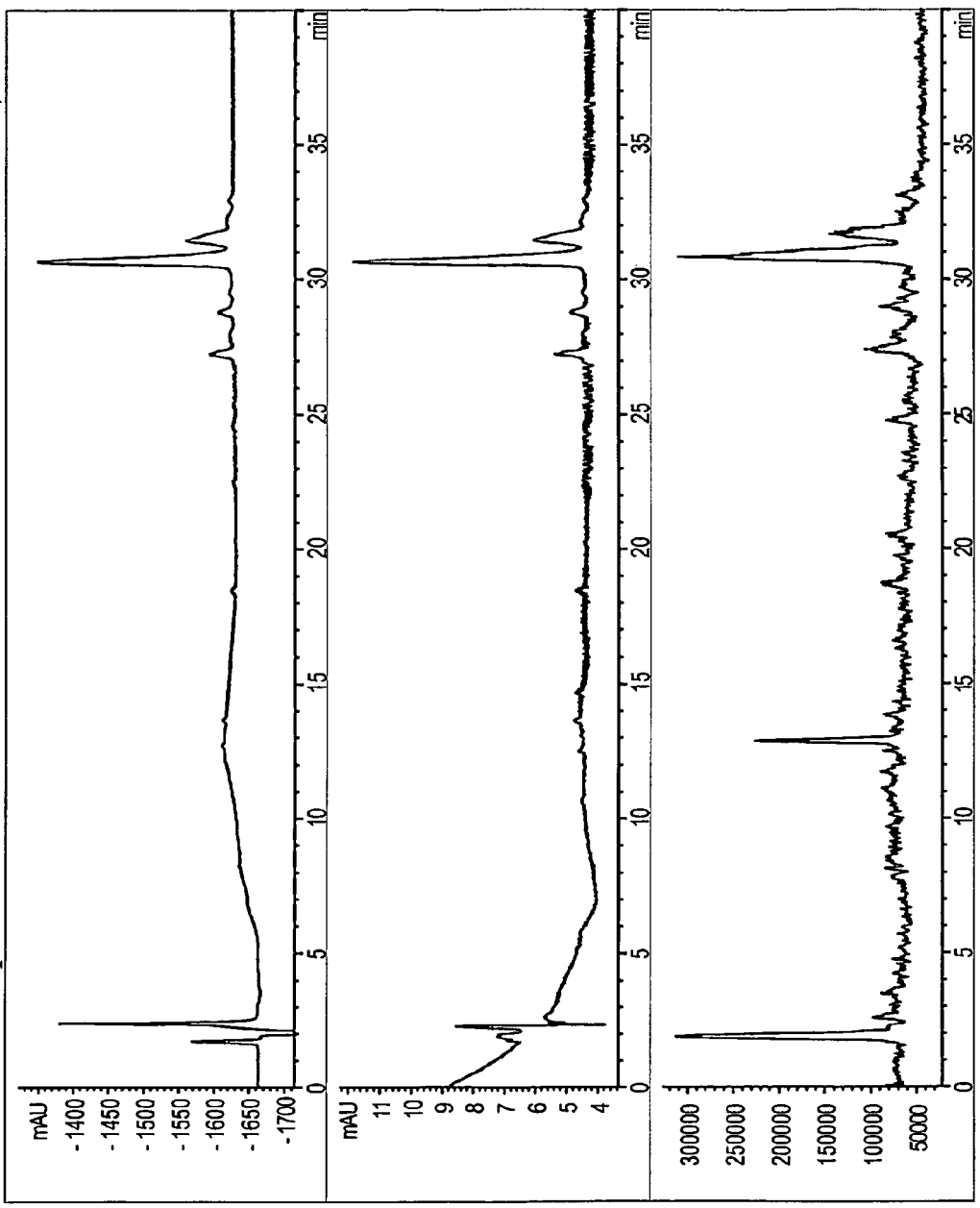

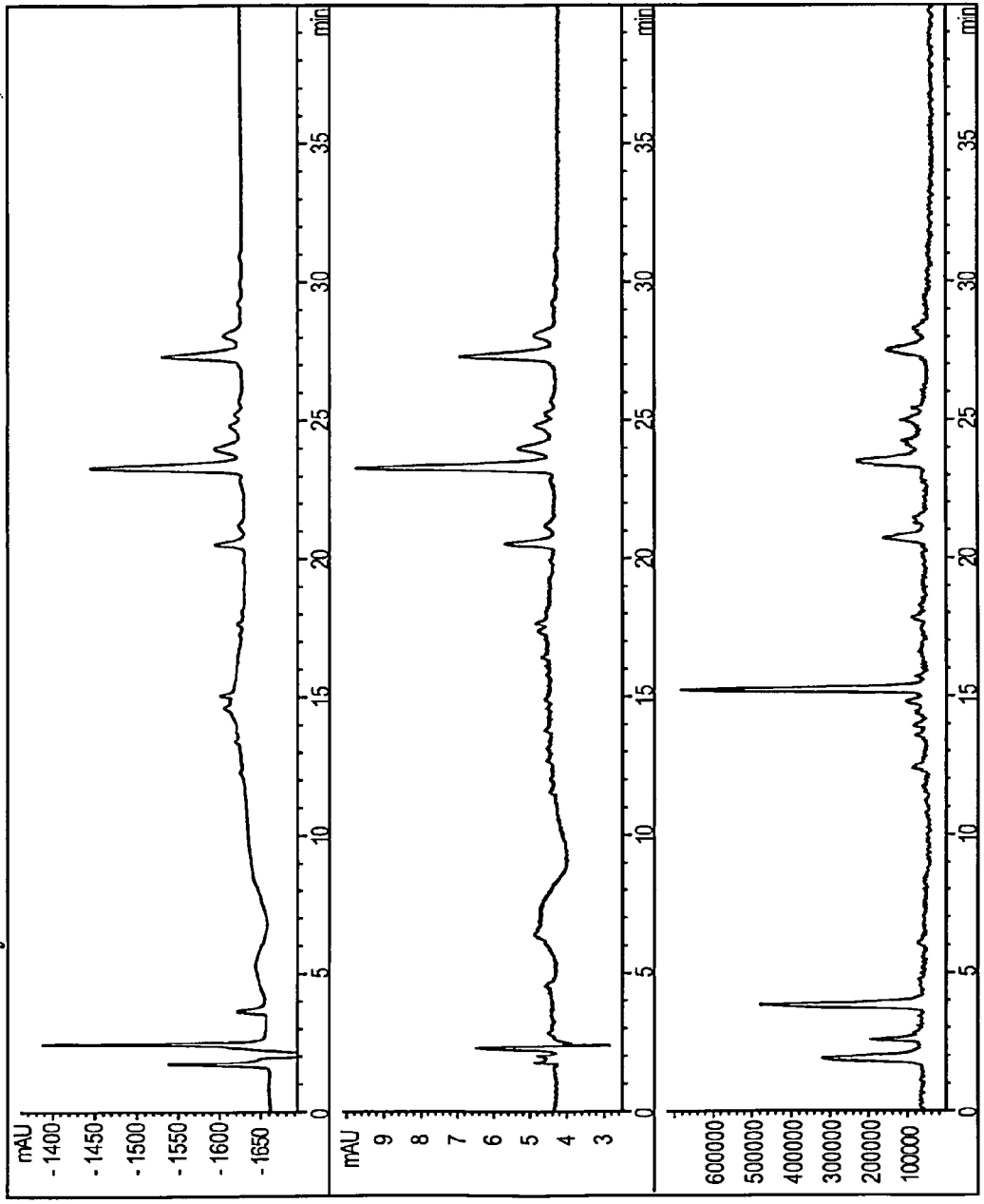
FIG. 21, cont.

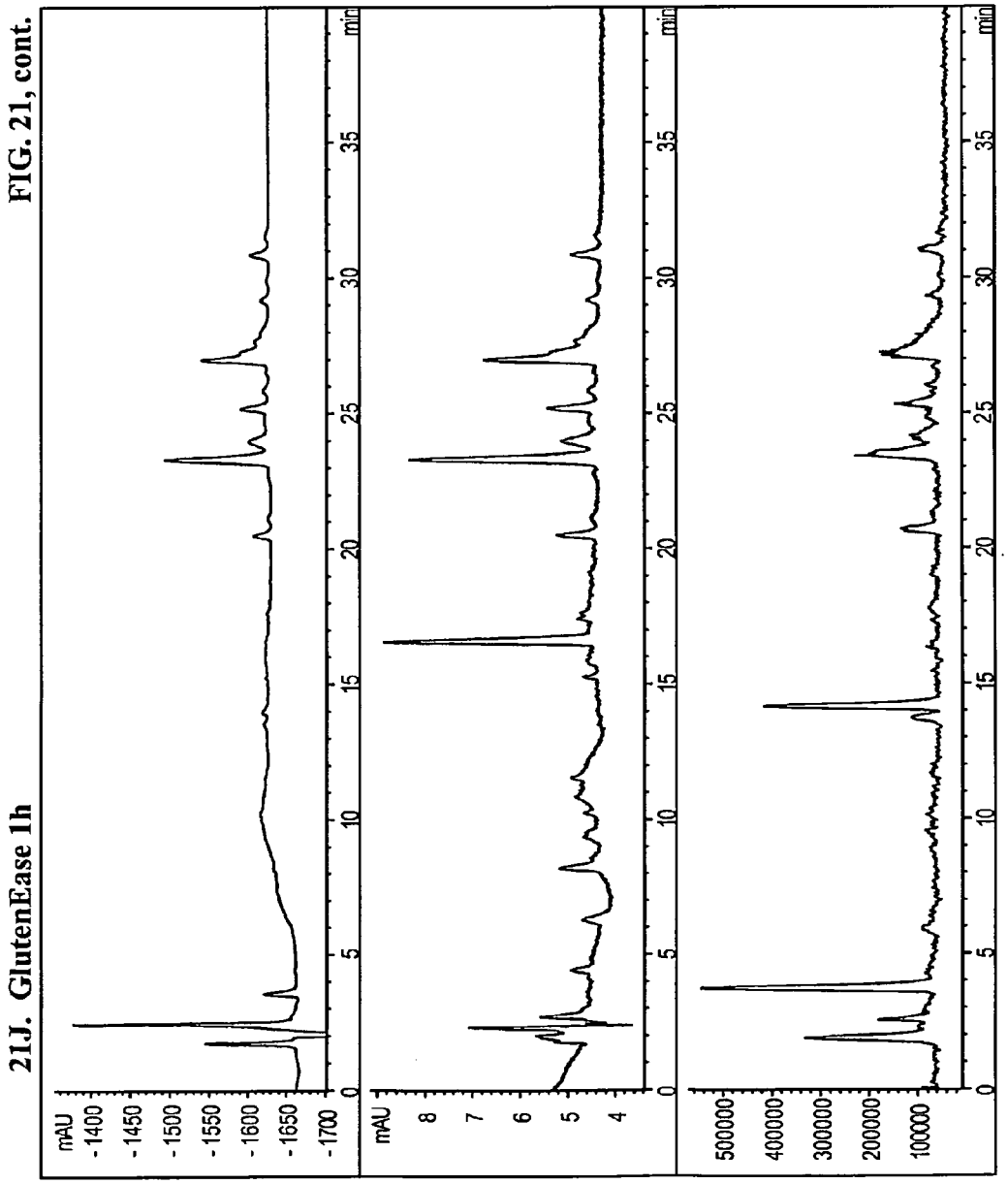
FIG. 21, cont.

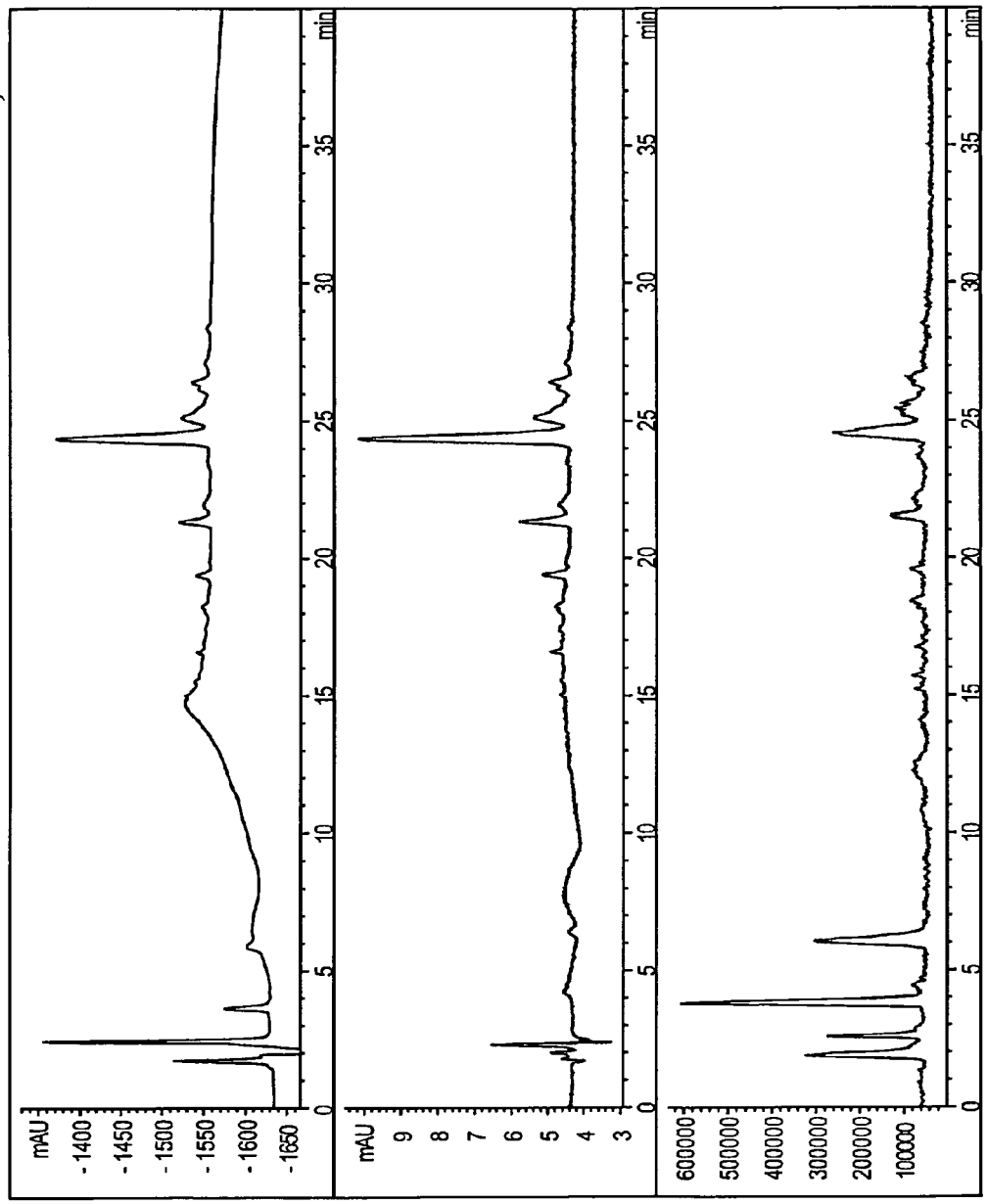
FIG. 21, cont.

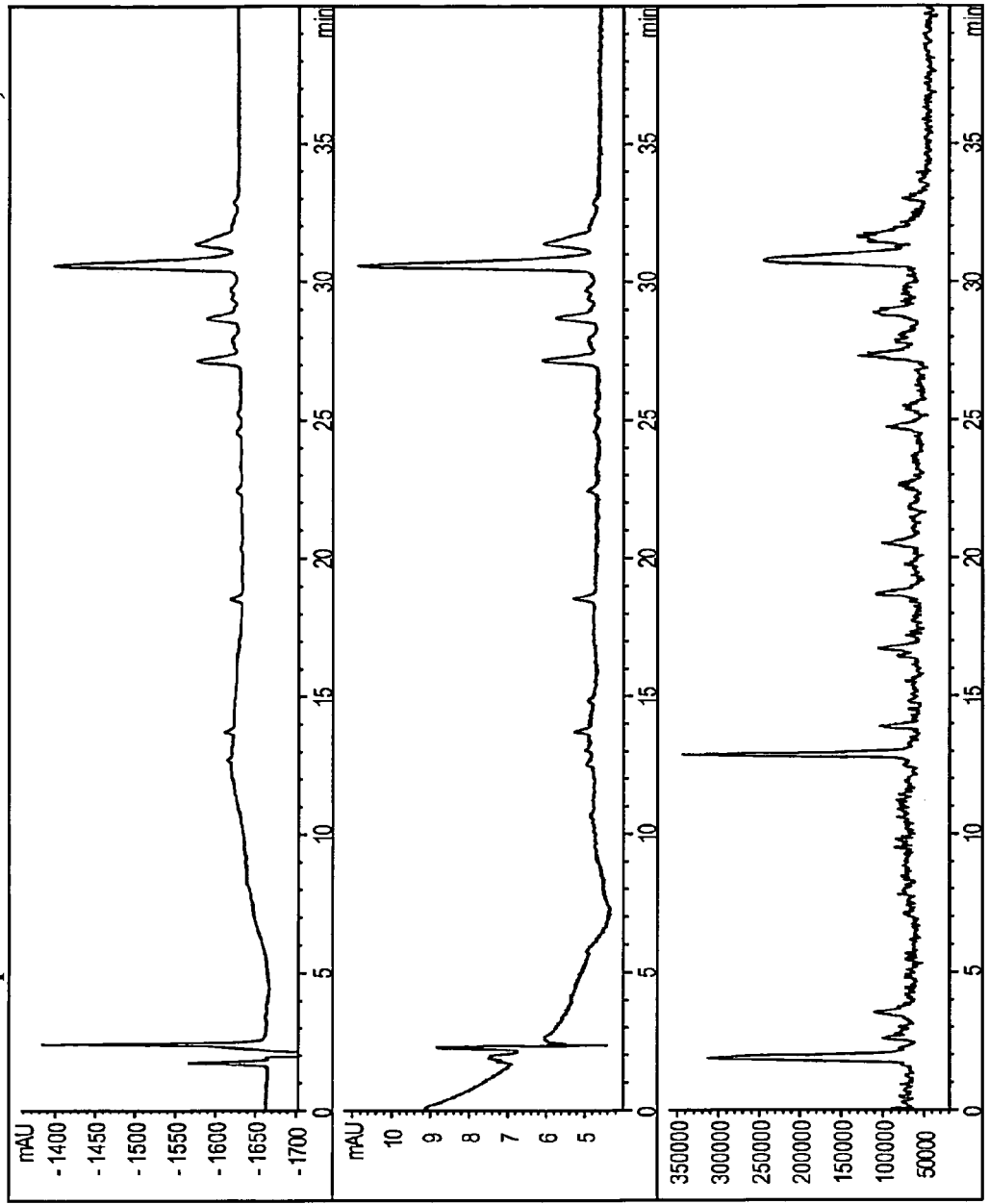
FIG. 21, cont.

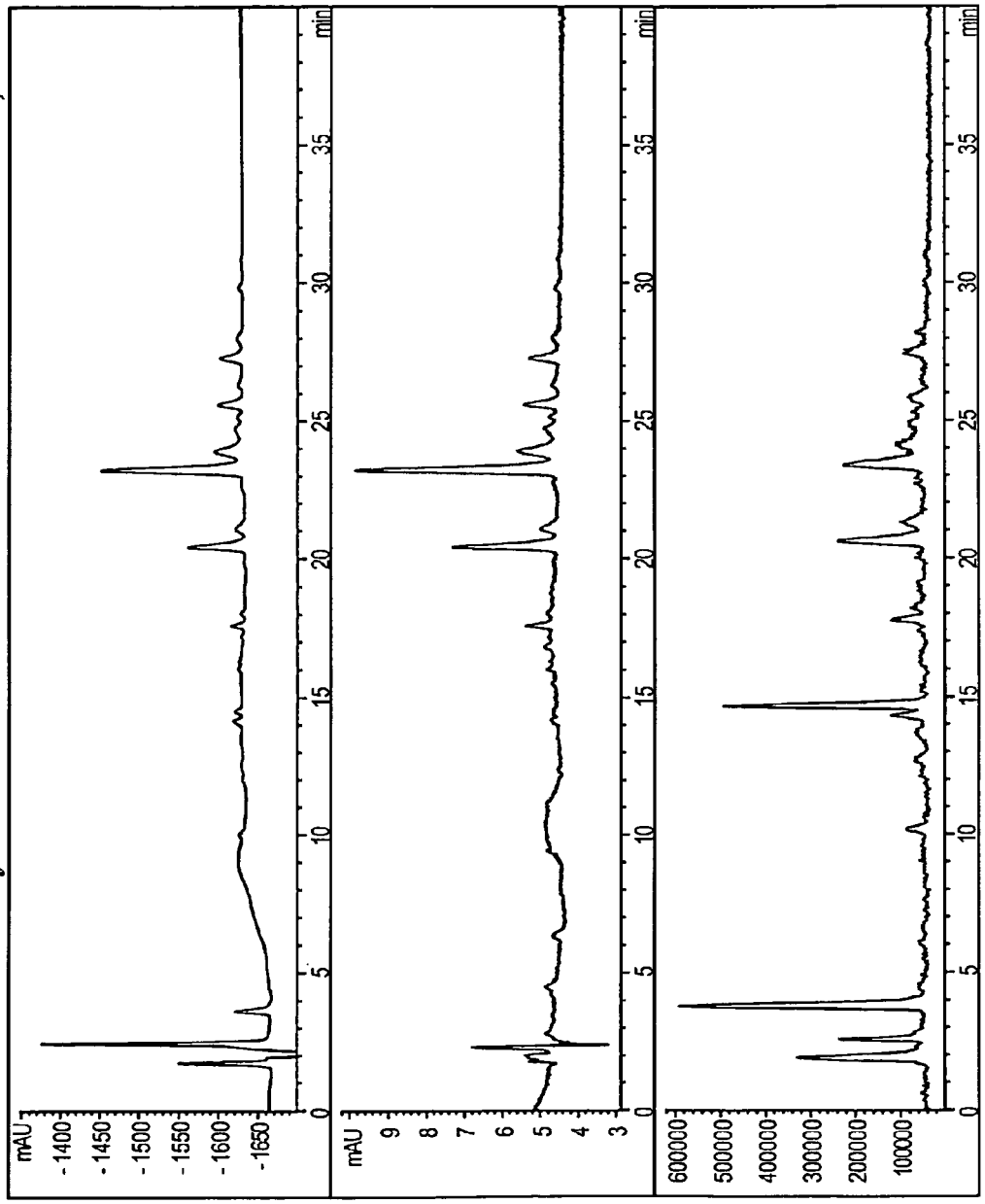
FIG. 21, cont.

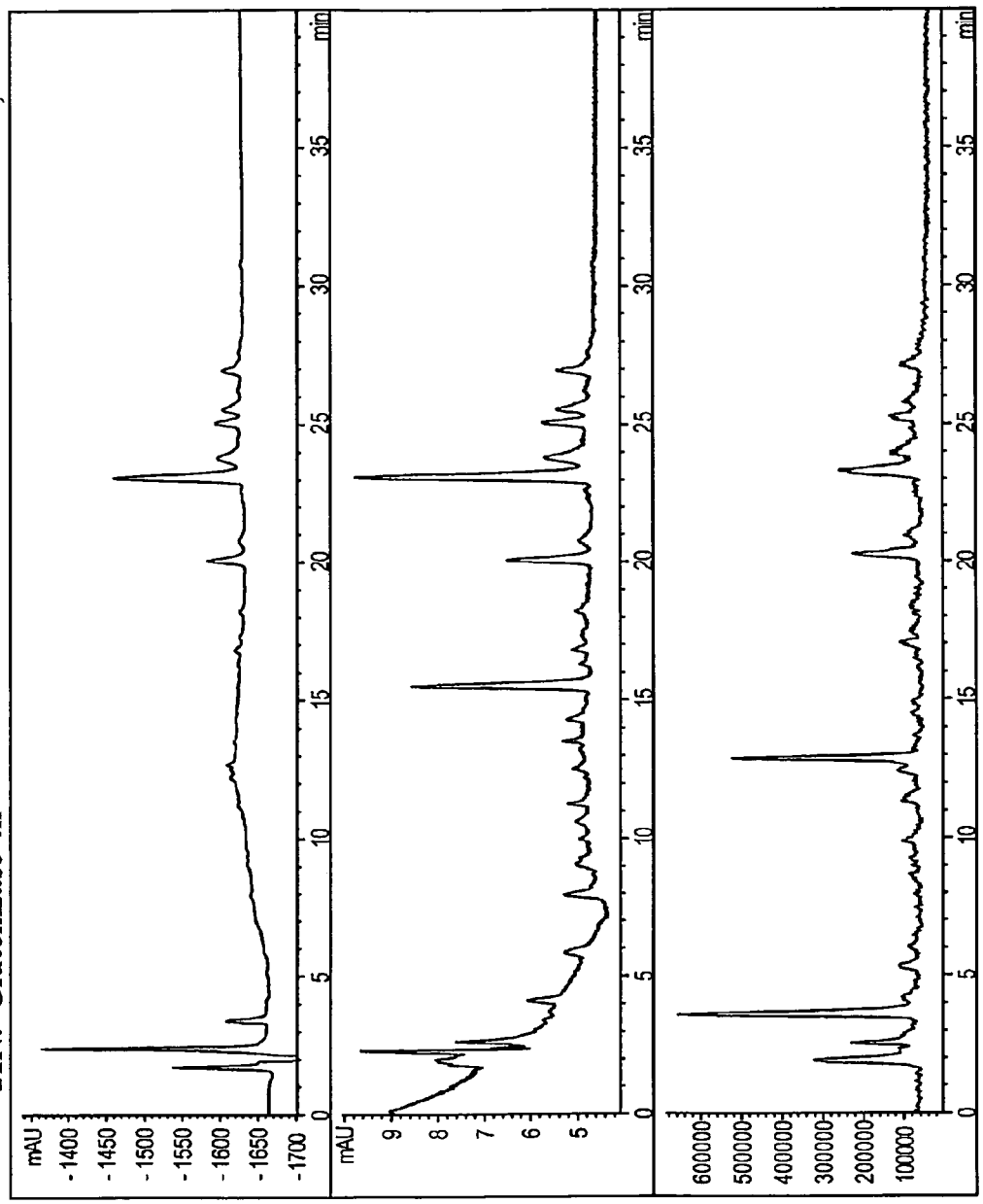
FIG. 21, cont.

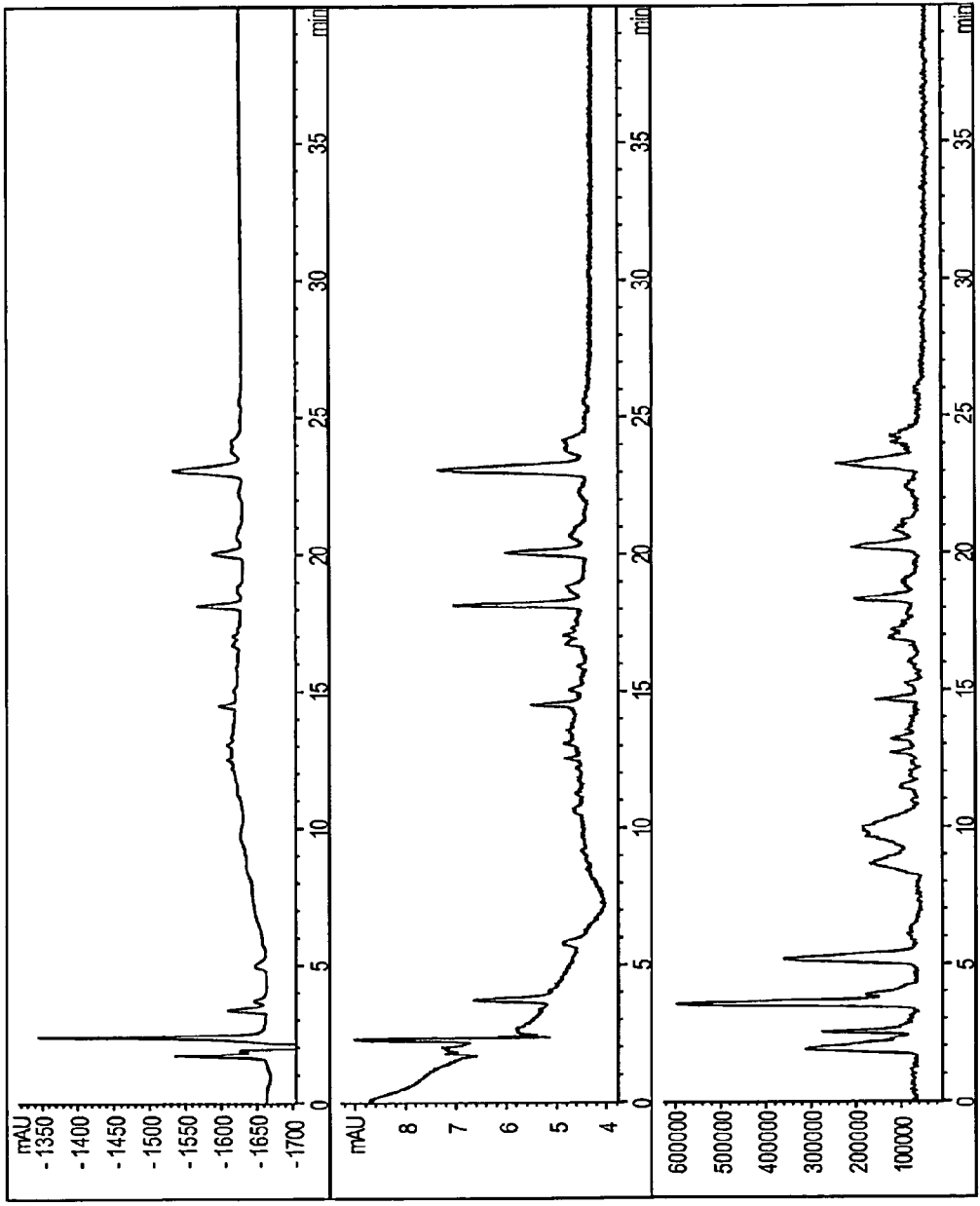
FIG. 21, cont.

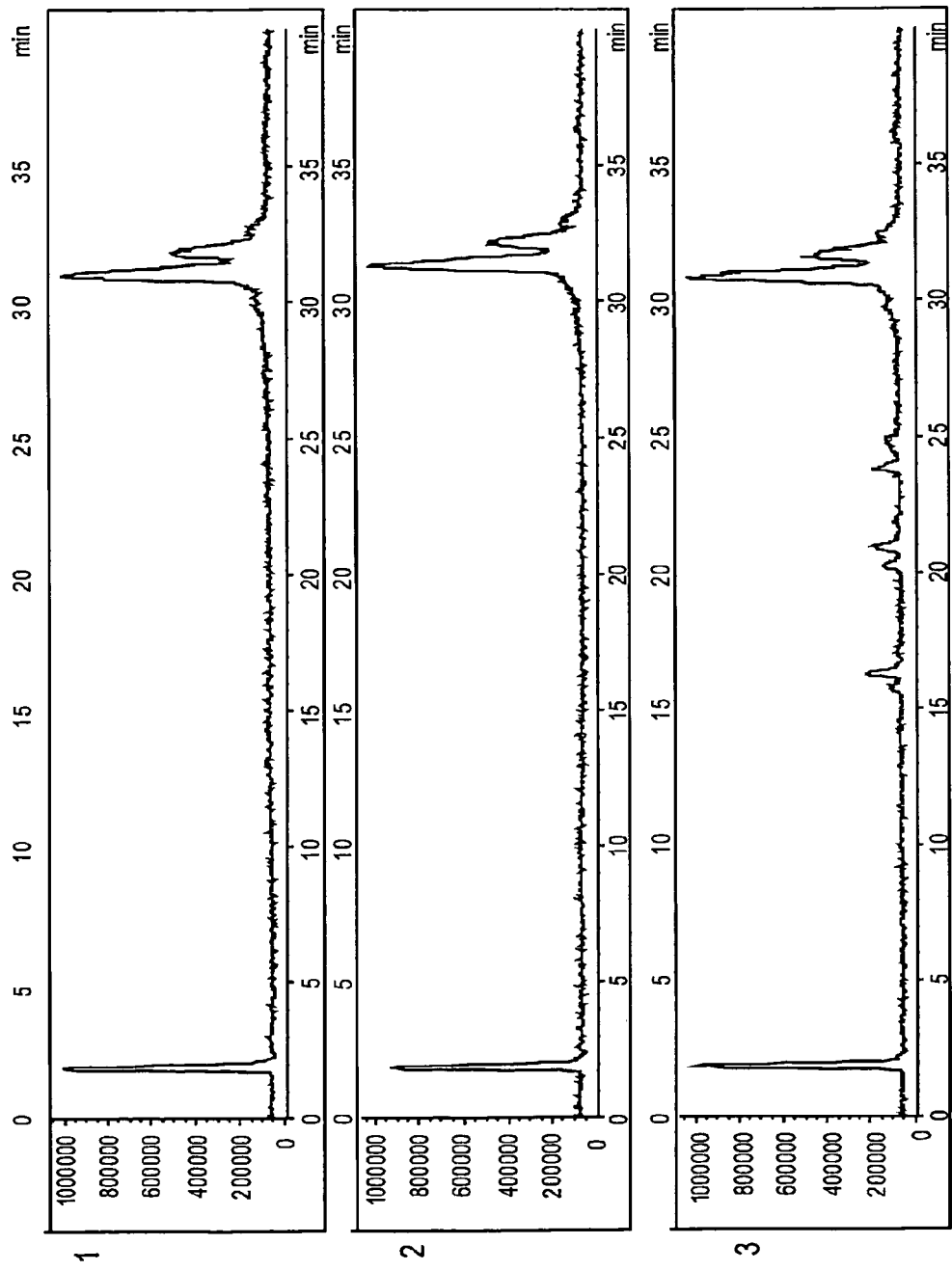
FIG. 23, cont.

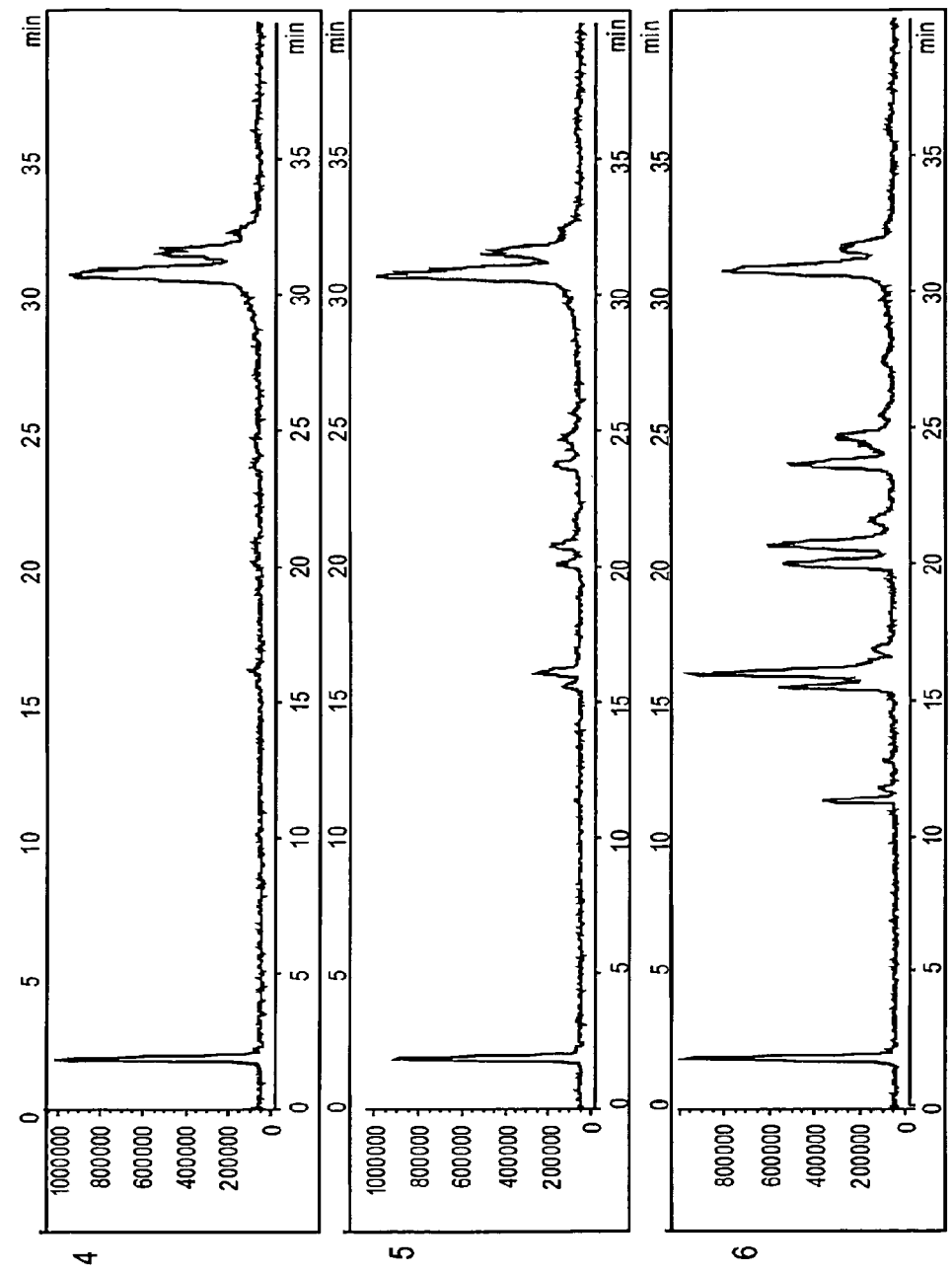
FIG. 23, cont.

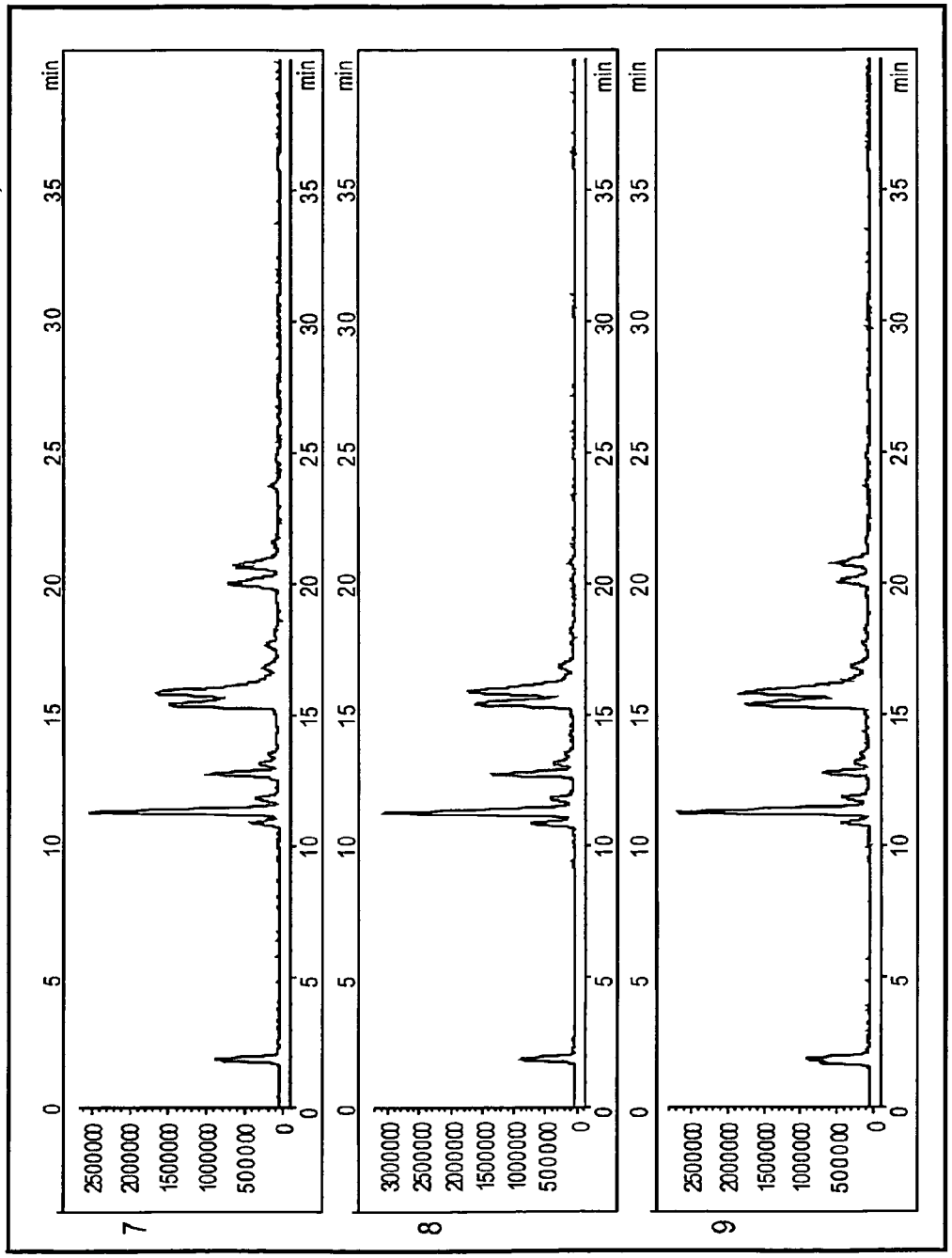

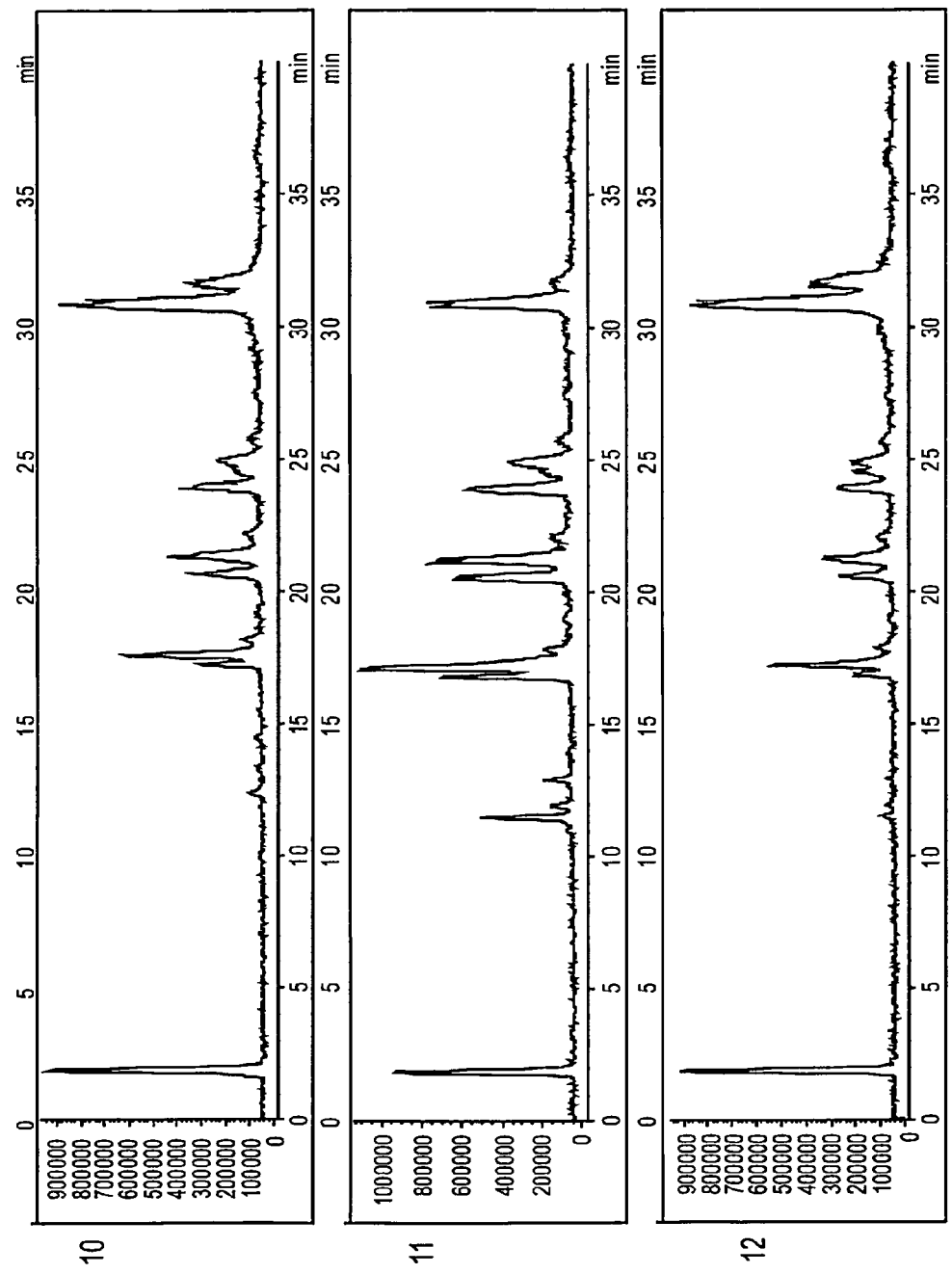
FIG. 23, cont.

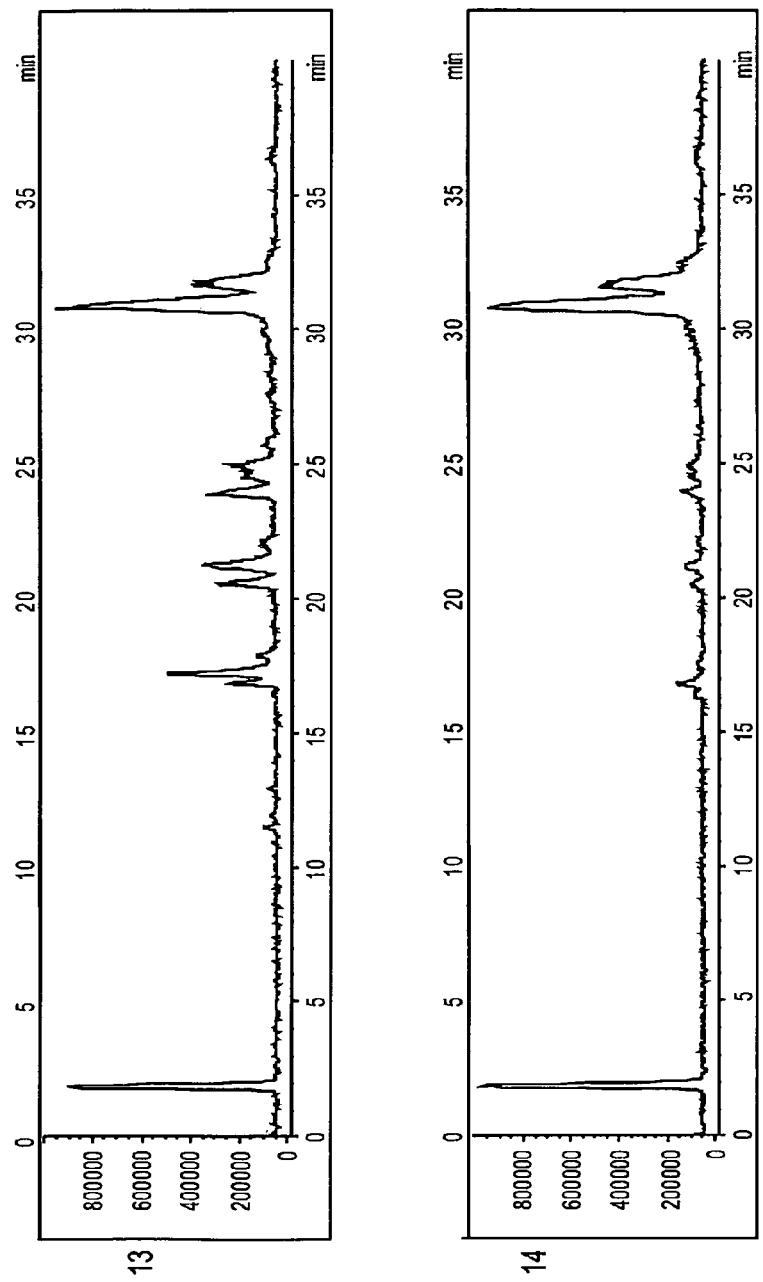
FIG. 23, cont.

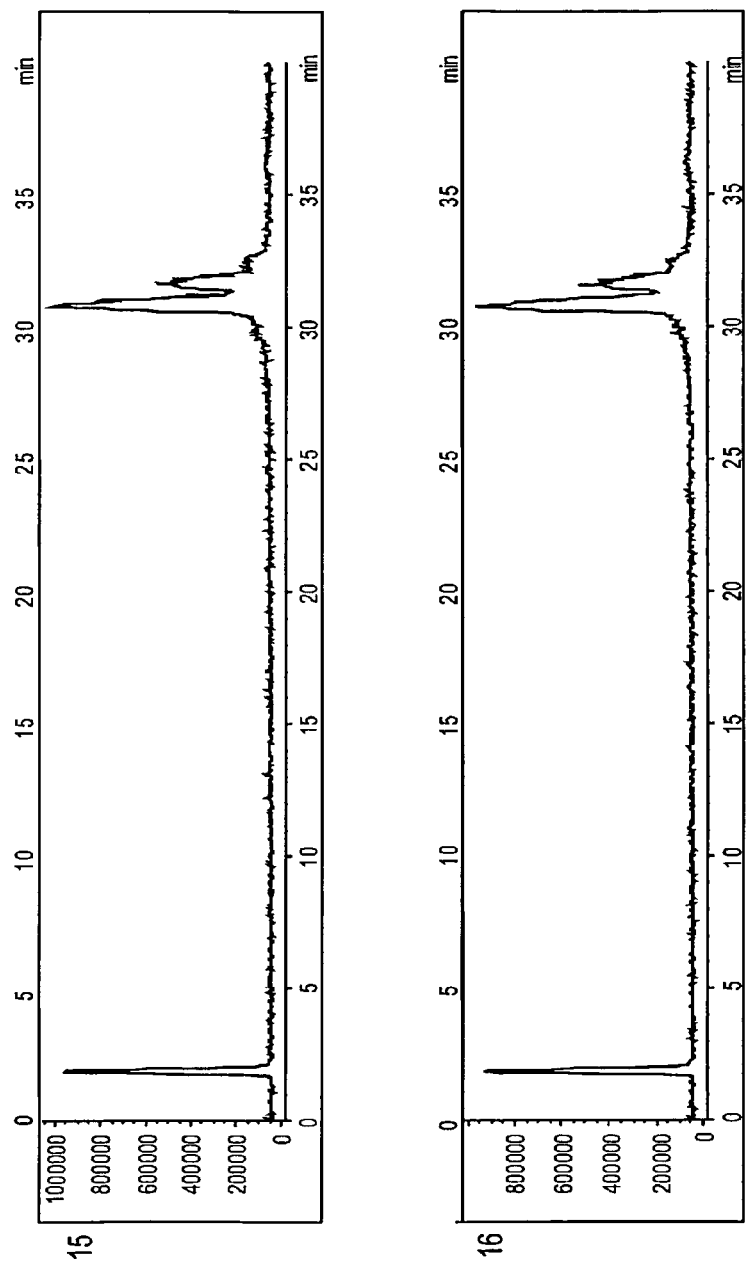
FIG. 23, cont.

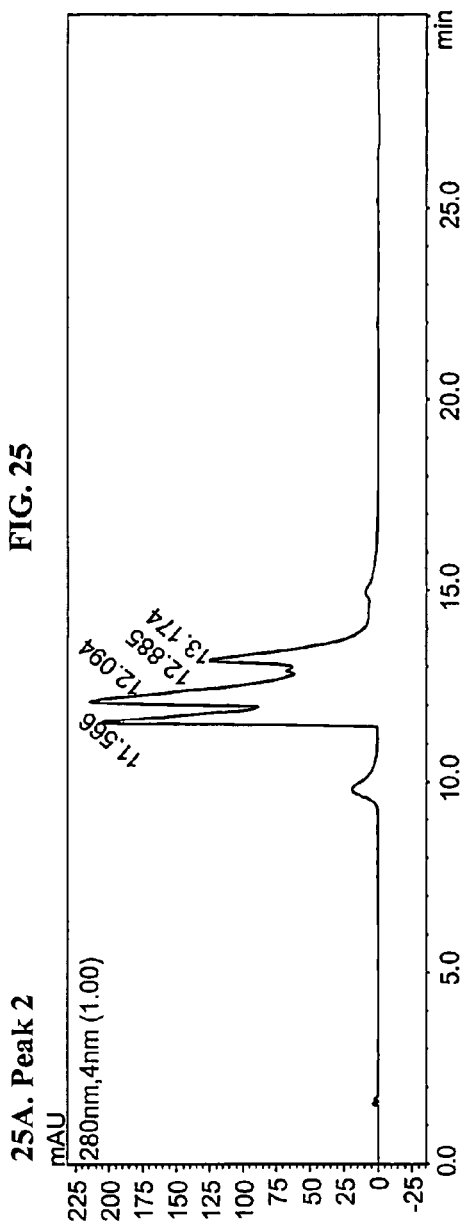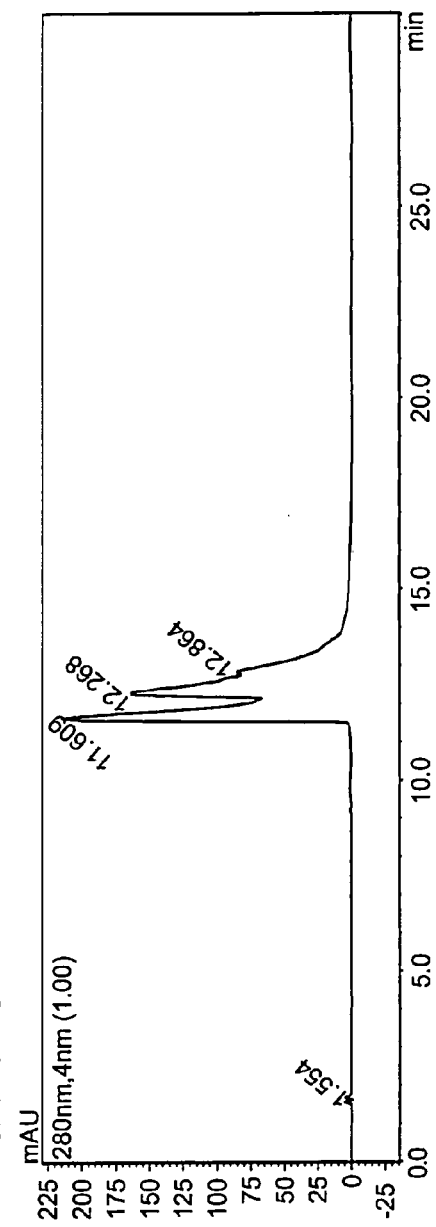
FIG. 25

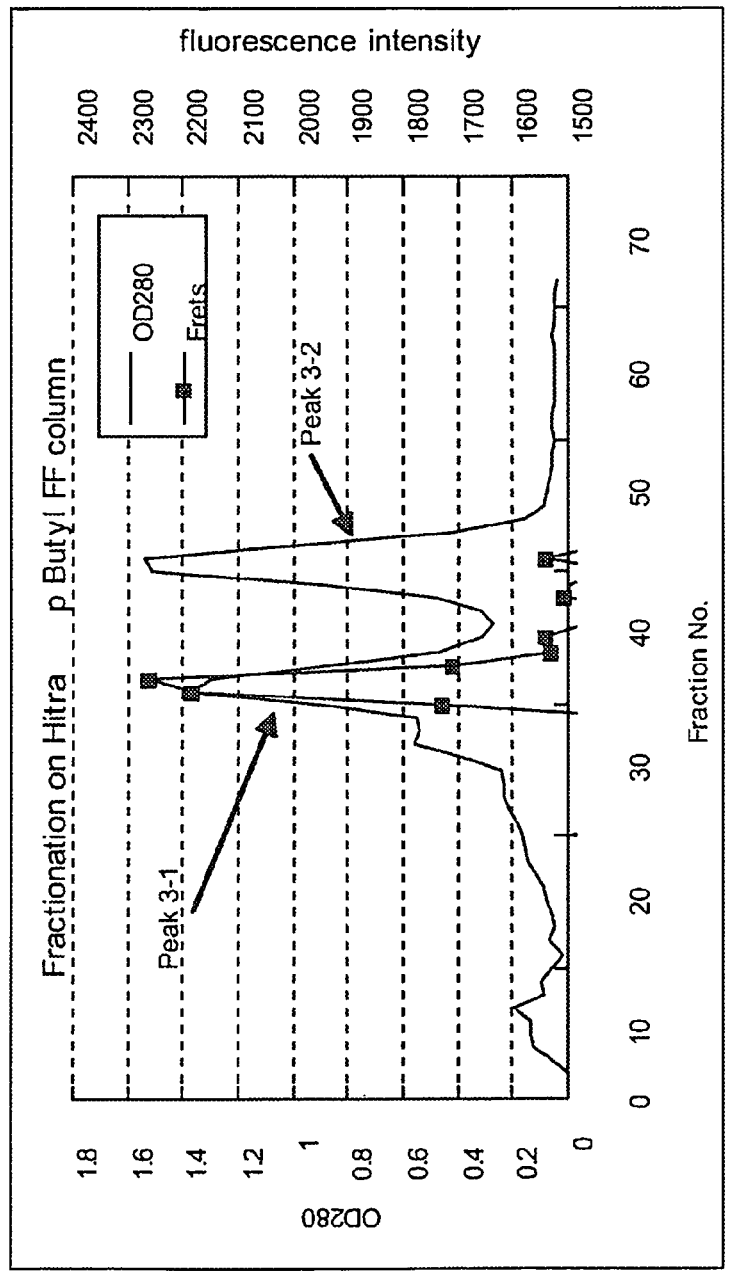
FIG. 26, cont.

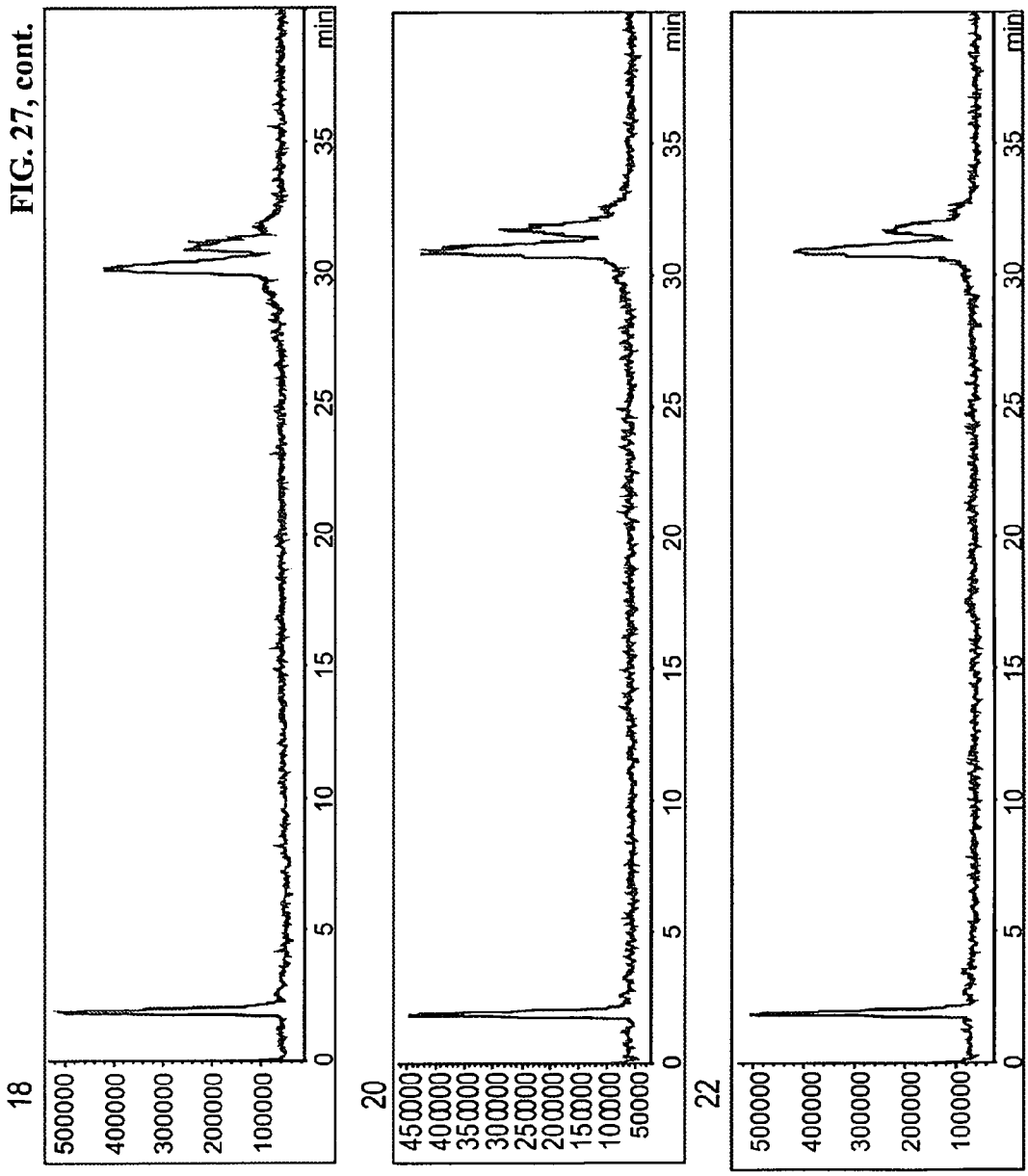

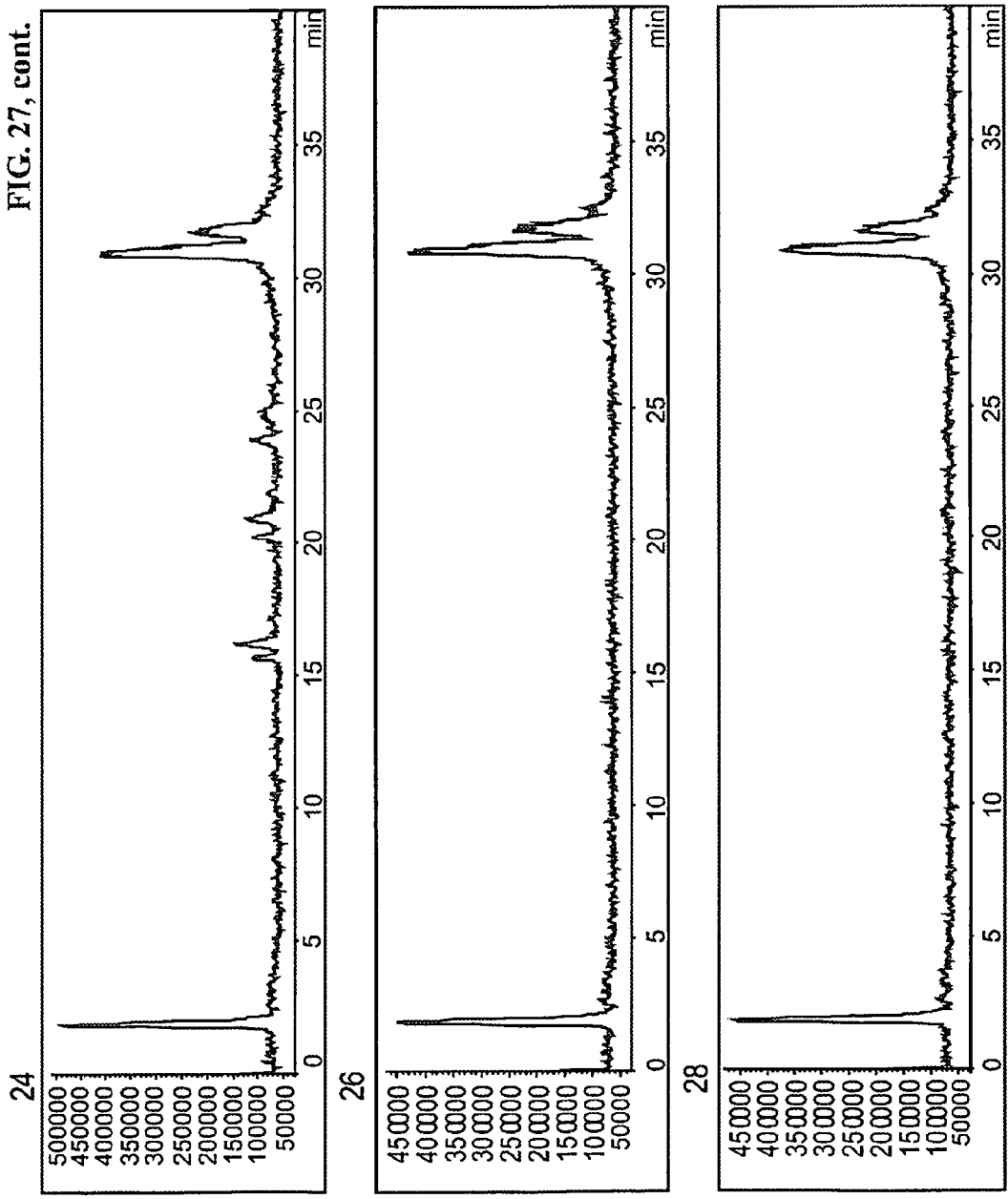

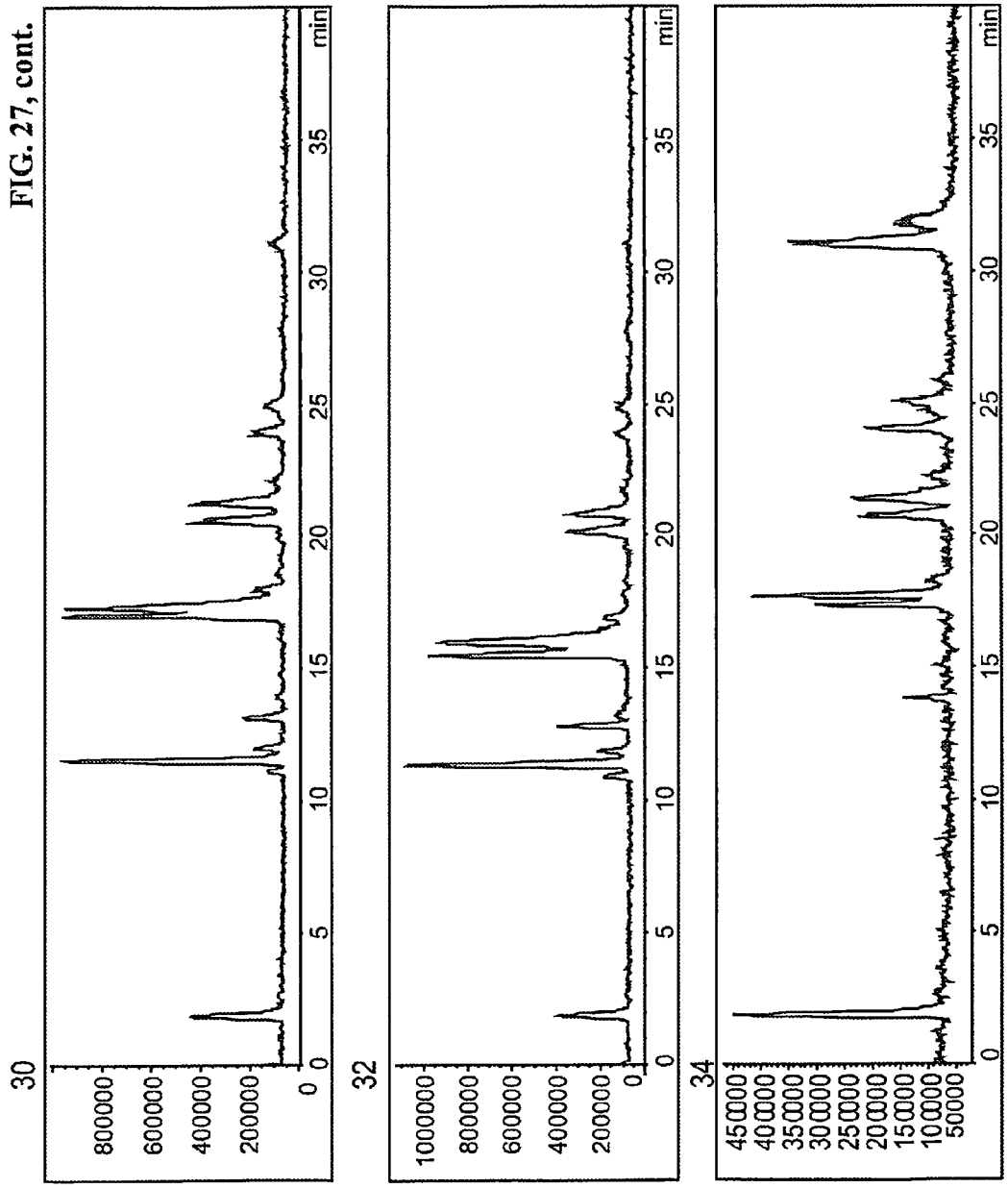
FIG. 27, cont.

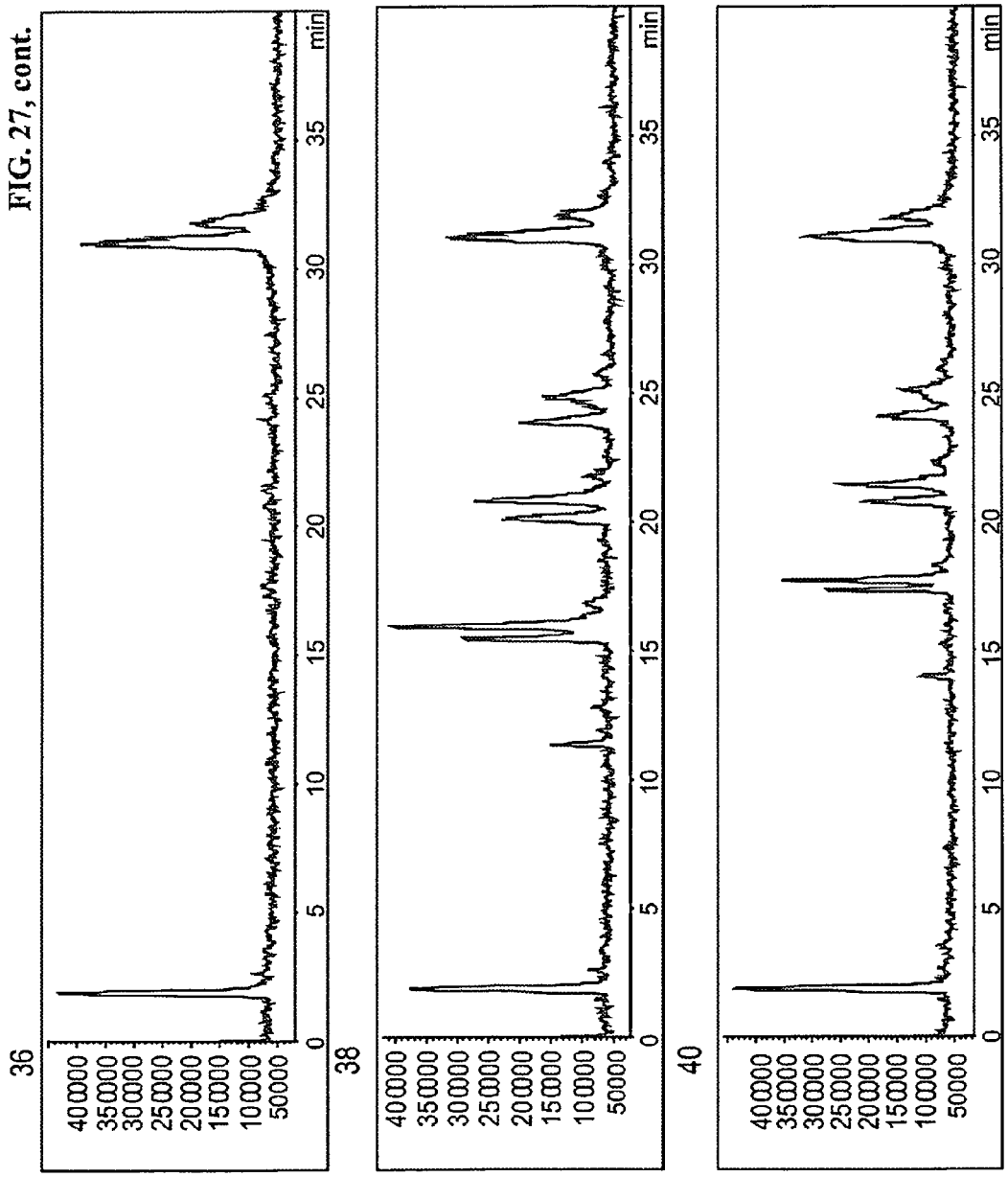
FIG. 27, cont.

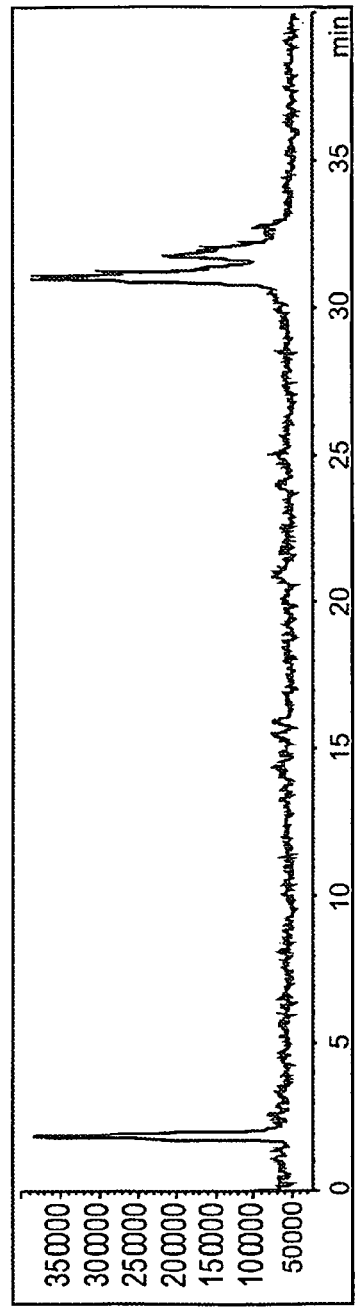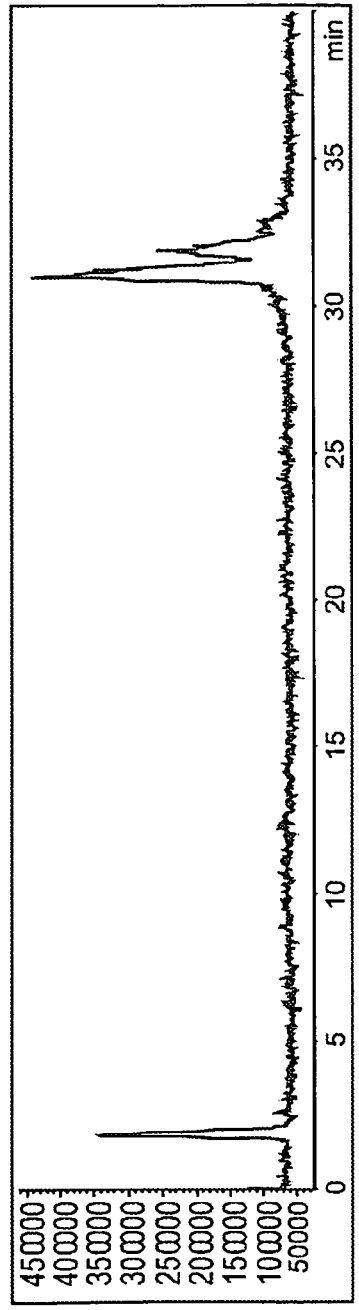
FIG. 27, cont.

FIG. 28
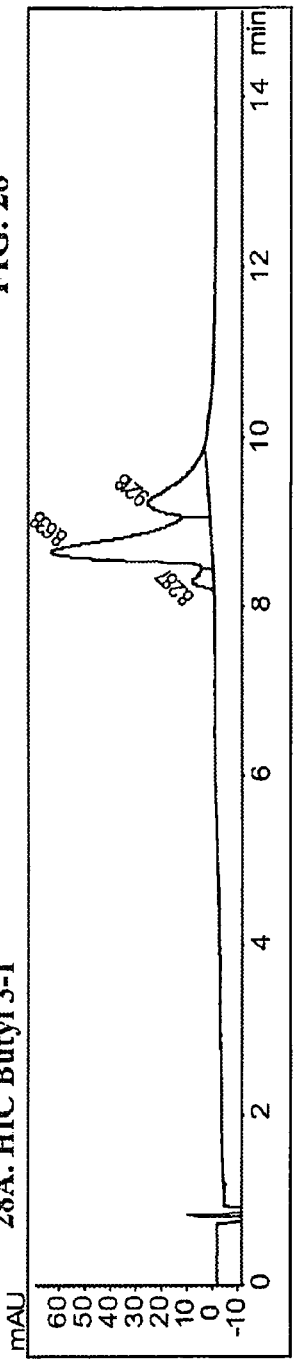
28A. HIC Butyl 3-1
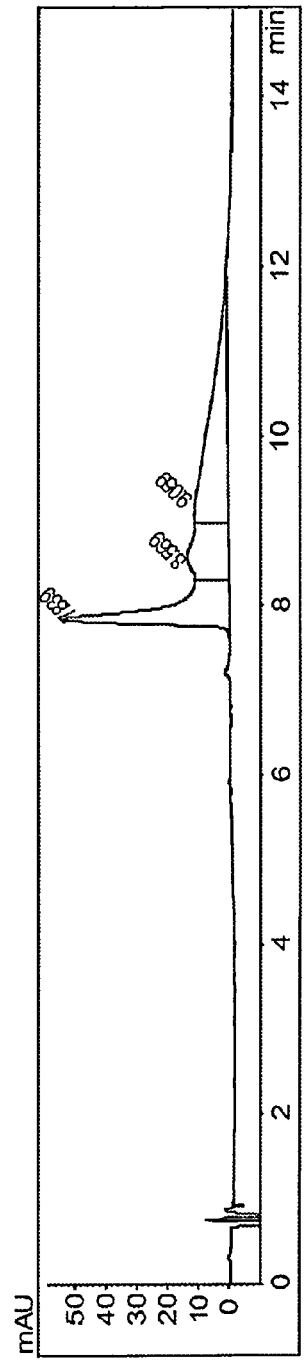
28B. HIC Butyl 3-2
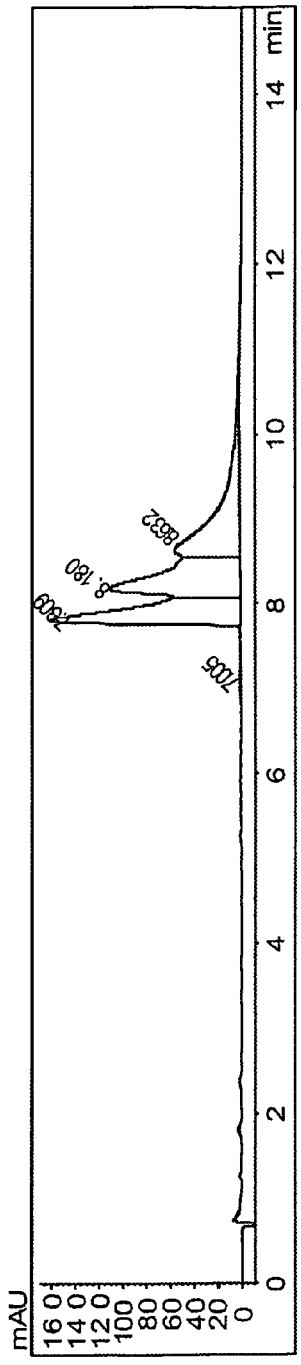
28C. SP-Sepharose Peak 3

30A.  FIG. 30
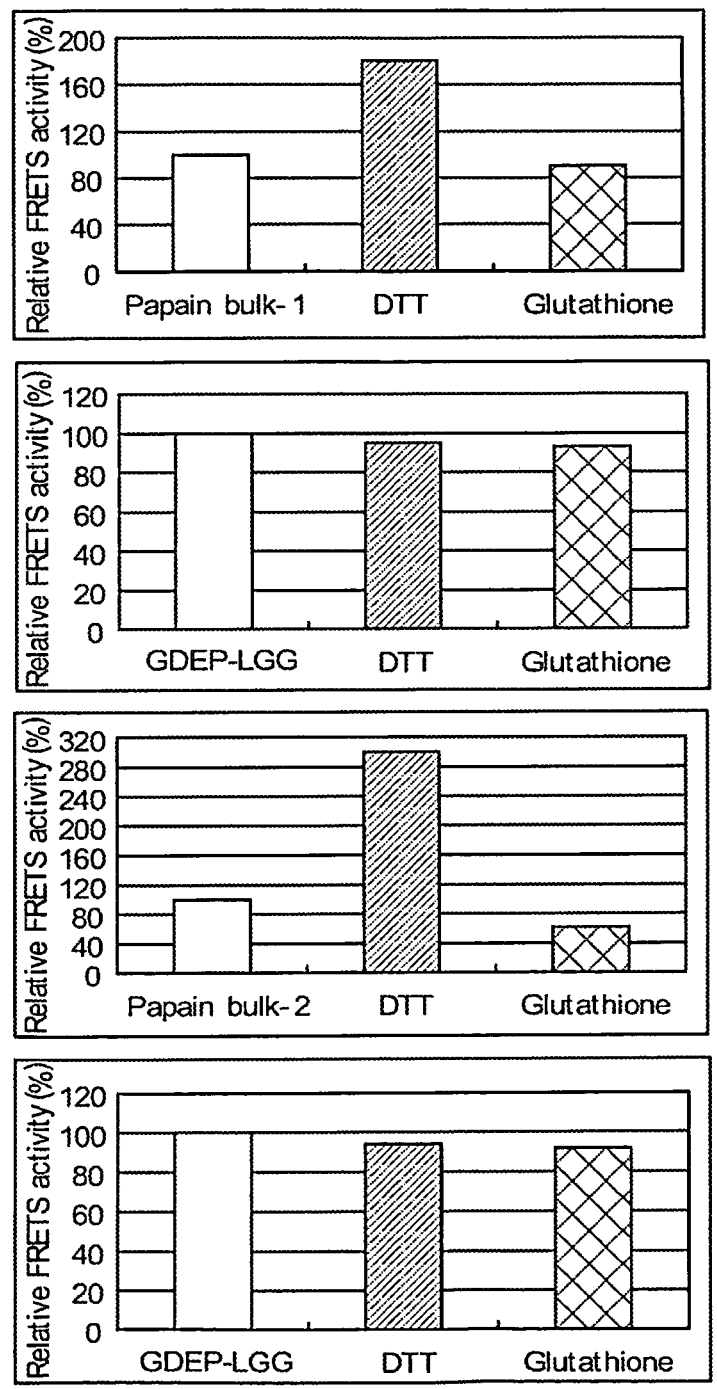

FIG. 30, cont.
30B.
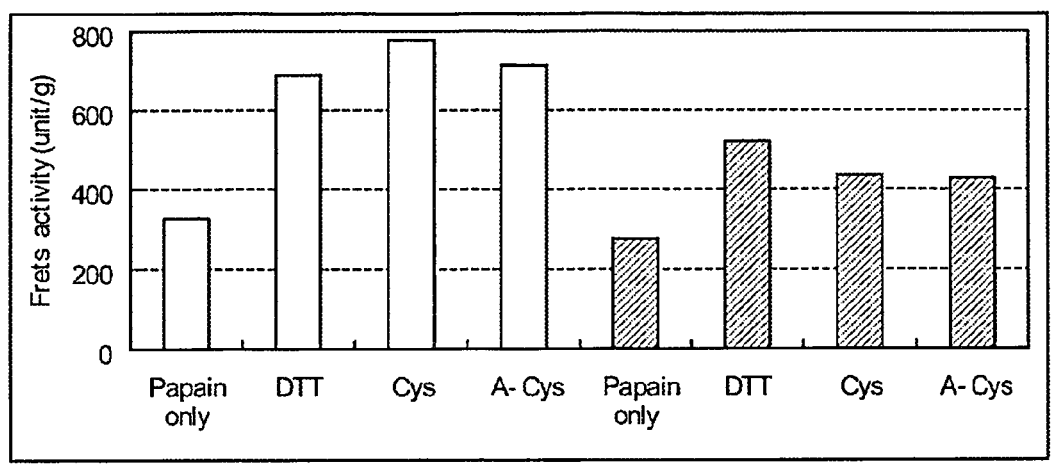
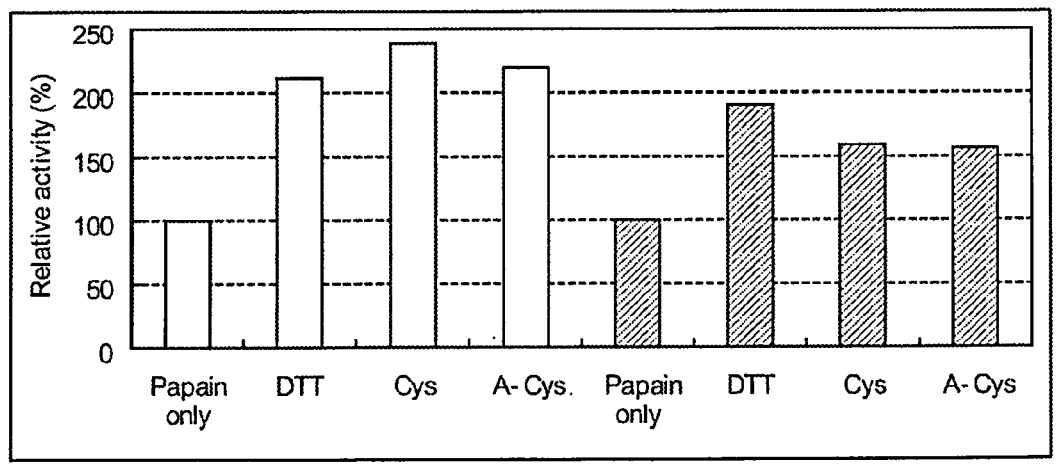

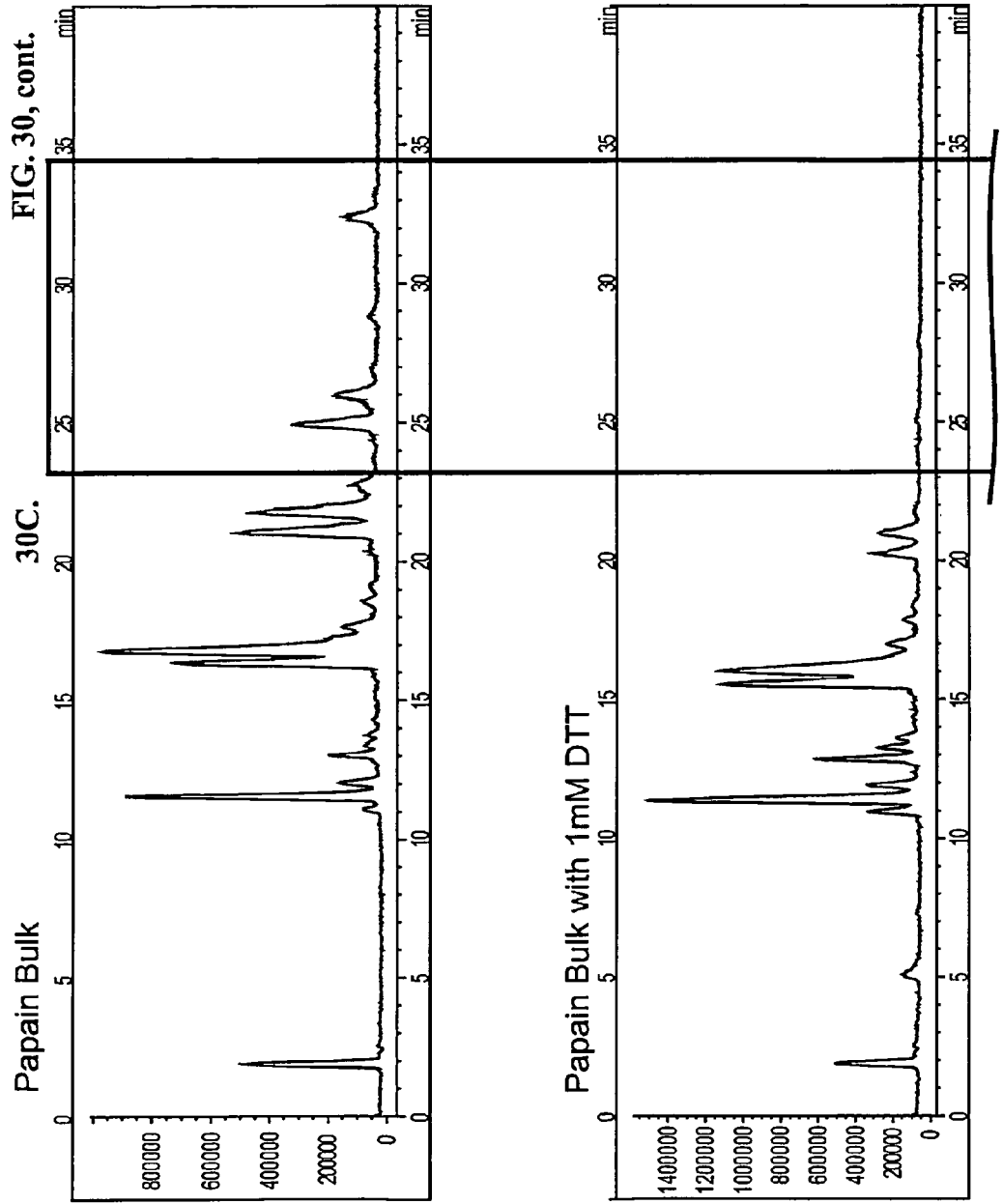
FIG. 30, cont.

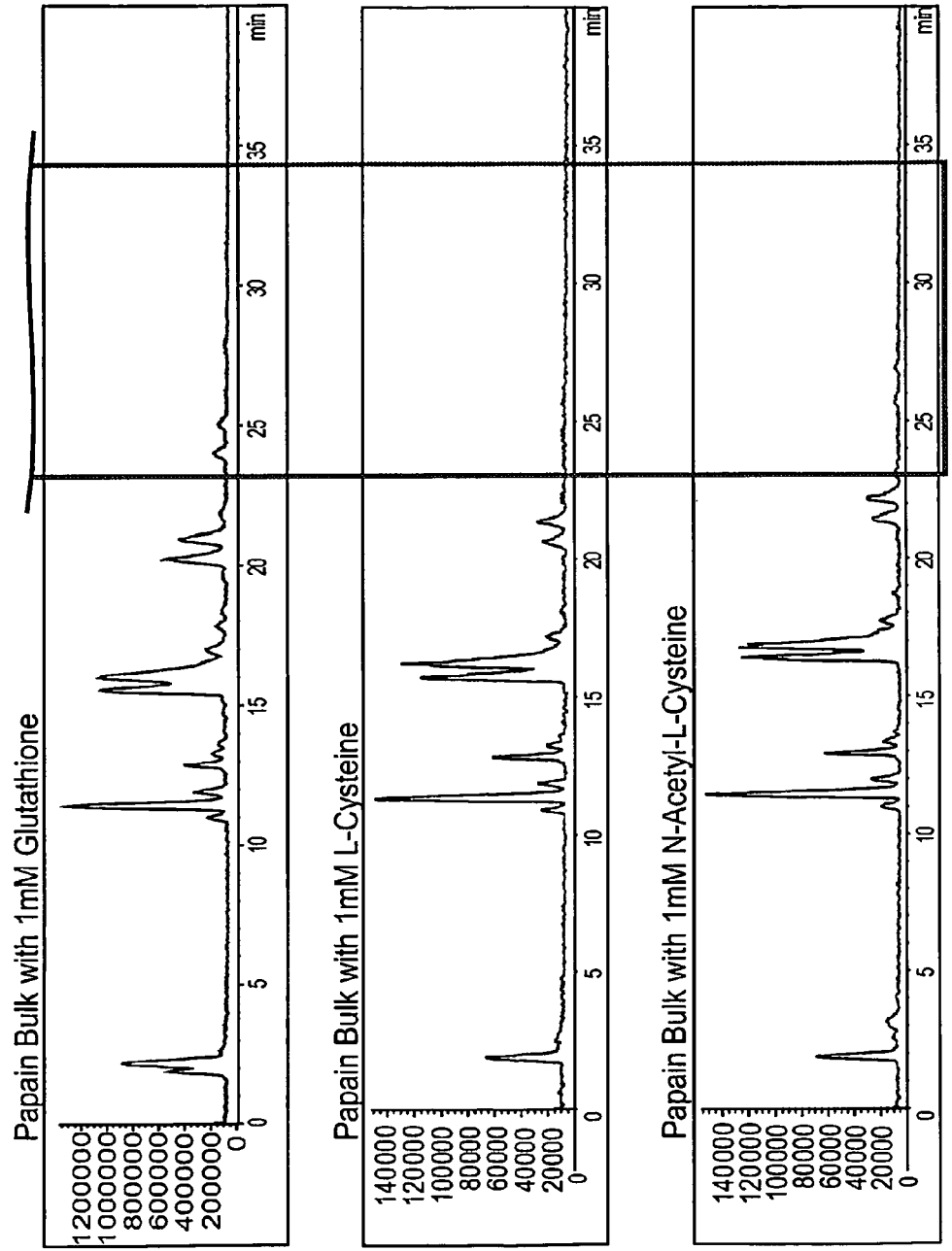

31A.    FIG. 31
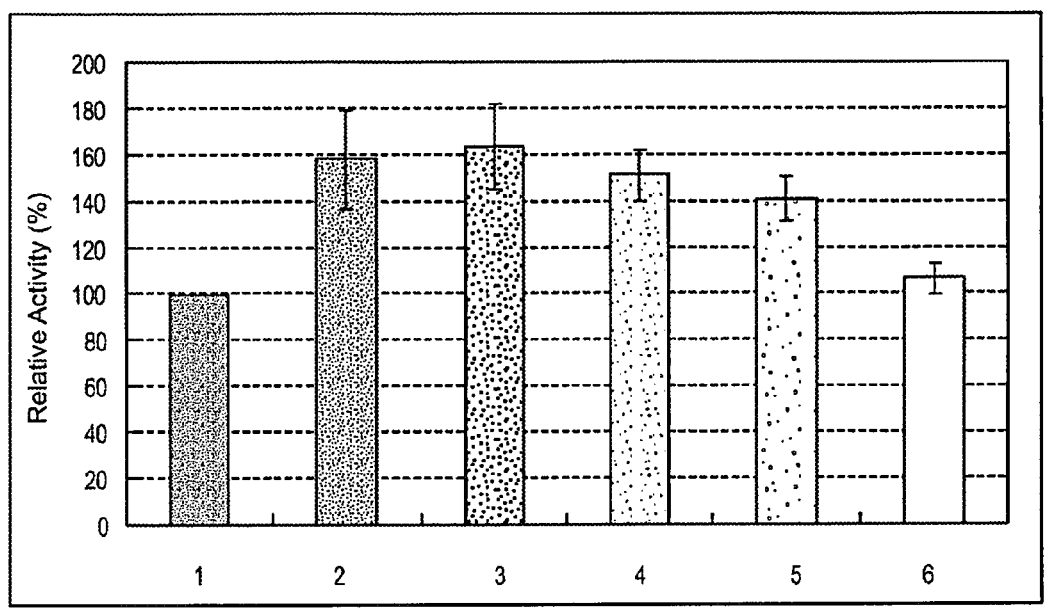
A; 0.057 unit/mL GDEP-LGG
B; 0.060 unit/mL Papain
1; 100% A
2; 80% A + 20% B
3; 60% A + 40% B
4; 40% A + 60% B
5; 20% A + 80% B
6; 100% B

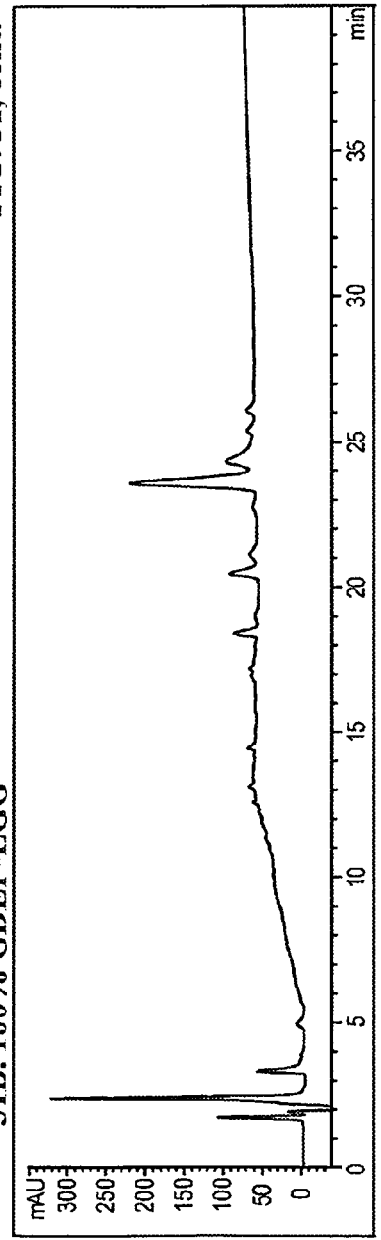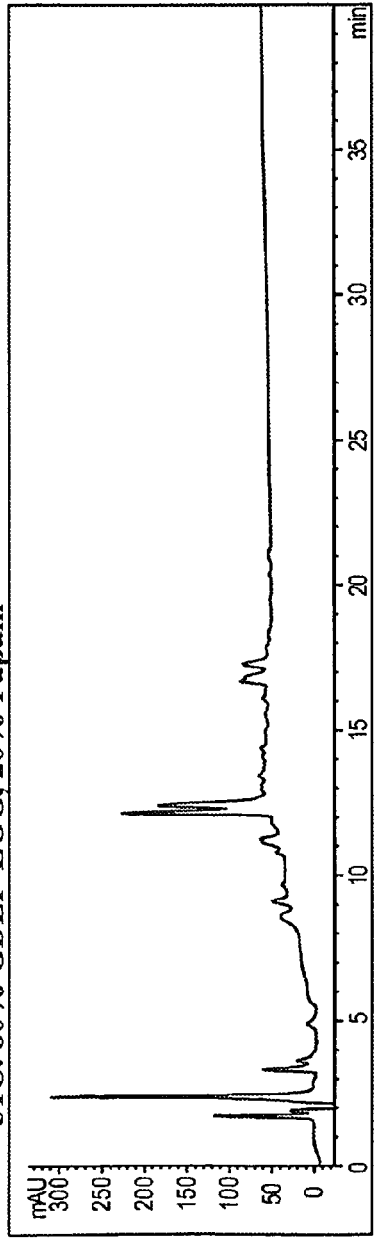
FIG. 31, cont.

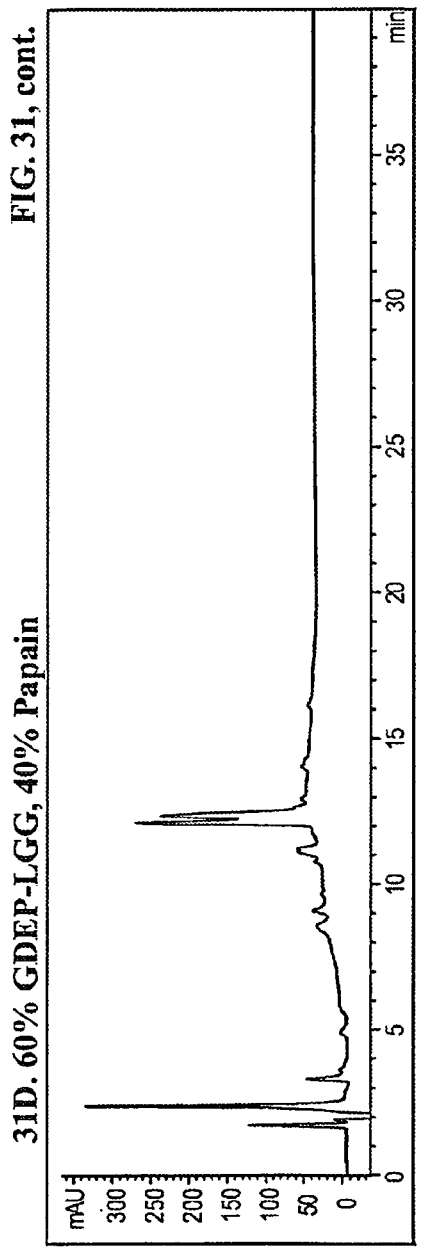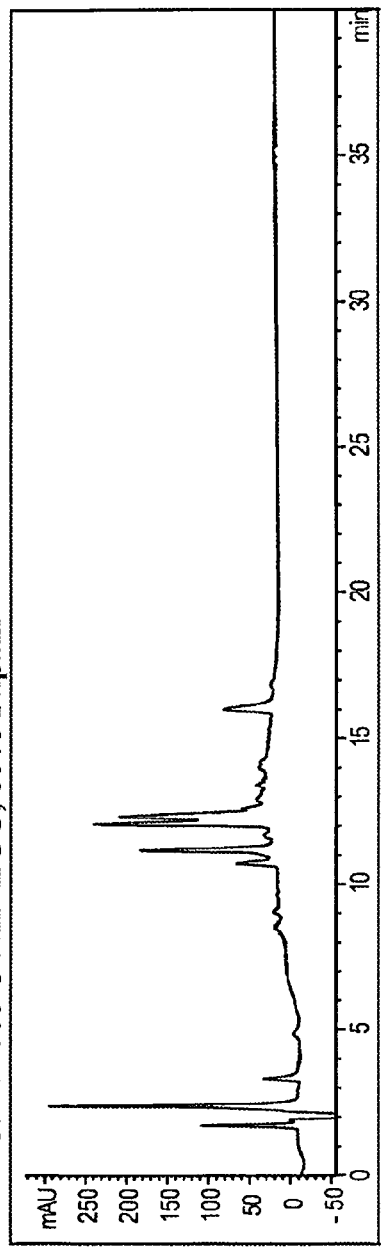
FIG. 31, cont.

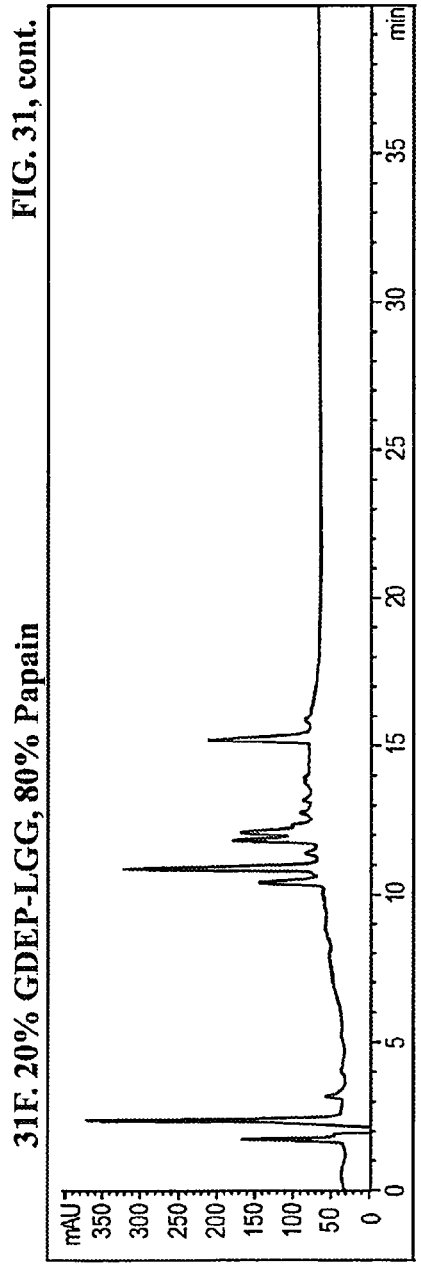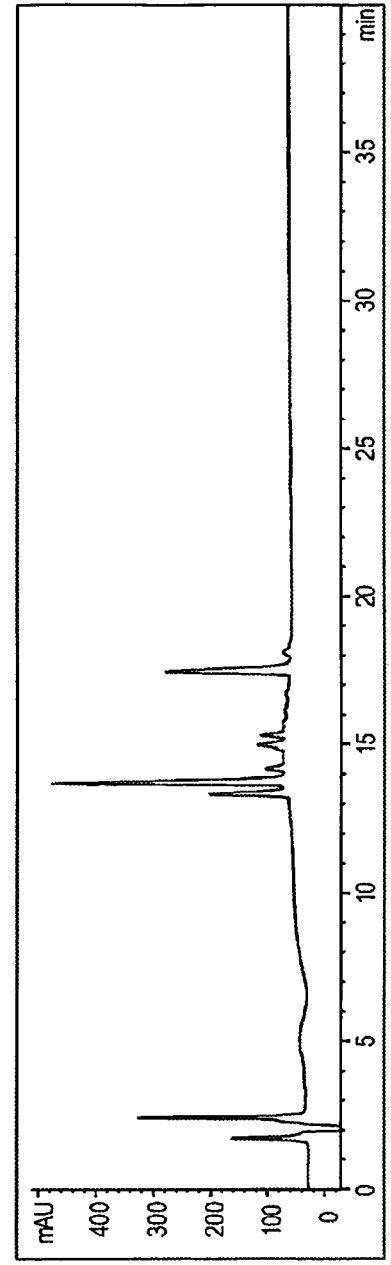
FIG. 31, cont.

| Enzyme name | Enzyme Activity (unit/gram) | | | | | | | | | | | No. of digestion |
|---|---|---|---|---|---|---|---|---|---|---|---|---|
| | LQLQPF | QPFPQP | PQPQLP | QLPYPQ | YPQPQL | PQLPYP | PYPQPQ | QPQLPY | LPYPQP | PQPQPF | | |
| GDEP-M (spray dried) | 5,700 | 6,900 | 1,400 | 6,400 | 9,200 | 6,700 | 2,600 | 15,100 | 2,700 | 4,100 | | 10 |
| Dextrozyme plus L | 6,500 | 7,100 | 7,900 | 10,600 | 3,200 | 6,000 | 2,900 | 8,900 | 4,900 | 0 | | 9 |
| Smiteam PM | 3,000 | 9,600 | 3,100 | 19,300 | 3,800 | 11,600 | 2,400 | 18,500 | 6,100 | (100) | | 9 |
| UPR-N | 7,200 | 2,800 | 18,800 | 11,200 | 1,600 | 10,900 | 3,000 | 2,700 | 2,700 | 0 | | 9 |
| GDEP-M | 4,400 | 3,900 | 900 | 4,500 | 7,000 | 2,800 | 1,500 | 11,900 | 1,700 | 2,600 | | 9 |
| GDEP-2A | 6,600 | 2,400 | (500) | 2,300 | 3,600 | 1,300 | 1,800 | 3,100 | 1,100 | 2,500 | | 9 |
| GDEP-2A (spray dried) | 10,500 | 6,000 | (400) | 6,000 | 5,700 | 4,800 | 3,900 | 4,700 | 3,100 | 5,000 | | 9 |
| GDEP-LNA | 10,900 | 4,000 | (400) | 2,800 | 5,300 | 3,100 | 4,700 | 2,800 | 2,100 | 4,900 | | 9 |
| GDEP-AH | 10,500 | 3,700 | (600) | 4,700 | 4,700 | 2,800 | 3,000 | 2,600 | 1,500 | 7,300 | | 9 |
| BHS5-N | 900 | 3,000 | (600) | 3,500 | 1,200 | 3,100 | 2,600 | 2,500 | 1,300 | 2,500 | | 7 |
| GDEP-LGG | 6,600 | 1,300 | (700) | 4,700 | 3,900 | 700 | 3,000 | 1,300 | 700 | 2,500 | | 5 |
| AGS(SD)-N | 1,200 | (500) | 1,600 | 1,400 | 0 | 1,600 | 900 | 3,100 | 300 | (300) | | 5 |
| Papain (Asahi) | 31,300 | (200) | (500) | 1,200 | 500 | 3,700 | 900 | 2,200 | (200) | (100) | | 4 |
| PZH(SD)-N | 24,400 | (500) | (900) | (300) | 7,000 | (500) | 7,400 | 100 | (400) | 9,500 | | 4 |
| MOR-N | 400 | (200) | 3,000 | 1,100 | 4,500 | 800 | 300 | 2,800 | 100 | (900) | | 4 |
| Preperation from P. citrinum | 1000 | 3,400 | (200) | 600 | 4,100 | 1,200 | 300 | 2,100 | (100) | 900 | | 4 |
| Papain (GSM) | 37,100 | (100) | 2,000 | 1,000 | 600 | 4,100 | 300 | 2,000 | (300) | (100) | | 4 |
| DRP-SD | 1,400 | 200 | (300) | 0 | 1,500 | (300) | 100 | 1,200 | (400) | 100 | | 8 |
| ATF-200 | 2,700 | (200) | (100) | (100) | 1,700 | (100) | 500 | 0 | (200) | 11,000 | | 8 |
| BHS3-N | 200 | 600 | (700) | 900 | 500 | 500 | 1,500 | 1,700 | 300 | 400 | | 2 |

FIG. 32A

|  |  |  |  |  |  |  |  |  |  |  |  |
|---|---|---|---|---|---|---|---|---|---|---|---|
| Orientase 10NL | 16,300 | (100) | (300) | 400 | 800 | (100) | 2,600 | 0 | (200) | 0 | 2 |
| DNN-N | 600 | 600 | (500) | 1,400 | 900 | 200 | 2,000 | 100 | 300 | 700 | 2 |
| PN-N | 800 | 0 | (100) | 1,100 | (100) | 500 | 600 | 1,300 | 100 | (900) | 2 |
| MIP-Y | 4,600 | (300) | (500) | (300) | 1,200 | (100) | 0 | 0 | (300) | (400) | 2 |
| CGTR-Y | 200 | (100) | 0 | 0 | 0 | 0 | 400 | 0 | (300) | 1,300 | 1 |
| NP-D | 1,000 | (700) | (900) | (300) | (400) | (600) | 300 | 0 | (300) | (500) | 1 |
| TG-D | (400) | 600 | (900) | 800 | (300) | 700 | 1,100 | 900 | 200 | (500) | 1 |
| BHS1-N | 0 | 500 | (700) | 400 | 400 | 500 | 900 | 0 | 200 | 300 | 1 |
| β-amylase L | 1,300 | (300) | (200) | (100) | (200) | (100) | 0 | 0 | 200 | (100) | 1 |
| Smiteam ACH | (200) | (700) | (500) | (500) | (600) | (200) | 900 | 1,500 | (300) | (600) | 1 |
| C-N | 500 | (100) | 1,800 | 500 | 0 | 900 | 200 | 200 | 100 | (600) | 1 |
| BBR | 17,900 | (900) | (600) | (200) | (600) | 0 | 0 | 100 | (500) | (500) | 1 |
| Smiteam LPL(DS) | (200) | (900) | (500) | (900) | 500 | (600) | 100 | 3,100 | (200) | (600) | 1 |

FIG. 32B

USE OF PROTEASES FOR GLUTEN INTOLERANCE

RELATED APPLICATIONS

This application claims priority to and benefit from U.S. provisional patent application No. 61/300,726, filed on Feb. 2, 2010, which is hereby incorporated by reference in its entirety.

BACKGROUND OF THE INVENTION

Gluten is a common complex of proteins found in certain grass-related grains, including wheat, barley, and rye. Gluten is a mixture of proteins comprising gliadin and glutenin. A 33-mer peptide derived from α-2 gliadin (residues 57-89), which is not digested in the human digestive system, has been identified as an initiator of the inflammatory response to gluten in, for example, Celiac disease. The 33-mer derived from α-2 gliadin is particularly rich in proline and glutamine residues. It stimulates a T-cell immune response in susceptible subjects, resulting in an inflammation that damages the intestinal wall. This, in turn, impairs the ability of the intestine to absorb nutrients, leading to malnutrition and a variety of other symptoms.

Gluten intolerance, or gluten sensitivity, is a collective term which includes all kinds of sensitivity to gluten. A small proportion of gluten intolerant people will test positive for Celiac disease. The standard diagnostic for celiac disease is villus atrophy detected in duodenal biopsies. In addition, antibodies to tissue transglutaminase (tTG) and gliadin appear in almost 100% of the patients with active Celiac disease, and the presence of such antibodies, particularly of the IgA class, has been used in diagnosis of the disease. The large majority of Celiac patients express the HLA-DQ2 [DQA1*0501, DQB1*02] and/or DQ8 [DQA1*0301, DQB1*0302] molecules. Clinical symptoms of Celiac disease include, for example, fatigue, chronic diarrhea, malabsorption of nutrients, weight loss, abdominal distension, anemia, as well as a substantially enhanced risk for the development of osteoporosis and intestinal malignancies (lymphoma and carcinoma).

However, most gluten intolerant, or gluten sensitive, people test negative (or inconclusive) for Celiac disease. Up to approximately 15% of the population (or 1 in 7 people) are non-Celiac gluten sensitive or non-Celiac gluten intolerant. These subjects are non-Celiac gluten sensitive or non-Celiac gluten intolerant in that they suffer symptoms and illness similar to celiac disease patients without meeting diagnostic criteria for celiac disease. Thus, non-Celiac gluten sensitivity ("NCGS"), non-Celiac gluten intolerance ("NCGI"), or gluten related disease ("GRD"), refer to a condition or disorder in which individuals suffer symptoms very similarly to people with Celiac disease, but the diagnostic tests (including blood tests) which identify and diagnose Celiac disease are negative or inconclusive. Thus, as much as 15% of the US population (or 1 in 7 people) may have NCGS.

Moreover, 15-30 million people in United States buy gluten-free products in an attempt to reduce gluten exposure for a variety of reasons.

U.S. Pat. No. 7,320,788 ("Shan") has proposed administering certain enzymes, termed "glutenases," to Celiac or dermatitis herpetiformis patients. According to Shan, glutenases include endoproteases found in wheat, barley, and rye, such as an endoprotease from *Hordeum vulgare*; prolyl endopeptidases ("PEP"), and specifically PEP from *Flavobacterium meningoscepticum* (Genbank ID# D10980) and *Myxococcus xanthus* (Genbank ID# AF127082); and brush border enzymes that catalyze the removal of dipeptides, including dipeptidyl peptidase IV and dipeptidyl carboxypeptidase. Shan also mentions that the X-Pro dipeptidase from *Aspergillus oryzae* (GenBank ID# BD191984) and the carboxypeptidase from *Aspergillus saitoi* (GenBank ID# D25288) can improve gluten digestion in the Celiac intestine. Shan teaches that the oligopeptides such as Gly-Pro-pNA, Z-Gly-Pro-pNA, and Hip-His-Leu can be used to determine whether a candidate enzyme will digest a toxic gluten oligopeptide. In fact, Shan teaches that the dose of a PEP enzyme is determined by the amount of that enzyme required to hydrolyze 1 micromol Z-Gly-Pro-pNA.

U.S. Pat. No. 7,534,426 ("Piper") is directed to methods of determining the therapeutic efficacy of candidate glutenase enzyme by detecting the ability of a candidate enzyme to digest one or more selected oligopeptides. US Patent Application Publication No. 2008/0213245 ("Hausch") refers to enzyme treatment of foodstuffs and also mentions mscreening methods that employ toxic oligopeptides to identify active glutenases. Like Shan, both Piper and Hausch mention PEPs for treatment of Celiac Sprue and/or dermatitis herpetiformis and teach that the oligopeptide Z-Gly-Pro-pNA can be used to determine whether a candidate enzyme will digest a toxic gluten oligopeptide. U.S. Pat. No. 7,462,688 ("Khosla") is directed to methods for diagnosing Celiac disease and/or dermatitis herpetiformis by detecting toxic gluten oligopeptides, or T cells and/or antibodies reactive thereto. Kholsa suggests treating such patients by administering peptides that interfere with the binding of toxic gluten oligopeptides to T cells and/or HLA molecules.

International Publication No. WO 2005/027953 ("Edens") is directed to processes for the proteolytic hydrolysis of a peptide or a polypeptide and mentions using proline specific endopeptidases, such as PEP from *Aspergillus* species, to produce food devoid of Celiac related epitopes. Likewise, U.S. Pat. No. 7,563,864 ("Marti") mentions an in vitro proteolytic protocol to detoxify gluten employing pepsin, trypsin/chymotrypsin, elastase, carboxypeptidase A, PEP, and rat brush border membrane enzymes. Rizello et al. (Applied and Environmental Microbiology, July 2007, p. 4499-4507) uses a combination of lactobacilli and proteases from *Aspergillus oryzae* (supplied by BIO-CAT) to reduce gluten concentration during food processing. Doumas et al. (Applied and Environmental Microbiology, December 1998, p. 4809-4815) provides the sequence of *Aspergillus oryzae* prolyl dipeptidyl peptidase (DPPIV) and suggests that the DPPIV enzyme may be of importance in industrial hydrolysis of wheat gluten-based substrates.

Ehren et al. (PLoS ONE 4(7):e6313) discuss a food-grade enzyme preparation with modest gluten detoxification properties. Ehren et al. note that aspergillopepsin from *Aspergillus niger* markedly enhances gluten digestion. Ehren et al. employed peptidase P from *Aspergillus oryzae*, which contains the exopeptidase DPPIV, to augment the extent to which ASP hydrolyzes gluten. Ehren et al. teach that DPPIV alone is unable to detoxify gluten oligopeptides, including a synthetic 33-mer from α2-gliadin or the 26-mer from γ5-gliadin and that DPPIV is ineffective at low pH and, therefore, would not be effective in vivo in the absence of an antacid adjuvant.

"Oral Papain in Gluten Intolerance" ("Messer et al.") mentions that the treatment of a patient regarded as having celiac disease with oral papain resulted in the patient being able to consume a gluten-containing diet with no further symptoms of celiac disease. Australian Patent Application No. 2008100719 ("Cornell and Stelmasiak") mentions compositions and methods for the prophylaxis or treatment of celiac disease. Cornell et al. mentions compositions and methods that include an extract of papaya resin or a functional analogue thereof "Papaya latex enzymes capable of detoxification of gliadin" ("Cornell et al.") mentions that the activity of papaya is due largely to caricain, and to a lesser extent chymopapain and glutamine cyclotransferase.

BRIEF SUMMARY OF THE INVENTION

Certain embodiments of the present technology provide an enzyme cocktail comprising a gluten degrading enzyme preparation and papain. The enzyme cocktail of the present technology is capable of cleaving a gluten oligopeptide, such as a 33-mer peptide fragment of α-gliadin. The enzyme cocktail may comprise activated papain. For example, papain can be activated by a reductant. The enzyme cocktail may be formulated for oral delivery and/or contained in a formulation that contains an enteric coating. The enzyme cocktail may be contained in a formulation that includes a pharmaceutically acceptable carrier, such as a solid, a capsule, or a liquid.

Certain embodiments of the present technology provide an enzyme cocktail comprising a gluten degrading enzyme preparation and an acidic serine protease polypeptide having an amino acid sequence at least about 80% homologous to Aorsin, or a fragment thereof. The enzyme cocktail of the present technology is capable of cleaving a gluten oligopeptide, such as a 33-mer peptide fragment of α-gliadin. The enzyme cocktail may further comprise papain (including activated papain, chymopapain, and/or purified papain), carboxypeptidase Y ("CPY"), and/or an enzyme having an amino acid sequence at least about 80% homologous to CPY, or a fragment thereof. The CPY may be *Saccharomyces cerevisiae* CPY, *Aspergillus niger* CPY, *Schizosaccharomyces pombe* CPY, or *Aspergillus fumigatus* CPY. The enzyme cocktail may be formulated in a pharmaceutically acceptable excipient. The enzyme cocktail may be formulated for oral delivery and/or contained in a formulation that contains an enteric coating. The enzyme cocktail may be contained in a formulation that includes a pharmaceutically acceptable carrier, such as a solid, a capsule, or a liquid.

Certain embodiments of the present technology provide a formulation for use in reducing gluten exposure or treating gluten intolerance comprising an enzyme composition capable of cleaving an immunogenic gluten oligopeptide into non-toxic fragments in vitro. The enzyme composition may include gluten degrading enzyme preparation; papain (including activated papain, chymopapain, and/or purified papain); Aorsin; an acidic serine protease polypeptide having an amino acid sequence at least about 80% homologous to Aorsin, or a fragment thereof; CPY; an enzyme having an amino acid sequence at least 80% homologous to CPY; a protease from *Aspergillus melleus*; and/or a preparation from *Penicillium citrinum*. The formulation may be capable of cleaving at least about 70%, at least about 80%, or at least about 90% of the immunogenic gluten oligopeptide into non-toxic fragments in vitro. The formulation may include a pharmaceutically acceptable carrier, such as a solid, a capsule, or a liquid.

Certain embodiments of the present technology provide a formulation for use in reducing gluten exposure or treating gluten intolerance. The formulation is capable of digesting a gluten oligopeptide in an in vitro gastrointestinal model and includes at least two enzyme compositions. The enzyme compositions may be gluten degrading enzyme preparation; papain (including activated papain, chymopapain, and/or purified papain); Aorsin; an acidic serine protease polypeptide having an amino acid sequence at least about 80% homologous to Aorsin, or a fragment thereof; CPY; an enzyme having an amino acid sequence at least 80% homologous to CPY; a protease from *Aspergillus melleus*; and/or a preparation from *Penicillium citrinum*. The in vitro gastrointestinal model may include incubating the enzyme compositions with a gluten oligopeptide in simulated gastric fluid at about 37° C. for a period representative of in vivo contact with gastric fluids and/or incubating the enzyme compositions with a gluten oligopeptide in simulated intestinal fluid at about 37° C. for a period representative of in vivo contact with intestinal fluids. The simulated gastric fluid may include gastric mucosa mucin, pepsin, gelatinase, amylase, and/or lipase. The simulated intestinal fluid may include one or more pancreatic enzymes and a bile salt. The pancreatic enzymes may be trypsin, chymotrypsin, amylase, and/or lipase. The gluten oligopeptide may be a 33-mer peptide fragment of α-gliadin, such as a peptide having the amino acid sequence LQLQPF-PQPQLPYPQPQLPYPQPQLPYPQPQPF (SEQ ID NO:1).

Certain embodiments of the present technology provide a method of treating gluten intolerance in a human subject comprising providing the subject with a therapeutically effective amount of an enzyme cocktail that is capable of cleaving a gluten oligopeptide at acidic conditions. The enzyme cocktail may include a gluten degrading enzyme preparation; papain (including activated papain, chymopapain, and/or purified papain); Aorsin; an acidic serine protease polypeptide having an amino acid sequence at least about 80% homologous to Aorsin, or a fragment thereof; CPY; an enzyme having an amino acid sequence at least 80% homologous to CPY; a protease from *Aspergillus melleus*; and/or a preparation from *Penicillium citrinum*. The enzyme cocktail may include a composition derived from *Aspergillus oryzae*. The enzyme cocktail may be formulated in a pharmaceutically acceptable excipient. The enzyme cocktail may be formulated for oral delivery and/or contained in a formulation that contains an enteric coating. The enzyme cocktail may be contained in a formulation that includes a pharmaceutically acceptable carrier, such as a solid, a capsule, or a liquid.

Certain embodiments of the present technology provide a method of reducing gluten exposure in a subject, comprising providing the subject with an enzyme cocktail that is capable of cleaving a gluten oligopeptide at acidic conditions. The enzyme cocktail may include a gluten degrading enzyme preparation; papain (including activated papain, chymopapain, and/or purified papain); Aorsin; an acidic serine protease polypeptide having an amino acid sequence at least about 80% homologous to Aorsin, or a fragment thereof; CPY; an enzyme having an amino acid sequence at least 80% homologous to CPY; a protease from *Aspergillus melleus*; and/or a preparation from *Penicillium citrinum*. The enzyme cocktail may include a composition derived from *Aspergillus oryzae*. The enzyme cocktail may be formulated in a pharmaceutically acceptable excipient. The enzyme cocktail may be formulated for oral delivery and/or contained in a formulation that contains an enteric coating. The enzyme cocktail may be contained in a formulation that includes a pharmaceutically acceptable carrier, such as a solid, a capsule, or a liquid.

Certain embodiments of the present technology provide a method of assessing the efficacy of an enzyme composition, comprising the steps of (i) incubating a mixture comprising a candidate enzyme composition and a gluten oligopeptide in simulated gastric fluid at about 37° C. for a period representative of in vivo contact with gastric fluids; (ii) adding an acid neutralizing substance to the mixture; (iii) incubating the mixture in simulated intestinal fluid at about 37° C. for a period representative of in vivo contact with intestinal fluids; and (iv) determining the amount of intact gluten oligopeptide in the mixture. The period representative of in vivo contact with gastric fluids may be about 120 minutes. The period representative of in vivo contact with intestinal fluids may be about 60 minutes. The simulated gastric fluid may include gastric mucosa mucin, pepsin, gelatinase, amylase, and lipase. The simulated intestinal fluid comprises one or more pancreatic enzymes and a bile salt. The pancreatic enzymes may be trypsin, chymotrypsin, amylase, and/or lipase. The gluten oligopeptide may be a 33-mer peptide fragment of α-gliadin, such as a peptide having the amino acid sequence LQLQPFPQPQLPYPQPQLPYPQPQLPYPQPQPF (SEQ ID NO:1).

BRIEF DESCRIPTION OF SEVERAL VIEWS OF THE DRAWINGS

FIG. 4 shows chromatographs of HPLC analysis with 280 nm and 210 nm (panels 1 and 2) and mass spectral analysis (panel 3) of a 33-mer peptide after treatment with pepsin (FIG. 4A), proteinase K (FIG. 4B), and GDEP-LGG (FIG. 4C). Amino acid sequences corresponding to sequence identification numbers 1-10 are included in FIG. 4A; corresponding to sequence identification numbers 1, and 10-20 are included in FIG. 4B; and corresponding to sequence identification numbers 21-26 are included in FIG. 4C.

FIG. 7 also shows chromatographs of HPLC analysis (panels 1 and 2) and mass spectral analysis (panel 3) of a 33-mer peptide after treatment with GDEP-M alone (FIG. 7E) and GDEP-M in the presence of PMSF (FIG. 7F), pepstatin (FIG. 7G), and EDTA (FIG. 7H). Amino acid sequences corresponding to sequence identification numbers 27-31, 72-84, and 89 are included in FIG. 7A; corresponding to sequence identification numbers 1, 27-31, 46, 48, and 89 are included in FIG. 7B; corresponding to sequence identification numbers 27-31, 51-53, 77-84, and 89 are included in FIG. 7C; corresponding to sequence identification numbers 27-31, 77-84, and 89 are included in FIG. 7D; corresponding to sequence identification numbers 27-31, 51-53, 58-66, and 72-84 are included in FIG. 7E; corresponding to sequence identification numbers 26, 47, and 90-92 are included in FIG. 7F; corresponding to sequence identification numbers 27-31, 47, 51-53, 62-65, 72-84, and 90-92 are included in FIG. 7G; and corresponding to sequence identification numbers 27-31, 51-53, 62-65, 72-84 are included in FIG. 7H.

FIG. 10 shows chromatographs of HPLC analysis (panels 1 and 2) and mass spectral analysis (panel 3) of a 33-mer peptide after treatment with Carboxypeptidase Y ("CPY") at a pH ranging from 4.0 to 7.0 (FIG. 10A-10D) and with *Myxococcus xanthus* prolyl endopeptidase ("MX-PEP") at a pH ranging from 4.0 to 7.0 (FIG. 10E-10H). Amino acid sequences corresponding to sequence identification numbers 10 are included in FIG. 10A; corresponding to sequence identification numbers 10 are included in FIG. 10B; corresponding to sequence identification numbers 10 are included in FIG. 10C; corresponding to sequence identification numbers 10, 12, 50, 112, and 114-117 are included in FIG. 10D; corresponding to sequence identification numbers 1 are included in FIG. 10E; corresponding to sequence identification numbers 1 are included in FIG. 10F; corresponding to sequence identification numbers 10, 62-65, 67-71, and 118-

Figure 1:
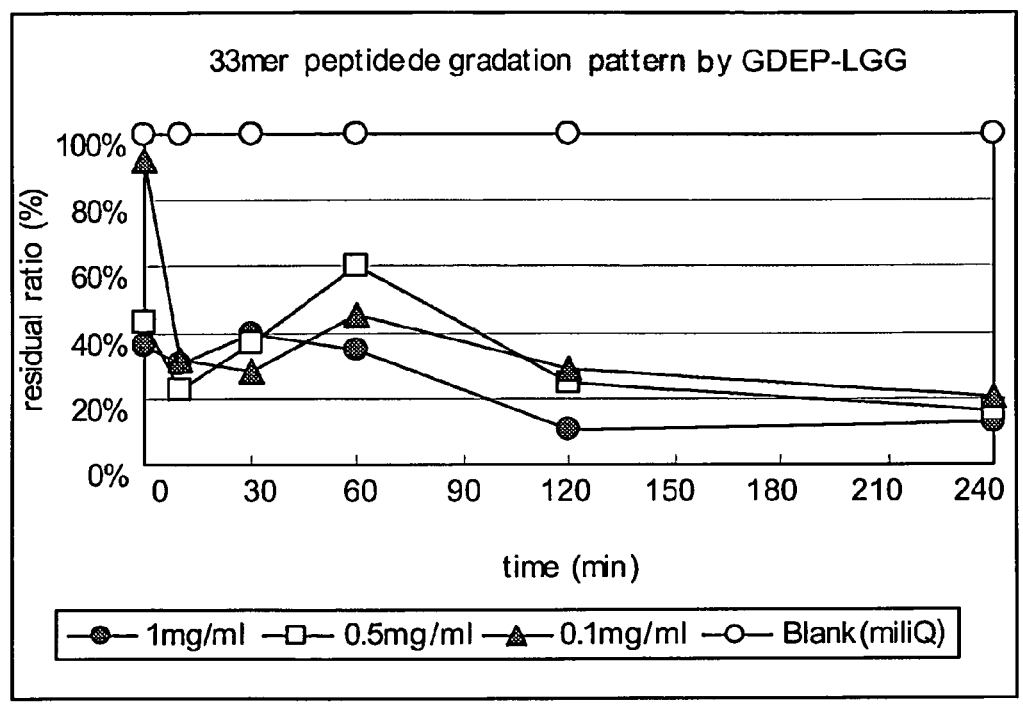
FIG. 1 shows degradation of a 33-mer peptide (as assessed by measuring the levels of intact 33-mer peptide by ELISA) by GDEP-LGG at various doses and times.

120 are included in FIG. 10G; and corresponding to sequence identification numbers 10, 67-71, and 118-120 are included in FIG. 10H.

FIG. 11 shows chromatographs of HPLC analysis (panels 1 and 2) and mass spectral analysis (panel 3) of a 33-mer peptide after treatment with various amounts of CPY (FIG. 11A-11D), MX-PEP (FIG. 11E-11H), and *Aspergillus niger* prolyl endopeptidase ("AN-PEP") (FIG. 11I-11L). FIG. 11 also shows chromatographs of HPLC analysis (panels 1 and 2) and mass spectral analysis (panel 3) of a 33-mer peptide after treatment with CPY (FIG. 11M-11P), MX-PEP (FIG. 11Q-11T), and AN-PEP (FIG. 11U-11V). Amino acid sequences corresponding to sequence identification number 10 is included in FIG. 11A; corresponding to sequence identification numbers 10, 12, and 121 are included in FIG. 11B; corresponding to sequence identification numbers 12, 50, 112, 116-117, and 121 are included in FIG. 11C; corresponding to sequence identification numbers 26, 48, 50, 112, 114-116, and 122 are included in FIG. 11D; corresponding to sequence identification numbers 10, 62-65, 67-71, 118-120, and 123 are included in FIG. 11E; corresponding to sequence identification numbers 1, 10, 62-65, 67-71, 89, 93-99, and 123 are included in FIG. 11F; corresponding to sequence identification numbers 1, 10, 62-65, 89, and 93-99 are included in FIG. 11G; corresponding to sequence identification numbers 1, 10, 62-65, 89, and 93-99 are included in FIG. 11H; corresponding to sequence identification numbers 10, 62-65, 67-71, and 118-120 are included in FIG. 11I; corresponding to sequence identification numbers 10, 62-65, and 67-71 are included in FIG. 11J; corresponding to sequence identification numbers 10, 62-65, 67-71, 118-120, and 123 are included in FIG. 11K; corresponding to sequence identification numbers 10, 62-65, 67-71, 118-120, and 123 are included in FIG. 11L; corresponding to sequence identification numbers 26, 48, 50, 112, 114-116, and 122 are included in FIG. 11M; corresponding to sequence identification numbers 12, 26, 48, 50, 112, 114-117, and 122 are included in FIG. 11N; corresponding to sequence identification numbers 10, 12, 50, 112, 117, and 121 are included in FIG. 11O; corresponding to sequence identification numbers 10 are included in FIG. 11P; corresponding to sequence identification numbers 1, 10, 62-65, 67-71, 89, 93-99, and 123 are included in FIG. 11Q; corresponding to sequence identification numbers 1, 10, 62-65, 67-71, 89, 93-99, and 123 are included in FIG. 11R; corresponding to sequence identification numbers 1, 10, 62-65, 67-71, 89, 93-99, and 123 are included in FIG. 11S; corresponding to sequence identification numbers 10, 62-65, 67-71, 89, 93-99, and 123 are included in FIG. 11T; corresponding to sequence identification numbers 10, 62-65, 67-71, 118-120, and 123 are included in FIG. 11U; and corresponding to sequence identification numbers 10, 62-65, 67-71, 118-120 are included in FIG. 11V.

Figure 12A:
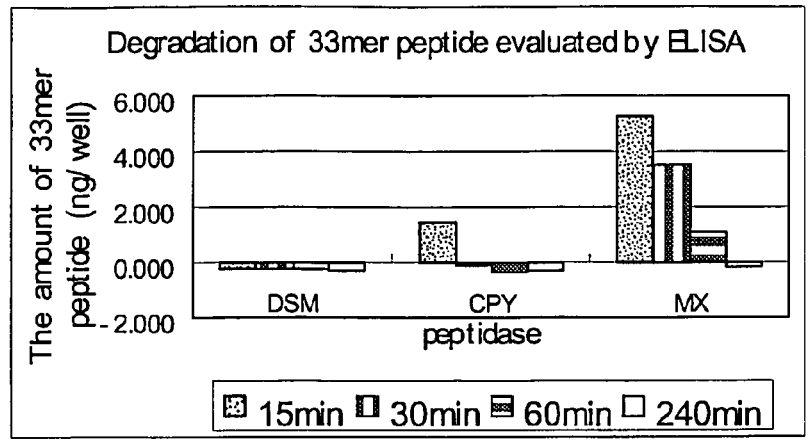
Figure 12B:
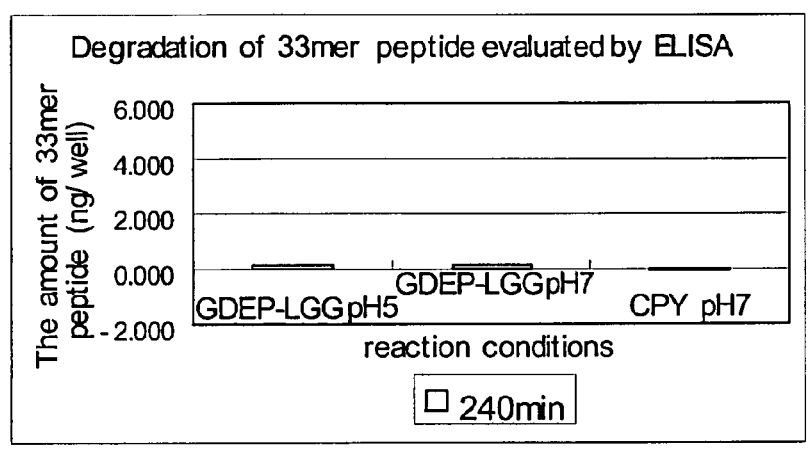
Figure 12C:
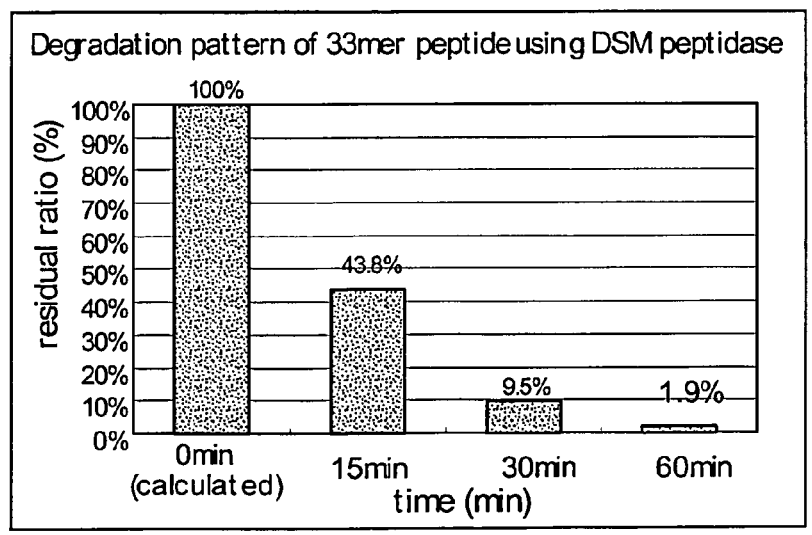

FIG. 12 shows degradation of a 33-mer peptide (as assessed by measuring the levels of intact 33-mer peptide by ELISA) by CPY and the prolyl endopeptidases MX-PEP and AN-PEP (FIG. 12A). FIG. 12 also shows degradation of a 33-mer peptide (as assessed by measuring the levels of intact 33-mer peptide by ELISA) by GDEP-LGG and CPY (FIG. 12B). FIG. 12 also shows degradation of a 33-mer peptide (as assessed by measuring the levels of intact 33-mer peptide by ELISA) by AN-PEP (FIG. 12C).

Figure 13:
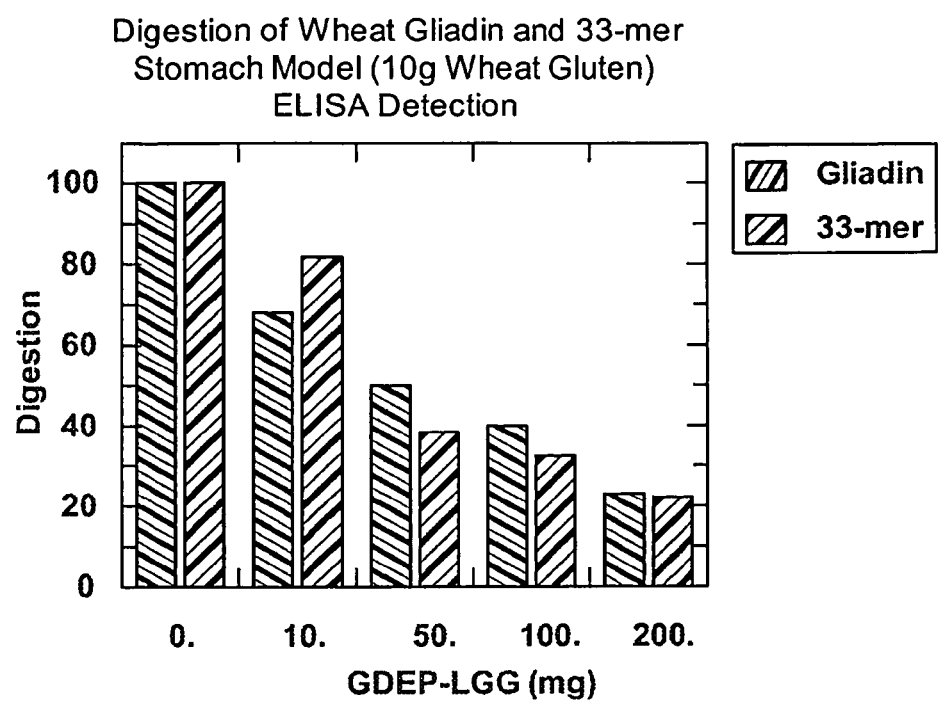

FIG. 13 shows degradation of wheat gliadin and a 33-mer peptide (as assessed by measuring the levels of intact 33-mer peptide by ELISA) by GDEP-LGG in an in vitro gastrointestinal model.

Figure 14:
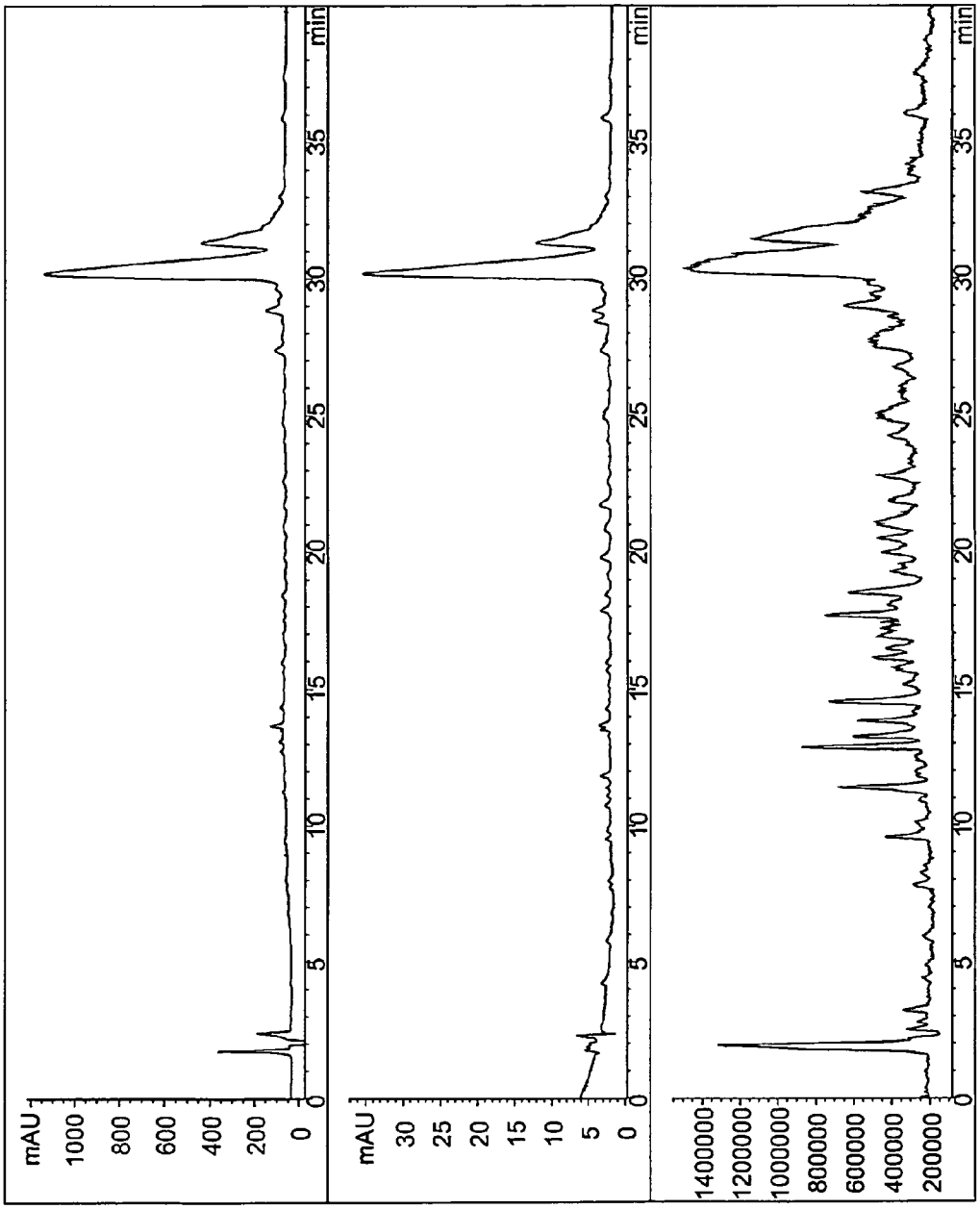

FIG. 14 shows chromatographs of HPLC analysis (panels 1 and 2) and mass spectral analysis (panel 3) of a 33-mer peptide after treatment with digestive enzymes alone (FIG. 14A), CPY (FIG. 14B), GDEP-M (FIG. 14C), and a combination of CPY and GDEP-M (FIG. 14D) in an in vitro gastrointestinal model.

Figure 15:
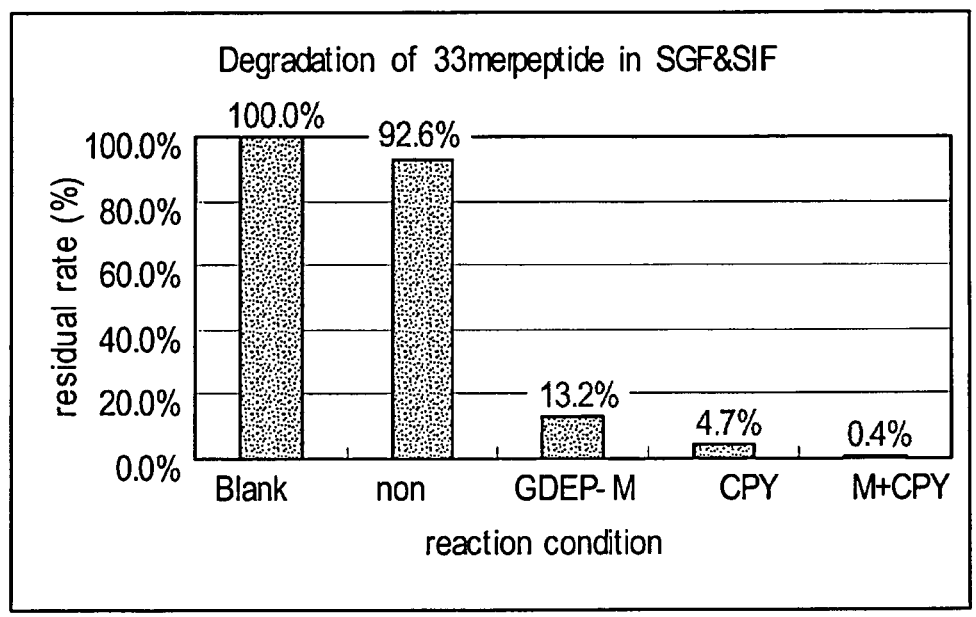

FIG. 15 shows degradation of wheat gliadin and a 33-mer peptide (as assessed by measuring the levels of intact 33-mer peptide by ELISA) by CPY and GDEP-M in an in vitro gastrointestinal model.

Figure 16:
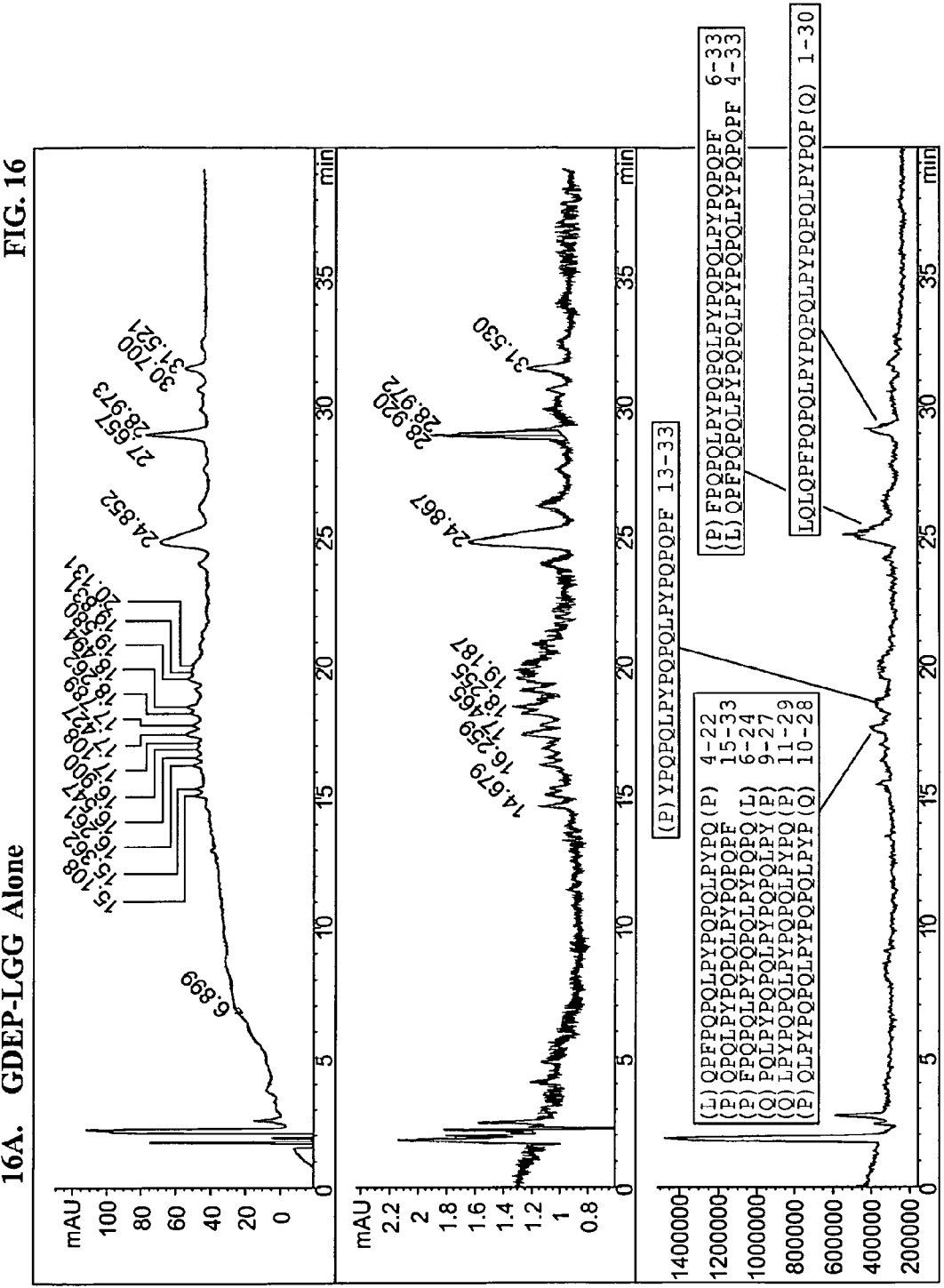

FIG. 16 shows chromatographs of HPLC analysis (panels 1 and 2) and mass spectral analysis (panel 3) of a 33-mer peptide after treatment with GDEP-LGG (FIG. 16A), CPY (FIG. 16B), and a combination of GDEP-LGG and CPY (FIG. 16C). Amino acid sequences corresponding to sequence identification numbers 26, 43-47, and 124-127 are included in FIG. 16A; corresponding to sequence identification numbers 12, 50, 88, 112, and 114-117 are included in FIG. 16B; and corresponding to sequence identification numbers 43-45, and 125-155 are included in FIG. 16C.

FIG. 17 shows protein concentration (A280), 33-mer peptide degradation activity, prolyl endopeptidase activity, and protease activity of fractionated GDEP-LGG.

FIG. 18 shows residual ratio comparisons after analysis by ELISA for gluten digestion with CPY and AN-PEP (FIG. 18A), GDEP-M and GDEP-LGG (FIG. 18B), Aorsin A and Aorsin B (FIG. 18C), a Combination of GDEP-M and some peptidases (FIG. 18D), and a Combination of GDEP-LGG and GDEP-M (FIG. 18E) all at varying amounts of enzyme.

FIG. 19 shows degradation of 33-mer peptide (as assessed by measuring the levels of intact 33-mer peptide by ELISA) from a commercial preparation of the 33-mer peptide (FIG. 19A), ravioli (FIG. 19B), cheese macaroni (FIG. 19C), white bread (FIG. 19D) and roll of bread (FIG. 19E) at various doses (50 mg, 100 mg, 200 mg, and 400 mg) of GDEP-LGG.

FIG. 20 shows degradation of 33-mer peptide (as assessed by measuring the levels of intact 33-mer peptide by ELISA) from ravioli (FIG. 20A), macaroni (FIG. 20B), white bread (FIG. 20C), roll of bread (FIG. 20D), lasagna (FIG. 20E) and pasta (FIG. 20F) at various doses (50 mg, 100 mg, 200 mg, and 400 mg) of GDEP-LGG and GDEP-M. FIG. 20G and FIG. 20H show summaries of degradation of 33-mer peptide (as assessed by measuring the levels of intact 33-mer peptide by ELISA) from ravioli, macaroni, white bread, roll of bread, lasagna, and pasta at various doses (50 mg, 100 mg, 200 mg, and 400 mg) of GDEP-LGG and GDEP-M.

Figure 21:
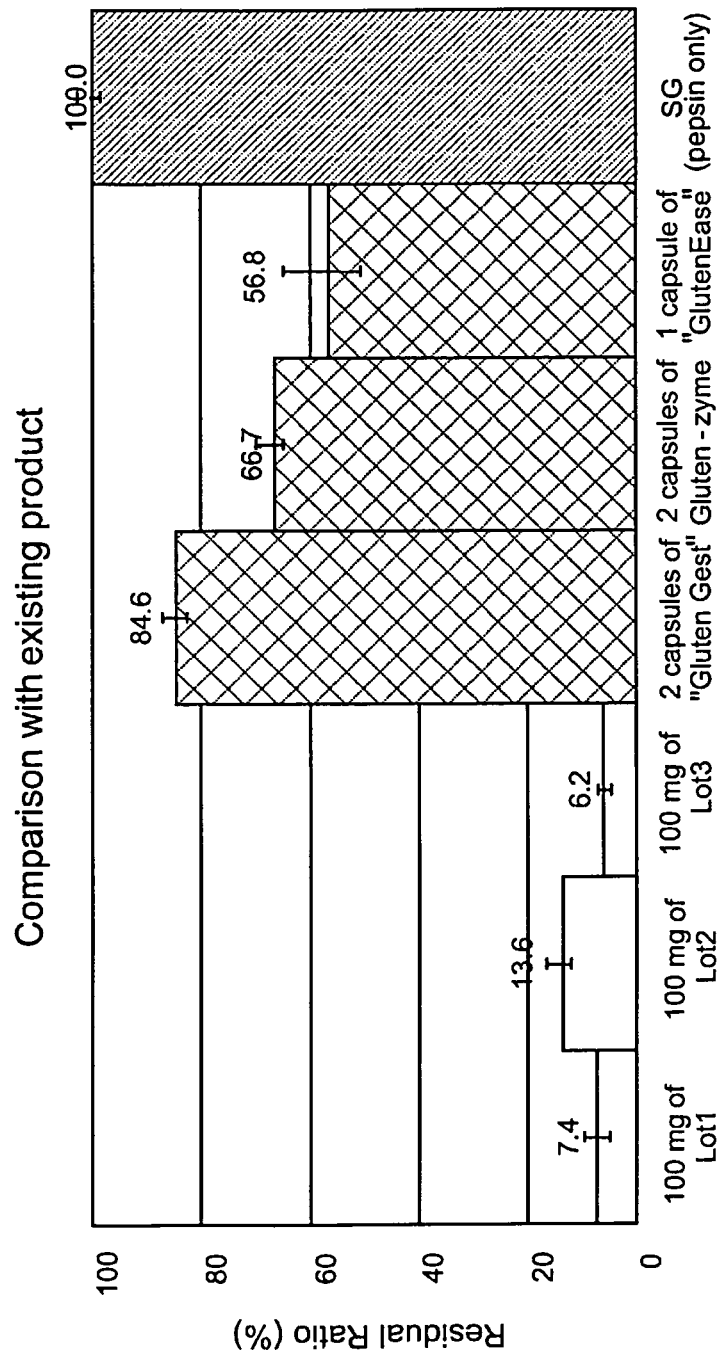

FIG. 21 shows a comparison of residual ratios after degradation of a 33-mer peptide (as assessed by measuring the levels of intact 33-mer peptide by ELISA) by three lots of GDEP-LGG and three existing products ("Gluten Gest," "Gluten-zyme" and "GlutenEase") as well as chromatographs after analysis by HPLC-MS for existing products ("Gluten Gest", "Spectrumzyme", "Gluten-zyme Plus", "Gluten-zyme" and "GlutenEase"), pepsin, a 33-mer control and gluten degrading enzyme preparation at various times throughout the reaction.

Figure 22:
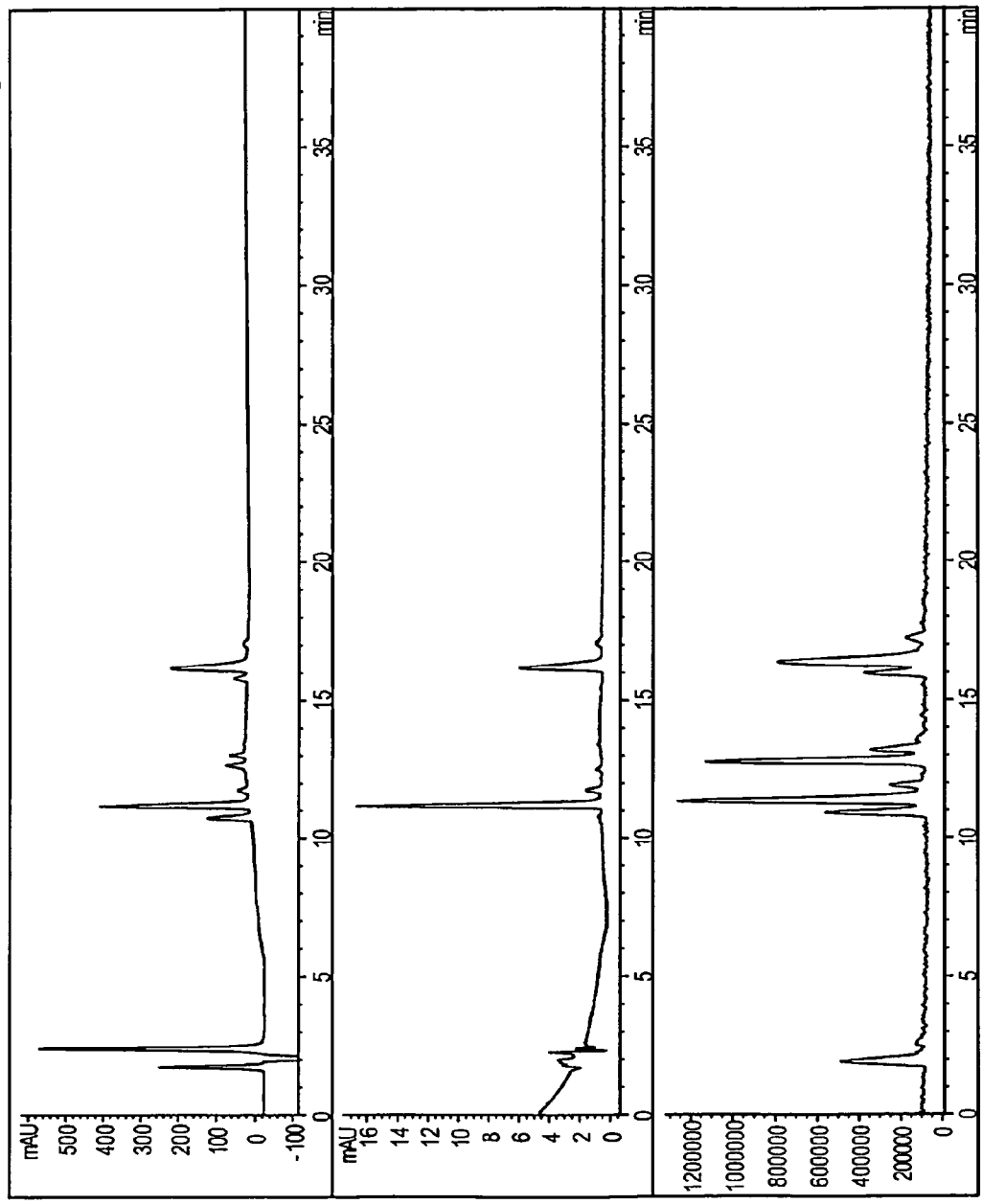

FIG. 22 shows chromatographs of HPLC analysis (panels 1 and 2) and mass spectral analysis (panel 3) of a 33-mer peptide after treatment with papain.

Figure 23:
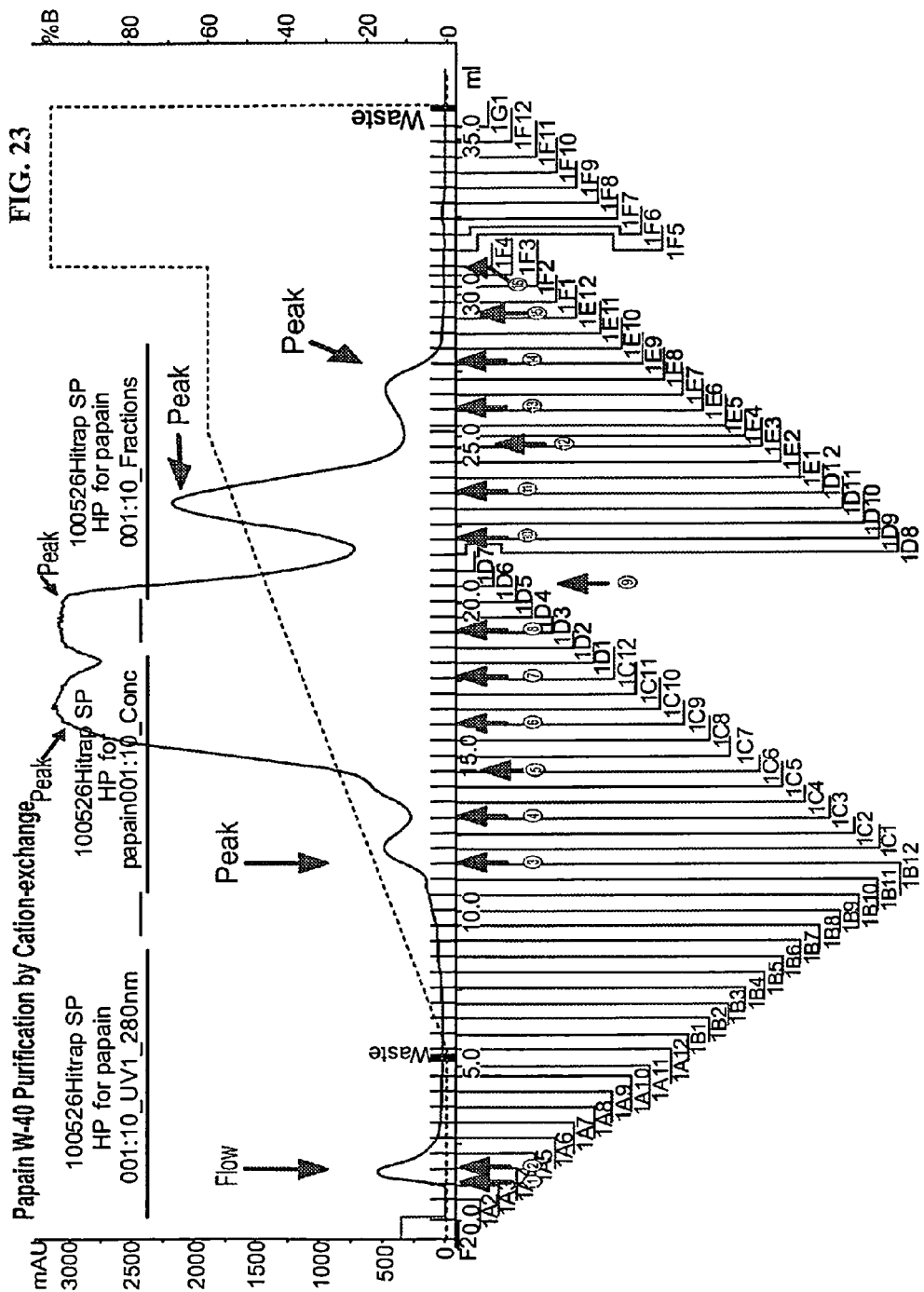

FIG. 23 shows a chromatograph of cation-exchange analysis of papain and mass spectral analysis of a 33-mer peptide after treatment with the papain fractions resultant from the cation-exchange chromatography.

Figure 24:
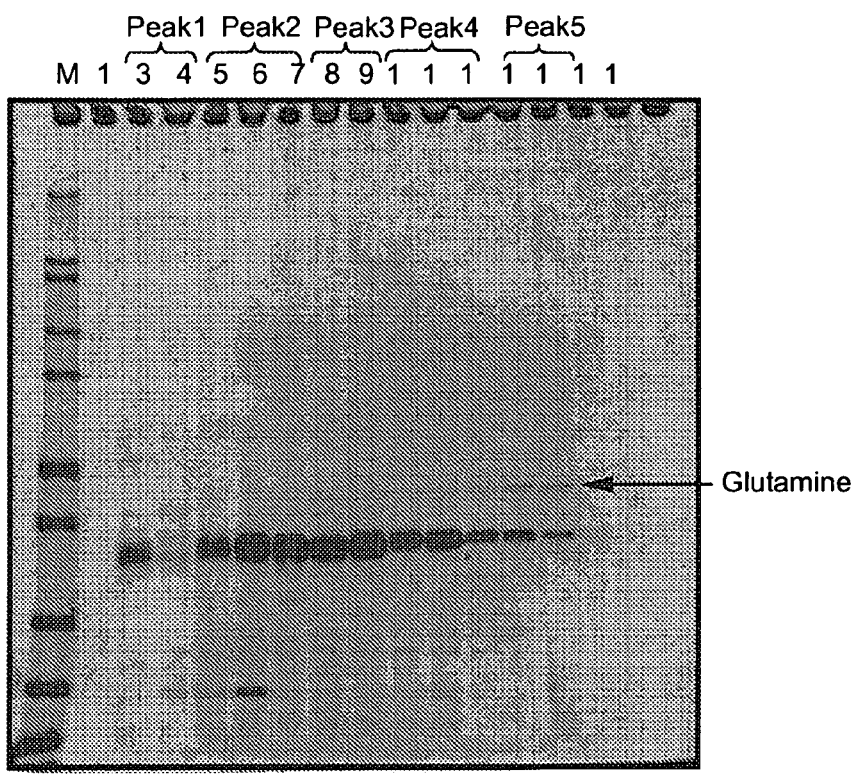

FIG. 24 shows SDS-PAGE gels of papain after fractionation by cation-exchange chromatography.

FIG. 25 shows chromatographs of HPLC analysis for Peak 2 (FIG. 25A) and Peak 3 (FIG. 25B) fractions from papain after purification by cation-exchange chromatography.

Figure 26:
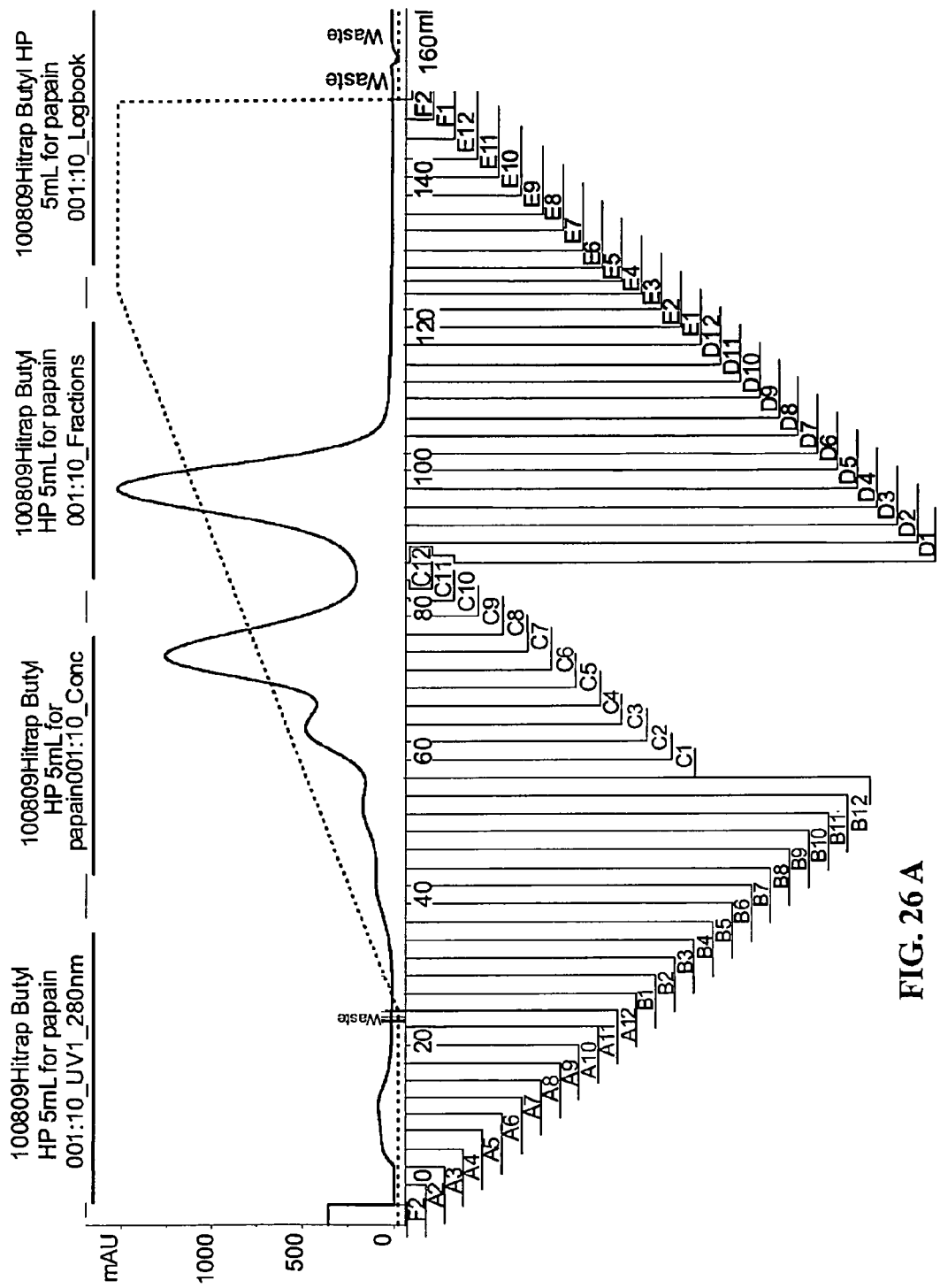

FIG. 26 shows a chromatograph of HPLC analysis for the E9 fraction of the papain purification by cation-exchange chromatography after further hydrophobic interaction chromatography (FIG. 26A) and FRETS analysis (FIG. 26B).

Figure 27:
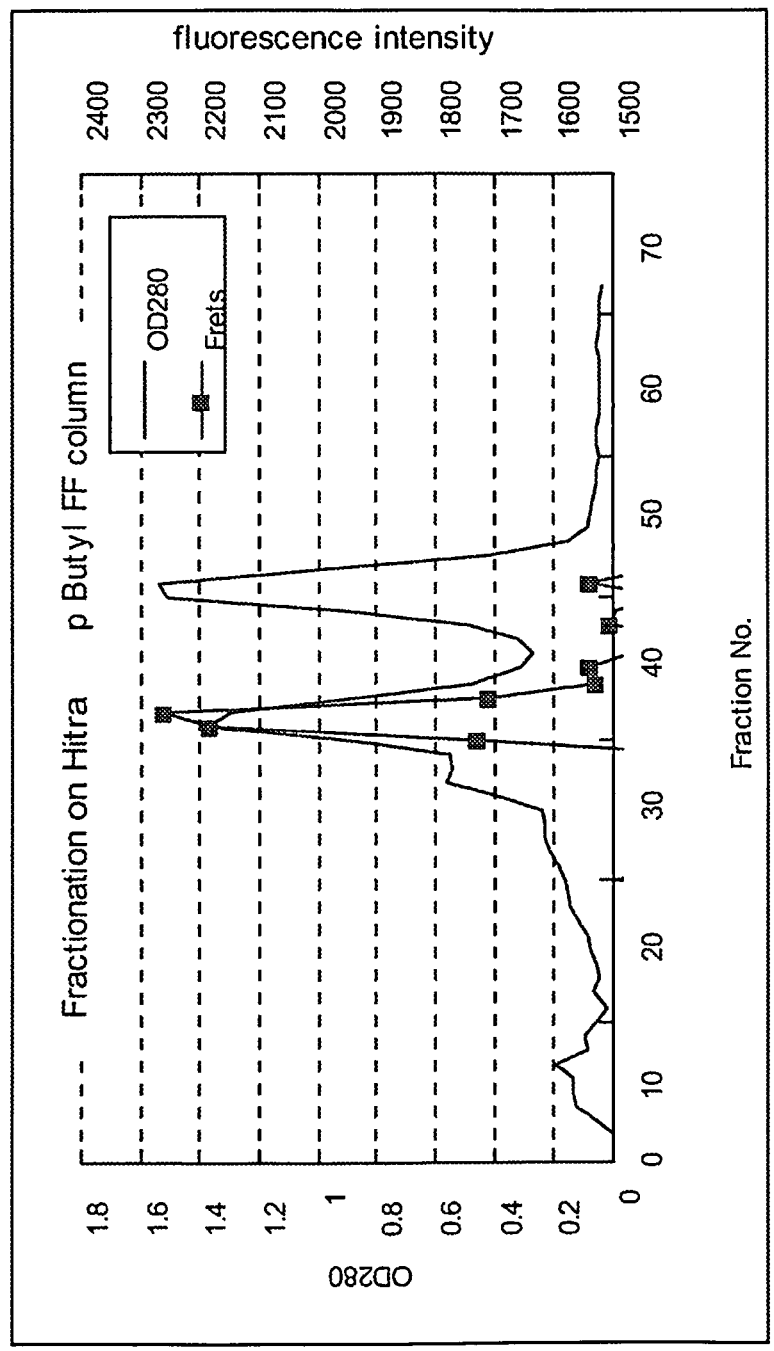

FIG. 27 shows FRETS analysis and chromatographs of mass spectral analysis of a 33-mer peptide after treatment with the resulting fractions.

FIG. 28 shows chromatographs of HPLC analysis for Peaks 3-1 (FIG. 28A), 3-2 (FIG. 28B) and 3 (FIG. 28C) by reverse phase chromatography.

Figure 29:
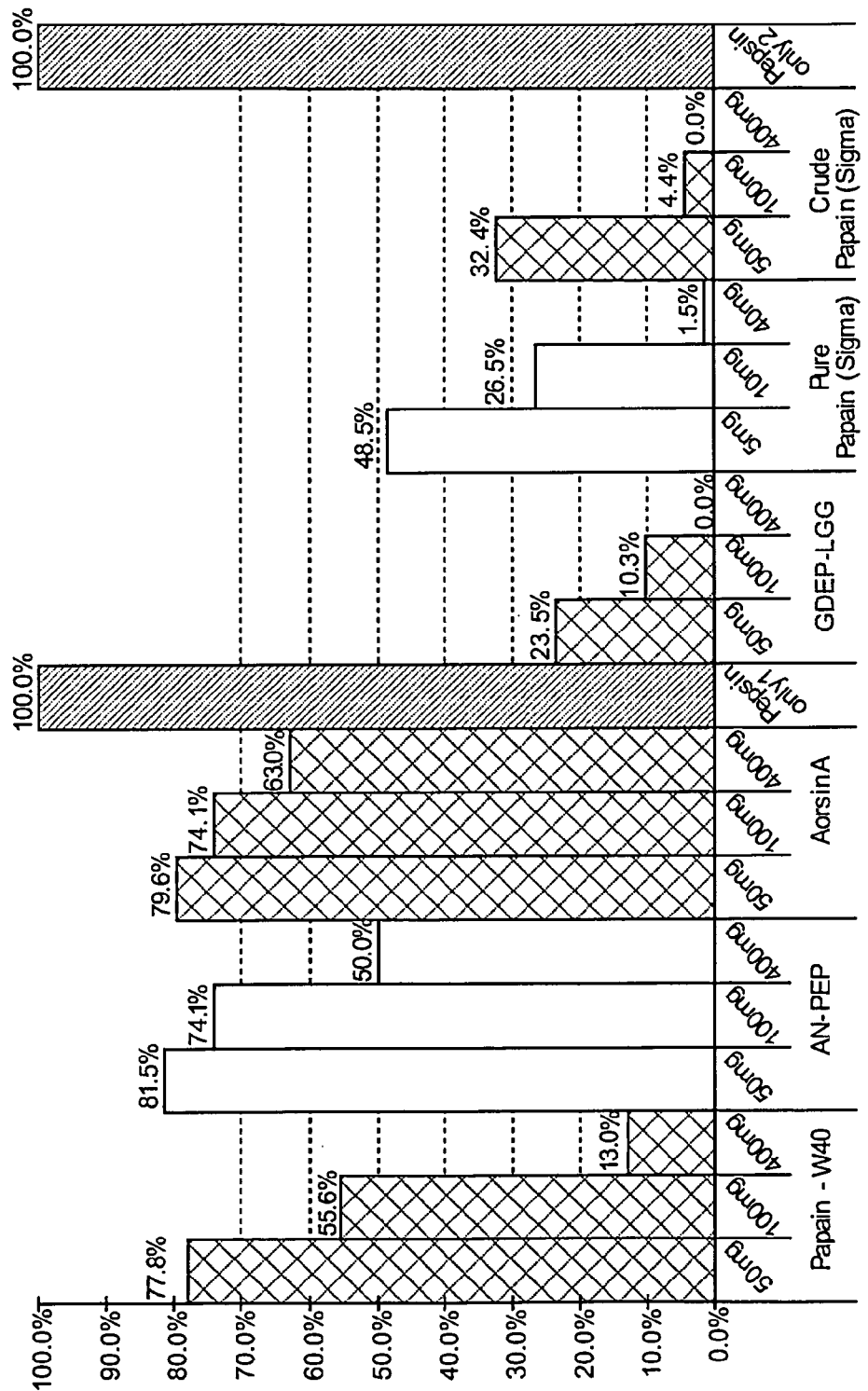

FIG. 29 shows residual ratio comparisons of papain and other enzymes after analysis by ELISA.

FIG. 30 shows the protease activity and hydrolysis activity of papain and GDEP-LGG with a reductant (Glutathione, dithiothreitol, L-Cysteine, or N-Acetyl-L-Cysteine).

FIG. 31 shows the relative activity of an enzyme cocktail comprising GDEP-LGG and papain at various concentrations (FIG. 31A) and chromatographs of HPLC analysis for each concentration (FIGS. 31B-31G).

FIG. 32 shows the results of a FRETS assay screening using a set of 6-mers to for various compositions.

Figure 33:
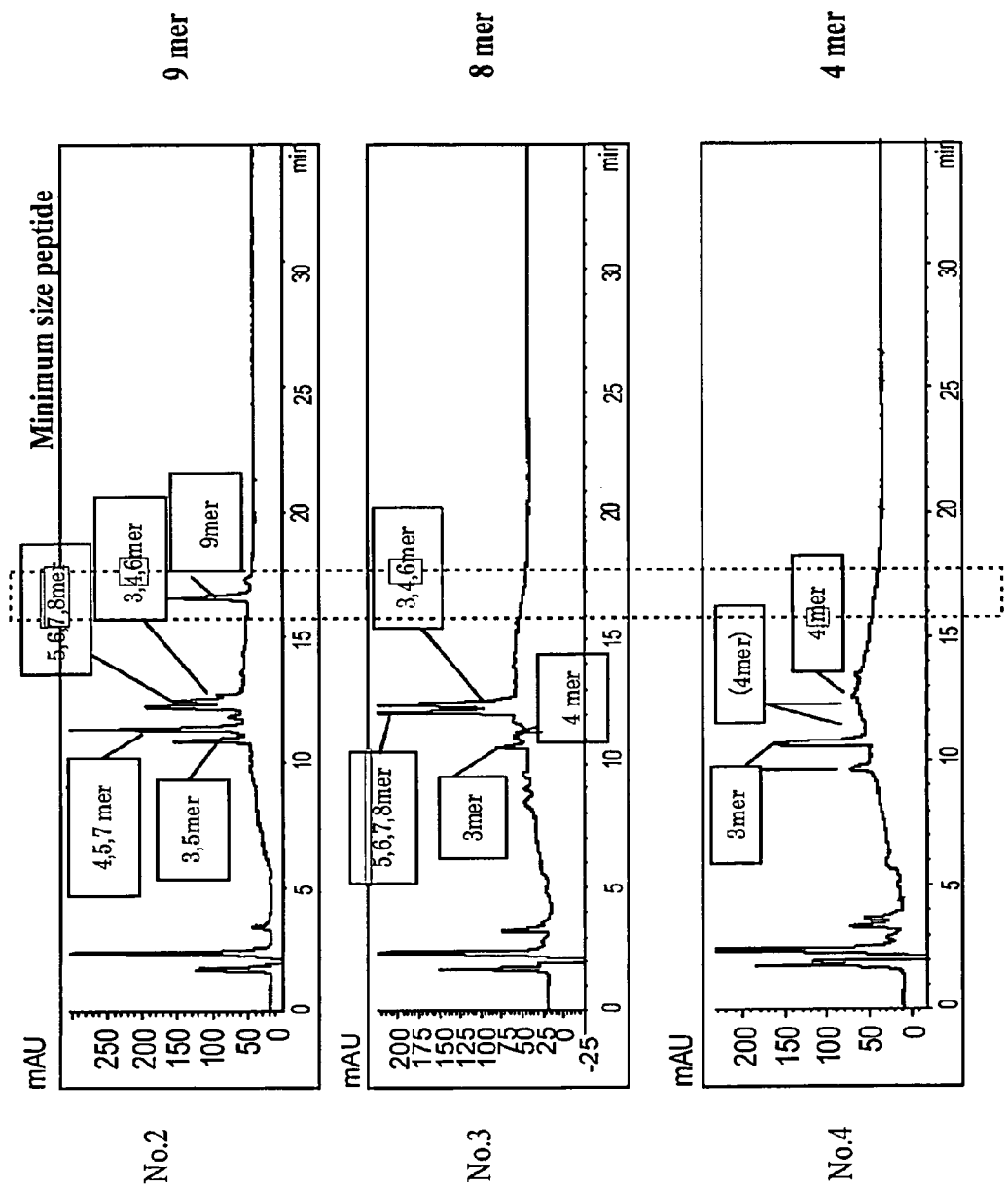

FIG. 33 shows chromatographs of HPLC analysis for the hydrolysis activity of compositions selected from the FRETS assay screening (FIG. 32).

The following table lists all of the amino acid sequences and their corresponding sequence identification numbers.

| Amino Acid Sequence | Seq. ID |
| --- | --- |
| LQLQPFPQPQLPYPQPQLPYPQPQLPYPQPQPF | SEQ ID NO: 1 |
| QPQLPYPQPQL | SEQ ID NO: 2 |
| LQLQPFPQPQL | SEQ ID NO: 3 |
| PFPQPQLPYPQPQLP | SEQ ID NO: 4 |
| PYPQPQLPYPQPQPF | SEQ ID NO: 5 |
| LQLQPFPQPQLPYPQPQLPYPQPQL | SEQ ID NO: 6 |
| PYPQPQPF | SEQ ID NO: 7 |
| QPQLPYPQPQLPYPQPQL | SEQ ID NO: 8 |
| LQLQPFPQPQLPYPQPQL | SEQ ID NO: 9 |
| LQLQP | SEQ ID NO: 10 |
| QPQLPYPQPQ | SEQ ID NO: 11 |
| LQLQPFPQPQ | SEQ ID NO: 12 |
| QLQPFPQPQL | SEQ ID NO: 13 |
| LQPFPQPQLPYPQPQ | SEQ ID NO: 14 |
| QPFPQPQLPYPQPQL | SEQ ID NO: 15 |
| QLQPFPQPQLPYPQP | SEQ ID NO: 16 |
| QLQPFPQPQLPYPQPQLPYPQP | SEQ ID NO: 17 |
| LQPFPQPQLPYPQPQLPYPQPQ | SEQ ID NO: 18 |
| QPFPQPQLPYPQPQLPYPQPQL | SEQ ID NO: 19 |
| LQPFPQPQLPYPQPQLPYPQPQLPYPQPQPF | SEQ ID NO: 20 |
| LQPFPQPQLPYPQPQLPYPQPQLPYP | SEQ ID NO: 21 |
| PQPQLPYPQPQLPYP | SEQ ID NO: 22 |
| PQLPYPQPQLPYPQP | SEQ ID NO: 23 |
| LPYPQPQLPYPQPQP | SEQ ID NO: 24 |
| PYPQPQLPYPQPQLP | SEQ ID NO: 25 |
| LQLQPFPQPQLPYPQPQLPYPQPQLPYPQP | SEQ ID NO: 26 |
| QPFPQPQLPYPQPQLPYPQPQLPYPQP | SEQ ID NO: 27 |
| PQPQLPYPQPQLPYPQPQLPYPQPQPF | SEQ ID NO: 28 |
| PFPQPQLPYPQPQLPYPQPQLPYPQPQ | SEQ ID NO: 29 |
| FPQPQLPYPQPQLPYPQPQLPYPQPQP | SEQ ID NO: 30 |
| QPFPQPQLPYPQPQLPYPQPQLPYPQPQP | SEQ ID NO: 31 |
| QPFPQPQLPYP | SEQ ID NO: 32 |
| PFPQPQLPYPQ | SEQ ID NO: 33 |
| FPQPQLPYPQP | SEQ ID NO: 34 |
| PQLPYPQPQPF | SEQ ID NO: 35 |
| LPYPQPQLPYP | SEQ ID NO: 36 |
| YPQPQLPYPQPQPF | SEQ ID NO: 37 |
| QPQLPYPQPQPF | SEQ ID NO: 38 |
| QPFPQPQLPYPQ | SEQ ID NO: 39 |
| FPQPQLPYPQPQ | SEQ ID NO: 40 |
| QPFPQPQLPYPQPQLPYPQPQLPYPQ | SEQ ID NO: 41 |
| FPQPQLPYPQPQLPYPQPQLPYPQPQ | SEQ ID NO: 42 |
| PQLPYPQPQLPYPQPQLPY | SEQ ID NO: 43 |
| LPYPQPQLPYPQPQLPYPQ | SEQ ID NO: 44 |
| QLPYPQPQLPYPQPQLPYP | SEQ ID NO: 45 |
| FPQPQLPYPQPQLPYPQPQLPYPQPQPF | SEQ ID NO: 46 |
| QPFPQPQLPYPQPQLPYPQPQLPYPQPQPF | SEQ ID NO: 47 |
| LQLQPFPQPQLPYPQPQLPYPQPQLPYPQPQP | SEQ ID NO: 48 |
| LQPFPQPQLPYPQPQL | SEQ ID NO: 49 |
| LQLQPFPQPQLPYPQP | SEQ ID NO: 50 |
| PQPQLPYPQPQLPYPQPQ | SEQ ID NO: 51 |
| QPQLPYPQPQLPYPQPQP | SEQ ID NO: 52 |
| QLQPFPQPQLPYPQPQLP | SEQ ID NO: 53 |
| QLQPFPQPQLPYPQPQLPYPQPQLPYPQPQP | SEQ ID NO: 54 |
| QPFPQPQLPYPQPQLPYPQPQLPYPQPQ | SEQ ID NO: 55 |
| LQLQPFPQPQLPYPQPQLPYPQPQLPYP | SEQ ID NO: 56 |
| QLQPFPQPQLPYPQPQLPYPQPQLPYPQPQPF | SEQ ID NO: 57 |
| PQPQLPYP | SEQ ID NO: 58 |
| PQLPYPQP | SEQ ID NO: 59 |
| PYPQPQLP | SEQ ID NO: 60 |
| LPYPQPQP | SEQ ID NO: 61 |

-continued

| Amino Acid Sequence | Seq. ID |
|---|---|
| QPFP | SEQ ID NO: 62 |
| PFPQ | SEQ ID NO: 63 |
| PQPF | SEQ ID NO: 64 |
| FPQP | SEQ ID NO: 65 |
| LPYP | SEQ ID NO: 66 |
| QPFQP | SEQ ID NO: 67 |
| PFPQP | SEQ ID NO: 68 |
| PQPQPF | SEQ ID NO: 69 |
| PQLPYP | SEQ ID NO: 70 |
| LPYPQP | SEQ ID NO: 71 |
| PYPQPQLPYPQPQ | SEQ ID NO: 72 |
| YPQPQLPYPQPQP | SEQ ID NO: 73 |
| LQPFPQPQLPYPQ | SEQ ID NO: 74 |
| QLQPFPQPQLPYP | SEQ ID NO: 75 |
| FPQPQLPYPQPQL | SEQ ID NO: 76 |
| PQLPYPQPQLPYPQPQLPYPQP | SEQ ID NO: 77 |
| LPYPQPQLPYPQPQLPYPQP | SEQ ID NO: 78 |
| PQPQLPYPQPQLPYPQPQLPYP | SEQ ID NO: 79 |
| PYPQPQLPYPQPQLPYPQPQ | SEQ ID NO: 80 |
| YPQPQLPYPQPQLPYPQPQP | SEQ ID NO: 81 |
| QLQPFPQPQLPYPQPQLPYP | SEQ ID NO: 82 |
| LQPFPQPQLPYPQPQLPYPQ | SEQ ID NO: 83 |
| FPQPQLPYPQPQLPYPQPQL | SEQ ID NO: 84 |
| QPQLPY | SEQ ID NO: 85 |
| QLPYPQ | SEQ ID NO: 86 |
| YPQPQL | SEQ ID NO: 87 |
| LQLQPF | SEQ ID NO: 88 |
| LQLQPFP | SEQ ID NO: 89 |
| LPYPQPQLPYPQPQLPYPQPQPF | SEQ ID NO: 90 |
| FPQPQLPYPQPQLPYPQPQLPYP | SEQ ID NO: 91 |
| PFPQPQLPYPQPQLPYPQPQLPY | SEQ ID NO: 92 |
| PQPQLPY | SEQ ID NO: 93 |
| QPQLPYP | SEQ ID NO: 94 |
| PQLPYPQ | SEQ ID NO: 95 |
| QLPYPQP | SEQ ID NO: 96 |
| LPYPQPQ | SEQ ID NO: 97 |
| PYPQPQL | SEQ ID NO: 98 |
| YPQPQLP | SEQ ID NO: 99 |
| PFPQPQLPYPQPQLPY | SEQ ID NO: 100 |
| FPQPQLPYPQPQLPYP | SEQ ID NO: 101 |
| LPYPQPQLPYPQPQPF | SEQ ID NO: 102 |
| PFPQPQLPY | SEQ ID NO: 103 |
| FPQPQLPYP | SEQ ID NO: 104 |
| LPYPQPQPF | SEQ ID NO: 105 |
| QPFPQPQ | SEQ ID NO: 106 |
| QPFPQ | SEQ ID NO: 107 |
| QPQPF | SEQ ID NO: 108 |
| FPQPQ | SEQ ID NO: 109 |
| PQPQP | SEQ ID NO: 110 |
| QPQLPYPQPQLPYPQPQ | SEQ ID NO: 111 |
| LQLQPFPQPQLPYPQPQ | SEQ ID NO: 112 |
| QLQPFPQPQLPYPQPQL | SEQ ID NO: 113 |
| LQLQPFPQPQLPYPQPQLPYPQPQ | SEQ ID NO: 114 |
| LQLQPFPQPQLPYPQPQLPYPQ | SEQ ID NO: 115 |
| LQLQPFPQPQLPYPQPQLPYPQP | SEQ ID NO: 116 |
| LQLQPFPQPQLPYPQ | SEQ ID NO: 117 |
| PYPQ | SEQ ID NO: 118 |
| YPQP | SEQ ID NO: 119 |
| LQPF | SEQ ID NO: 120 |
| LQLQPFPQP | SEQ ID NO: 121 |
| LQLQPFPQPQLPYPQPQLPYPQPQLPYPQPQ | SEQ ID NO: 122 |
| PQPQLP | SEQ ID NO: 123 |
| YPQPQLPYPQPQLPYPQPQPF | SEQ ID NO: 124 |
| QPFPQPQLPYPQPQLPYPQ | SEQ ID NO: 125 |
| QPQLPYPQPQLPYPQPQPF | SEQ ID NO: 126 |
| FPQPQLPYPQPQLPYPQPQ | SEQ ID NO: 127 |
| QPFPQPQLPYPQPQ | SEQ ID NO: 128 |
| PQPQLPYPQPQLPY | SEQ ID NO: 129 |
| QPQLPYPQPQLPYP | SEQ ID NO: 130 |
| PQLPYPQPQLPYPQ | SEQ ID NO: 131 |
| QLPYPQPQLPYPQP | SEQ ID NO: 132 |
| LPYPQPQLPYPQPQ | SEQ ID NO: 133 |
| PYPQPQLPYPQPQL | SEQ ID NO: 134 |
| YPQPQLPYPQPQLP | SEQ ID NO: 135 |
| LQLQPFPQPQLPYP | SEQ ID NO: 136 |
| QPFPQPQLPYPQPQLPYP | SEQ ID NO: 137 |
| PQLPYPQPQLPYPQPQPF | SEQ ID NO: 138 |

| Amino Acid Sequence | Seq. ID |
|---|---|
| PFPQPQLPYPQPQLPYPQ | SEQ ID NO: 139 |
| FPQPQLPYPQPQLPYPQP | SEQ ID NO: 140 |
| LPYPQPQLPYPQPQLPYP | SEQ ID NO: 141 |
| PYPQPQLPYPQPQLPYPQPQP | SEQ ID NO: 142 |
| LQPFPQPQLPYPQPQLPYPQP | SEQ ID NO: 143 |
| PFPQPQLPYPQPQLPYPQPQL | SEQ ID NO: 144 |
| FPQPQLPYPQPQLPYPQPQLP | SEQ ID NO: 145 |
| PQPQLPYPQPQLPYPQ | SEQ ID NO: 146 |
| QPQLPYPQPQLPYPQP | SEQ ID NO: 147 |
| PQLPYPQPQLPYPQPQ | SEQ ID NO: 148 |
| QLPYPQPQLPYPQPQP | SEQ ID NO: 149 |
| PQLPYPQPQLPYPQPQLPYPQ | SEQ ID NO: 150 |
| LPYPQPQLPYPQPQLPYPQPQ | SEQ ID NO: 151 |
| PQPQLPYPQPQLPYPQPQLPY | SEQ ID NO: 152 |
| QPQLPYPQPQLPYPQPQLPYP | SEQ ID NO: 153 |
| QLPYPQPQLPYPQPQLPYPQP | SEQ ID NO: 154 |
| LQLQPFPQPQLPYPQPQLPYP | SEQ ID NO: 155 |
| LQLQPEPQPQLPYPQPQLPYQPQLPYPQPQPF | SEQ ID NO: 156 |

DETAILED DESCRIPTION OF THE INVENTION

The present technology generally relates to an enzyme composition. The enzyme composition may be used to treat gluten intolerant and/or gluten sensitive subjects, including subjects suffering from non-Celiac gluten sensitivity ("NCGS") and/or non-Celiac gluten intolerance ("NCGI"). The enzyme composition may also be used to reduce gluten exposure in certain individuals. For example, the enzyme composition may also be used as a prophylactic to reduce or prevent exposure to gluten oligopeptides, such as a 33-mer peptide derived from α-2 gliadin, to limit, reduce, prevent, or control the development of gluten intolerance and/or gluten insensitivity. A 33-mer peptide fragment of an α-gliadin, LQLQPFPQPQLPYPQPQLPYPQPQLPYPQPQPF (SEQ ID NO:1), is naturally formed by digestion with gastric and pancreatic enzymes and is resistant to further degradation by digestive enzymes.

Many food and beverages include gluten oligopeptides, such as a 33-mer peptide derived from α-2 gliadin. The digestion of gluten-related peptides, including the 33-mer peptide derived from α-2 gliadin, offers physiological benefits, such as reduced exposure to gluten and gluten-related peptides. This may be particularly beneficial for populations or specific individuals (including human or animal subjects) that do not effectively or efficiently hydrolyze gluten (e.g., whose digestive systems lack the enzyme activity needed to effectively or efficiently hydrolyze gluten and/or gluten-related peptides) and to individuals desiring to reduce their exposure to gluten and gluten-related peptides.

In certain embodiments, the enzyme composition of the present technology is a nutraceutical. The term "nutraceutical" has been used to refer to any food product or substance that is intended to be, or reasonably expected to be, ingested and may provide medical or health benefits, including the prevention and/or treatment of NCGS and/or NCGI and/or related symptoms, including, but not limited to, abdominal pain, bloating, bowel discomfort, diarrhea, flatulence, and nutrient malabsorption. Compositions falling under the label "nutraceutical" may range from isolated nutrients, dietary supplements, and enzyme compositions to genetically engineered designer foods, herbal products, and processed foods such as cereals, soups and beverages. In a more technical sense, the term "nutraceutical" refers to an ingestible food product generally sold in medicinal forms and demonstrated to have a physiological benefit by, for example, ameliorating, treating, prevent, reducing the incidence of, or providing protection against, an acute or chronic disease, disorder, or other symptomology.

In certain embodiments, one or more enzyme compositions of the present technology may be used to treat any disease amenable to treatment by a prevention of and/or reduction in gluten exposure, including, for example Celiac disease, thyroid diseases, such as hypothyroidism and neurological diseases, such as autism, cerebellar ataxia, peripheral neuropathies, and schizophrenia.

In certain embodiments, the enzyme compositions of the present technology may comprise any enzyme or mixture of enzymes. In certain embodiments, an enzyme of the enzyme compositions of the present technology is a protein reducing enzyme, including, for example, proteases and peptidases such as exoproteases, endoproteases, and acid stable proteases. In certain embodiments, the enzyme composition can include a protease. Generally, proteases are enzymes that break peptide bonds between the amino acids of proteins. A suitable subset of enzymes includes enzymes derived from *Aspergillus oryzae*. For example, the enzyme composition may comprise a gluten degrading enzyme preparation, papain, purified papain, activated papain, chymopapain, or a combination thereof. The enzyme composition may also include a carboxypeptidase, such as Carboxypeptidase Y ("CPY"). The enzyme composition may also include a semi-alkali protease. The preparation may also include a preparation from *Penicillium citrinum*. Enzyme compositions of the present technology are useful, for example, in the treatment of gluten intolerance, and in reducing exposure to gluten oligopeptides, including the 33-mer derived from α-2 gliadin.

As used herein, the term "gluten degrading enzyme preparation" ("GDEP") is used to refer to an enzyme preparation that contains at least Oryzin, Neutral protease I ("NPI") and Neutral protease II ("NPII").

GDEP having not less than about 70 unit/g peptidase activity at a neutral pH by the leucyl-glycyl-glycine ("LGG") method is referred to herein as "GDEP-LGG". GDEP having not less than about 1,400 u/g peptidase activity at a neutral pH by the leucylnaphthylamide ("LNA") method is referred to herein as "GDEP-LNA". GDEP having not less than about 5,500 unit/g protease activity at an acidic pH is referred to herein as "GDEP-M". GDEP having not less than about 20,000 unit/g protease activity at a neutral pH is referred to herein as "GDEP-2A". GDEP having not less than about 10,000 unit/g protease activity at a neutral pH is referred to herein as "GDEP-AH".

In one embodiment, a GDEP-LGG is a peptidase preparation derived from Koji mold (*Aspergillus oryzae*). The gluten degrading enzyme preparation production strain is derived by subjecting *Aspergillus oryzae* to a course of mutigenesis, including UV mutagenesis. For example, yellow Koji mold, which contains *Aspergillus oryzae*, is subjected to UV mutagenesis to produce "A strain," which is subjected to UV mutagenesis to produce 90-76, which has a proteolytic activity of about 500-600 u/g. The 90-76 strain is further subjected to UV mutagenesis to produce the 90-51 strain, which has a proteolytic activity of about 800-1000 u/g. Following UV mutagenesis, Mono Spore Isolation (M.S.I.) is performed to obtain a mono-colony on the medium plate. This procedure yields the gluten degrading enzyme preparation production strain. The proteolytic activity of the gluten degrading enzyme preparation production strain is about 2 times as much as that of the parent strain.

An exemplary GDEP-LGG composition has not less than about 70 u/g peptidase activity at a pH of about 7.0. GDEP-LGG can be obtained from *Aspergillus oryzae* by methods known in the art, and diluted or concentrated prior to use. Preparations with GDEP-LGG can be obtained by spray drying to avoid inactivation of peptidases. The production process includes, for example, solid fermentation, followed by water extraction, filtration, ultra-filtration, and, finally, spray-drying.

In at least some embodiments of the present technology, GDEP-LGG cuts at the carboxyl side of Gln, Ser, Thr, Met, Arg, Ala, Lys, Phe, and Leu. As determined by assessing activity against substrate Z-Gly-Pro-pNA, GDEP-LGG does not possess prolyl-endopeptidase activity. Nonetheless, GDEP-LGG partially hydrolyzes a 33-mer peptide and remains effective even at an acidic pH. Using a 33-mer peptide as a substrate, gluten degrading enzyme preparation digests approximately 90% of the 33-mer. In an in vitro gastrointestinal model, 200 mg gluten degrading enzyme preparation digests approximately 80% of the 33-mer from 10 g of wheat gluten as compared to the 33-mer level present without added enzyme (control).

In certain embodiments, the enzyme composition of the present technology includes papain. A typical commercial preparation of papain is commercially available as Papain W-40 bulk. This commercial preparation may be used at the given concentration, or the commercial preparation may be diluted or concentrated for use.

In certain embodiments, the enzyme composition of the present technology includes purified papain. Purification methods include cation-exchange chromatography and hydrophobic interaction chromatography.

In certain embodiments, the enzyme composition of the present technology includes chymopapain.

In certain embodiments, the enzyme composition of the present technology includes activated papain. For example, papain can be activated by a reductant. Suitable reductants for use in the present technology include, but are not limited to, Glutathione, dithiothreitol ("DTT"), L-Cysteine, and N-Acetyl-L-Cysteine.

In certain embodiments, the enzyme composition of the present technology is a mixture of enzymes or enzyme compositions. In certain embodiments, the components of the mixture have an additive. In certain other embodiments, the components of the mixture have a synergistic effect, for example, an enzyme composition comprising a mixture of gluten degrading enzyme preparation and papain has an unexpectedly synergistic effect on 33-mer peptide degradation.

In certain embodiments, the enzyme composition of the present technology includes GDEP-M. GDEP-M can be obtained from *Aspergillus oryzae* by methods known in the art, and diluted or concentrated prior to use. Preparations with GDEP-M can be obtained by spray drying or by ethanol precipitation. Spray drying produces more peptidase activity compared to ethanol precipitation protease activity. In certain embodiments, the GDEP-M used has a protease activity of not less than about 5,500 u/g at a pH of about 3.0. This preparation may be used at the given concentration, or the preparation may be diluted or concentrated for use.

In certain embodiments, the enzyme composition of the present technology includes GDEP-2A. GDEP-2A can be obtained from *Aspergillus oryzae* by methods known in the art, and diluted or concentrated prior to use. Preparations with GDEP-2A can be obtained by spray drying or by ethanol precipitation. Spray drying produces more peptidase activity compared to ethanol precipitation protease activity. In certain embodiments, the GDEP-2A used has a protease activity of not less than about 20,000 u/g at a pH of about 7.0. This preparation may be used at the given concentration, or the preparation may be diluted or concentrated for use.

In certain embodiments, the enzyme composition of the present technology includes GDEP-AH. GDEP-AH can be obtained from *Aspergillus oryzae* by methods known in the art, and diluted or concentrated prior to use. Preparations with GDEP-AH can be obtained by spray drying. In certain embodiments, the GDEP-AH used has a protease activity of not less than about 10,000 u/g at a pH of about 7.0. This preparation may be used at the given concentration, or the preparation may be diluted or concentrated for use.

In certain embodiments, the enzyme composition of the present technology includes GDEP-LNA. GDEP-LNA can be obtained from *Aspergillus oryzae* by methods known in the art, and diluted or concentrated prior to use. Preparations with GDEP-LNA can be obtained by spray drying. In certain embodiments, the GDEP-LNA has not less than about 1,400 u/g peptidase activity at a pH of about 7.0 by leucylnaphthylamide ("LNA") method. This preparation may be used at the given concentration, or the preparation may be diluted or concentrated for use.

In certain embodiments, the enzyme composition of the present technology comprises specific protease components of GDEP-M. For example, Aorsin is a serine proteinase with trypsin-like specificity at an acidic pH that is purified from GDEP-M. Aorsin A and Aorsin B are characterized in Japanese Patent Nos. JP4401555 and JP2009-232835A, each of which are incorporated by reference in their entireties. Aorsin efficiently hydrolyzes a 33-mer peptide at an acidic pH. The nucleotide and amino acid sequence of Aorsin was published in Lee, et al., Biochem. J. 371 (PT 2), 541-548 (2003). The nucleotide sequence for Aorsin A has the GenBank Accession Number AB084899.1, and the corresponding amino acid sequence has the GenBank Accession Number BAB97387. The nucleotide sequence for Aorsin B has the GenBank Accession Number XM 001820783.1, and the corresponding amino acid sequence has the GenBank Accession Number XP_001820835.1.

In certain embodiments, the enzyme composition of the present technology comprises an enzyme having the amino acid sequence of Aorsin or an amino acid sequence having at least about 70% identity with the amino acid sequence of Aorsin. In certain embodiments, the amino acid may have at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity with the amino acid sequence of Aorsin.

In certain embodiments, the enzyme composition of the present technology comprises an enzyme having an amino acid sequence substantially homologous to Aorsin. Two amino acid sequences are "substantially homologous" when at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of the amino acids are identical; or at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of the amino acids are similar in that they are functionally identical. Homologous sequences may be identified by alignment using, for example, the GCG (Genetics Computer Group, Program Manual for the GCG Package, Version 7, Madison, Wis.) pileup program, or any of sequence comparison algorithms such as BLAST or FASTA.

The present technology also includes enzyme compositions exhibiting an enzyme activity profile similar to that of GDEP-M. For example, in certain embodiments the enzyme composition exhibits a protease activity of about 4,000 to about 8,000 u/g. In one non-limiting example, such a composition has an enzyme activity profile comprising a protease activity of about 6,500 u/g.

In certain embodiments, the enzyme composition of the present technology includes CPY, which is also known as proteinase C or yscY. CPY is a broad-specificity vacuolar exopeptidase that removes amino acids from the carboxy termini of proteins and peptides. It belongs to a family of serine carboxypeptidases that are ubiquitous proteolytic enzymes characterized by highly conserved and catalytically essential serine and histidine residues around their active sites. CPY useful in the present technology may be CPY from, for example, yeast or fungi such as *saccharomyces, schizosaccharomyces, aspergillus, candida*, and *pichia*. For example, CPY used in the present technology have at least about 20% sequence identity at the amino acid level, alternatively at least about 40% sequence identity, alternatively at least about 50% sequence identity, alternatively at least about 60% sequence identity, alternatively at least about 70% sequence identity, alternatively at least about 80% sequence identity, alternatively at least about 90% sequence identity, to one of the following CPY: *Saccharomyces cerevisiae* CPY, *Aspergillus niger* CPY, *Schizosaccharomyces pombe* CPY, *Aspergillus fumigatus* CPY.

In certain embodiments, the enzyme composition of the present technology comprises an enzyme having the amino acid sequence of a CPY or an amino acid sequence having at least about 70% identity with the amino acid sequence of a CPY. In certain embodiments, the amino acid may have at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity with the amino acid sequence of a CPY. In certain embodiments, the enzyme composition comprises an enzyme having an amino acid sequence substantially homologous to a CPY.

In another embodiment, gluten degrading activity has been surprisingly found in an enzyme preparation from *Penicillium citrinum*. In particular, the enzyme preparation from *Penicillium citrinum* has gluten digesting activity in which at least 4 of the 10 6-mer substrates identified in Example 24 are digested >1000 u/g, where 1 unit is equal to 1 µmol of FRET substrate digested/min. A preparation having this activity may also be obtained from other fungi, such as *Aspergillus niger*, and certain Actinomyces, such as *Streptomyces aureus*. In certain embodiments, the enzyme composition of the present technology comprises a preparation from *Penicillium citrinum* that has gluten degrading activity as well as 5'-phosphodiesterase ("5'-PDE") activity.

In another embodiment, gluten degrading activity has been surprisingly found in an enzyme composition including a preparation containing a semi-alkali protease. As used herein, semi-alkali protease refers to an enzyme, which is derived from a fungal source and is capable of breaking down proteins and their degradation products, polypeptides and peptides, by hydrolysis, and is active in an environment ranging from a pH of 6.0 to a pH of 11. Sources of semi-alkali protease include certain fungi, such as *Aspergillus melleus*. Semi-alkali protease may also be obtained from certain plant germs such as barley or sorghum germ.

In certain embodiments, the enzyme composition of the present technology may be generated by any of a number of methods. For example, individual enzymes may be combined to achieve the desired enzyme composition with a desired enzyme activity profile.

Additionally or alternatively, the enzyme composition may be obtained from a microorganism that produces enzymes naturally or that is genetically modified to produce one or more enzymes, using methods well known in the art. For example, the enzyme composition of the present technology may include at least two of the following: GDEP, GDEP-LGG, GDEP-LNA, GDEP-M, GDEP-2A, GDEP-AH, oryzin, NPI, NPII, Aorsin A, Aorsin B, CPY, papain, activated papain, purified papain, or chymopapain. The enzyme composition of the present technology may further include a preparation from *Penicillium citrinum* and/or a semi-alkali protease. In certain embodiments, the enzyme composition may comprise GDEP-LGG and papain. In another embodiment, the enzyme composition may comprise GDEP-LGG, papain, and a preparation from *Penicillium citrinum*. In another embodiment, the enzyme composition may comprise GDEP-LGG, papain, a preparation from *Penicillium citrinum* and a semi-alkali protease. In still other embodiments the enzyme composition may comprise GDEP-LGG and activated papain. In another embodiment, the enzyme composition may comprise GDEP-LGG, activated papain, and a preparation from *Penicillium citrinum*. In another embodiment, the enzyme composition may comprise GDEP-LGG, activated papain, a preparation from *Penicillium citrinum* and a semi-alkali protease. In still other embodiments the enzyme composition may comprise GDEP-LGG and chymopapain. In another embodiment, the enzyme composition may comprise GDEP-LGG, chymopapain, and a preparation from *Penicillium citrinum*. In another embodiment, the enzyme composition may comprise GDEP-LGG, chymopapain, a preparation from *Penicillium citrinum* and a semi-alkali protease.

As noted above, enzymes and enzyme compositions of the present technology may also be obtained from transformed or transfected cells by methods well known in the art. For example, a nucleic acid sequence encoding a desired enzyme can be inserted into an expression vector, which can be used to transform or transfect a host cell for production of the enzyme. Enzymes or enzyme compositions can then be obtained from the host cell by methods well known in the art.

The amount of a given enzyme or enzyme activity in a composition may vary based on the desired effect of the composition, and may be determined or measured by a variety of methods known in the art. The amount of enzymes present in a composition may be stated in molar amounts or molar ratios (e.g., nanomoles or micromoles of enzyme), weight amounts or weight ratio (micrograms or nanograms of enzyme), or activity amounts or activity ratios (e.g., "units" of enzyme or enzyme activity/weight or mole of enzyme). In particular embodiments, compositions may include protease and peptidase activities.

In certain embodiments of the present technology, the efficacies of various protease compositions are assessed. Thus, the present technology includes an in vitro model to assess these protease compositions. The in vitro model may include, for example, a gastric model, an intestinal model, or a gastrointestinal model.

In vitro gastric model. An in vitro gastric model may comprise, for example, a simulated gastric fluid ("SGF"). The SGF may contain serum albumin, gastric mucosa mucin, and/or a buffer. The buffer may be an acetate buffer. The SGF may include a physiological salt solution comprising, for example, sodium chloride (NaCl) and calcium chloride ($CaCl_2$). The SGF may be maintained at an appropriate pH to simulate gastric conditions, such an acidic pH including pH ranging from about 1.0 to about 7.0, and including about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, or about 6.9. An acid, such as hydrochloric acid, may be added to the SGF at periodic intervals during the incubation phase to maintain the acidity of the SGF.

The SGF may also include one or more gastric enzymes, such as pepsin, gelatinase, amylase, and lipase, as well as other enzymes such as lactase and alpha-galactosidase to further simulate gastric conditions. Commercially available digestive enzyme products, such as EZ-GEST® (Shaklee) may be used to supplement the simulated gastric mixture.

To assess the efficacy of a candidate enzyme composition, an amount of the enzyme composition and a peptide-containing substance may be added to the SGF. The peptide-containing substance may be a homogenous peptide preparation, such as a preparation containing natural or synthetic gluten oligopeptide, or a heterogeneous preparation comprising, for example, any substance, including foodstuffs, intended to be, or reasonably expected to be, ingested by an animal. Exemplary gluten oligopeptides include the 32 and 33-mer peptides: LQLQPEPQPQLPYPQPQLPYQPQLPYPQPQPF (SEQ ID NO:156) and LQLQPFPQPQLPYPQPQLPYPQPQLPYPQPQPF (SEQ ID NO:1), as well as peptides identified in, for example, U.S. Pat. No. 7,563,864.

The mixture comprising SGF, the enzyme composition, and the peptide-containing substance may be incubated at about 37° C. for a period that is representative of in vivo contact with gastric fluids; for example, about 20, about 25, about 30, about 35, about 40, about 45, about 50, about 55, about 60, about 65, about 70, about 80, about 85, about 90, about 95, about 100, about 105, about 110, about 115, or about 120 minutes. The mixture comprising the SGF, the enzyme composition, and the peptide-containing substance may be sampled at regular intervals to assess digestion efficiency. Digestion efficiency may be assessed by, for example, measuring the amount of 33-mer present in the mixture or measuring the amount of free tyrosine production by the Folin method.

In vitro intestinal model. An in vitro intestinal model may comprise, for example, a simulated intestinal fluid ("SIF"). The SIF may be maintained at an appropriate pH to simulate intestinal conditions, such as a slightly acidic, neutral, or basic pH including pH ranging from about 6.0 to about 14.0 and including about 7.0, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, or about 13.9. The SIF may also include substances to neutralize acid such as sodium bicarbonate ($NaHCO_3$) or disodium hydrogen phosphate ($Na_2HPO_4$).

The SIF may include one or more pancreatic enzymes such as trypsin, chymotrypsin, and amylase, and intestinal enzymes such as sucrase, maltase, isomaltase, and lactase. For example, the SIF may also contain pancreatin. Pancreatin contains the pancreatic enzymes trypsin, amylase, and lipase. Pancreatin is commercially available as Creon® (Solvay), Nutrizym 100® (Merck), Pancrease® (Janssen-Ortho) and Pancrex® (Paines & Byrne).

The SIF may also include one or more bile salts, such as cholates including taurodeoxycholate ("TDCA") and deoxycholate ("DCA"), or bile acids, such as cholic acid, glyocholic acid, taurocholic acid, deoxycholic acid, or lithocholic acid.

To assess the efficacy of a candidate enzyme composition, an amount of the enzyme composition and a peptide-containing substance may be added to the SIF. The peptide-containing substance may be a homogenous peptide preparation, such as a preparation containing natural or synthetic gluten oligopeptide, or a heterogeneous preparation comprising, for example, include any substance, including foodstuffs, intended to be, or reasonably expected to be, ingested by a human or an animal. Exemplary gluten oligopeptides include the 32 and 33-mer peptides: LQLQPEPQPQLPYPQPQLPYQPQLPYPQPQPF (SEQ ID NO:156) and LQLQPFPQPQLPYPQPQLPYPQPQLPYPQPQPF (SEQ ID NO:1), as well as peptides identified in, for example, U.S. Pat. No. 7,563,864.

The mixture comprising SIF, the enzyme composition, and the peptide-containing substance may be incubated at about 37° C. for a period that is representative of in vivo contact with intestinal fluids, for example, about 20, about 25, about 30, about 35, about 40, about 45, about 50, about 55, about 60, about 65, about 70, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, or about 240 minutes. The mixture comprising the SIF, the enzyme composition, and the peptide-containing substance may be sampled at regular intervals to assess digestion efficiency. Digestion efficiency may be assessed by, for example, measuring the amount of 33-mer present in the mixture or measuring the amount of free tyrosine production by the Folin method.

In vitro gastrointestinal model. An in vitro gastrointestinal model may comprise sequential treatment in the gastric and intestinal models described above. For example, a candidate enzyme composition and a peptide-containing substance may be incubated in SGF at about 37° C. for a period that is representative of in vivo contact with gastric fluids, for example, about 20, about 25, about 30, about 35, about 40, about 45, about 50, about 55, about 60, about 65, about 70, about 80, about 85, about 90, about 95, about 100, about 105, about 110, about 115, or about 120 minutes. A substance to neutralize acid, such as sodium bicarbonate ($NaHCO_3$) or sodium phosphate (e.g., $Na_2HPO_4$), may be added to the mixture. The mixture may then be incubated in SIF at about 37° C. for a period that is representative of in vivo contact with intestinal fluids, for example, about 20, about 25, about 30, about 35, about 40, about 45, about 50, about 55, about 60, about 65, about 70, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, or about 240 minutes. Preferably, the candidate enzyme composition and peptide-containing substance may be incubated for about 60 minutes in SGF and about 60 minutes in SIF. Alternatively, the candidate enzyme composition and peptide-containing substance may be incubated for about 120 minutes in SGF and about 60 minutes in SIF. Gastrointestinal fluids from suitable animal models and/or simulated fluids such as Simulated Gastric and Intestinal Fluids USP may be used.

A "pharmaceutical composition" refers to a mixture of one or more of the enzymes or enzyme compositions of the present technology described herein, along with other chemical components, such as physiologically acceptable carriers and excipients as described below. The purpose of a pharmaceutical composition is to facilitate administration of an enzyme or enzyme composition to an organism.

While the enzymes or enzyme compositions can be administered in their essentially pure forms, it may be desirable to formulate the enzymes into pharmaceutical compositions prior to administration in order to increase, for example, enzyme palatability, subject compliance with a treatment regimen, and/or general ease of administration. Thus, in certain embodiments, the enzyme compositions of the present technology comprise other components in addition to one or more enzymes with activity against gluten oligopeptides, such as one or more pharmaceutically acceptable coatings, binding agents, lubricating agents, suspending agents, sweeteners, flavoring agents, preservatives, buffers, wetting agents, disintegrants, effervescent agents, and other excipients. Such excipients are known in the art and can be readily selected by the skilled artisan. The amount of additional component present in addition to one or more enzymes may vary, ranging from about 0.1 wt. % to about 99 wt. %, preferably from about 5 wt. % to about 80 wt. %, more preferably from about 10 wt. % to about 70 wt. % of the total composition. For example, the amount of additional component present in addition to one or more enzymes may be about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, or about 65 wt. %.

According to some embodiments of the present technology, a pharmaceutical composition may include a pharmaceutically acceptable carrier. The term "pharmaceutically acceptable carrier" relates to one or more compatible solid or liquid fillers, diluents, or capsule substances which are suitable for administration to, for example, a human subject. The term "carrier" relates to an organic or inorganic ingredient, natural or synthetic in nature, in which the active ingredient is combined in order to facilitate use. The ingredients of the pharmaceutical composition are ordinarily of such a nature that no interaction which substantially impairs the desired pharmaceutical efficacy occurs. In certain embodiments, the carriers for use within such compositions are biocompatible and/or biodegradable. In certain embodiments, a carrier may be a composition comprising at least one mucoadhesive polymer that is capable of forming a hydrogel such as those described in US 2008/0020036.

In one embodiment, the enzyme composition is blended with at least one pharmaceutically acceptable excipient, diluted by an excipient or enclosed within a carrier that can be in the form of a capsule, sachet, tablet, buccal, lozenge, oral thin film, paper, or other container. When the excipient serves as a diluent, it may be a solid, semi-solid, suspension, slurry, or liquid material which acts as a vehicle, carrier, or medium for the balance of the composition. Thus, the composition can be formulated into tablets, pills, pastilles, powders, elixirs, suspensions, emulsions, syrups, capsules (such as, for example, soft and hard gelatin capsules), suppositories, lozenges, buccal dosage forms, sterile injectable solutions, and sterile packaged powders.

In certain embodiments, a pharmaceutical composition may comprise salts, buffer substances, preservatives, carriers and, where appropriate, other therapeutic active ingredients. For use in medicine, the salts should be pharmaceutically acceptable. Other salts can, however, be used to prepare pharmaceutically acceptable salts and are included as part of the present technology. Such pharmacologically and pharmaceutically acceptable salts include, for example, those prepared from the following acids: hydrobromic, sulfuric, nitric, perchloric, fumaric, maleic, phosphoric, glycollic, lactic, salicylic, succinic, toluene-p-sulphonic, tartaric, acetic, citric, formic, benzoic, malonic, naphthalene-2-sulphonic, benzenesulphonic acids and the like. Pharmaceutically acceptable salts can also be prepared as alkali metal or alkaline earth metal salts such as sodium, potassium or calcium salts.

In certain embodiments, a pharmaceutical composition may comprise buffer substances such as acetic acid in a salt, citric acid in a salt, boric acid in a salt and phosphoric acid in a salt.

The pharmaceutical compositions may also include where appropriate suitable preservatives such as parabens, including polyparaben and methylparaben, potassium sorbate, benzoic acid and its salts, other esters of parahydroxybenzoic acid such as butylparaben, alcohols such as ethyl or benzyl alcohol, phenolic compounds such as phenol, or quarternary compounds such as benzalkonium chloride, chlorobutanol, and thimerosal.

The pharmaceutical compositions are ordinarily supplied in a standard dose form and can be produced in a manner known to those of skill in the art. Pharmaceutical compositions may for example be in the form of capsules, tablets, pastilles, suspensions, slurries, syrups, elixirs or emulsions.

Examples of binding agents include various celluloses and cross-linked polyvinylpyrrolidone, microcrystalline cellulose (such as Avicel PH), silicidized microcrystalline cellulose (SMCC), and mannitol.

Suitable lubricants, including agents that act on the flowability of the powder formulation to be compressed, include colloidal silicon dioxide (such as Aerosil® 200), talc, stearic acid, magnesium stearate, calcium stearate, and silica gel.

Examples of sweeteners include natural or artificial sweeteners, such as sucrose, xylitol, lactose, saccharin, cyclamate, aspartame, and acesulfame and salts thereof. Examples of flavoring agents are Magnasweet® (MAFCO), acacia syrup, cardamom, caraway, vanilla, saccharin, glucose, glycerin, glycyrrhiza, bubble gum flavor, peppermint, oil of wintergreen, and fruit flavors, such as cherry or orange flavoring.

Suitable diluents include pharmaceutically acceptable inert fillers, such as colloidal silicon dioxide, microcrystalline cellulose (such as Avicel PH); dibasic calcium phosphate; saccharides, including mannitol, sorbitol, lactose, sucrose, and glucose; and/or mixtures of any of the foregoing.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents include effervescent couples, such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

In certain embodiments, the pharmaceutical composition of the present technology is an immediate release composition. In other embodiments, the pharmaceutical composition is a controlled release composition. The pharmaceutical composition may provide a relatively constant level of release of one active component. In other embodiments, however, a more rapid rate of release immediately upon administration may be desired. In other embodiments, release of active compounds may be event-triggered. Events triggering the release of the active components may be exposure to moisture, lower pH or temperature threshold. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated.

Various other materials may be present as coatings or to otherwise modify the physical form of the dosage unit. For instance, tablets, pills, or capsules may be coated with shellac, sugar, or both.

In some embodiments, the enzyme composition of the present technology is formed into dosage units suitable for oral administration, wherein the active compounds may be incorporated with excipients and used in the form of ingestible tablets, lozenges, buccal tablets, troches, capsules, elixirs, suspensions, syrups, wafers, and the like.

For example, an enzyme composition can be mixed with a solid, pulverant carrier such as, for example, sorbitol, mannitol, starch, amylopectin, cellulose derivatives or gelatin, as well as with an antifriction agent such as, for example, magnesium stearate, calcium stearate, and polyethylene glycol waxes. The mixture then can be pressed into tablets. If coated tablets are desired, the above prepared tablets may be coated, such as with a concentrated solution of sugar, which may contain gum arabic, gelatin, talc, titanium dioxide, or with a lacquer dissolved in volatile organic solvent or mixture of solvents. To this coating, various dyes can be added in order to distinguish among tablets with different enzymes or with different amounts of an enzyme present.

In certain embodiments the dosage unit form is a capsule. The capsule may contain a liquid carrier. For example, the dosage unit form may be a soft capsule suitable for oral administration, such as capsules which contain a mixture of the one or more enzymes with vegetable oil or non-aqueous, water miscible materials such as, for example, polyethylene glycol and the like. Alternatively, the enzyme(s) can be provided in hard capsules that can contain granules of the enzyme composition in combination with a solid, pulverant carrier, such as, for example, sorbitol, mannitol, potato starch, corn starch, amylopectin, cellulose derivatives, or gelatin.

Other embodiments of the present technology include granulated forms of the enzyme compositions described herein. Granulated forms are useful for preparing tablets for oral use, and are typically prepared in the following manner, although other techniques well known in the art can be employed. The solid substances (including the one or more enzymes) are gently ground or sieved to a desired particle size, and the resulting mass is gently pressed through a stainless steel sieve having a desired size. The layers of the mixture are then dried in controlled drying units for a determined length of time to achieve a desired particle size and consistency. The granules of the dried mixture are gently sieved to remove any powder. To this mixture can be added optional disintegrating, anti-friction, and/or anti-adhesive agents. Finally, the mixture is pressed into tablets using a machine with the appropriate punches and dies to obtain the desired tablet size. The operating parameters of the machine can be selected by the skilled artisan.

Other embodiments of the present technology include powders for inhalation.

The one or more enzymes or enzyme compositions of the present technology also can be formulated in compositions that release the enzyme or enzyme compositions over an extended period of time, such as, for example, between about two to about sixteen hours. In some embodiments, the enzyme or enzyme compositions are released over a time of between about 3 to about 12 hours. For example, the enzyme or enzyme compositions may be released over about 4, about 5, about 6, about 7, about 8, about 9, about 10, or about 11 hours. In yet other embodiments, the enzyme or enzyme compositions are released over a time of between about four to about eight hours. Those who are skilled in the art can prepare such sustained release formulation by methods that are known in the art.

In certain embodiments, the enzyme composition of the present technology is stabilized to resist digestion in acidic stomach conditions. In certain embodiments, the enzyme composition may be contained in an enteric coating that allows delivery of the active agent(s) to the intestine. In certain embodiments, the enzyme composition may be present in a core surrounded by one or more layers including, for example, an enteric coating layer with or without a protective sub-coating as known to the ordinarily skilled artisan relative to pharmaceutical formulations. If no sub-coating is employed, then the enteric coating can be selected such that it does not degrade the active ingredient in the core.

The enteric layer typically comprises a polymer with enteric properties. Exemplary enteric polymers include, but are not limited to, methacrylic acid copolymer, hydroxypropyl methylcellulose phtalate and hydroxypropyl methylcellulose acetate succinate. Different types of methacrylic acid copolymers can be used, such as, for example, methacrylic acid copolymer type A (Eudragit® L-100), methacrylic acid copolymer type B (Eudragit® S 100), methacrylic acid copolymer type C (Eudragit® L 100-55), methacrylic acid copolymer dispersion (Eudragit® L 30 D-55), a copolymer of methacrylic acid methyl methacrylate and methyl methacrylate (Eudragit® FS) and mixtures thereof, for instance, a mixture of Eudragit® L 100-55 and Eudragit® S 100 at a weight ratio of about 3:1 to about 2:1, or a mixture of Eudragit® L 30 D-55 and Eudragit® FS at a weight ratio of about 3:1 to about 5:1.

The enteric layer may further comprise other agents such as cellulose acetate phthalate, polyvinyl acetate phthalate, cellulose acetate trimellitate, shellac and/or zein. Optionally, the enteric layer further comprises anti-tackiness agents such as talc or glyceryl monostearate; plasticizers such as triethylcitrate or polyethylene glycol; and/or pigments such as titanium dioxide or ferric oxides. The enteric layer may further comprise one or more plasticizers including, but not limited to, acetyl triethyl citrate, acetyltributyl citrate, acetylated monoglycerides, glycerin, triacetin, propylene glycol, phthalate esters (e.g., diethyl phthalate, dibutyl phthalate), castor oil, sorbitol and dibutyl seccate. Certain embodiments provide an enterically coated formulation where the enteric layer comprises hydroxypropyl methylcellulose phthalate, triacetin, silica and stearic acid.

Dosage units for rectal administration also are contemplated. These can be prepared in the form of suppositories which contain the enzyme(s) and a neutral fat base. Alternatively, they can be prepared in the form of gelatin-rectal capsules which contain the enzyme(s) in a mixture with a vegetable oil or paraffin oil.

Compositions suitable for parenteral administration include ordinarily a sterile aqueous or nonaqueous preparation of the active ingredient, which is preferably isotonic with the recipient's blood. Suitable carriers and solvents are for example Ringer's solution and isotonic sodium chloride solution. Ordinarily employed additionally as dissolving or suspending medium are sterile, fixed oils.

Methods and compositions are provided herein for the administration of one or more enzyme compositions to a gluten intolerant subject or a subject desiring to reduce his or her gluten exposure. In certain embodiments, these methods and compositions will allow a subject to ingest gluten-containing food without serious health consequences, much the same as individuals that do not suffer from gluten intolerance. In certain embodiments, a subject not suffering from Celiac disease may wish to reduce or limit his or her exposure to gluten without strict adherence to a gluten-free diet. As further examples, the enzyme composition may also be administered to subjects to treat any disease amenable to treatment by a reduction in gluten exposure, including, for example thyroid diseases, such as hypothyroidism and neurological diseases, such as autism, cerebellar ataxia, peripheral neuropathies, and schizophrenia.

In certain embodiments, enzymes or enzyme compositions can be administered alone or in combination with each other, or with other active or inactive agents. When combinations of enzymes or enzyme compositions are used, simultaneous or sequential administration of at least two different enzymes or enzyme compositions is contemplated.

In certain embodiments simultaneous administration is contemplated and the combination of enzymes or enzyme compositions is present in a dosage unit form suitable for oral administration, wherein the active compounds may be incorporated with excipients and used in the form of ingestible tablets, lozenges, buccal tablets, troches, capsules, elixirs, suspensions, syrups, wafers and the like. The combination of enzymes or enzyme compositions may include at least two of GDEP-LGG, GDEP-LNA, GDEP-M, GDEP-2A, GDEP-AH, oryzin, NPI, NPII, Aorsin A, Aorsin B, CPY, papain, activated papain, purified papain, or chymopapain. The enzyme composition of the present technology may further include a preparation from *Penicillium citrinum*.

As used herein, the phrase a "therapeutically effective amount" connotes an amount effective to treat gluten intolerance, including NCGS or NCGI. In certain embodiments, the phrase a "therapeutically effective amount" may also be used to refer to an amount effective to reduce a subject's exposure to gluten oligopeptides, including the 33-mer derived from α-2 gliadin, or to reduce the antigenicity of gluten oligopeptides, including the 33-mer derived from α-2 gliadin. This amount may vary from subject to subject, and may generally range from about 20 to about 1000 mg per dose for a human subject. In another embodiment, the amounts range from about 100 to about 500 mg per dose for a human subject. For example, the amount may be about 50, about 100, about 150, about 200, about 250, about 300, about 350, about 400, or about 450 mg per dose for a human subject. An exemplary dosage is about 200 mg for a human subject. A therapeutically effective amount of an enzyme composition of the present technology can be administered once daily. Alternatively, a therapeutically effective amount can be administered in divided amounts multiple times per day. An illustrative dosing regimen is about 200 mg of the enzyme composition given twice per day. Another illustrative dosing regimen for a human subject is about 200 mg of the enzyme composition given whenever gluten-containing food is ingested. Alternate suitable dosing regimens can be determined by the skilled artisan.

One skilled in the art will recognize that a therapeutically effective amount of active ingredient will vary depending upon a variety of factors including, for example, the activity of the specific compound employed; the age, body weight, general health, sex, and diet of a particular patient or patient population; the time of administration, rate of absorption, and rate of excretion; the potential interactions with other drugs taken separately or in combination; and the severity of the particular disease, condition, or disorder for which a therapeutic effect is desired. The size of the dose will also be determined by the existence, nature, and extent of any adverse side effects that might accompany the administration of a particular compound. Other factors, which affect the specific dosage, include, for example, bioavailability, metabolic profile, and the pharmacodynamics associated with the particular compound to be administered in a particular subject. For example, a therapeutically effective amount can include the amount or quantity of an enzyme composition, which is sufficient to elicit the required or desired therapeutic response, e.g., an amount, which is sufficient to elicit a biological or therapeutic response when administered to a subject.

In certain embodiments, the term "administering" refers to bringing a subject in contact with the compositions provided herein. For example, in certain embodiments, the compositions provided herein are suitable for oral administration, whereby bringing the subject in contact with the composition comprises ingesting the compositions. In other embodiments, a method of administration may include genetic modification of cells, such as enterocytes, to express increased levels of particular enzymes or the introduction of microorganisms expressing enzyme compositions to the subject's intestinal tract. Such cells (which include cells that are not derived from the patient but that are not immunologically rejected when administered to the patient) and microorganisms are, in some embodiments, formulated in a pharmaceutically acceptable excipient, or introduced in foods. In still other embodiments, food may be pretreated or combined with an enzyme composition to reduce or to remove the toxic oligopeptides of gluten.

A person skilled in the art would readily recognize that the methods of bringing the subject in contact with the compositions provided herein, will depend on many variables such as, without any intention to limit the modes of administration; age, pre-existing conditions, other agents administered to the subject, the severity of symptoms, subject weight or propensity to gain weight, refraction to other medication and the like. In one embodiment, provided herein are embodiments of methods for administering the compounds of the present technology to a subject, through any appropriate route, as will be appreciated by one skilled in the art.

As used herein, the term "treating" refers to abrogating; preventing; substantially inhibiting, slowing or reversing the progression of; substantially ameliorating clinical and/or non-clinical symptoms of; or substantially preventing or delaying the appearance of clinical and/or non-clinical symptoms of a disease, disorder or condition.

In one embodiment, the term "subject" refers to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

In the preceding paragraphs, use of the singular may include the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

The disclosures of all patents, publications, including published patent applications, depository accession numbers, and database accession numbers are hereby incorporated by reference to the same extent as if each patent, publication, depository accession number, and database accession number were specifically and individually incorporated by reference.

It is to be understood that the scope of the present technology is not to be limited to the specific embodiments described above. The present technology may be practiced other than as particularly described and still be within the scope of the accompanying claims.

Likewise, the following examples are presented in order to more fully illustrate the present technology. They should in no way be construed, however, as limiting the broad scope of the technology disclosed herein.

EXAMPLES

Example 1

33-mer Peptide Degradation by GDEP-LGG

A 33-mer peptide (1 mg/ml; LQLQPF-PQPQLPYPQPQLPYPQPQLPYPQPQPF (SEQ ID NO:1)) was incubated with GDEP-LGG at various concentrations (0 mg/ml; 0.1 mg/ml, 0.5 mg/ml, and 1.0 mg/ml) in the presence of simulated intestinal fluid (SIF; pH≈6.8) from U.S. Pharmacopeia. A 30 µL reaction volume comprised 10 µL 33-mer peptide, 10 µL enzyme solution, and 10 µL 3×SIF buffer. The reactions were carried out for about 15, 30, 60, 120, and 240 minutes at about 37° C. and, then, 5 min at 90° C. to stop the enzyme reaction.

Samples of enzyme-treated 33-mer were analyzed by enzyme-linked immunosorbent assay ("ELISA") using a HRP-conjugated polyclonal antibody developed against the 33-mer peptide.

The results of the time-course and dose-response analysis of 33-mer peptide degradation by GDEP-LGG are shown in FIG. 1. Incubation with GDEP-LGG (at all concentrations) for about 120 minutes reduced the antigenicity of the 33-mer by at least about 70%.

Example 2

33-mer Peptide Degradation by Components of GDEP-LGG

Individual components of GDEP-LGG, including Oryzin, NP I, and NP II, were tested for enzymatic activity against the 33-mer. The 33-mer peptide (1 mg/ml) was incubated with 0.1 mg/ml enzyme solution comprising GDEP-LGG; 3×GDEP-LGG (i.e., 0.3 mg/ml); Oryzin; NP I; NP II; or combinations of Oryzin, NP I, and NP II (at ratios of 1:1:1 and 2:1:4) in the presence of simulated intestinal fluid (SIF; pH≈6.8). A 30 µL reaction volume comprised 10 µl 33-mer peptide, 10 µL enzyme solution, and 10 µL 3×SIF buffer. The reactions were carried out for about 20, 60, 120, and 240 minutes at about 37° C. and, then, 5 min at 90° C. to stop the enzyme reaction.

Figure 2:
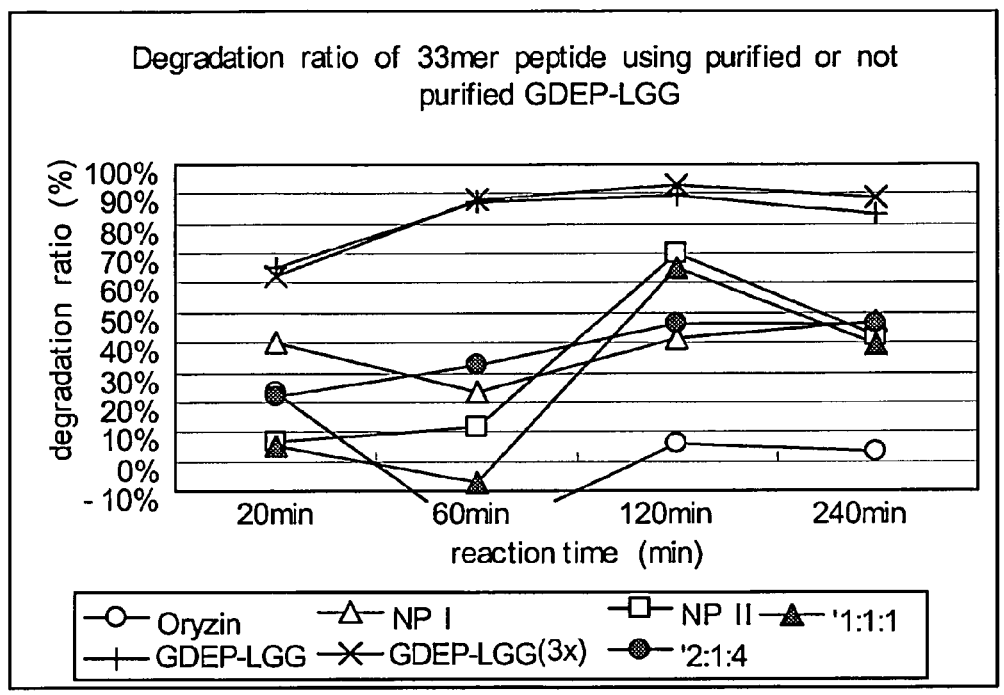
FIG. 2 shows degradation of a 33-mer peptide (as assessed by measuring the levels of intact 33-mer peptide by ELISA) by gluten degrading enzyme preparation and its individual component enzymes, Oryzin, NP I, and NP II.

Samples of enzyme-treated 33-mer were analyzed as in Example 1. Degradation of the 33-mer by GDEP-LGG and its individual component enzymes is shown in FIG. 2. Incubation with GDEP-LGG (at both concentrations tested) for about 60 minutes resulted in degradation of about 90% of the 33-mer peptide. Oryzin alone did not degrade the 33-mer peptide. NP I and NP II each exhibited a limited ability to degrade the 33-mer peptide. Re-construction of GDEP-LGG using the three purified enzymes (Oryzin, NP I, and NP II) resulted in about 50% degradation of the 33-mer peptide at 120 and 240 minutes.

Further combinations of Oryzin, NP I, and/or NP II were tested for their ability to degrade the 33-mer peptide. The 33-mer peptide (1 mg/ml) was incubated with various concentrations of enzyme solution (0.1 mg/ml, 0.2 mg/ml, 0.4 mg/ml, or 0.8 mg/ml) comprising gluten degrading enzyme preparation; Oryzin; NP I; and/or NP II in the presence of simulated intestinal fluid (SIF; pH≈6.8). A 30 µL reaction volume comprised 10 µL 33-mer peptide, 10 µL enzyme solution, and 10 µL 3×SIF buffer. The reactions were carried out for about 60 minutes at about 37° C. and, then, 5 min at 90° C. to stop the enzyme reaction.

Figure 3A:
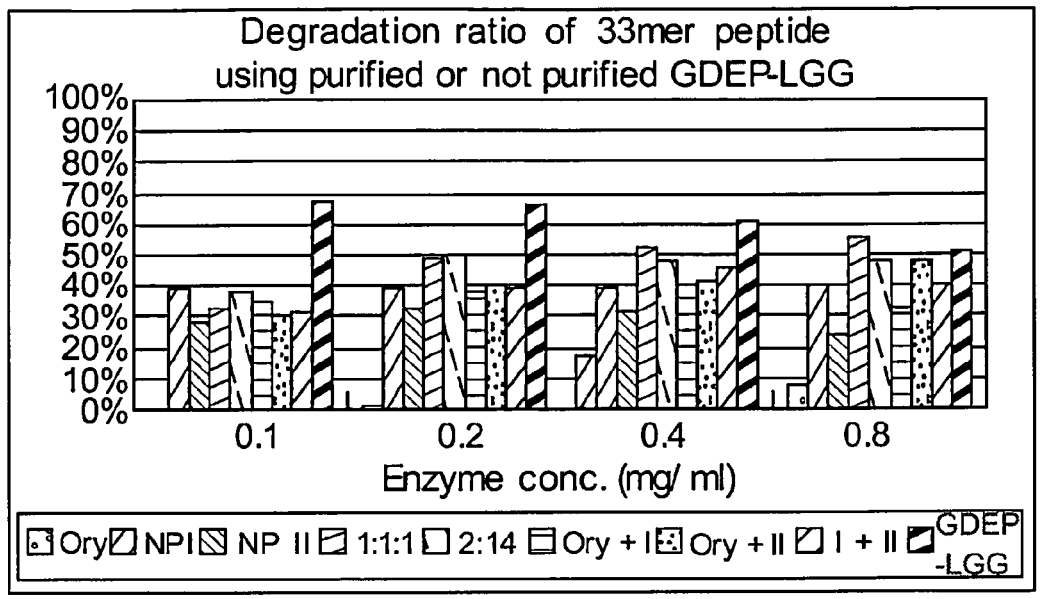
FIG. 3 shows degradation of a 33-mer peptide (as assessed by measuring the levels of intact 33-mer peptide by ELISA) by gluten degrading enzyme preparation and its individual component enzymes, Oryzin, NP I, and NP II, and various combinations thereof.
Figure 3B:
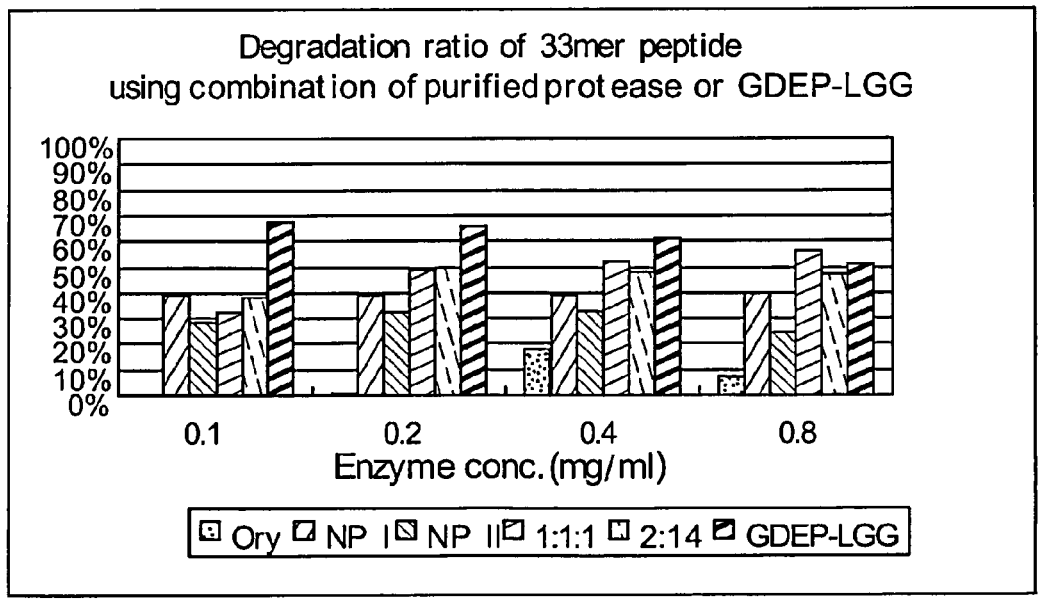
Figure 3C:
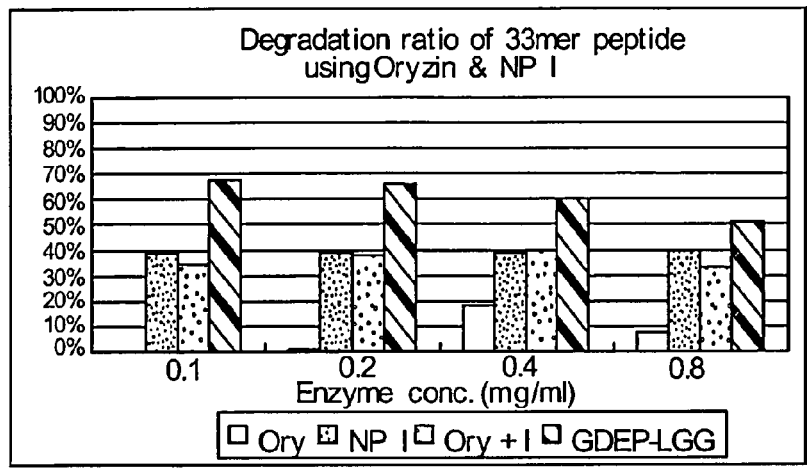
Figure 3D:
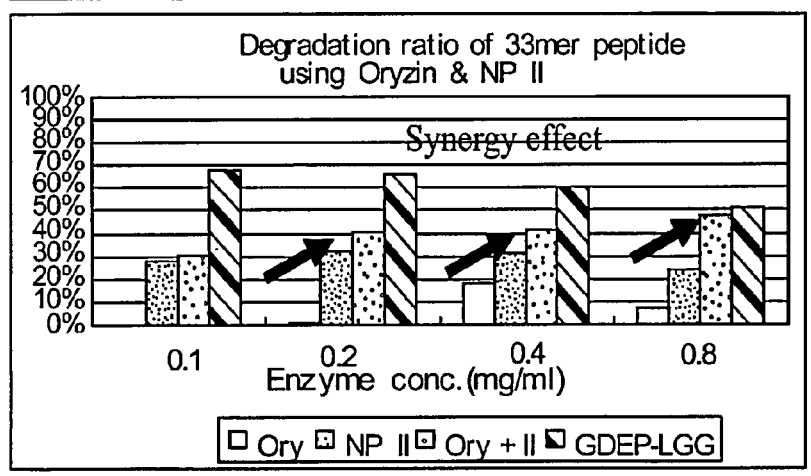
Figure 3E:
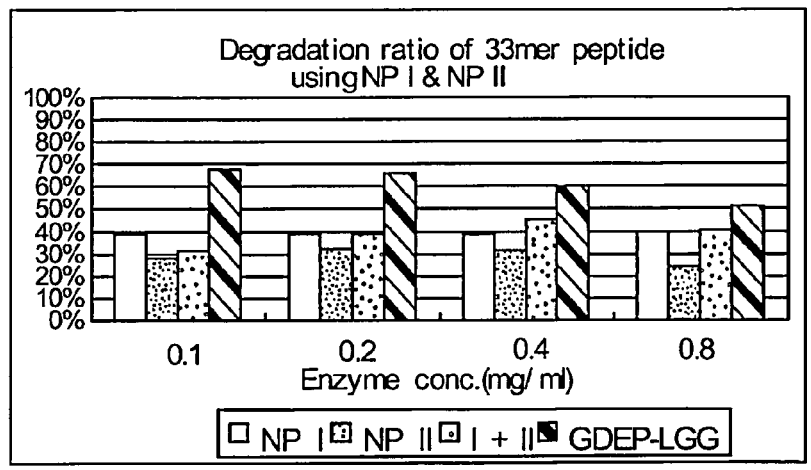

Samples of enzyme-treated 33-mer were analyzed as in Example 1. Degradation of the 33-mer by GDEP-LGG and its individual component enzymes and various combinations thereof is shown in FIG. 3. NP I alone degraded about 40% of the 33-mer peptide (FIG. 3B). NP II alone degraded about 20% to about 30% of the 33-mer peptide (FIG. 3B). Oryzin, at the lowest concentrations, did not degrade the 33-mer peptide (FIG. 3B). However, at higher concentrations (0.4 mg/ml and 0.8 mg/ml), Oryzin degraded about 10% to about 20% of the 33-mer peptide (FIG. 3B). Re-construction of GDEP-LGG using the three purified enzymes (Oryzin, NP I, and NP II) resulted in degradation of about 30% to about 50% of the 33-mer peptide. However, the combination did not achieve the same percentage of degradation of the 33-mer as GDEP-LGG (FIG. 3B). Thus, another protease or peptidase in GDEP-LGG might be involved in 33-mer digestion. Neither the combination of Oryzin and NP I nor the combination of NP I and NP II appear to result in a synergy effect (FIGS. 3C and 3E). However, the combination of Oryzin and NP II may achieve a synergy effect (FIG. 3D).

Example 3

Comparison of GDEP-LGG and Other Digestive Proteases

The 33-mer peptide (1 mg/ml) was incubated with 0.25 mg/ml enzyme solution (containing pepsin, proteinase K, or GDEP-LGG) in the presence of simulated intestinal fluid (SIF; pH≈6.8) or simulated gastric fluid (SGF; pH≈2.0). A 40 µL reaction volume comprised 10 µL 33-mer peptide, 10 µL enzyme solution, and 20 µL 2×SIF or SGF buffer. The reactions were carried out for about 15 hours at 37° C. and, then, 5 min at 90° C.

Samples of enzyme-treated 33-mer were analyzed by reverse phase high pressure liquid chromatography ("HPLC") using an Agilent 1100 HPLC system. Samples were loaded onto an Eclipse SB-C18 (ID2.1 mm×150 mm, 3.5 um) column. The mobile phase comprised of (A) distilled water with 0.1% formic acid and (B) acetonitril with 0.1% formic acid was used to elute targets in gradient mode (0 min, 2% B→10 min, 25% B→40 min, 40% B→45 min, 100% B→50 min, 100% B). Flow rate was set at 0.2 mL/min and the injection volume was 5 µL. Detection was performed with a diode array detector (210, 280) and a mass spectrometer.

The mass spectrometer was operated in API-ES positive mode using the following conditions: drying gas flow 13.0 L/min; drying gas temperature 280° C.; nebulizer pressure 60 psig; and capillary voltage 2000 V.

At gastric conditions (pH≈2.0), pepsin did not hydrolyze most of the 33-mer peptide (FIG. 4A). Similarly, at intestinal conditions (pH≈6.8), proteinase K did not hydrolyze most of the 33-mer peptide (FIG. 4B). At intestinal conditions, GDEP-LGG hydrolyzed the 33-mer peptide, but did not eliminate all peptide fragments (FIG. 4C).

Example 4

Comparison of Gluten Degrading Enzyme Preparation and Other *Aspergillus*-Derived Proteases The 33-mer peptide (1 mg/ml) was incubated with gluten GDEP-LGG, GDEP-2A, GDEP-LNA, GDEP-M, or Protease P, in the presence of SIF (pH≈6.8). A 30 µL reaction volume comprised 10 µL 33-mer peptide, 10 µL enzyme solution (0.1 mg/ml), and 10 µL 3×SIF buffer. The reactions were carried out for about 4 hours at 37° C. and, then, 5 min at 90° C. Analysis by HPLC-MS was as described in Example 3.

Protease P is a semi-alkali protease and a proteolytic enzyme preparation. Protease P is manufactured by a unique fermentation process with a selected strain of *Aspergillus*, which is cultured on the wheat bran. Protease P enzyme is extracted with water and purified by fractionation with ethanol. Protease P has high proteolytic activity.

PZH(SD) is a semi-alkali protease from *Aspergillus melleus*. This is also referred to as Protease P, Seaprose or Protease DS depending on the purification and application of the enzyme. Protease P is less purified; Seaprose (semi alkaline protease) has been used as a drug in Japan for lung related diseases; Protease DS is an enzyme preparation produced by *Aspergillus melleus*.

Figure 5:
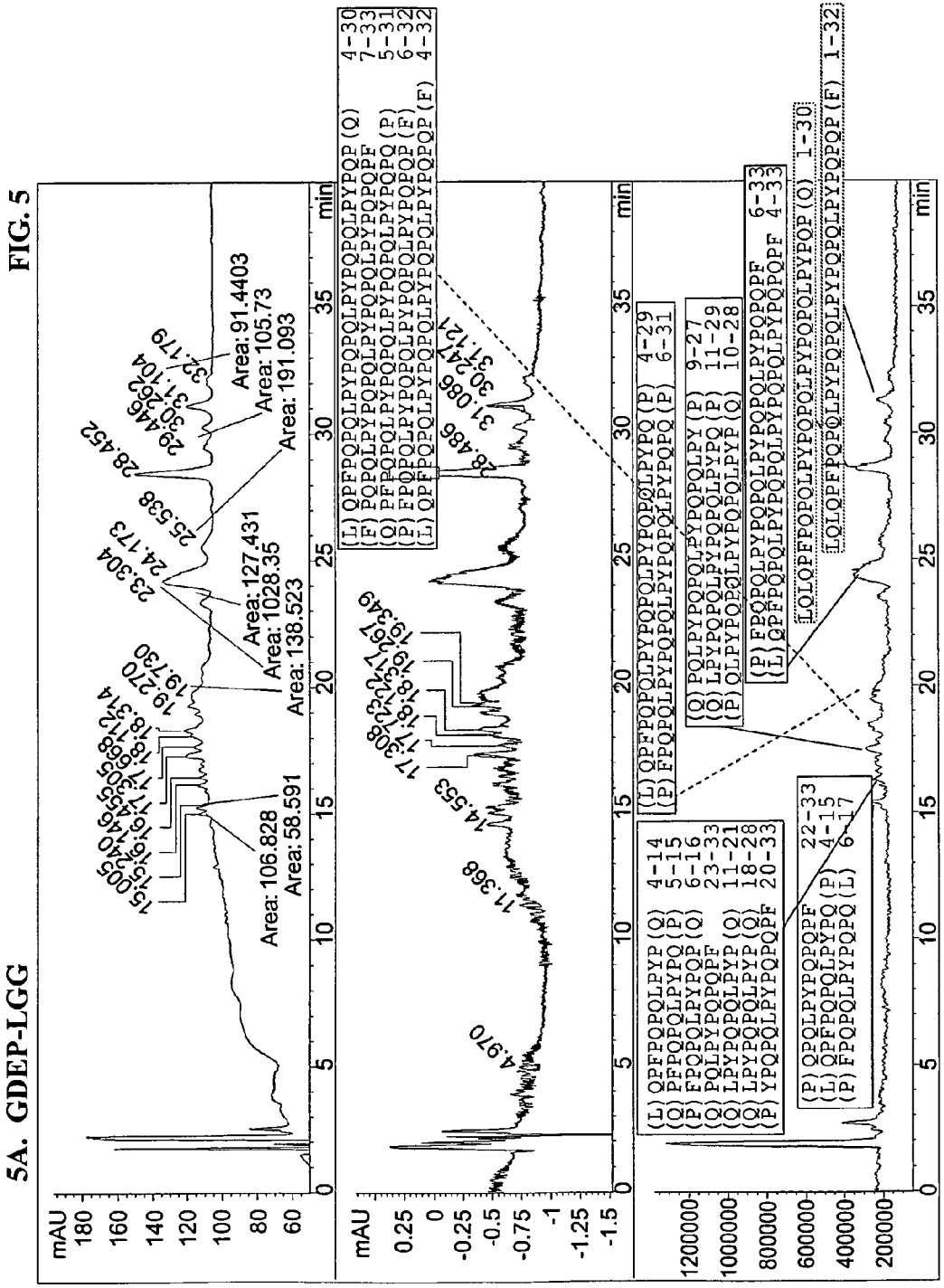
FIG. 5 shows chromatographs of HPLC analysis with 280 nm and 210 nm (panels 1 and 2) and mass spectral analysis (panel 3) of a 33-mer peptide after treatment with gluten degrading enzyme preparation (FIG. 5A) and other *Aspergillus*-derived proteases, GDEP-2A (FIG. 5B), GDEP-LNA (FIG. 5C), GDEP-M (FIG. 5D), and Protease P (FIG. 5E). Amino acid sequences corresponding to sequence identification numbers 26-48 are included in FIG. 5A; corresponding to sequence identification numbers 26-48 are included in FIG. 5B; corresponding to sequence identification numbers 26-48 are included in FIG. 5C; corresponding to sequence identification numbers 26-48 are included in FIG. 5D; and corresponding to sequence identification numbers 21, 26-27, and 48-57 are included in FIG. 5E.

When incubated with the 33-mer peptide for 4 hours at intestinal conditions (pH≈6.8), GDEP-LGG hydrolyzed the 33-mer (FIG. 5A). However, hydrolysis of the 33-mer by GDEP-LGG was less efficient when the reaction time was reduced to 4 hours as compared to 15 hours (see Example 3). The other *Aspergillus* proteases show similar hydrolysis of the 33-mer peptide as gluten degrading enzyme preparation. (FIG. 5B-5E).

Example 5

33-mer Hydrolysis Activity of GDEP-M and GDEP-LGG at Various pH

Figure 6:
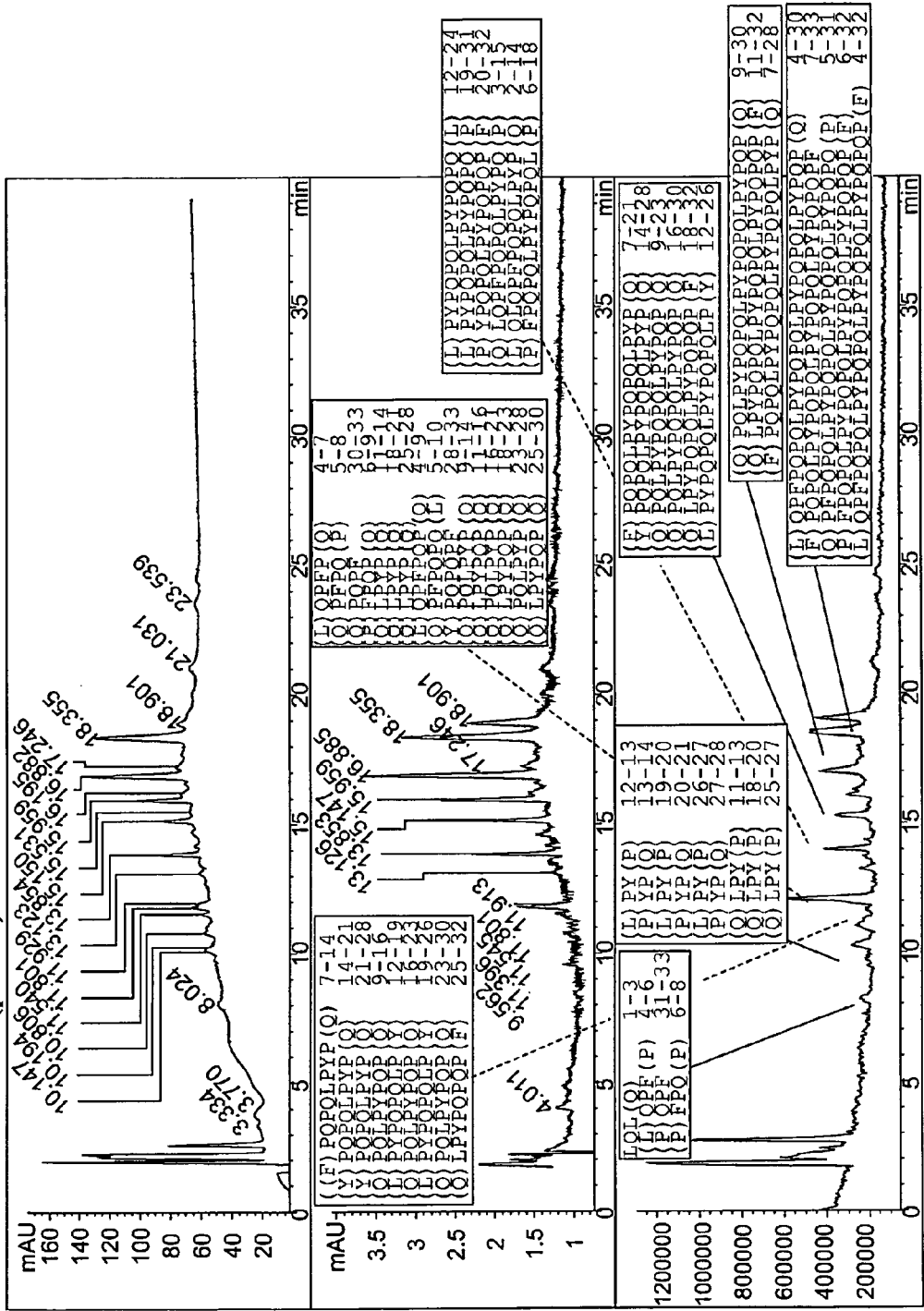
FIG. 6 shows chromatographs of HPLC analysis with 280 nm and 210 nm (panels 1 and 2) and mass spectral analysis (panel 3) of a 33-mer peptide after treatment with GDEP-M at a pH ranging from 3.0 to 6.0 (FIG. 6A-6D, 6H) and GDEP-LGG at a pH ranging from 4.0 to 6.0 (FIG. 6E-6G). Amino acid sequences corresponding to sequence identification numbers 22-25, 27-31, and sequence identification numbers 58-79 are included in FIG. 6A; corresponding to sequence identification numbers 22-25, 27-31, and 58-79 are included in FIG. 6B; corresponding to sequence identification numbers 22-25, 27-31, and 58-79 are included in FIG. 6C; corresponding to sequence identification numbers 22-25, 27-31, 41-42, 46-47, and 77-79 are included in FIG. 6D; corresponding to sequence identification numbers 27-31, and 58-84 are included in FIG. 6E; corresponding to sequence identification numbers 22-25, 27-31, and 72-84 are included in FIG. 6F; corresponding to sequence identification numbers 22-31, 46-47, 58-61, and 77-84 are included in FIG. 6G; and corresponding to sequence identification numbers 22-31, 62-65, 72-79, and 85-88 are included in FIG. 6H.

The 33-mer peptide (1 mg/ml) was incubated with GDEP-LGG or GDEP-M at various pH. A 30 µL reaction volume comprised 10 µL 33-mer peptide, 10 µL enzyme solution (0.1 mg/ml), and 10 µL 50 mM citrate buffer. The pH of the buffer for GDEP-M ranged from 3.0 to 6.0 (FIG. 6A-6D). The pH of the buffer for gluten degrading enzyme preparation ranged from 4.0 to 6.0 (FIG. 6E-6G). A half amount of GDEP-M was also tested at pH 4.0 (FIG. 6H). The reactions were carried out for about 4 hours at 37° C. and, then, 5 min at 90° C. Analysis by HPLC-MS was as described in Example 3.

Both GDEP-LGG and GDEP-M, individually, hydrolyzed the 33-mer peptide at high efficiency at acidic pH. GDEP-M exhibited more efficient hydrolysis than GDEP-LGG at acidic pH.

Example 6

Protease Inhibitor Analysis

The preceding examples show that GDEP-M and GDEP-LGG hydrolyze a 33-mer peptide, such as that derived from α-2 gliadin, efficiently at an acidic pH. Various protease inhibitors were used to evaluate the component of GDEP-M and GDEP-LGG effective for the degradation of the 33-mer.

The 33-mer peptide (1 mg/ml) was incubated with 0.1 mg/ml enzyme solution (either GDEP-LGG or GDEP-M). A 33 µL reaction volume comprised 10 µL 33-mer peptide, 10 µL enzyme solution (0.1 mg/ml), 10 µL 50 mM citrate buffer, and 3 µL protease inhibitor—PMSF, Pepstatin, or EDTA. The pH of the buffer was about 4.0. The reactions were carried out for about 4 hours at 37° C. and, then, 5 min at 90° C. Analysis by HPLC-MS was as described in Example 3.

Figure 7:
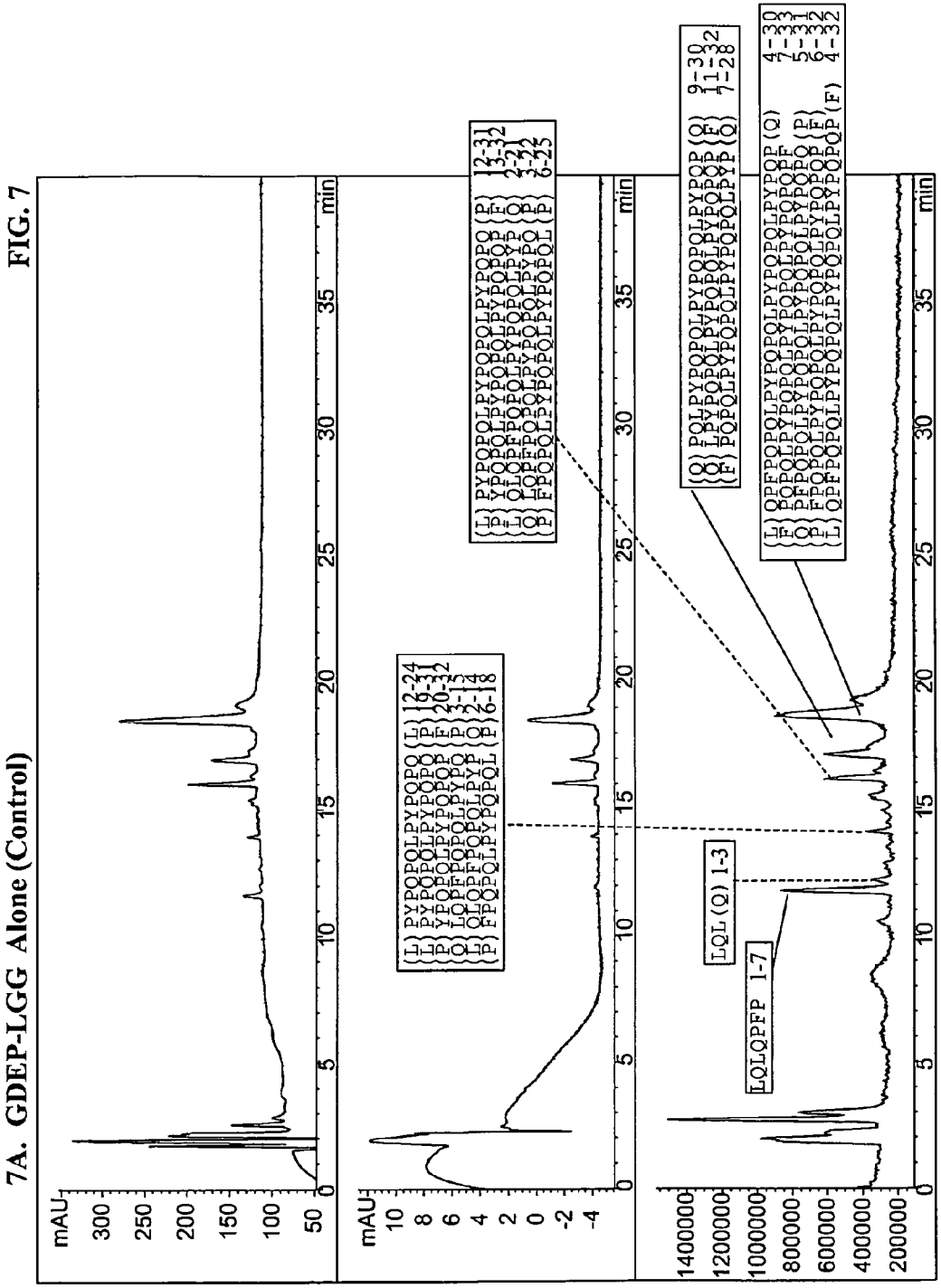
FIG. 7 shows chromatographs of HPLC analysis with 280 nm and 210 nm (panels 1 and 2) and mass spectral analysis (panel 3) of a 33-mer peptide after treatment with GDEP-LGG alone (FIG. 7A) and GDEP-LGG in the presence of PMSF (FIG. 7B), pepstatin (FIG. 7C), and EDTA (FIG. 7D).
Figure 8:
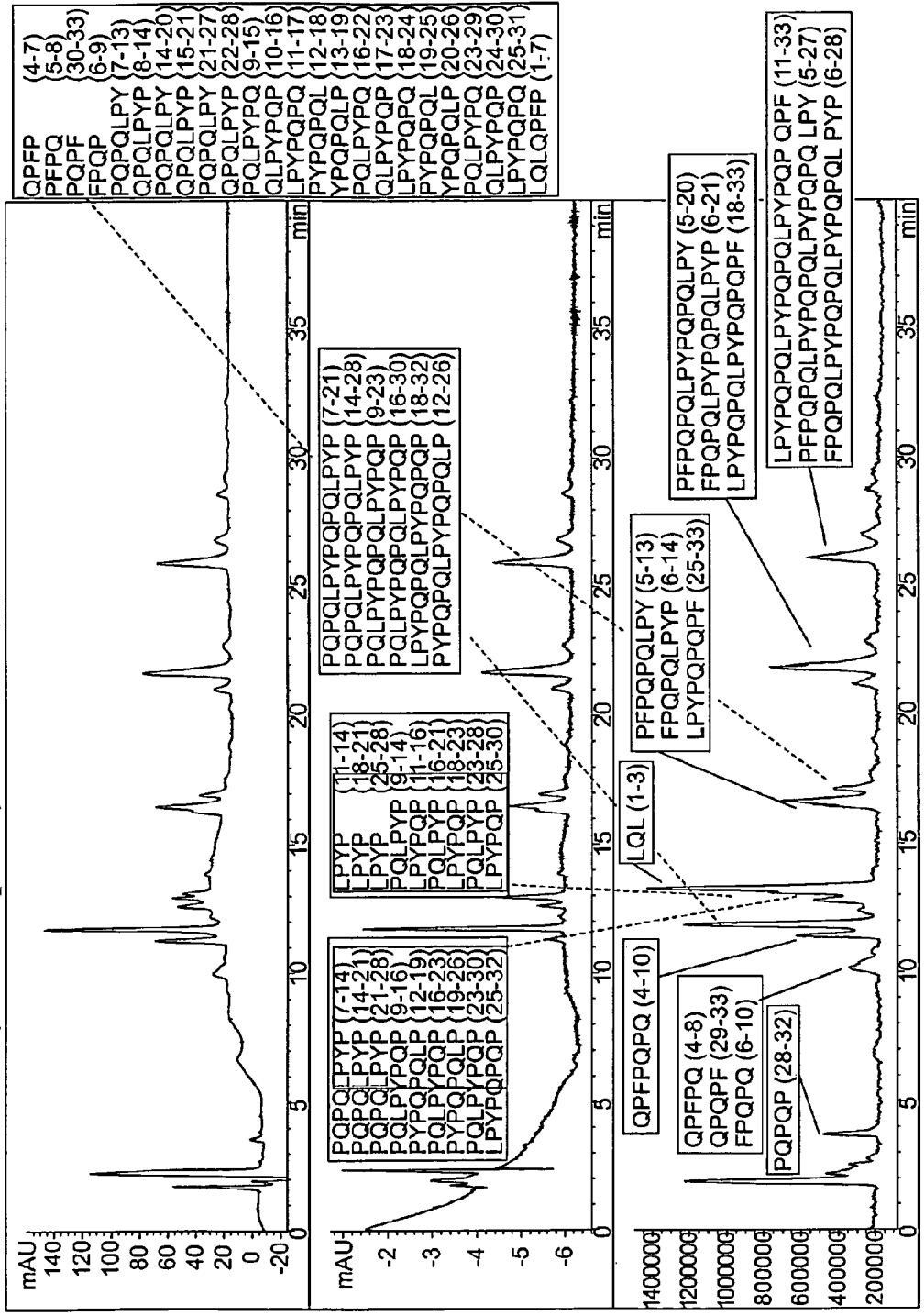
FIG. 8 shows chromatographs of HPLC analysis with 280 nm and 210 nm (panels 1 and 2) and mass spectral analysis (panel 3) of a 33-mer peptide after treatment with various amounts of Aorsin A (FIGS. 8A-8D) and Aorsin B (FIGS. 8E-8H). Amino acid sequences corresponding to sequence identification numbers 22-25, 58-66, 70-71, 89-110 are included in FIG. 8A; corresponding to sequence identification numbers 22-25, 58-66, 70-71, 89-110 are included in FIG. 8B; corresponding to sequence identification numbers 58-66, 70-71, 89, 93-99, and 103-110 are included in FIG. 8C; corresponding to sequence identification numbers 107-110 are included in FIG. 8D; corresponding to sequence identification numbers 1, 10, 89-106, and 111-113 are included in FIG. 8E; corresponding to sequence identification numbers 10, 89-106, and 111-113 are included in FIG. 8F; corresponding to sequence identification numbers 89, 93-106 are included in FIG. 8G; and corresponding to sequence identification numbers 89, and 93-106 are included in FIG. 8H.

When incubated with the 33-mer peptide for 4 hours in acidic conditions (pH≈4.0), GDEP-LGG hydrolyzed the 33-mer (FIG. 7A). However, hydrolysis of the 33-mer by GDEP-LGG was less efficient when in the presence of PMSF (FIG. 7B). Neither pepstatin nor EDTA inhibited 33-mer peptide hydrolysis by GDEP-LGG (FIGS. 7C and 7D).

When incubated with the 33-mer peptide for 4 hours in acidic conditions (pH≈4.0), GDEP-M hydrolyzed the 33-mer (FIG. 7E). However, hydrolysis of the 33-mer by GDEP-M was less efficient when in the presence of PMSF (FIG. 7F). Neither pepstatin nor EDTA inhibited 33-mer peptide hydrolysis by GDEP-M (FIGS. 7G and 7H).

Neither pepstatin nor EDTA inhibited 33-mer peptide hydrolysis by GDEP-LGG or GDEP-M. PMSF inhibited 33-mer peptide hydrolysis by gluten degrading enzyme preparation or GDEP-M. Thus, an acidic serine protease is the main component of 33-mer peptide hydrolysis by gluten degrading enzyme preparation or GDEP-M.

Example 7

33-mer Peptide Degradation by Aorsin, a Component of GDEP-M

The experiments presented above indicate that an acidic serine protease contributes to the hydrolytic activity of GDEP-M against the 33-mer. Aorsin is an acidic serine protease present in GDEP-M.

Individual components of GDEP-M, including Aorsin A and Aorsin B, were tested for enzymatic activity against the 33-mer. The 33-mer peptide (1 mg/ml) was incubated with 1.0 mg/ml enzyme solution comprising Aorsin A or Aorsin B in the presence of citrate buffer (pH≈4.0). A 30 µL reaction volume comprised 10 µL 33-mer peptide, 10 µL Aorsin solution, and 10 µL 50 mM citrate buffer. The reactions were carried out for about 15, 30, 60, and 240 minutes at about 37° C. and, then, 5 min at 90° C. to stop the enzyme reaction.

Analysis by HPLC-MS was as described in Example 3. When incubated with the 33-mer peptide in acidic conditions (pH≈4.0), Aorsin A hydrolyzed the 33-mer. (FIGS. 8A-8D). Similarly, when incubated with the 33-mer peptide in acidic conditions (pH≈4.0), Aorsin B hydrolyzed the 33-mer. (FIGS. 8E-8H).

Figure 9:
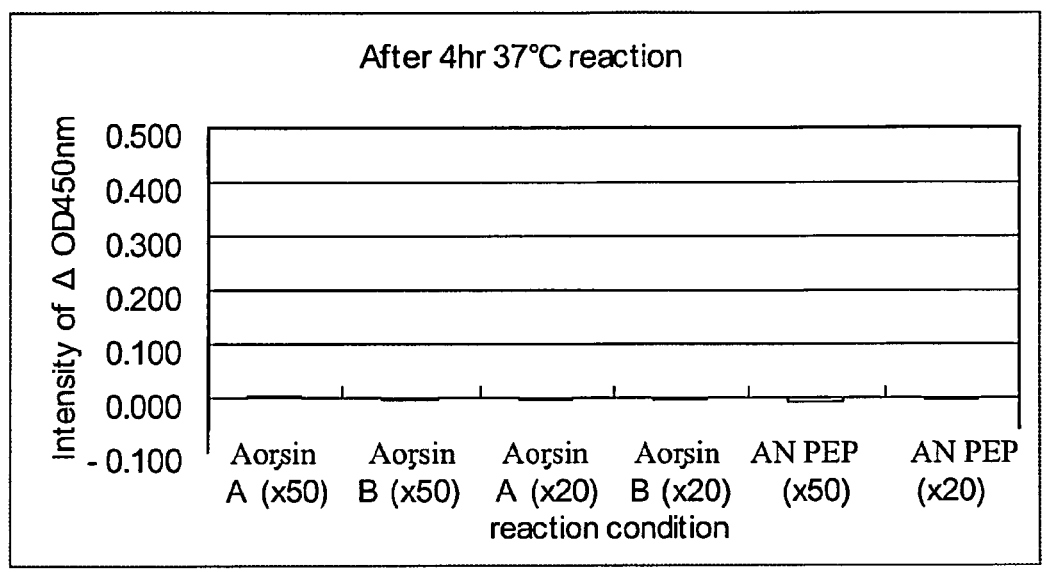
FIG. 9 shows degradation of a 33-mer peptide (as assessed by measuring the levels of intact 33-mer peptide by ELISA) by Aorsin.

Samples of 33-mer treated with Aorsin for about 240 minutes were also analyzed as in Example 1. Degradation of the 33-mer by Aorsin is shown in FIG. 9. Incubation with either Aorsin A or B for about 240 minutes resulted in complete degradation of the 33-mer peptide.

Example 8

33-mer Hydrolysis Activity of Carboxypeptidase Y and *Myxococcus Xanthus* Prolyl Endopeptidase at Various pH The 33-mer peptide (1 mg/ml) was incubated with a CPY derived from *Saccharomyces cerevisiae* or *Myxococcus xanthus* prolyl endopeptidase ("MX-PEP") at various pH. A 30 µL reaction volume comprised 10 µL 33-mer peptide, 10 µL enzyme solution (0.1 mg/ml), and 10 µL buffer. The pH of the buffer ranged from 4.0 to 7.0 (FIGS. 10A-10D for CPY and 10E-10H for MX-PEP). The reactions were carried out for about 4 hours at 37° C. and, then, 5 min at 90° C. Analysis by HPLC-MS was as described in Example 3.

MX-PEP did not hydrolyze the 33-mer peptide at an acidic pH. CPY completely hydrolyzed the 33-mer peptide at acidic pH. This result is surprising because CPY is known as an exo-peptidase having a neutral pH optimum. However, the data presented here show that CPY has an acidic pH optimum against the 33-mer peptide.

Example 9

Comparison of Carboxypeptidase Y and Prolyl Endopeptidases

The 33-mer peptide (1 mg/ml) was incubated with enzyme solution (containing CPY, MX-PEP, or *Aspergillus niger* prolyl endopeptidase ("AN-PEP")). AN-PEP is commercially available as, for example, Brewers Clarex™ (DSM). CPY and AN-PEP were incubated at an acidic pH (pH≈5.0). MX-PEP was incubated in the presence of SIF (pH≈6.8). A 30 µL reaction volume comprised 10 µL 33-mer peptide, 10 µL enzyme solution, and 10 µL buffer.

Each enzyme was tested at 4 concentrations: 0.1 mg/ml, 0.05 mg/ml; 0.025 mg/ml, and 0.0125 mg/ml. The reactions were carried out for about 4 hours at about 37° C. and, then, 5 min at 90° C. to stop the enzyme reaction. The results of the dose response for CPY, MX-PEP, and AN-PEP are presented in FIGS. 11A-11D (CPY), 11E-11H (MX-PEP), and 11I-11L (AN-PEP).

Each enzyme (at a concentration of 0.1 mg/ml) was also tested at 4 time points: about 15 min, 30 min, 60 min, and 240 min. Analysis by HPLC-MS was as described in Example 3 and the results of this analysis for CPY, MX-PEP, and AN-PEP are presented in FIGS. 11M-11P (CPY), 11Q-11T (MX-PEP), and 11U-11V (AN-PEP). Analysis by ELISA was also performed as described in Example 1 and the results of this analysis are presented in FIG. 12.

CPY, MX-PEP, and AN-PEP hydrolyze the 33-mer peptide. AN-PEP appears to have the strongest activity against the 33-mer peptide, followed by CPY and then MX-PEP.

Example 10

In Vitro Gastrointestinal Model

In vitro gastrointestinal models were used to assess digestion efficiency of various enzymes, including GDEP-LGG, GDEP-M, and CPY.

To examine the digestion efficiency of GDEP-LGG against wheat gluten and commercially available foodstuffs, intended to be, or reasonably expected to be, ingested by an animal, the following model was employed.

A 135 ml solution was prepared using 100 ml of 2.7% bovine serum albumin; 5 ml of 3% gastric mucosa mucin; 10 ml NaCl 13.2 g+CaCl$_2$ 2H2o 0.22 g/100 ml; and 20 ml of pH 4.0 acetate buffer. The solution was incubated at 37° C. for about 20 min. After this pre-incubation, 5 ml of 0.2% pepsin and 10 ml of 1.47% EZ-GEST® (Shaklee) were added to the solution. At t=0 min a peptide-containing substance (e.g., wheat gluten or a commercially available food) was added to the solution and incubated for about 120 min. During the incubation phase, 4 ml of 0.2N HCl was added to the mixture to maintain the acidity of the mixture (at t=5 min, t=20 min, t=35 min, t=50 min, t=65 min).

At t=120 min, 3.0 g sodium bicarbonate (NaHCO$_3$), 0.31 g TDCA, and 150 mg pancreatin were added to the mixture to simulate intestinal conditions. The mixture was then be incubated at about 37° C. for about 60 minutes (until t=180 min). The mixture was sampled by removing 1 ml at t=0 min, t=30 min, t=60 min, t=90 min, t=120 min, t=130 min, t=140 min, t=150 min, and t=180 min.

The digestion efficiency of GDEP-LGG against the 33-mer peptide using various commercially available foods as a source of the 33-mer peptide are presented in Tables 1 and 2. The data in Table 1 reflect incubation of the indicated source of a 33-mer with 200 mg GDEP-LGG for 180 min. The data presented in Table 2 reflect incubation of the indicated source of a 33-mer with the indicated amount of GDEP-LGG for 180 min.

TABLE 1

Amount of 33-mer peptide digested by 200 GDEP-LGG.

| Source of 33-mer (Food) | Serving Size | Digestion Efficiency |
|---|---|---|
| Wheat Gluten | 10 g | 68% |
| Lasagna | 252 g | 89% |
| Easy Mac | 58 g | 51% |
| Cheez-It ® Crackers | 30 g | 81% |

TABLE 1-continued

Amount of 33-mer peptide digested by 200 GDEP-LGG.

| Source of 33-mer (Food) | Serving Size | Digestion Efficiency |
|---|---|---|
| Ramen Noodles | 43 g | 49% |
| Sesame Chicken | 283 g | 49% |
| Frozen Burrito | 142 g | 64% |

TABLE 2

Amount of 33-mer peptide digested by GDEP-LGG.

| Source of 33-mer (Food) | Serving Size | GDEP-LGG | Digestion Efficiency |
|---|---|---|---|
| Chicken & Cheddar Hot Pockets | 127 g | 7 μg | 37% |
| Turkey Pot Pie | 284 g | 10 μg | 83% |
| Chow Mein | 65 g | 10 μg | 62% |
| Oyster Sauce | 16 g | 5 μg | 39% |
| Onion Soup | 8 g | 6 μg | 39% |

In addition, various doses of GDEP-LGG, ranging from 0 mg to 200 mg, were tested against 10 g wheat gluten in the gastrointestinal model described above. FIG. 13 shows digestion of wheat gliadin and the 33-mer peptide by GDEP-LGG. A dose of about 200 mg GDEP-LGG digested approximately 80% of gliadin and approximately 80% of the 33-mer peptide.

An alternative in vitro gastrointestinal model was employed to examine the digestion efficiency of CPY and GDEP-M against the 33-mer peptide.

The 33-mer (300 μg) and pepsin (30 μg) were added to 100 μL of 20 mM acetate buffer (pH 4.5). CPY alone, GDEP-M alone, or a combination of CPY and GDEP-M were also added. The solution was incubated under these gastric conditions at 37° C. for about 60 min. The pH was then adjusted to 6.8 by the addition of 500 mM Na$_2$HPO$_4$. Intestinal enzymes, trypsin (20 μg) and chymotrypsin (20 μg), were also added at this time. The solution was further incubated under intestinal conditions at 37° C. for about 60 min and then, 5 min at 90° C. to stop the enzyme reaction. Analysis by HPLC-MS was as described in Example 3.

Analysis by HPLC-MS was as described in Example 3. The digestive enzymes only (pepsin, trypsin, and chymotrypsin) failed to digest the 33-mer peptide (FIG. 14A). GDEP-M, CPY, and the combination of GDEP-M and CPY efficiently digested the 33-mer peptide in the artificial gastrointestinal condition (FIGS. 14B-14D). Analysis was also carried out by ELISA as described in Example 1. GDEP-M alone digested about 87% of the 33-mer peptide, CPY alone digested about 95% of the 33-mer peptide, and the combination of GDEP-M and CPY digested about 99-100% of the 33-mer peptide (FIG. 15).

Example 11

Hydrolysis of 33-mer Peptide by CPY and GDEP-LGG

The 33-mer peptide (1 mg/ml) was incubated with GDEP-LGG, CPY or a combination of GDEP-LGG and CPY in the presence of SIF (pH≈6.8). A 30 μL reaction volume comprised 10 μL 33-mer peptide, 10 μL enzyme solution (0.1 mg/ml), and 10 μL 3×SIF buffer. The reactions were carried out for about 4 hours at 37° C. and, then, 5 min at 90° C. Analysis by HPLC-MS was as described in Example 3.

GDEP-LGG hydrolyzed the 33-mer peptide and produced residual peptides such as 1-30, 6-33, and 4-33 (FIG. 16A). CPY efficiently hydrolyzed the 33-mer peptide and residual peptides were approximately 20 amino acids in length (FIG. 16B). Treatment with GDEP-LGG and CPY hydrolyzed the 33-mer peptide; residual peptides were far fewer than with either enzyme composition alone (FIG. 16C).

Example 12

GDEP-LGG Protease Activity

GDEP-LGG was fractionated with DEAE chromatography. Each fraction was analyzed for protein concentration, 33-mer peptide degradation activity, prolyl endopeptidase activity, and protease activity. Protein concentration was assessed at 280 nm. Prolyl endopeptidase activity was assessed using the substrate Z-Gly-Pro-pNA. Protease activity was analyzed using azocasein and the commercially available Fluorescence Resonance Energy Transfer Substrates-25Xaa ("FRETS-25Xaa") Series.

FRETS-25Xaa products have the general structure:

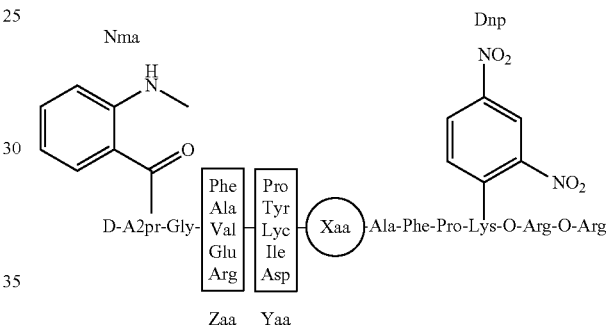

Each substrate (Code 3701-v-Code 3719-v) in the FRETS-25Xaa series contains a highly fluorescent 2-(N-methylamino)benzoyl (Nma) group linked to the side chain of the amino-terminal D-2,3-diamino propionic acid (D-A2pr) residue, which is efficiently quenched by a 2,4-dinitrophenyl (Dnp) group linked to the function of Lys. Xaa represents a fixed position of each of the 19 natural amino acids excluding Cys (noted in product name Code 3701-v-Code 3719-v). A mixture of 5 amino acid residues (P, Y, K, I, and D) is at the Yaa position, along with a mixture of 5 amino acid residues (F, A, V, E, and R) at the Zaa position for each fixed Xaa. This provides a peptide mixture of 25 combinations of each Xaa series resulting in a combinatorial library totaling 475 peptide substrates. Both Nma and Dnp groups are linked to the side chain of the individual residues, allowing for the determination of the cleavage site by a specific enzyme through mass spectrometric analysis and Edman degradation as well. When an enzyme of interest cleaves any peptide bond between D-A2pr(Nma) and Lys(Dnp) in the substrate, the fluorescence at λex=340 nm and λem=440 nm increases in proportion to the release of the Nma fluorophore form the internal Dnp quencher.

Figure 17A:
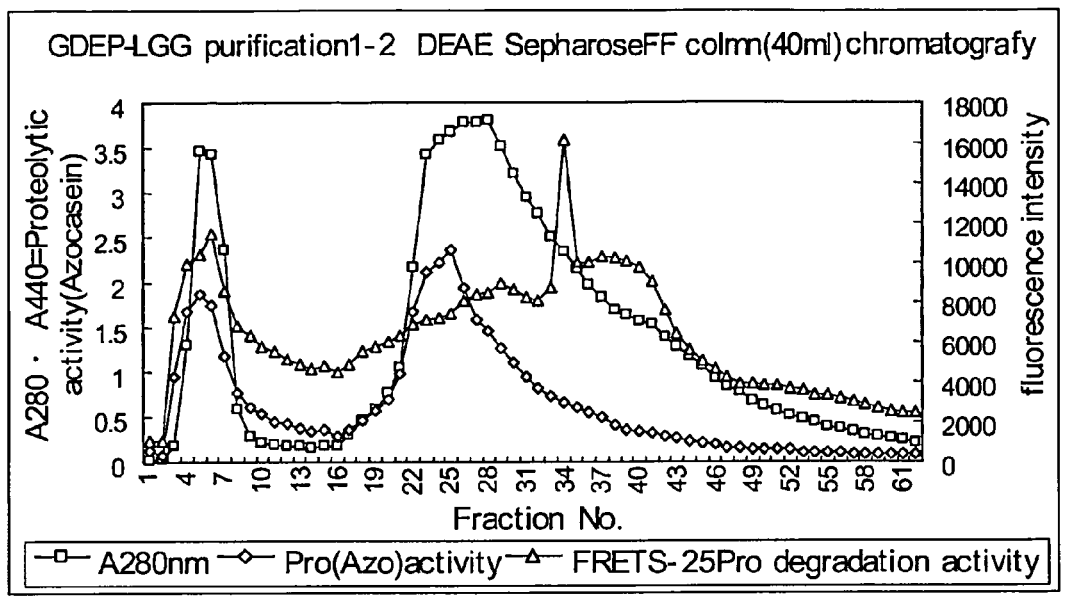
Figure 17B:
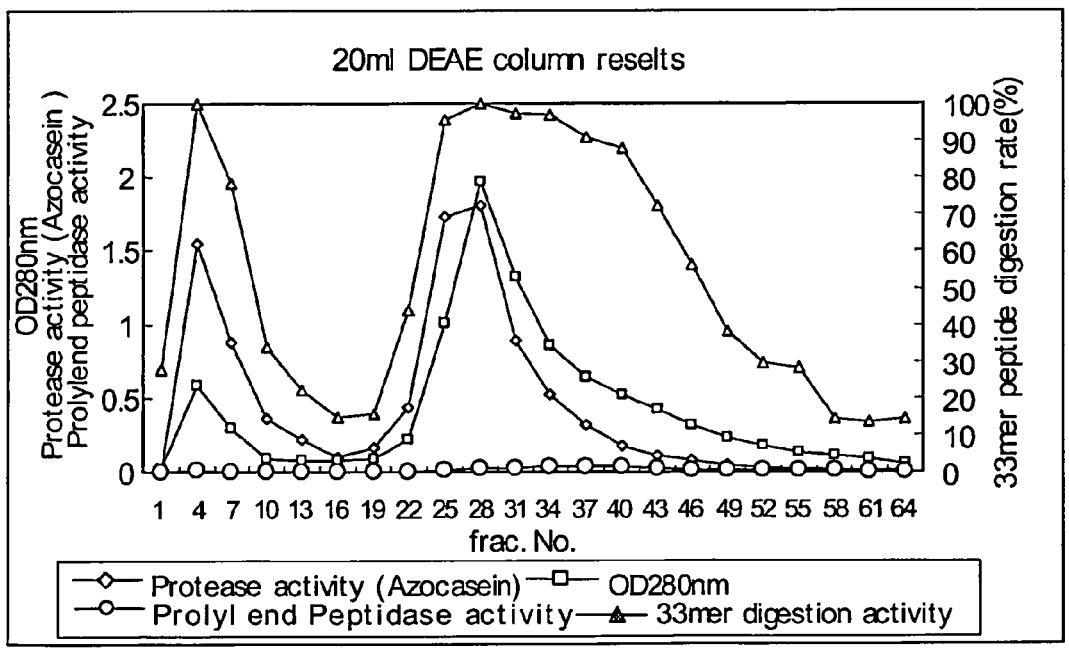

GDEP-LGG has significant protease activity as assessed by degradation of azocasein and FRETS-25Pro (FIG. 17A). Protease activity was divided in two major fractions, DEAE flow through fraction and DEAE absorbed fraction (FIG. 17A). GDEP-LGG has negligible prolyl endopeptidase activity as measured the substrate Z-Gly-Pro-pNA (FIG. 17B). Nonetheless, GDEP-LGG surprisingly has significant activity against the 33-mer peptide, which was divided in two major fractions, DEAE flow through fraction and DEAE absorbed fraction (FIG. 17B).

Example 13

In Vitro Gastrointestinal Model (Enzymes at Doses of 12.5 mg, 25 mg, 37.5 mg, 50 mg, 100 mg, 200 mg and 400 mg)

In vitro gastrointestinal models were used to assess digestion efficiency of various enzymes at doses of 12.5 mg, 25 mg, 37.5 mg, 50 mg, 100 mg, 200 mg and 400 mg.

To examine the digestion efficiency of various enzymes against gluten, intended to be, or reasonably expected to be, ingested by an animal, the following model was employed.

A 135 ml solution was prepared using 100 ml of 2.7% bovine serum albumin; 5 ml of 3% gastric mucosa mucin; 10 ml NaCl 13.2 g+CaCl$_2$ 2H2o 0.22 g/100 ml; and 20 ml of pH 4.0 acetate buffer. The solution was incubated at 37° C. for about 20 min. After this pre-incubation, 5 ml of 0.2% pepsin and 10 ml of various doses of enzyme (12.5 mg, 25 mg, 37.5 mg, 50 mg, 100 mg, 200 mg, or 400 mg) were added to the solution. At t=0 min gluten was added to the solution and incubated for about 120 min. During the incubation phase, 4 ml of 0.2N HCl aliquots were added to the mixture to maintain the acidity of the mixture (at t=5 min, t=20 min, t=35 min, t=50 min, t=65 min).

At t=120 min, 3.0 g sodium bicarbonate (NaHCO$_3$), 0.81 g deoxycholate, and 150 mg pancreatin were added to the mixture to simulate intestinal conditions. The mixture was then incubated at about 37° C. for about 60 minutes (until t=180 min). The mixture was sampled by removing 1 ml at t=0 min, t=30 min, t=60 min, t=90 min, t=120 min, t=130 min, t=140 min, t=150 min, and t=180 min.

The residual ratio of enzyme against the 33-mer peptide using gluten as a source of the 33-mer peptide is presented in FIGS. 18A-18E. The figures reflect incubation of gluten with 12.5 mg, 25 mg, 37.5 mg, 50 mg, 100 mg, 200 mg, or 400 mg of the indicated enzyme or enzymes for 180 min. Analysis by ELISA was as described in Example 1.

GDEP-LGG was effective to greatly reduce or eliminate the 33-mer from the gluten source of 33-mer peptide (FIG. 18B, 18E).

Example 14

In Vitro Gastrointestinal Model (Gluten Degrading Enzyme Preparation at Doses of 50 mg, 100 mg, 200 mg and 400 mg)

In vitro gastrointestinal models were used to assess digestion efficiency of GDEP-LGG at doses of 50 mg, 100 mg, 200 mg and 400 mg.

To examine the digestion efficiency of gluten degrading enzyme preparation against commercially available foodstuffs, intended to be, or reasonably expected to be, ingested by an animal, the following model was employed.

A 135 ml solution was prepared using 100 ml of 2.7% bovine serum albumin; 5 ml of 3% gastric mucosa mucin; 10 ml NaCl 13.2 g+CaCl$_2$ 2H2o 0.22 g/100 ml; and 20 ml of pH 4.0 acetate buffer. The solution was incubated at 37° C. for about 20 min. After this pre-incubation, 5 ml of 0.2% pepsin and 10 ml of various doses of GDEP-LGG (50, 100, 200 or 400 mg) were added to the solution. At t=0 min a peptide-containing substance (e.g., a commercially available food) was added to the solution and incubated for about 120 min. During the incubation phase, 4 ml of 0.2N HCl aliquots were added to the mixture to maintain the acidity of the mixture (at t=5 min, t=20 min, t=35 min, t=50 min, t=65 min).

At t=120 min, 3.0 g sodium bicarbonate (NaHCO$_3$), 0.81 g deoxycholate, and 150 mg pancreatin were added to the mixture to simulate intestinal conditions. The mixture was then incubated at about 37° C. for about 60 minutes (until t=180 min). The mixture was sampled by removing 1 ml at t=0 min, t=30 min, t=60 min, t=90 min, t=120 min, t=130 min, t=140 min, t=150 min, and t=180 min.

The residual ratio of the 33-mer peptide from commercially available foods as a source of the 33-mer peptide following treatment with GDEP-LGG is presented in FIGS. 19A-19E and summarized in Table 3. The data in Table 3 reflect incubation of the indicated source of the 33-mer with 50 mg, 100 mg, 200 mg or 400 mg GDEP-LGG for 180 min. Analysis by ELISA was as described in Example 1.

TABLE 3

Amount of 33-mer peptide digested by GDEP-LGG

| Source of 33-mer (Food) | GDEP-LGG Dose | Residual Ratio |
|---|---|---|
| Commercial 33-mer peptide | 50 mg | 10% |
| | 100 mg | −1% |
| | 200 mg | 1% |
| | 400 mg | 1% |
| Ravioli (Chef Boyardee Mini Beef Ravioli) | 50 mg | 11.7% |
| | 100 mg | 7.8% |
| | 200 mg | 7.6% |
| | 400 mg | 4.9% |
| Cheese Macaroni (Kraft Easy Mac) | 50 mg | 6.7% |
| | 100 mg | 1.4% |
| | 200 mg | 3.7% |
| | 400 mg | 2.3% |
| White Bread | 50 mg | 8.6% |
| | 100 mg | 7.2% |
| | 200 mg | 7.8% |
| | 400 mg | 0.8% |
| Roll of Bread | 50 mg | −4.0% |
| | 100 mg | −1.9% |
| | 200 mg | −5.2% |
| | 400 mg | −1.2% |

GDEP-LGG was effective to greatly reduce or eliminate the 33-mer from various commercial sources of 33-mer peptide. The residual ratio of 33-mer generally decreased with higher doses of GDEP-LGG across all sources (FIG. 19A-19E).

Example 15

In Vitro Gastrointestinal Model: Comparison of GDEP-LGG and GDEP-M at Doses of 50 mg, 100 mg, 200 mg and 400 mg In vitro gastrointestinal models were used to compare digestion efficiency of each of GDEP-LGG and GDEP-M at doses of 50 mg, 100 mg, 200 mg and 400 mg.

To examine the digestion efficiency of GDEP-LGG and GDEP-M against commercially available foodstuffs, intended to be, or reasonably expected to be, ingested by an animal, the following model was employed.

A 135 ml solution was prepared using 100 ml of 2.7% bovine serum albumin; 5 ml of 3% gastric mucosa mucin; 10 ml NaCl 13.2 g+CaCl$_2$ 2H2o 0.22 g/100 ml; and 20 ml of pH 4.0 acetate buffer. The solution was incubated at 37° C. for about 20 min. After this pre-incubation, 5 ml of 0.2% pepsin and 10 ml of various doses of GDEP-LGG or GDEP-M (50, 100, 200 or 400 mg) were added to the solution. At t=0 min a peptide-containing substance (e.g., a commercially available food) was added to the solution and incubated for about 120 min. During the incubation phase, 4 ml of 0.2N HCl aliquots were added to the mixture to maintain the acidity of the mixture (at t=5 min, t=20 min, t=35 min, t=50 min, t=65 min).

At t=120 min, 3.0 g sodium bicarbonate (NaHCO$_3$), 0.81 g deoxycholate, and 150 mg pancreatin were added to the mixture to simulate intestinal conditions. The mixture was then incubated at about 37° C. for about 60 minutes (until t=180 min). The mixture was sampled by removing 1 ml at t=0 min, t=30 min, t=60 min, t=90 min, t=120 min, t=130 min, t=140 min, t=150 min, and t=180 min.

The residual ratio of the 33-mer peptide from commercially available foods as a source of the 33-mer peptide following treatment with GDEP-LGG or GDEP-M is presented in FIGS. 20A-20H and summarized in Table 4. The data in Table 4 reflect incubation of the indicated source of a 33-mer with 50 mg, 100 mg, 200 mg or 400 mg GDEP-LGG or GDEP-M for 180 min. Analysis by ELISA was as described in Example 1.

TABLE 4

Amount of 33-mer peptide digested by GDEP-LGG or GDEP-M

| Source of 33-mer (Food) | GDEP-LGG or GDEP-M Dose | Residual Ratio GDEP-LGG | Residual Ratio GDEP-M |
|---|---|---|---|
| Ravioli (Chef Boyardee Mini Beef Ravioli) | 50 mg | 11.7% | 38.6% |
| | 100 mg | 7.8% | 20.8% |
| | 200 mg | 7.6% | 8.9% |
| | 400 mg | 4.9% | 7.2% |
| Cheese Macaroni (Kraft Easy Mac) | 50 mg | 6.7% | 18.3% |
| | 100 mg | 1.4% | 10.6% |
| | 200 mg | 3.7% | 3.6% |
| | 400 mg | 2.3% | 4.0% |
| White Bread | 50 mg | 8.6% | 19.8% |
| | 100 mg | 7.2% | 15.2% |
| | 200 mg | 7.8% | 2.7% |
| | 400 mg | 0.8% | −1.1% |
| Roll of Bread | 50 mg | −4.0% | 8.0% |
| | 100 mg | −1.9% | 0.9% |
| | 200 mg | −5.2% | −1.9% |
| | 400 mg | −1.2% | −4.5% |
| Lasagna | 50 mg | 20.6% | 44.2% |
| | 100 mg | 13.3% | 40.6% |
| | 200 mg | 3.0% | 29.7% |
| | 400 mg | −0.6% | 10.3% |
| Pasta | 50 mg | 20.0% | 49.3% |
| | 100 mg | 8.3% | 27.8% |
| | 200 mg | 4.5% | 10.3% |
| | 400 mg | 2.5% | 5.3% |

GDEP-LGG was effective to greatly reduce or eliminate the 33-mer from various commercial sources of 33-mer peptide and was more effective than GDEP-M at reducing or eliminating the 33-mer from various commercial sources of 33-mer peptide. The residual ratio of the 33-mer generally decreased with higher doses of GDEP-LGG or GDEP-M across all sources (FIG. 20A-20H).

Example 16

Comparison of GDEP-LGG with Existing Products

In order to assess the digestion efficiency of GDEP-LGG as compared to existing products, the following in vitro model was employed.

A 135 ml solution was prepared using 100 ml of 2.7% bovine serum albumin; 5 ml of 3% gastric mucosa mucin; 10 ml NaCl 13.2 g+CaCl$_2$ 2H2o 0.22 g/100 ml; and 20 ml of pH 4.0 acetate buffer. The solution was incubated at 37° C. for about 20 min. After this pre-incubation, 5 ml of 0.2% pepsin and 10 ml of an enzyme composition (100 mg GDEP-LGG; 2 capsules of "Gluten Gest," available from Allergy Research Group; 2 capsules of "Gluten-zyme," available from BioCare; or 1 capsule of "GlutenEase," available from Enzymedica; 2 capsules of "Gluten-zyme Plus" available from BioCare; or 2 capsules of "Spectrumzyme" available from BioCare) were added to the solution. At t=0 min a commercially available 33-mer peptide was added to the solution and incubated for about 120 min. During the incubation phase, 4 ml of 0.2N HCl aliquots were added to the mixture to maintain the acidity of the mixture (at t=5 min, t=20 min, t=35 min, t=50 min, t=65 min).

At t=120 min, 3.0 g sodium bicarbonate (NaHCO$_3$), 0.81 g deoxycholate, and 150 mg pancreatin were added to the mixture to simulate intestinal conditions. The mixture was then be incubated at about 37° C. for about 60 minutes (until t=180 min). The mixture was sampled by removing 1 ml at t=0 min, t=30 min, t=60 min, t=90 min, t=120 min, t=130 min, t=140 min, t=150 min, and t=180 min.

Analysis was performed by ELISA as described in Example 1 and HPLC-MS as described in Example 3. The results are presented in FIG. 21A and summarized in Table 4.

TABLE 5

Comparison of gluten degrading enzyme preparation with existing products

| Product | Residual Ratio |
|---|---|
| 100 mg Lot1 GDEP-LGG | 7.4% |
| 100 mg Lot2 GDEP-LGG | 13.6% |
| 100 mg Lot3 GDEP-LGG | 6.2% |
| 2 Capsules of "Gluten Gest" | 84.6% |
| 2 Capsules of "Gluten-zyme" | 66.7% |
| 1 Capsule of "GlutenEase" | 56.8% |

All 3 lots of GDEP-LGG greatly reduced or eliminated the 33-mer peptide. All 3 lots of gluten degrading enzyme preparation had a significantly lower residual ratio than the three tested existing products, with Lot3 presenting the lowest residual ratio at 6.2%. Individual chromatographs for each commercial product are presented in FIGS. 21B-21O.

Example 17

33-mer Peptide Degradation by Papain

The 33-mer peptide (1 mg/ml) was incubated with papain at a pH of about 4.5. A 30 µL reaction volume comprised 10 µL 33-mer peptide, 10 µL enzyme solution (0.1 mg/ml) and 10 µL buffer. The pH of the buffer was about 4.5. The reaction was carried out for about 1 hour at 37° C. and, then, 5 min at 90° C. to stop the enzyme reaction. Analysis by HPLC-MS was as described in Example 3.

The results of the analysis are presented in FIG. 22. Papain completely hydrolyzed the 33-mer peptide at a pH of about 4.5.

Example 18

Papain Purification by Cation-Exchange Chromatography

Papain was purified by cation-exchange chromatography using an AKTA purifier from GE Health Care. A 20% enzyme solution of papain W-40 bulk in a 50 mM Acetate buffer at a pH of about 5.0 was desalted using a PD10 column with 50 mM Acetate buffer at a pH of about 5.0. The sample was diluted about 1.4 times. Samples were loaded onto a 40 ml SP Sepharose FF column. The mobile phase comprised of (A) 50 mM Bis-Tris HCl buffer at a pH of about 5.0 and (B) 50 mM Bis-Tris HCl buffer at a pH of about 5.0 with 1M NaCl was used to elute targets in gradient mode (40 mL application; 80 mL flow through; 600 mL elution 1 with 0→600 mM NaCl; 120 mL elution 2 with 600 mM NaCl; 120 mL wash with 1M NaCl). Flow rate was set at 5.0 mL/min, the injection volume was 10 mL and the fraction size was 10 mL. Detection was performed at an optical density of 280 nm.

The results of the purification are presented in FIG. 23. Each fraction was incubated with the 33-mer peptide at a pH of about 4.5. A 30 µL reaction volume comprised 10 µL 33-mer peptide, 10 µL enzyme solution (0.1 mg/ml) and 10 µL buffer. The pH of the buffer was about 4.5. The reaction was carried out for about 1 hour at 37° C. and, then, 5 min at 90° C. to stop the enzyme reaction. Analysis by HPLC-MS was as described in Example 3.

The results of the analysis are presented in FIG. 23. The fractions from peak 3 completely hydrolyzed the 33-mer peptide at a pH of about 4.5.

SDS-PAGE gels were prepared for each fraction of the cation-exchange chromatography analysis. The results of the SDS-PAGE gels are presented in FIG. 24. Each peak (protein) shows consistent molecular weight.

Peaks 2 and 3 from the cation-exchange chromatography purification results were further purified by reverse phase chromatography and identification was performed by N-Terminal Sequence analysis. The results of the analysis are presented in FIGS. 25A and 25B.

Example 19

Papain Purification by Hydrophobic Interaction Chromatography

The E9 fraction of the cation-exchange chromatography analysis performed in Example 18 was further purified by hydrophobic interaction chromatography using an AKTA purifier from GE health care. The enzyme solution of the E9 fraction was added to the same volume of 2.4M ammonium sulfate in 50 mM Pipes buffer at a pH of about 6.5 to form a final sample of 1.2M ammonium sulfate in 25 mM Pipes buffer at a pH of about 6.5. Samples were loaded onto a 5 mL HiTrap Butyl FF column. The mobile phase comprised of (A) 1.2M ammonium sulfate in 25 mM Pipes buffer at a pH of about 6.5 and (B) 25 mM Pipes buffer at a pH of about 6.5 was used to elute targets in gradient mode (20 mL application; 5 mL flow through; 100 mL elution 1 with 1.2M→0 mM ammonium sulfate; 25 mL elution 2 with 0 mM ammonium sulfate). Flow rate was set at 4.0 mL/min, the injection volume was 10 mL and the fraction size was 2.5 mL. Detection was performed at an optical density of 280 nm.

The results of the purification are presented in FIG. 26. Unlike the results of the cation-exchange chromatography of Example 18, Peak 3 presents as two separate peaks. The peaks are labeled Peak 3-1 and Peak 3-2 in Figure (FIG. 26A-26B).

The fractions were hydrolyzed using the FRETS-25Xaa method as described in Example 18. 10 µL of enzyme solution was added to 100 µL of 10 µM substrate in 50 mM acetate buffer and incubated at 37° C. for about 1 hour and, then, 5 min at 90° C. to stop the enzyme reaction.

The results of the FRETS-25Xaa analysis are presented in FIG. 27. The fractions represented by Peak 3-1 completely hydrolyzed the 33-mer peptide.

Example 20

Papain Purification by Reverse Phase Chromatography

The enzyme solutions presented as Peaks 3-1 and 3-2 in Example 19 were further purified using reverse phase chromatography.

The results of the reverse phase chromatography analysis are presented in FIG. 28.

Example 21

Comparison of Papain and Other Enzymes

In vitro gastrointestinal models were used to assess digestion efficiency of papain and other enzymes at varying doses.

A 135 ml solution was prepared using 100 ml of 2.7% bovine serum albumin; 5 ml of 3% gastric mucosa mucin; 10 ml NaCl 13.2 g+$CaCl_2$ $2H_2o$ 0.22 g/100 ml; and 20 ml of pH 4.0 acetate buffer. The solution was incubated at 37° C. for about 20 min. After this pre-incubation, 5 ml of 0.2% pepsin and 10 ml of various doses of enzyme (5, 10, 40, 50, 100 and 400 mg) were added to the solution. At t=0 min a commercially available 33-mer peptide was added to the solution and incubated for about 120 min. During the incubation phase, 4 ml of 0.2N HCl aliquots were added to the mixture to maintain the acidity of the mixture (at t=5 min, t=20 min, t=35 min, t=50 min, t=65 min).

At t=120 min, 3.0 g sodium bicarbonate ($NaHCO_3$), 0.81 g deoxycholate, and 150 mg pancreatin were added to the mixture to simulate intestinal conditions. The mixture was then incubated at about 37° C. for about 60 minutes (until t=180 min). The mixture was sampled by removing 1 ml at t=0 min, t=30 min, t=60 min, t=90 min, t=120 min, t=130 min, t=140 min, t=150 min, and t=180 min.

The residual ratio of the enzyme against the 33-mer peptide is presented in FIG. 29. Analysis by ELISA was as described in Example 1.

All forms of papain were effective to greatly reduce or eliminate the 33-mer from. The residual ratio of 33-mer generally decreased with higher doses of enzyme (FIG. 29).

Example 22

Activation of Papain by Reducing Agent

In order to test the activity of papain in the presence of a reductant, the following test method was employed.

Papain and GDEP-LGG with and without the presence of a reductant (Glutathione, dithiothreitol ("DTT"), L-Cysteine, or N-Acetyl-L-Cysteine) were analyzed for protease activity using the FRETS-25Xaa method as described in Example 16. 10 ut, of enzyme solution was added to 100 µL of 10 µM Nma-YPQPQLPYPK(Dnp)-DArg-DArg-NH2 peptide in 50 mM Acetate buffer at pH 4.5 or 50 mM Acetate buffer with 1 mM reductant. The solution was incubated for about 1 hour at 37° C. and, then, 5 min at 90° C. to stop the enzyme reaction.

The DTT and Glutathione reductants activated the FRETS activity of papain but did not significantly activate the FRETS activity of GDEP-LGG (FIG. 30A). All reductants activated papain (FIG. 30B).

The 33-mer hydrolysis activity of the enzyme solutions with reductants was further tested. A 30 μL reaction volume comprised of 10 μL of 1 mg/mL 33-mer peptide, 10 μL of enzyme solution (papain or GDEP-LGG) and 10 μL of 50 mM acetate buffer at pH 4.5 or 50 mM Acetate buffer with 1 mM reductant was incubated for about 1 hour at 37° C. and, then, 5 min at 90° C. to stop the enzyme reaction. Analysis by HPLC-MS was as described in Example 3. All reductants activated the 33-mer hydrolysis activity of papain (FIG. 30C).

Example 23

Comparison of GDEP-LGG, Various Papain GDEP-LGG Combinations, and Papain

The FRETS activity of various concentrations of enzyme solution (100% GDEP-LGG, 80% GDEP-LGG with 20% papain, 60% GDEP-LGG with 40% papain, 40% GDEP-LGG with 60% papain, 20% GDEP-LGG with 80% papain, and 100% papain) was measured using the FRETS-25Xaa method as described in Example 16. GDEP-LGG concentration was 0.057 unit/mL and papain concentration was 0.060 unit/mL.

10 μL of enzyme solution was added to 100 μL of 10 μM Nma-YPQPQLPYPK(Dnp)-DArg-DArg-NH2 peptide in 50 mM Acetate buffer at pH 4.5. The solution was incubated for 1 hour at 37° C. and, then, 5 min at 90° C. to stop the enzyme reaction.

Relative activity (%) of GDEP-LGG and papain at various concentrations is shown in FIG. 31A. GDEP-LGG and papain alone showed a relative activity of about 100%. The combination of GDEP-LGG and papain resulted in a synergistic effect (FIG. 31A) with the combination of GDEP-LGG and papain having activity in excess of 100%. The sample with 60% GDEP-LGG and 40% papain resulted in the highest relative activity at about 150% to about 170%.

The 33-mer hydrolysis activity of the enzyme solutions was further tested. A 60 μL reaction volume comprised of 20 μL of 1 mg/mL 33-mer peptide, 20 μL of enzyme solution (100% GDEP-LGG, 80% GDEP-LGG with 20% papain, 60% GDEP-LGG with 40% papain, 40% GDEP-LGG with 60% papain, 20% GDEP-LGG with 80% papain, and 100% papain) and 20 μL of 150 mM acetate buffer at pH 4.5 was incubated for 1 hour at 37° C. and, then, 5 min at 90° C. to stop the enzyme reaction. Analysis by HPLC-MS was as described in Example 3. The results of the hydrolysis experiment are presented in FIG. 31B-31G. The sample with 60% GDEP-LGG and 40% papain resulted in the highest 33-mer hydrolysis activity.

Example 24

Comparison of Various Enzyme Preparations

The 33-mer hydrolysis activity of various enzyme preparations was tested according to the method described in Example 23. A set of 6-mers were used in a FRETS assay to screen various compositions for activity against the 33-mer. FIG. 32 summarizes the results of the screening. Enzymes with the best activity were selected. It was surprisingly found that certain preparations from *Penicillium citrinum* had activity against the 33-mer. Table 6 summarizes the reaction blends and maximum residual peptides found.

TABLE 6

Comparison of various gluten degrading enzyme preparation containing enzyme blends

| Enzyme Blend | Dose/serve | Maximum Residual Peptide |
| --- | --- | --- |
| GDEP-LGG | 100 mg | >10 mer |
| GDEP-LGG and papain | 100 mg | 9 mer |
| GDEP-LGG, papain and Protease P | 150 mg | 8 mer |
| GDEP-LGG, papain, Protease P and a preparation from *Penicillium citrinum* | 200 mg | 4 mer |

Chromatographs showing the results of the hydrolysis experiment are presented in FIG. 33. Analysis by HPLC/MC was as described in Example 3. The products of the hydrolysis experiment are smallest for the blend comprising GDEP-LGG, papain, Protease P and a preparation from *Penicillium citrinum*.

Specific Embodiments

An enzyme cocktail described herein can be illustrated by the following embodiments enumerated in the numbered sentences that follow:

1. An enzyme cocktail comprising:
   (a) GDEP-LGG; and
   (b) papain;
wherein the enzyme cocktail is capable of cleaving a gluten oligopeptide.

2. The enzyme cocktail of sentence 1, further comprising a semi-alkali protease and/or a preparation from *Penicillium citrinum*.

3. The enzyme cocktail of any one of the preceding sentences, wherein the papain is activated papain or chymopapain.

4. The enzyme cocktail of sentence 3, wherein the activated papain has been activated by a reductant.

5. The enzyme cocktail of any one of the preceding sentences, further comprising a reductant.

6. A pharmaceutical composition comprising the enzyme cocktail of any one of the preceding sentences.

7. The enzyme cocktail of any one of the preceding sentences, wherein the enzyme cocktail further comprises GDEP-M.

8. The enzyme cocktail of any one of the preceding sentences, wherein the enzyme cocktail further comprises an enzyme having an amino acid sequence at least about 80% homologous to CPY, or a fragment thereof.

9. The enzyme cocktail of any one of the preceding sentences, wherein the enzyme cocktail further comprises an enzyme having an amino acid sequence at least about 90% homologous to CPY, or a fragment thereof.

10. The enzyme cocktail of any one of the preceding sentences, wherein the enzyme cocktail further comprises CPY.

11. The enzyme cocktail of sentence 10, wherein the CPY is selected from the group consisting essentially of *Saccharomyces cerevisiae* CPY, *Aspergillus niger* CPY, *Schizosaccharomyces pombe* CPY, *Aspergillus fumigatus* CPY.

12. The enzyme cocktail of any one of the preceding sentences, wherein the gluten oligopeptide is a 33-mer peptide fragment of α-gliadin.

13. The enzyme cocktail of sentence 12, wherein the 33-mer peptide fragment has the amino acid sequence LQLQPFPQPQLPYPQPQLPYPQPQLPYPQPQPF (SEQ ID NO:1).

14. The enzyme cocktail of any one of the preceding sentences, wherein the enzyme cocktail is stable in acid conditions.

15. The enzyme cocktail of any one of the preceding sentences, wherein the enzyme cocktail is formulated in a pharmaceutically acceptable excipient.

16. The enzyme cocktail of any one of the preceding sentences, wherein the enzyme cocktail is formulated for oral delivery.

17. The enzyme cocktail of any one of the preceding sentences, wherein the enzyme cocktail is contained in a formulation that contains an enteric coating.

18. The enzyme cocktail of any one of the preceding sentences, wherein the enzyme cocktail is contained in a formulation that includes a pharmaceutically acceptable carrier.

19. The enzyme cocktail of sentence 18, wherein the pharmaceutically acceptable carrier is a solid.

20. The enzyme cocktail of sentence 18, wherein the pharmaceutically acceptable carrier is a capsule.

21. The enzyme cocktail of sentence 18, wherein the pharmaceutically acceptable carrier is a liquid.

An enzyme cocktail described herein can be illustrated by the following embodiments enumerated in the numbered sentences that follow:

1. An enzyme cocktail comprising:
   (a) GDEP-LGG; and
   (b) an acidic serine protease polypeptide having an amino acid sequence at least about 80% homologous to Aorsin, or a fragment thereof
   wherein the enzyme cocktail is capable of cleaving a gluten oligopeptide.

2. The enzyme cocktail of sentence 1, wherein the acidic serine protease polypeptide has an amino acid sequence at least about 90% homologous to Aorsin, or a fragment thereof 3. The enzyme cocktail of any one of the preceding sentences, wherein the enzyme cocktail comprises GDEP-M.

4. The enzyme cocktail of any one of the preceding sentences, wherein the enzyme cocktail further comprises an enzyme having an amino acid sequence at least about 80% homologous to CPY, or a fragment thereof.

5. The enzyme cocktail of any one of the preceding sentences, wherein the enzyme cocktail further comprises an enzyme having an amino acid sequence at least about 90% homologous to CPY, or a fragment thereof.

6. The enzyme cocktail of any one of the preceding sentences, wherein the enzyme cocktail further comprises CPY.

7. The enzyme cocktail of sentence 6, wherein the CPY is selected from the group consisting essentially of *Saccharomyces cerevisiae* CPY, *Aspergillus niger* CPY, *Schizosaccharomyces pombe* CPY, *Aspergillus fumigatus* CPY.

8. The enzyme cocktail of any one of the preceding sentences, wherein the gluten oligopeptide is a 33-mer peptide fragment of α-gliadin.

9. The enzyme cocktail of sentence 8, wherein the 33-mer peptide fragment has the amino acid sequence LQLQPF-PQPQLPYPQPQLPYPQPQLPYPQPQPF (SEQ ID NO:1).

10. The enzyme cocktail of any one of the preceding sentences, wherein the enzyme cocktail is stable in acid conditions.

11. The enzyme cocktail of any one of the preceding sentences, wherein the enzyme cocktail is formulated in a pharmaceutically acceptable excipient.

12. The enzyme cocktail of any one of the preceding sentences, wherein the enzyme cocktail is formulated for oral delivery.

13. The enzyme cocktail of any one of the preceding sentences, wherein the enzyme cocktail is contained in a formulation that contains an enteric coating.

14. The enzyme cocktail of any one of the preceding sentences, wherein the enzyme cocktail is contained in a formulation that includes a pharmaceutically acceptable carrier.

15. The enzyme cocktail of sentence 14, wherein herein the pharmaceutically acceptable carrier is a solid.

16. The enzyme cocktail of sentence 14, wherein herein the pharmaceutically acceptable carrier is a capsule.

17. The enzyme cocktail of sentence 14, wherein herein the pharmaceutically acceptable carrier is a liquid.

A formulation described herein can be illustrated by the following embodiments enumerated in the numbered sentences that follow:

1. A formulation for use in reducing gluten exposure or treating gluten intolerance comprising:
   an enzyme composition selected from the group consisting essentially of GDEP-LGG, papain, activated papain, purified papain, chymopapain, GDEP-M, Aorsin, CPY, a semi-alkali protease, and a preparation from *Penicillium citrinum*;
   wherein the enzyme composition is capable of cleaving an immunogenic gluten oligopeptide into non-toxic fragments in vitro.

2. The formulation of sentence 1, wherein the enzyme composition capable of cleaving at least about 70% of an immunogenic gluten oligopeptide into non-toxic fragments in vitro.

3. The formulation of any one of the preceding sentences, wherein the enzyme composition capable of cleaving at least about 80% of an immunogenic gluten oligopeptide into non-toxic fragments in vitro.

4. The formulation of any one of the preceding sentences, wherein the enzyme composition capable of cleaving at least about 90% of an immunogenic gluten oligopeptide into non-toxic fragments in vitro.

5. The formulation of any one of the preceding sentences, wherein the formulation is suitable for oral administration.

6. The formulation of any one of the preceding sentences, wherein the formulation includes a pharmaceutically acceptable carrier.

7. The formulation of sentence 6, wherein the pharmaceutically acceptable carrier is a solid.

8. The formulation of sentence 6, wherein the pharmaceutically acceptable carrier is a capsule.

9. The formulation of sentence 6, wherein the pharmaceutically acceptable carrier is a liquid.

A formulation described herein can be illustrated by the following embodiments enumerated in the numbered sentences that follow:

1. A formulation for use in reducing gluten exposure or treating gluten intolerance comprising:
   at least two enzyme compositions selected from the group consisting essentially of GDEP; GDEP-LGG; GDEP-M; GDEP-LNA; GDEP-2A; GDEP-AH; papain; Aorsin; an acidic serine protease polypeptide having an amino acid sequence at least about 80% homologous to Aorsin, or a fragment thereof; CPY; an enzyme having an amino acid sequence at least about 80% homologous to CPY; a semi-alkali protease; and a preparation from *Penicillium citrinum*;
   wherein the at least two enzyme compositions are capable of digesting a gluten oligopeptide in an in vitro gastrointestinal model.

3. The formulation of sentence 1, wherein the at least two enzyme compositions are GDEP-LGG and papain.

3. The formulation of sentence 1, wherein the at least two enzyme compositions are Carboxypeptidase Y and Aorsin.

4. The formulation of any one of the preceding sentences, wherein the model comprises incubating the at least two enzyme compositions with the gluten oligopeptide in simulated gastric fluid at about 37° C. for a period representative of in vivo contact with gastric fluids.

5. The formulation of sentence 4, wherein the period representative of in vivo contact with gastric fluids is about 120 minutes.

6. The formulation of any one of sentences 4 or 5, wherein the simulated gastric fluid comprises gastric mucosa mucin, pepsin, gelatinase, amylase, and lipase.

7. The formulation of any one of the preceding sentences, wherein the model comprises incubating the at least two enzyme compositions with the gluten oligopeptide in simulated intestinal fluid at about 37° C. for a period representative of in vivo contact with intestinal fluids.

8. The formulation of sentence 7, wherein the period representative of in vivo contact with intestinal fluids is about 60 minutes.

9. The formulation of any one of the preceding sentences, wherein the simulated intestinal fluid comprises one or more pancreatic enzymes and a bile salt.

10. The formulation of sentence 9, wherein the one or more pancreatic enzymes are selected from the group consisting essentially of trypsin, chymotrypsin, amylase, and lipase.

11. The formulation of any one of the preceding sentences, wherein the model comprises:
incubating a mixture comprising the at least two enzyme compositions, the gluten oligopeptide, gastric mucosa mucin, pepsin, gelatinase, amylase, and lipase in acidic conditions at about 37° C. for about 120 minutes;
adding an acid neutralizing substance to the mixture; and
incubating the mixture with trypsin, amylase, and lipase, and a bile salt in neutral conditions at about 37° C. for about 60 minutes.

12. The formulation of any one of the preceding sentences, wherein the model comprises:
incubating a mixture comprising the at least two enzyme compositions, the gluten oligopeptide, and pepsin in acidic conditions at about 37° C. for about 60 minutes;
adding an acid neutralizing substance to the mixture; and
incubating the mixture with trypsin and chymotrypsin in neutral conditions at about 37° C. for about 60 minutes.

13. The formulation of any one of the preceding sentences, wherein the gluten oligopeptide is a 33-mer peptide fragment of α-gliadin.

14. The formulation of sentence 13, wherein the 33-mer peptide fragment has the amino acid sequence LQLQPF-PQPQLPYPQPQLPYPQPQLPYPQPQPF (SEQ ID NO:1).

A method described herein can be illustrated by the following embodiments enumerated in the numbered sentences that follow:

1. A method of treating gluten intolerance or reducing gluten exposure in a human subject comprising:
providing the subject with a therapeutically effective amount of an enzyme cocktail,
wherein the enzyme cocktail is capable of cleaving a gluten oligopeptide at acidic conditions.

2. The method of sentence 1, wherein the enzyme cocktail comprises a composition selected from the group consisting essentially of at least two enzyme compositions selected from the group consisting essentially of GDEP; GDEP-LGG; GDEP-M; GDEP-LNA; GDEP-2A; GDEP-AH; papain; Aorsin; an acidic serine protease polypeptide having an amino acid sequence at least about 80% homologous to Aorsin, or a fragment thereof; CPY; an enzyme having an amino acid sequence at least about 80% homologous to CPY, or a fragment thereof; a semi-alkali protease; and a preparation from *Penicillium citrinum*.

3. The method of any one of the preceding sentences, wherein the enzyme cocktail includes a composition derived from *Aspergillus oryzae*.

4. The method of any one of the preceding sentences, wherein the enzyme cocktail is formulated in a pharmaceutically acceptable excipient.

5. The method of any one of the preceding sentences, wherein the enzyme cocktail is formulated for oral delivery.

6. The method of any one of the preceding sentences, wherein the enzyme cocktail is contained in a formulation that contains an enteric coating.

7. The method of any one of the preceding sentences, wherein enzyme cocktail is contained in a formulation that includes a pharmaceutically acceptable carrier.

8. The method of sentence 7, wherein the pharmaceutically acceptable carrier is a solid.

9. The method of sentence 7, wherein the pharmaceutically acceptable carrier is a capsule.

10. The method of sentence 7, wherein the pharmaceutically acceptable carrier is a liquid.

A method described herein can be illustrated by the following embodiments enumerated in the numbered sentences that follow:

1. A method of assessing the efficacy of an enzyme composition, comprising the steps of:
(i) incubating a mixture comprising the enzyme composition and a gluten oligopeptide in simulated gastric fluid at about 37° C. for a period representative of in vivo contact with gastric fluids;
(ii) adding an acid neutralizing substance to the mixture;
(iii) incubating the mixture in simulated intestinal fluid at about 37° C. for a period representative of in vivo contact with intestinal fluids; and
(iv) determining the amount of intact gluten oligopeptide in the mixture.

2. The method of sentence 1, wherein the period representative of in vivo contact with gastric fluids is about 120 minutes.

3. The method of any one of the preceding sentences, wherein the simulated gastric fluid comprises gastric mucosa mucin, pepsin, gelatinase, amylase, and lipase.

4. The method of any one of the preceding sentences, wherein the period representative of in vivo contact with intestinal fluids is about 60 minutes.

5. The method of any one of the preceding sentences, wherein the simulated intestinal fluid comprises one or more pancreatic enzymes and a bile salt.

6. The method of sentence 5, wherein the one or more pancreatic enzymes are selected from the group consisting essentially of trypsin, chymotrypsin, amylase, and lipase.

7. The method of any one of the preceding sentences, wherein the gluten oligopeptide is a 33-mer peptide fragment of α-gliadin.

8. The method of sentence 7, wherein the 33-mer peptide fragment has the amino acid sequence LQLQPF-PQPQLPYPQPQLPYPQPQLPYPQPQPF (SEQ ID NO:1).

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

What is claimed is:

1. An enzyme cocktail comprising:
a gluten degrading enzyme preparation with specificity for peptide substrate leucyl-glycyl-glycine (GDEP-LGG) and papain in a percent relative activity ratio of 80:20 to 20:80;
wherein the enzyme cocktail degrades a gluten oligopeptide into peptide fragments of nine amino acids or less.

2. The enzyme cocktail of claim 1, wherein the enzyme cocktail further comprises a semi-alkali protease and an enzyme preparation from *Penicillium citrinum*.

3. The enzyme cocktail of claim 2, wherein the semi-alkali protease is Protease P.

4. The enzyme cocktail of claim 1, wherein the papain has been activated by a reductant.

5. The enzyme cocktail of claim 1, wherein the gluten oligopeptide is a 33-mer peptide fragment of α-gliadin.

6. The enzyme cocktail of claim 5, wherein the 33-mer peptide fragment has the amino acid sequence LQLQPFPQPQLPYPQPQLPYPQPQLPYPQPQPF (SEQ ID NO:1).

7. The enzyme cocktail of claim 1, wherein the enzyme cocktail is stable in acid conditions.

8. The enzyme cocktail of claim 1, wherein the enzyme cocktail is formulated in a pharmaceutically acceptable excipient.

9. The enzyme cocktail of claim 1, wherein the enzyme cocktail further comprises a semi-alkali protease.

10. The enzyme cocktail of claim 1, wherein the percent relative activity ratio is 80:20 to 40:60.

11. The enzyme cocktail of claim 1, wherein the percent relative activity ratio is 80:20 to 60:40.

12. The enzyme cocktail of claim 1, wherein the percent relative activity ratio is 60:40.

13. A method of treating gluten intolerance or reducing the effects of ingestion of a gluten oligopeptide in a human subject in need thereof, comprising:
orally administering said subject with a therapeutically effective amount of the enzyme cocktail according to claim 1,
wherein the enzyme cocktail degrades the gluten oligopeptide at acidic conditions.

* * * * *

SEQUENCE LISTING

<160> NUMBER OF SEQ ID NOS: 156

<210> SEQ ID NO 1
<211> LENGTH: 33
<212> TYPE: PRT
<213> ORGANISM: Triticum aestivum

<400> SEQUENCE: 1

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 2
<211> LENGTH: 11
<212> TYPE: PRT
<213> ORGANISM: Triticum aestivum

<400> SEQUENCE: 2

Gln Pro Gln Leu Pro Tyr Pro Gln Pro Gln Leu
1               5                   10

<210> SEQ ID NO 3
<211> LENGTH: 11
<212> TYPE: PRT
<213> ORGANISM: Triticum aestivum

<400> SEQUENCE: 3

Leu Gln Leu Gln Pro Phe Pro Gln Pro Gln Leu
1               5                   10

<210> SEQ ID NO 4
<211> LENGTH: 15
<212> TYPE: PRT
<213> ORGANISM: Triticum aestivum

<400> SEQUENCE: 4

Pro Phe Pro Gln Pro Gln Leu Pro Tyr Pro Gln Pro Gln Leu Pro
1               5                   10                  15

<210> SEQ ID NO 5
<211> LENGTH: 15
<212> TYPE: PRT
<213> ORGANISM: Triticum aestivum

<400> SEQUENCE: 5

Pro Tyr Pro Gln Pro Gln Leu Pro Tyr Pro Gln Pro Gln Pro Phe
1               5                   10                  15

<210> SEQ ID NO 6
<211> LENGTH: 25
<212> TYPE: PRT
<213> ORGANISM: Triticum aestivum

<400> SEQUENCE: 6

Leu Gln Leu Gln Pro Phe Pro Gln Pro Gln Leu Pro Tyr Pro Gln Pro
1               5                   10                  15

Gln Leu Pro Tyr Pro Gln Pro Gln Leu
            20                  25

<210> SEQ ID NO 7
<211> LENGTH: 8

```
<212> TYPE: PRT
<213> ORGANISM: Triticum aestivum

<400> SEQUENCE: 7

Pro Tyr Pro Gln Pro Gln Pro Phe
1               5

<210> SEQ ID NO 8
<211> LENGTH: 18
<212> TYPE: PRT
<213> ORGANISM: Triticum aestivum

<400> SEQUENCE: 8

Gln Pro Gln Leu Pro Tyr Pro Gln Pro Gln Leu Pro Tyr Pro Gln Pro
1               5                   10                  15

Gln Leu

<210> SEQ ID NO 9
<211> LENGTH: 18
<212> TYPE: PRT
<213> ORGANISM: Triticum aestivum

<400> SEQUENCE: 9

Leu Gln Leu Gln Pro Phe Pro Gln Pro Gln Leu Pro Tyr Pro Gln Pro
1               5                   10                  15

Gln Leu

<210> SEQ ID NO 10
<211> LENGTH: 5
<212> TYPE: PRT
<213> ORGANISM: Triticum aestivum

<400> SEQUENCE: 10

Leu Gln Leu Gln Pro
1               5

<210> SEQ ID NO 11
<211> LENGTH: 10
<212> TYPE: PRT
<213> ORGANISM: Triticum aestivum

<400> SEQUENCE: 11

Gln Pro Gln Leu Pro Tyr Pro Gln Pro Gln
1               5                   10

<210> SEQ ID NO 12
<211> LENGTH: 10
<212> TYPE: PRT
<213> ORGANISM: Triticum aestivum

<400> SEQUENCE: 12

Leu Gln Leu Gln Pro Phe Pro Gln Pro Gln
1               5                   10

<210> SEQ ID NO 13
<211> LENGTH: 10
<212> TYPE: PRT
<213> ORGANISM: Triticum aestivum

<400> SEQUENCE: 13

Gln Leu Gln Pro Phe Pro Gln Pro Gln Leu
1               5                   10
```

```
<210> SEQ ID NO 14
<211> LENGTH: 15
<212> TYPE: PRT
<213> ORGANISM: Triticum aestivum

<400> SEQUENCE: 14

Leu Gln Pro Phe Pro Gln Pro Gln Leu Pro Tyr Pro Gln Pro Gln
1               5                   10                  15

<210> SEQ ID NO 15
<211> LENGTH: 15
<212> TYPE: PRT
<213> ORGANISM: Triticum aestivum

<400> SEQUENCE: 15

Gln Pro Phe Pro Gln Pro Gln Leu Pro Tyr Pro Gln Pro Gln Leu
1               5                   10                  15

<210> SEQ ID NO 16
<211> LENGTH: 15
<212> TYPE: PRT
<213> ORGANISM: Triticum aestivum

<400> SEQUENCE: 16

Gln Leu Gln Pro Phe Pro Gln Pro Gln Leu Pro Tyr Pro Gln Pro
1               5                   10                  15

<210> SEQ ID NO 17
<211> LENGTH: 22
<212> TYPE: PRT
<213> ORGANISM: Triticum aestivum

<400> SEQUENCE: 17

Gln Leu Gln Pro Phe Pro Gln Pro Gln Leu Pro Tyr Pro Gln Pro Gln
1               5                   10                  15

Leu Pro Tyr Pro Gln Pro
            20

<210> SEQ ID NO 18
<211> LENGTH: 22
<212> TYPE: PRT
<213> ORGANISM: Triticum aestivum

<400> SEQUENCE: 18

Leu Gln Pro Phe Pro Gln Pro Gln Leu Pro Tyr Pro Gln Pro Gln Leu
1               5                   10                  15

Pro Tyr Pro Gln Pro Gln
            20

<210> SEQ ID NO 19
<211> LENGTH: 22
<212> TYPE: PRT
<213> ORGANISM: Triticum aestivum

<400> SEQUENCE: 19

Gln Pro Phe Pro Gln Pro Gln Leu Pro Tyr Pro Gln Pro Gln Leu Pro
1               5                   10                  15

Tyr Pro Gln Pro Gln Leu
            20

<210> SEQ ID NO 20
<211> LENGTH: 31
<212> TYPE: PRT
<213> ORGANISM: Triticum aestivum
```

```
<400> SEQUENCE: 20

Leu Gln Pro Phe Pro Gln Pro Gln Leu Pro Tyr Pro Gln Pro Gln Leu
1               5                   10                  15

Pro Tyr Pro Gln Pro Gln Leu Pro Tyr Pro Gln Pro Gln Pro Phe
            20                  25                  30

<210> SEQ ID NO 21
<211> LENGTH: 26
<212> TYPE: PRT
<213> ORGANISM: Triticum aestivum

<400> SEQUENCE: 21

Leu Gln Pro Phe Pro Gln Pro Gln Leu Pro Tyr Pro Gln Pro Gln Leu
1               5                   10                  15

Pro Tyr Pro Gln Pro Gln Leu Pro Tyr Pro
            20                  25

<210> SEQ ID NO 22
<211> LENGTH: 15
<212> TYPE: PRT
<213> ORGANISM: Triticum aestivum

<400> SEQUENCE: 22

Pro Gln Pro Gln Leu Pro Tyr Pro Gln Pro Gln Leu Pro Tyr Pro
1               5                   10                  15

<210> SEQ ID NO 23
<211> LENGTH: 15
<212> TYPE: PRT
<213> ORGANISM: Triticum aestivum

<400> SEQUENCE: 23

Pro Gln Leu Pro Tyr Pro Gln Pro Gln Leu Pro Tyr Pro Gln Pro
1               5                   10                  15

<210> SEQ ID NO 24
<211> LENGTH: 15
<212> TYPE: PRT
<213> ORGANISM: Triticum aestivum

<400> SEQUENCE: 24

Leu Pro Tyr Pro Gln Pro Gln Leu Pro Tyr Pro Gln Pro Gln Pro
1               5                   10                  15

<210> SEQ ID NO 25
<211> LENGTH: 15
<212> TYPE: PRT
<213> ORGANISM: Triticum aestivum

<400> SEQUENCE: 25

Pro Tyr Pro Gln Pro Gln Leu Pro Tyr Pro Gln Pro Gln Leu Pro
1               5                   10                  15

<210> SEQ ID NO 26
<211> LENGTH: 30
<212> TYPE: PRT
<213> ORGANISM: Triticum aestivum

<400> SEQUENCE: 26

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro
```

<210> SEQ ID NO 27
<211> LENGTH: 27
<212> TYPE: PRT
<213> ORGANISM: Triticum aestivum

<400> SEQUENCE: 27

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro
            20                  25

<210> SEQ ID NO 28
<211> LENGTH: 27
<212> TYPE: PRT
<213> ORGANISM: Triticum aestivum

<400> SEQUENCE: 28

Pro Gln Pro Gln Leu Pro Tyr Pro Gln Pro Gln Leu Pro Tyr Pro Gln
1               5                   10                  15

Pro Gln Leu Pro Tyr Pro Gln Pro Gln Pro Phe
            20                  25

<210> SEQ ID NO 29
<211> LENGTH: 27
<212> TYPE: PRT
<213> ORGANISM: Triticum aestivum

<400> SEQUENCE: 29

Pro Phe Pro Gln Pro Gln Leu Pro Tyr Pro Gln Pro Gln Leu Pro Tyr
1               5                   10                  15

Pro Gln Pro Gln Leu Pro Tyr Pro Gln Pro Gln
            20                  25

<210> SEQ ID NO 30
<211> LENGTH: 27
<212> TYPE: PRT
<213> ORGANISM: Triticum aestivum

<400> SEQUENCE: 30

Phe Pro Gln Pro Gln Leu Pro Tyr Pro Gln Pro Gln Leu Pro Tyr Pro
1               5                   10                  15

Gln Pro Gln Leu Pro Tyr Pro Gln Pro Gln Pro
            20                  25

<210> SEQ ID NO 31
<211> LENGTH: 29
<212> TYPE: PRT
<213> ORGANISM: Triticum aestivum

<400> SEQUENCE: 31

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln Pro
            20                  25

<210> SEQ ID NO 32
<211> LENGTH: 11
<212> TYPE: PRT
<213> ORGANISM: Triticum aestivum

<400> SEQUENCE: 32

```
Gln Pro Phe Pro Gln Pro Gln Leu Pro Tyr Pro
1               5                   10
```

<210> SEQ ID NO 33
<211> LENGTH: 11
<212> TYPE: PRT
<213> ORGANISM: Triticum aestivum

<400> SEQUENCE: 33

```
Pro Phe Pro Gln Pro Gln Leu Pro Tyr Pro Gln
1               5                   10
```

<210> SEQ ID NO 34
<211> LENGTH: 11
<212> TYPE: PRT
<213> ORGANISM: Triticum aestivum

<400> SEQUENCE: 34

```
Phe Pro Gln Pro Gln Leu Pro Tyr Pro Gln Pro
1               5                   10
```

<210> SEQ ID NO 35
<211> LENGTH: 11
<212> TYPE: PRT
<213> ORGANISM: Triticum aestivum

<400> SEQUENCE: 35

```
Pro Gln Leu Pro Tyr Pro Gln Pro Gln Pro Phe
1               5                   10
```

<210> SEQ ID NO 36
<211> LENGTH: 11
<212> TYPE: PRT
<213> ORGANISM: Triticum aestivum

<400> SEQUENCE: 36

```
Leu Pro Tyr Pro Gln Pro Gln Leu Pro Tyr Pro
1               5                   10
```

<210> SEQ ID NO 37
<211> LENGTH: 14
<212> TYPE: PRT
<213> ORGANISM: Triticum aestivum

<400> SEQUENCE: 37

```
Tyr Pro Gln Pro Gln Leu Pro Tyr Pro Gln Pro Gln Pro Phe
1               5                   10
```

<210> SEQ ID NO 38
<211> LENGTH: 12
<212> TYPE: PRT
<213> ORGANISM: Triticum aestivum

<400> SEQUENCE: 38

```
Gln Pro Gln Leu Pro Tyr Pro Gln Pro Gln Pro Phe
1               5                   10
```

<210> SEQ ID NO 39
<211> LENGTH: 12
<212> TYPE: PRT
<213> ORGANISM: Triticum aestivum

<400> SEQUENCE: 39

```
Gln Pro Phe Pro Gln Pro Gln Leu Pro Tyr Pro Gln
```

```
<210> SEQ ID NO 40
<211> LENGTH: 12
<212> TYPE: PRT
<213> ORGANISM: Triticum aestivum

<400> SEQUENCE: 40

Phe Pro Gln Pro Gln Leu Pro Tyr Pro Gln Pro Gln
1               5                   10

<210> SEQ ID NO 41
<211> LENGTH: 26
<212> TYPE: PRT
<213> ORGANISM: Triticum aestivum

<400> SEQUENCE: 41

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln
            20                  25

<210> SEQ ID NO 42
<211> LENGTH: 26
<212> TYPE: PRT
<213> ORGANISM: Triticum aestivum

<400> SEQUENCE: 42

Phe Pro Gln Pro Gln Leu Pro Tyr Pro Gln Pro Gln Leu Pro Tyr Pro
1               5                   10                  15

Gln Pro Gln Leu Pro Tyr Pro Gln Pro Gln
            20                  25

<210> SEQ ID NO 43
<211> LENGTH: 19
<212> TYPE: PRT
<213> ORGANISM: Triticum aestivum

<400> SEQUENCE: 43

Pro Gln Leu Pro Tyr Pro Gln Pro Gln Leu Pro Tyr Pro Gln Pro Gln
1               5                   10                  15

Leu Pro Tyr

<210> SEQ ID NO 44
<211> LENGTH: 19
<212> TYPE: PRT
<213> ORGANISM: Triticum aestivum

<400> SEQUENCE: 44

Leu Pro Tyr Pro Gln Pro Gln Leu Pro Tyr Pro Gln Pro Gln Leu Pro
1               5                   10                  15

Tyr Pro Gln

<210> SEQ ID NO 45
<211> LENGTH: 19
<212> TYPE: PRT
<213> ORGANISM: Triticum aestivum

<400> SEQUENCE: 45

Gln Leu Pro Tyr Pro Gln Pro Gln Leu Pro Tyr Pro Gln Pro Gln Leu
1               5                   10                  15

Pro Tyr Pro
```

```
<210> SEQ ID NO 46
<211> LENGTH: 28
<212> TYPE: PRT
<213> ORGANISM: Triticum aestivum

<400> SEQUENCE: 46

Phe Pro Gln Pro Gln Leu Pro Tyr Pro Gln Pro Gln Leu Pro Tyr Pro
1               5                   10                  15

Gln Pro Gln Leu Pro Tyr Pro Gln Pro Gln Pro Phe
            20                  25

<210> SEQ ID NO 47
<211> LENGTH: 30
<212> TYPE: PRT
<213> ORGANISM: Triticum aestivum

<400> SEQUENCE: 47

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln Pro Phe
            20                  25                  30

<210> SEQ ID NO 48
<211> LENGTH: 32
<212> TYPE: PRT
<213> ORGANISM: Triticum aestivum

<400> SEQUENCE: 48

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

<210> SEQ ID NO 49
<211> LENGTH: 16
<212> TYPE: PRT
<213> ORGANISM: Triticum aestivum

<400> SEQUENCE: 49

Leu Gln Pro Phe Pro Gln Pro Gln Leu Pro Tyr Pro Gln Pro Gln Leu
1               5                   10                  15

<210> SEQ ID NO 50
<211> LENGTH: 16
<212> TYPE: PRT
<213> ORGANISM: Triticum aestivum

<400> SEQUENCE: 50

Leu Gln Leu Gln Pro Phe Pro Gln Pro Gln Leu Pro Tyr Pro Gln Pro
1               5                   10                  15

<210> SEQ ID NO 51
<211> LENGTH: 18
<212> TYPE: PRT
<213> ORGANISM: Triticum aestivum

<400> SEQUENCE: 51

Pro Gln Pro Gln Leu Pro Tyr Pro Gln Pro Gln Leu Pro Tyr Pro Gln
1               5                   10                  15

Pro Gln
```

-continued

```
<210> SEQ ID NO 52
<211> LENGTH: 18
<212> TYPE: PRT
<213> ORGANISM: Triticum aestivum

<400> SEQUENCE: 52

Gln Pro Gln Leu Pro Tyr Pro Gln Pro Gln Leu Pro Tyr Pro Gln Pro
1               5                   10                  15

Gln Pro

<210> SEQ ID NO 53
<211> LENGTH: 18
<212> TYPE: PRT
<213> ORGANISM: Triticum aestivum

<400> SEQUENCE: 53

Gln Leu Gln Pro Phe Pro Gln Pro Gln Leu Pro Tyr Pro Gln Pro Gln
1               5                   10                  15

Leu Pro

<210> SEQ ID NO 54
<211> LENGTH: 31
<212> TYPE: PRT
<213> ORGANISM: Triticum aestivum

<400> SEQUENCE: 54

Gln Leu Gln Pro Phe Pro Gln Pro Gln Leu Pro Tyr Pro Gln Pro Gln
1               5                   10                  15

Leu Pro Tyr Pro Gln Pro Gln Leu Pro Tyr Pro Gln Pro Gln Pro
            20                  25                  30

<210> SEQ ID NO 55
<211> LENGTH: 28
<212> TYPE: PRT
<213> ORGANISM: Triticum aestivum

<400> SEQUENCE: 55

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln
            20                  25

<210> SEQ ID NO 56
<211> LENGTH: 28
<212> TYPE: PRT
<213> ORGANISM: Triticum aestivum

<400> SEQUENCE: 56

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro
            20                  25

<210> SEQ ID NO 57
<211> LENGTH: 32
<212> TYPE: PRT
<213> ORGANISM: Triticum aestivum

<400> SEQUENCE: 57

Gln Leu Gln Pro Phe Pro Gln Pro Gln Leu Pro Tyr Pro Gln Pro Gln
1               5                   10                  15

Leu Pro Tyr Pro Gln Pro Gln Leu Pro Tyr Pro Gln Pro Gln Pro Phe
```

```
                    20              25              30
```

<210> SEQ ID NO 58
<211> LENGTH: 8
<212> TYPE: PRT
<213> ORGANISM: Triticum aestivum

<400> SEQUENCE: 58

Pro Gln Pro Gln Leu Pro Tyr Pro
1               5

<210> SEQ ID NO 59
<211> LENGTH: 8
<212> TYPE: PRT
<213> ORGANISM: Triticum aestivum

<400> SEQUENCE: 59

Pro Gln Leu Pro Tyr Pro Gln Pro
1               5

<210> SEQ ID NO 60
<211> LENGTH: 8
<212> TYPE: PRT
<213> ORGANISM: Triticum aestivum

<400> SEQUENCE: 60

Pro Tyr Pro Gln Pro Gln Leu Pro
1               5

<210> SEQ ID NO 61
<211> LENGTH: 8
<212> TYPE: PRT
<213> ORGANISM: Triticum aestivum

<400> SEQUENCE: 61

Leu Pro Tyr Pro Gln Pro Gln Pro
1               5

<210> SEQ ID NO 62
<211> LENGTH: 4
<212> TYPE: PRT
<213> ORGANISM: Triticum aestivum

<400> SEQUENCE: 62

Gln Pro Phe Pro
1

<210> SEQ ID NO 63
<211> LENGTH: 4
<212> TYPE: PRT
<213> ORGANISM: Triticum aestivum

<400> SEQUENCE: 63

Pro Phe Pro Gln
1

<210> SEQ ID NO 64
<211> LENGTH: 4
<212> TYPE: PRT
<213> ORGANISM: Triticum aestivum

<400> SEQUENCE: 64

Pro Gln Pro Phe
1

```
<210> SEQ ID NO 65
<211> LENGTH: 4
<212> TYPE: PRT
<213> ORGANISM: Triticum aestivum

<400> SEQUENCE: 65

Phe Pro Gln Pro
1

<210> SEQ ID NO 66
<211> LENGTH: 4
<212> TYPE: PRT
<213> ORGANISM: Triticum aestivum

<400> SEQUENCE: 66

Leu Pro Tyr Pro
1

<210> SEQ ID NO 67
<211> LENGTH: 6
<212> TYPE: PRT
<213> ORGANISM: Triticum aestivum

<400> SEQUENCE: 67

Gln Pro Phe Pro Gln Pro
1               5

<210> SEQ ID NO 68
<211> LENGTH: 6
<212> TYPE: PRT
<213> ORGANISM: Triticum aestivum

<400> SEQUENCE: 68

Pro Phe Pro Gln Pro Gln
1               5

<210> SEQ ID NO 69
<211> LENGTH: 6
<212> TYPE: PRT
<213> ORGANISM: Triticum aestivum

<400> SEQUENCE: 69

Pro Gln Pro Gln Pro Phe
1               5

<210> SEQ ID NO 70
<211> LENGTH: 6
<212> TYPE: PRT
<213> ORGANISM: Triticum aestivum

<400> SEQUENCE: 70

Pro Gln Leu Pro Tyr Pro
1               5

<210> SEQ ID NO 71
<211> LENGTH: 6
<212> TYPE: PRT
<213> ORGANISM: Triticum aestivum

<400> SEQUENCE: 71

Leu Pro Tyr Pro Gln Pro
1               5

<210> SEQ ID NO 72
```

```
<211> LENGTH: 13
<212> TYPE: PRT
<213> ORGANISM: Triticum aestivum

<400> SEQUENCE: 72

Pro Tyr Pro Gln Pro Gln Leu Pro Tyr Pro Gln Pro Gln
1               5                   10

<210> SEQ ID NO 73
<211> LENGTH: 13
<212> TYPE: PRT
<213> ORGANISM: Triticum aestivum

<400> SEQUENCE: 73

Tyr Pro Gln Pro Gln Leu Pro Tyr Pro Gln Pro Gln Pro
1               5                   10

<210> SEQ ID NO 74
<211> LENGTH: 13
<212> TYPE: PRT
<213> ORGANISM: Triticum aestivum

<400> SEQUENCE: 74

Leu Gln Pro Phe Pro Gln Pro Gln Leu Pro Tyr Pro Gln
1               5                   10

<210> SEQ ID NO 75
<211> LENGTH: 13
<212> TYPE: PRT
<213> ORGANISM: Triticum aestivum

<400> SEQUENCE: 75

Gln Leu Gln Pro Phe Pro Gln Pro Gln Leu Pro Tyr Pro
1               5                   10

<210> SEQ ID NO 76
<211> LENGTH: 13
<212> TYPE: PRT
<213> ORGANISM: Triticum aestivum

<400> SEQUENCE: 76

Phe Pro Gln Pro Gln Leu Pro Tyr Pro Gln Pro Gln Leu
1               5                   10

<210> SEQ ID NO 77
<211> LENGTH: 22
<212> TYPE: PRT
<213> ORGANISM: Triticum aestivum

<400> SEQUENCE: 77

Pro Gln Leu Pro Tyr Pro Gln Pro Gln Leu Pro Tyr Pro Gln Pro Gln
1               5                   10                  15

Leu Pro Tyr Pro Gln Pro
            20

<210> SEQ ID NO 78
<211> LENGTH: 22
<212> TYPE: PRT
<213> ORGANISM: Triticum aestivum

<400> SEQUENCE: 78

Leu Pro Tyr Pro Gln Pro Gln Leu Pro Tyr Pro Gln Pro Gln Leu Pro
1               5                   10                  15

Tyr Pro Gln Pro Gln Pro
```

```
                    20

<210> SEQ ID NO 79
<211> LENGTH: 22
<212> TYPE: PRT
<213> ORGANISM: Triticum aestivum

<400> SEQUENCE: 79

Pro Gln Pro Gln Leu Pro Tyr Pro Gln Pro Gln Leu Pro Tyr Pro Gln
1               5                   10                  15

Pro Gln Leu Pro Tyr Pro
            20

<210> SEQ ID NO 80
<211> LENGTH: 20
<212> TYPE: PRT
<213> ORGANISM: Triticum aestivum

<400> SEQUENCE: 80

Pro Tyr Pro Gln Pro Gln Leu Pro Tyr Pro Gln Pro Gln Leu Pro Tyr
1               5                   10                  15

Pro Gln Pro Gln
            20

<210> SEQ ID NO 81
<211> LENGTH: 20
<212> TYPE: PRT
<213> ORGANISM: Triticum aestivum

<400> SEQUENCE: 81

Tyr Pro Gln Pro Gln Leu Pro Tyr Pro Gln Pro Gln Leu Pro Tyr Pro
1               5                   10                  15

Gln Pro Gln Pro
            20

<210> SEQ ID NO 82
<211> LENGTH: 20
<212> TYPE: PRT
<213> ORGANISM: Triticum aestivum

<400> SEQUENCE: 82

Gln Leu Gln Pro Phe Pro Gln Pro Gln Leu Pro Tyr Pro Gln Pro Gln
1               5                   10                  15

Leu Pro Tyr Pro
            20

<210> SEQ ID NO 83
<211> LENGTH: 20
<212> TYPE: PRT
<213> ORGANISM: Triticum aestivum

<400> SEQUENCE: 83

Leu Gln Pro Phe Pro Gln Pro Gln Leu Pro Tyr Pro Gln Pro Gln Leu
1               5                   10                  15

Pro Tyr Pro Gln
            20

<210> SEQ ID NO 84
<211> LENGTH: 20
<212> TYPE: PRT
<213> ORGANISM: Triticum aestivum

<400> SEQUENCE: 84
```

-continued

Phe Pro Gln Pro Gln Leu Pro Tyr Pro Gln Pro Gln Leu Pro Tyr Pro
1               5                   10                  15

Gln Pro Gln Leu
            20

<210> SEQ ID NO 85
<211> LENGTH: 6
<212> TYPE: PRT
<213> ORGANISM: Triticum aestivum

<400> SEQUENCE: 85

Gln Pro Gln Leu Pro Tyr
1               5

<210> SEQ ID NO 86
<211> LENGTH: 6
<212> TYPE: PRT
<213> ORGANISM: Triticum aestivum

<400> SEQUENCE: 86

Gln Leu Pro Tyr Pro Gln
1               5

<210> SEQ ID NO 87
<211> LENGTH: 6
<212> TYPE: PRT
<213> ORGANISM: Triticum aestivum

<400> SEQUENCE: 87

Tyr Pro Gln Pro Gln Leu
1               5

<210> SEQ ID NO 88
<211> LENGTH: 6
<212> TYPE: PRT
<213> ORGANISM: Triticum aestivum

<400> SEQUENCE: 88

Leu Gln Leu Gln Pro Phe
1               5

<210> SEQ ID NO 89
<211> LENGTH: 7
<212> TYPE: PRT
<213> ORGANISM: Triticum aestivum

<400> SEQUENCE: 89

Leu Gln Leu Gln Pro Phe Pro
1               5

<210> SEQ ID NO 90
<211> LENGTH: 23
<212> TYPE: PRT
<213> ORGANISM: Triticum aestivum

<400> SEQUENCE: 90

Leu Pro Tyr Pro Gln Pro Gln Leu Pro Tyr Pro Gln Pro Gln Leu Pro
1               5                   10                  15

Tyr Pro Gln Pro Gln Pro Phe
            20

<210> SEQ ID NO 91
<211> LENGTH: 23

<212> TYPE: PRT
<213> ORGANISM: Triticum aestivum

<400> SEQUENCE: 91

Phe Pro Gln Pro Gln Leu Pro Tyr Pro Gln Pro Gln Leu Pro Tyr Pro
1               5                   10                  15
Gln Pro Gln Leu Pro Tyr Pro
            20

<210> SEQ ID NO 92
<211> LENGTH: 23
<212> TYPE: PRT
<213> ORGANISM: Triticum aestivum

<400> SEQUENCE: 92

Pro Phe Pro Gln Pro Gln Leu Pro Tyr Pro Gln Pro Gln Leu Pro Tyr
1               5                   10                  15
Pro Gln Pro Gln Leu Pro Tyr
            20

<210> SEQ ID NO 93
<211> LENGTH: 7
<212> TYPE: PRT
<213> ORGANISM: Triticum aestivum

<400> SEQUENCE: 93

Pro Gln Pro Gln Leu Pro Tyr
1               5

<210> SEQ ID NO 94
<211> LENGTH: 7
<212> TYPE: PRT
<213> ORGANISM: Triticum aestivum

<400> SEQUENCE: 94

Gln Pro Gln Leu Pro Tyr Pro
1               5

<210> SEQ ID NO 95
<211> LENGTH: 7
<212> TYPE: PRT
<213> ORGANISM: Triticum aestivum

<400> SEQUENCE: 95

Pro Gln Leu Pro Tyr Pro Gln
1               5

<210> SEQ ID NO 96
<211> LENGTH: 7
<212> TYPE: PRT
<213> ORGANISM: Triticum aestivum

<400> SEQUENCE: 96

Gln Leu Pro Tyr Pro Gln Pro
1               5

<210> SEQ ID NO 97
<211> LENGTH: 7
<212> TYPE: PRT
<213> ORGANISM: Triticum aestivum

<400> SEQUENCE: 97

Leu Pro Tyr Pro Gln Pro Gln
1               5

<210> SEQ ID NO 98
<211> LENGTH: 7
<212> TYPE: PRT
<213> ORGANISM: Triticum aestivum

<400> SEQUENCE: 98

Pro Tyr Pro Gln Pro Gln Leu
1               5

<210> SEQ ID NO 99
<211> LENGTH: 7
<212> TYPE: PRT
<213> ORGANISM: Triticum aestivum

<400> SEQUENCE: 99

Tyr Pro Gln Pro Gln Leu Pro
1               5

<210> SEQ ID NO 100
<211> LENGTH: 16
<212> TYPE: PRT
<213> ORGANISM: Triticum aestivum

<400> SEQUENCE: 100

Pro Phe Pro Gln Pro Gln Leu Pro Tyr Pro Gln Pro Gln Leu Pro Tyr
1               5                   10                  15

<210> SEQ ID NO 101
<211> LENGTH: 16
<212> TYPE: PRT
<213> ORGANISM: Triticum aestivum

<400> SEQUENCE: 101

Phe Pro Gln Pro Gln Leu Pro Tyr Pro Gln Pro Gln Leu Pro Tyr Pro
1               5                   10                  15

<210> SEQ ID NO 102
<211> LENGTH: 16
<212> TYPE: PRT
<213> ORGANISM: Triticum aestivum

<400> SEQUENCE: 102

Leu Pro Tyr Pro Gln Pro Gln Leu Pro Tyr Pro Gln Pro Gln Pro Phe
1               5                   10                  15

<210> SEQ ID NO 103
<211> LENGTH: 9
<212> TYPE: PRT
<213> ORGANISM: Triticum aestivum

<400> SEQUENCE: 103

Pro Phe Pro Gln Pro Gln Leu Pro Tyr
1               5

<210> SEQ ID NO 104
<211> LENGTH: 9
<212> TYPE: PRT
<213> ORGANISM: Triticum aestivum

<400> SEQUENCE: 104

Phe Pro Gln Pro Gln Leu Pro Tyr Pro
1               5

```
<210> SEQ ID NO 105
<211> LENGTH: 9
<212> TYPE: PRT
<213> ORGANISM: Triticum aestivum

<400> SEQUENCE: 105

Leu Pro Tyr Pro Gln Pro Gln Pro Phe
1               5

<210> SEQ ID NO 106
<211> LENGTH: 7
<212> TYPE: PRT
<213> ORGANISM: Triticum aestivum

<400> SEQUENCE: 106

Gln Pro Phe Pro Gln Pro Gln
1               5

<210> SEQ ID NO 107
<211> LENGTH: 5
<212> TYPE: PRT
<213> ORGANISM: Triticum aestivum

<400> SEQUENCE: 107

Gln Pro Phe Pro Gln
1               5

<210> SEQ ID NO 108
<211> LENGTH: 5
<212> TYPE: PRT
<213> ORGANISM: Triticum aestivum

<400> SEQUENCE: 108

Gln Pro Gln Pro Phe
1               5

<210> SEQ ID NO 109
<211> LENGTH: 5
<212> TYPE: PRT
<213> ORGANISM: Triticum aestivum

<400> SEQUENCE: 109

Phe Pro Gln Pro Gln
1               5

<210> SEQ ID NO 110
<211> LENGTH: 5
<212> TYPE: PRT
<213> ORGANISM: Triticum aestivum

<400> SEQUENCE: 110

Pro Gln Pro Gln Pro
1               5

<210> SEQ ID NO 111
<211> LENGTH: 17
<212> TYPE: PRT
<213> ORGANISM: Triticum aestivum

<400> SEQUENCE: 111

Gln Pro Gln Leu Pro Tyr Pro Gln Pro Gln Leu Pro Tyr Pro Gln Pro
1               5                   10                  15

Gln
```

<210> SEQ ID NO 112
<211> LENGTH: 17
<212> TYPE: PRT
<213> ORGANISM: Triticum aestivum

<400> SEQUENCE: 112

Leu Gln Leu Gln Pro Phe Pro Gln Pro Gln Leu Pro Tyr Pro Gln Pro
1               5                   10                  15

Gln

<210> SEQ ID NO 113
<211> LENGTH: 17
<212> TYPE: PRT
<213> ORGANISM: Triticum aestivum

<400> SEQUENCE: 113

Gln Leu Gln Pro Phe Pro Gln Pro Gln Leu Pro Tyr Pro Gln Pro Gln
1               5                   10                  15

Leu

<210> SEQ ID NO 114
<211> LENGTH: 24
<212> TYPE: PRT
<213> ORGANISM: Triticum aestivum

<400> SEQUENCE: 114

Leu Gln Leu Gln Pro Phe Pro Gln Pro Gln Leu Pro Tyr Pro Gln Pro
1               5                   10                  15

Gln Leu Pro Tyr Pro Gln Pro Gln
            20

<210> SEQ ID NO 115
<211> LENGTH: 22
<212> TYPE: PRT
<213> ORGANISM: Triticum aestivum

<400> SEQUENCE: 115

Leu Gln Leu Gln Pro Phe Pro Gln Pro Gln Leu Pro Tyr Pro Gln Pro
1               5                   10                  15

Gln Leu Pro Tyr Pro Gln
            20

<210> SEQ ID NO 116
<211> LENGTH: 23
<212> TYPE: PRT
<213> ORGANISM: Triticum aestivum

<400> SEQUENCE: 116

Leu Gln Leu Gln Pro Phe Pro Gln Pro Gln Leu Pro Tyr Pro Gln Pro
1               5                   10                  15

Gln Leu Pro Tyr Pro Gln Pro
            20

<210> SEQ ID NO 117
<211> LENGTH: 15
<212> TYPE: PRT
<213> ORGANISM: Triticum aestivum

<400> SEQUENCE: 117

Leu Gln Leu Gln Pro Phe Pro Gln Pro Gln Leu Pro Tyr Pro Gln
1               5                   10                  15

```
<210> SEQ ID NO 118
<211> LENGTH: 4
<212> TYPE: PRT
<213> ORGANISM: Triticum aestivum

<400> SEQUENCE: 118

Pro Tyr Pro Gln
1

<210> SEQ ID NO 119
<211> LENGTH: 4
<212> TYPE: PRT
<213> ORGANISM: Triticum aestivum

<400> SEQUENCE: 119

Tyr Pro Gln Pro
1

<210> SEQ ID NO 120
<211> LENGTH: 4
<212> TYPE: PRT
<213> ORGANISM: Triticum aestivum

<400> SEQUENCE: 120

Leu Gln Pro Phe
1

<210> SEQ ID NO 121
<211> LENGTH: 9
<212> TYPE: PRT
<213> ORGANISM: Triticum aestivum

<400> SEQUENCE: 121

Leu Gln Leu Gln Pro Phe Pro Gln Pro
1               5

<210> SEQ ID NO 122
<211> LENGTH: 31
<212> TYPE: PRT
<213> ORGANISM: Triticum aestivum

<400> SEQUENCE: 122

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln
            20                  25                  30

<210> SEQ ID NO 123
<211> LENGTH: 6
<212> TYPE: PRT
<213> ORGANISM: Triticum aestivum

<400> SEQUENCE: 123

Pro Gln Pro Gln Leu Pro
1               5

<210> SEQ ID NO 124
<211> LENGTH: 21
<212> TYPE: PRT
<213> ORGANISM: Triticum aestivum

<400> SEQUENCE: 124

Tyr Pro Gln Pro Gln Leu Pro Tyr Pro Gln Pro Gln Leu Pro Tyr Pro
1               5                   10                  15
```

```
Gln Pro Gln Pro Phe
            20

<210> SEQ ID NO 125
<211> LENGTH: 19
<212> TYPE: PRT
<213> ORGANISM: Triticum aestivum

<400> SEQUENCE: 125

Gln Pro Phe Pro Gln Pro Gln Leu Pro Tyr Pro Gln Pro Gln Leu Pro
1               5                   10                  15

Tyr Pro Gln

<210> SEQ ID NO 126
<211> LENGTH: 19
<212> TYPE: PRT
<213> ORGANISM: Triticum aestivum

<400> SEQUENCE: 126

Gln Pro Gln Leu Pro Tyr Pro Gln Pro Gln Leu Pro Tyr Pro Gln Pro
1               5                   10                  15

Gln Pro Phe

<210> SEQ ID NO 127
<211> LENGTH: 19
<212> TYPE: PRT
<213> ORGANISM: Triticum aestivum

<400> SEQUENCE: 127

Phe Pro Gln Pro Gln Leu Pro Tyr Pro Gln Pro Gln Leu Pro Tyr Pro
1               5                   10                  15

Gln Pro Gln

<210> SEQ ID NO 128
<211> LENGTH: 14
<212> TYPE: PRT
<213> ORGANISM: Triticum aestivum

<400> SEQUENCE: 128

Gln Pro Phe Pro Gln Pro Gln Leu Pro Tyr Pro Gln Pro Gln
1               5                   10

<210> SEQ ID NO 129
<211> LENGTH: 14
<212> TYPE: PRT
<213> ORGANISM: Triticum aestivum

<400> SEQUENCE: 129

Pro Gln Pro Gln Leu Pro Tyr Pro Gln Pro Gln Leu Pro Tyr
1               5                   10

<210> SEQ ID NO 130
<211> LENGTH: 14
<212> TYPE: PRT
<213> ORGANISM: Triticum aestivum

<400> SEQUENCE: 130

Gln Pro Gln Leu Pro Tyr Pro Gln Pro Gln Leu Pro Tyr Pro
1               5                   10

<210> SEQ ID NO 131
<211> LENGTH: 14
<212> TYPE: PRT
```

<213> ORGANISM: Triticum aestivum

<400> SEQUENCE: 131

Pro Gln Leu Pro Tyr Pro Gln Pro Gln Leu Pro Tyr Pro Gln
1               5                   10

<210> SEQ ID NO 132
<211> LENGTH: 14
<212> TYPE: PRT
<213> ORGANISM: Triticum aestivum

<400> SEQUENCE: 132

Gln Leu Pro Tyr Pro Gln Pro Gln Leu Pro Tyr Pro Gln Pro
1               5                   10

<210> SEQ ID NO 133
<211> LENGTH: 14
<212> TYPE: PRT
<213> ORGANISM: Triticum aestivum

<400> SEQUENCE: 133

Leu Pro Tyr Pro Gln Pro Gln Leu Pro Tyr Pro Gln Pro Gln
1               5                   10

<210> SEQ ID NO 134
<211> LENGTH: 14
<212> TYPE: PRT
<213> ORGANISM: Triticum aestivum

<400> SEQUENCE: 134

Pro Tyr Pro Gln Pro Gln Leu Pro Tyr Pro Gln Pro Gln Leu
1               5                   10

<210> SEQ ID NO 135
<211> LENGTH: 14
<212> TYPE: PRT
<213> ORGANISM: Triticum aestivum

<400> SEQUENCE: 135

Tyr Pro Gln Pro Gln Leu Pro Tyr Pro Gln Pro Gln Leu Pro
1               5                   10

<210> SEQ ID NO 136
<211> LENGTH: 14
<212> TYPE: PRT
<213> ORGANISM: Triticum aestivum

<400> SEQUENCE: 136

Leu Gln Leu Gln Pro Phe Pro Gln Pro Gln Leu Pro Tyr Pro
1               5                   10

<210> SEQ ID NO 137
<211> LENGTH: 18
<212> TYPE: PRT
<213> ORGANISM: Triticum aestivum

<400> SEQUENCE: 137

Gln Pro Phe Pro Gln Pro Gln Leu Pro Tyr Pro Gln Pro Gln Leu Pro
1               5                   10                  15

Tyr Pro

<210> SEQ ID NO 138
<211> LENGTH: 18
<212> TYPE: PRT

-continued

<213> ORGANISM: Triticum aestivum

<400> SEQUENCE: 138

Pro Gln Leu Pro Tyr Pro Gln Pro Gln Leu Pro Tyr Pro Gln Pro Gln
1               5                   10                  15

Pro Phe

<210> SEQ ID NO 139
<211> LENGTH: 18
<212> TYPE: PRT
<213> ORGANISM: Triticum aestivum

<400> SEQUENCE: 139

Pro Phe Pro Gln Pro Gln Leu Pro Tyr Pro Gln Pro Gln Leu Pro Tyr
1               5                   10                  15

Pro Gln

<210> SEQ ID NO 140
<211> LENGTH: 18
<212> TYPE: PRT
<213> ORGANISM: Triticum aestivum

<400> SEQUENCE: 140

Phe Pro Gln Pro Gln Leu Pro Tyr Pro Gln Pro Gln Leu Pro Tyr Pro
1               5                   10                  15

Gln Pro

<210> SEQ ID NO 141
<211> LENGTH: 18
<212> TYPE: PRT
<213> ORGANISM: Triticum aestivum

<400> SEQUENCE: 141

Leu Pro Tyr Pro Gln Pro Gln Leu Pro Tyr Pro Gln Pro Gln Leu Pro
1               5                   10                  15

Tyr Pro

<210> SEQ ID NO 142
<211> LENGTH: 21
<212> TYPE: PRT
<213> ORGANISM: Triticum aestivum

<400> SEQUENCE: 142

Pro Tyr Pro Gln Pro Gln Leu Pro Tyr Pro Gln Pro Gln Leu Pro Tyr
1               5                   10                  15

Pro Gln Pro Gln Pro
            20

<210> SEQ ID NO 143
<211> LENGTH: 21
<212> TYPE: PRT
<213> ORGANISM: Triticum aestivum

<400> SEQUENCE: 143

Leu Gln Pro Phe Pro Gln Pro Gln Leu Pro Tyr Pro Gln Pro Gln Leu
1               5                   10                  15

Pro Tyr Pro Gln Pro
            20

<210> SEQ ID NO 144
<211> LENGTH: 21

<212> TYPE: PRT
<213> ORGANISM: Triticum aestivum

<400> SEQUENCE: 144

Pro Phe Pro Gln Pro Gln Leu Pro Tyr Pro Gln Pro Gln Leu Pro Tyr
1               5                   10                  15

Pro Gln Pro Gln Leu
            20

<210> SEQ ID NO 145
<211> LENGTH: 21
<212> TYPE: PRT
<213> ORGANISM: Triticum aestivum

<400> SEQUENCE: 145

Phe Pro Gln Pro Gln Leu Pro Tyr Pro Gln Pro Gln Leu Pro Tyr Pro
1               5                   10                  15

Gln Pro Gln Leu Pro
            20

<210> SEQ ID NO 146
<211> LENGTH: 16
<212> TYPE: PRT
<213> ORGANISM: Triticum aestivum

<400> SEQUENCE: 146

Pro Gln Pro Gln Leu Pro Tyr Pro Gln Pro Gln Leu Pro Tyr Pro Gln
1               5                   10                  15

<210> SEQ ID NO 147
<211> LENGTH: 16
<212> TYPE: PRT
<213> ORGANISM: Triticum aestivum

<400> SEQUENCE: 147

Gln Pro Gln Leu Pro Tyr Pro Gln Pro Gln Leu Pro Tyr Pro Gln Pro
1               5                   10                  15

<210> SEQ ID NO 148
<211> LENGTH: 16
<212> TYPE: PRT
<213> ORGANISM: Triticum aestivum

<400> SEQUENCE: 148

Pro Gln Leu Pro Tyr Pro Gln Pro Gln Leu Pro Tyr Pro Gln Pro Gln
1               5                   10                  15

<210> SEQ ID NO 149
<211> LENGTH: 16
<212> TYPE: PRT
<213> ORGANISM: Triticum aestivum

<400> SEQUENCE: 149

Gln Leu Pro Tyr Pro Gln Pro Gln Leu Pro Tyr Pro Gln Pro Gln Pro
1               5                   10                  15

<210> SEQ ID NO 150
<211> LENGTH: 21
<212> TYPE: PRT
<213> ORGANISM: Triticum aestivum

<400> SEQUENCE: 150

Pro Gln Leu Pro Tyr Pro Gln Pro Gln Leu Pro Tyr Pro Gln Pro Gln
1               5                   10                  15

Leu Pro Tyr Pro Gln
            20

<210> SEQ ID NO 151
<211> LENGTH: 21
<212> TYPE: PRT
<213> ORGANISM: Triticum aestivum

<400> SEQUENCE: 151

Leu Pro Tyr Pro Gln Pro Gln Leu Pro Tyr Pro Gln Pro Gln Leu Pro
1               5                   10                  15

Tyr Pro Gln Pro Gln
            20

<210> SEQ ID NO 152
<211> LENGTH: 21
<212> TYPE: PRT
<213> ORGANISM: Triticum aestivum

<400> SEQUENCE: 152

Pro Gln Pro Gln Leu Pro Tyr Pro Gln Pro Gln Leu Pro Tyr Pro Gln
1               5                   10                  15

Pro Gln Leu Pro Tyr
            20

<210> SEQ ID NO 153
<211> LENGTH: 21
<212> TYPE: PRT
<213> ORGANISM: Triticum aestivum

<400> SEQUENCE: 153

Gln Pro Gln Leu Pro Tyr Pro Gln Pro Gln Leu Pro Tyr Pro Gln Pro
1               5                   10                  15

Gln Leu Pro Tyr Pro
            20

<210> SEQ ID NO 154
<211> LENGTH: 21
<212> TYPE: PRT
<213> ORGANISM: Triticum aestivum

<400> SEQUENCE: 154

Gln Leu Pro Tyr Pro Gln Pro Gln Leu Pro Tyr Pro Gln Pro Gln Leu
1               5                   10                  15

Pro Tyr Pro Gln Pro
            20

<210> SEQ ID NO 155
<211> LENGTH: 21
<212> TYPE: PRT
<213> ORGANISM: Triticum aestivum

<400> SEQUENCE: 155

Leu Gln Leu Gln Pro Phe Pro Gln Pro Gln Leu Pro Tyr Pro Gln Pro
1               5                   10                  15

Gln Leu Pro Tyr Pro
            20

<210> SEQ ID NO 156
<211> LENGTH: 32
<212> TYPE: PRT
<213> ORGANISM: Triticum aestivum -continued

```
<400> SEQUENCE: 156

Leu Gln Leu Gln Pro Glu Pro Gln Pro Gln Leu Pro Tyr Pro Gln Pro
1               5                   10                  15

Gln Leu Pro Tyr Gln Pro Gln Leu Pro Tyr Pro Gln Pro Gln Pro Phe
            20                  25                  30
```